(12) United States Patent
Boyle et al.

(10) Patent No.: US 11,913,023 B2
(45) Date of Patent: Feb. 27, 2024

(54) MODIFIED B CELLS AND METHODS OF USE THEREOF

(71) Applicant: Walking Fish Therapeutics, South San Francisco, CA (US)

(72) Inventors: Kathleen Boyle, Alameda, CA (US); Hangil Park, San Francisco, CA (US); Srinivas Kothakota, Pacifica, CA (US); Mark Selby, San Francisco, CA (US); Thomas Brennan, Cupertino, CA (US); Lewis T. Williams, Mill Valley, CA (US)

(73) Assignee: Walking Fish Therapeutics, Inc., South San Francisco, CA (US)

( * ) Notice: Subject to any disclaimer, the term of this patent is extended or adjusted under 35 U.S.C. 154(b) by 0 days.

(21) Appl. No.: 17/465,759

(22) Filed: Sep. 2, 2021

(65) Prior Publication Data

US 2022/0073876 A1    Mar. 10, 2022

Related U.S. Application Data

(63) Continuation of application No. PCT/US2021/025273, filed on Mar. 31, 2021.

(60) Provisional application No. 63/073,799, filed on Sep. 2, 2020, provisional application No. 63/003,120, filed on Mar. 31, 2020.

(51) Int. Cl.
*C12N 5/0781* (2010.01)
*A61K 35/17* (2015.01)
*C07K 16/30* (2006.01)

(52) U.S. Cl.
CPC .......... *C12N 5/0635* (2013.01); *A61K 35/17* (2013.01); *C07K 16/303* (2013.01); *C07K 16/3069* (2013.01); *C07K 2317/53* (2013.01); *C07K 2317/622* (2013.01); *C07K 2319/03* (2013.01); *C12N 2510/00* (2013.01)

(58) Field of Classification Search
None
See application file for complete search history.

(56) References Cited

U.S. PATENT DOCUMENTS

| | | | |
|---|---|---|---|
| 9,175,072 B2 | 11/2015 | Hyde et al. | |
| 9,512,213 B2 | 12/2016 | Hyde et al. | |
| 10,233,424 B2 | 3/2019 | Hyde et al. | |
| 10,597,442 B2 | 3/2020 | Hyde et al. | |
| 10,745,468 B2 | 8/2020 | Hyde et al. | |
| 2006/0165668 A1 | 7/2006 | Liu et al. | |
| 2006/0247191 A1 | 11/2006 | Finney et al. | |
| 2006/0263340 A1 | 11/2006 | Andrian et al. | |
| 2013/0004456 A1 | 1/2013 | Weinschenk et al. | |
| 2016/0158285 A1 | 6/2016 | Cooper et al. | |
| 2016/0289637 A1 | 10/2016 | Goldberg et al. | |
| 2017/0368098 A1* | 12/2017 | Chen .................. | C07K 16/2887 |
| 2018/0002664 A1 | 1/2018 | Scholz et al. | |
| 2019/0218299 A1 | 7/2019 | Pradines et al. | |
| 2019/0321403 A1 | 10/2019 | Levitsky | |
| 2019/0352385 A1* | 11/2019 | Hyde .................. | G01N 33/6854 |
| 2020/0061117 A1* | 2/2020 | Kitchen ............. | A61K 38/1774 |
| 2020/0281973 A1* | 9/2020 | Dranoff ............. | C07K 16/2803 |
| 2021/0077532 A1* | 3/2021 | Xiao ................. | A61K 39/00117 |
| 2021/0161954 A1* | 6/2021 | Smith .................... | C07K 14/47 |
| 2021/0301024 A1* | 9/2021 | Yu ......................... | C07K 14/705 |
| 2022/0184123 A1* | 6/2022 | Naso .................. | A61K 39/3955 |
| 2022/0275334 A1* | 9/2022 | Delaney ............. | C07K 16/2803 |
| 2022/0372101 A1* | 11/2022 | Roybal ............. | C07K 14/70517 |
| 2023/0032532 A1* | 2/2023 | Zhao .................... | C12N 5/0636 |

FOREIGN PATENT DOCUMENTS

| | | |
|---|---|---|
| WO | WO 02/092792 A2 | 11/2002 |
| WO | WO 2017/174329 A1 | 10/2017 |
| WO | WO 2018/140573 A1 | 8/2018 |
| WO | WO 2018/200585 A1 | 11/2018 |

OTHER PUBLICATIONS

Marks et al., Retinoic Acid Signaling in B Cells Is Required for the Generation of an Effective T-Independent Immune Response. Front Immunol. Dec. 23, 2016;7:643.

Pesch, Theresa, "Molecular Design, Optimization, and Genomic Integration of Chimeric B Cell Receptors in Murine B Cells", Frontiers in Immunology, Nov. 14, 2019, vol. 10, Article 2630, 16 pages, Zurich, Switzerland.

* cited by examiner

*Primary Examiner* — Michail A Belyavskyi
(74) *Attorney, Agent, or Firm* — McDermott Will & Emery LLP

(57) ABSTRACT

The present invention relates to genetically modified B cells and their uses thereof, for example, for the treatment of a variety of diseases and disorders, including cancer, heart disease, inflammatory disease, muscle wasting disease, neurological disease, and the like. In certain embodiments, the invention relates to an isolated modified B cell ("CAR-B cell), capable of expressing a chimeric receptor ("CAR-B receptor"), wherein said chimeric receptor comprises (a) an extracellular domain; (b) a transmembrane domain; and (c) a cytoplasmic domain that comprises at least one signaling domain. In various embodiments, the invention comprises an isolated modified B cell, wherein said B cell is capable of expressing and secreting a payload, wherein the payload is not naturally expressed in a B cell or is expressed at higher levels than is naturally expressed in a B cell. In various embodiments, the payload is an antibody or fragment thereof.

32 Claims, 18 Drawing Sheets

Specification includes a Sequence Listing.

Examples of cBCR (chimeric B cell receptor)

| Anti GPC3 scFv | Hinge | Trans-membrane | Signaling domain |

| Anti PSMA scFv | Hinge | Trans-membrane | Signaling domain |

FIG. 3

SEQUENCE LISTING

<160> NUMBER OF SEQ ID NOS: 150

<210> SEQ ID NO 1
<211> LENGTH: 81
<212> TYPE: DNA
<213> ORGANISM: Mus musculus

<400> SEQUENCE: 1
ttctgggccc ttgtggtggt tgccggagtg ctgttttgct atgggctcct ggttaccgtt     60
gccctttgtg tgatttggac c                                              81

<210> SEQ ID NO 2
<211> LENGTH: 27
<212> TYPE: PRT
<213> ORGANISM: Mus musculus

<400> SEQUENCE: 2

Phe Trp Ala Leu Val Val Val Ala Gly Val Leu Phe Cys Tyr Gly Leu
1               5                  10                  15

Leu Val Thr Val Ala Leu Cys Val Ile Trp Thr
            20                  25

<210> SEQ ID NO 3
<211> LENGTH: 81
<212> TYPE: DNA
<213> ORGANISM: Homo sapiens

<400> SEQUENCE: 3
ttttgggtat tggtagtggt gggcggagtt ttagcctgct acagcctcct ggtaacagtg     60
gcttttatca tctttgggt g                                               81

<210> SEQ ID NO 4
<211> LENGTH: 27
<212> TYPE: PRT
<213> ORGANISM: Homo sapiens

<400> SEQUENCE: 4

Phe Trp Val Leu Val Val Val Gly Gly Val Leu Ala Cys Tyr Ser Leu
1               5                  10                  15

Leu Val Thr Val Ala Phe Ile Ile Phe Trp Val
            20                  25

<210> SEQ ID NO 5
<211> LENGTH: 729
<212> TYPE: DNA
<213> ORGANISM: Homo sapiens

<400> SEQUENCE: 5
cagcgggctt tagtcttgcg gcgtaaacgt aaaagaatga cagatccaac tcgcaggttc     60
ttcaaagtga cccccccacc tgggtccgga ccgcagaacc aatatgggaa tgtcctgtct    120
ctgcctacgc ctacaagtgg actgggtagg gctcagaggt gggctgccgg tctcggcgga    180
actgcgccat cttacggaaa tccctcctcc gacgttcagg cagacggggc cctggggtct    240
cgatccccgc ctggtgttgg accagaagag gaagagggcg agggctacga agagcccgac    300
tccgaagagg acagtgagtt ttacgagaac acagcaacc tggggcagga tcagctgtca    360
caggatggct caggatatga aaaccctgag gacgagcctt ggggcctga agatgaggac    420 tccttttcta atgcagagtc atatgagaat gaggacgaag aattgactca acccgtggca    480
agaacaatgg atttcctcag tccacacggg agtgcatggg acccctccag agaggctact    540

```
agcctcggtt ctcaaagcta tgaggacatg aggggtattc tgtacgcagc gcctcagttg      600
aggtccatcc gcggccagcc aggcccaaac catgaggaag atgccgattc ttacgaaaac      660
atggacaacc ccgatggtcc tgaccccgca tgggggggcg gcgggaggat gggcacctgg      720
tctactcgc                                                             729
```

<210> SEQ ID NO 6
<211> LENGTH: 243
<212> TYPE: PRT
<213> ORGANISM: Homo sapiens

<400> SEQUENCE: 6

```
Gln Arg Ala Leu Val Leu Arg Arg Lys Arg Lys Arg Met Thr Asp Pro
1               5                   10                  15

Thr Arg Arg Phe Phe Lys Val Thr Pro Pro Gly Ser Gly Pro Gln
            20                  25                  30

Asn Gln Tyr Gly Asn Val Leu Ser Leu Pro Thr Pro Thr Ser Gly Leu
        35                  40                  45

Gly Arg Ala Gln Arg Trp Ala Ala Gly Leu Gly Thr Ala Pro Ser
    50                  55                  60

Tyr Gly Asn Pro Ser Ser Asp Val Gln Ala Asp Gly Ala Leu Gly Ser
65                  70                  75                  80

Arg Ser Pro Pro Gly Val Gly Pro Glu Glu Glu Gly Glu Gly Tyr
                85                  90                  95

Glu Glu Pro Asp Ser Glu Glu Asp Ser Glu Phe Tyr Glu Asn Asp Ser
            100                 105                 110

Asn Leu Gly Gln Asp Gln Leu Ser Gln Asp Gly Ser Gly Tyr Glu Asn
        115                 120                 125

Pro Glu Asp Glu Pro Leu Gly Pro Glu Asp Glu Asp Ser Phe Ser Asn
    130                 135                 140

Ala Glu Ser Tyr Glu Asn Glu Asp Glu Glu Leu Thr Gln Pro Val Ala
145                 150                 155                 160

Arg Thr Met Asp Phe Leu Ser Pro His Gly Ser Ala Trp Asp Pro Ser
                165                 170                 175

Arg Glu Ala Thr Ser Leu Gly Ser Gln Ser Tyr Glu Asp Met Arg Gly
            180                 185                 190

Ile Leu Tyr Ala Ala Pro Gln Leu Arg Ser Ile Arg Gly Gln Pro Gly
        195                 200                 205

Pro Asn His Glu Glu Asp Ala Asp Ser Tyr Glu Asn Met Asp Asn Pro
    210                 215                 220

Asp Gly Pro Asp Pro Ala Trp Gly Gly Gly Arg Met Gly Thr Trp
225                 230                 235                 240

Ser Thr Arg
```

<210> SEQ ID NO 7
<211> LENGTH: 186
<212> TYPE: DNA
<213> ORGANISM: Homo sapiens

<400> SEQUENCE: 7

```
aagaaggttg caaaaaaacc tactaataag gctccccatc ctaagcaaga gccccaagaa      60
attaactttc ccgatgatct tccgggttct aacacggcag ccccggtgca ggagaccctg     120
catggttgtc aacccgtcac tcaggaggac gggaaagagt ctcgtatctc cgtccaggag     180
agacag                                                               186
```

<210> SEQ ID NO 8
<211> LENGTH: 62
<212> TYPE: PRT
<213> ORGANISM: Homo sapiens

<400> SEQUENCE: 8

Lys Lys Val Ala Lys Lys Pro Thr Asn Lys Ala Pro His Pro Lys Gln
1               5                   10                  15

Glu Pro Gln Glu Ile Asn Phe Pro Asp Asp Leu Pro Gly Ser Asn Thr
            20                  25                  30

Ala Ala Pro Val Gln Glu Thr Leu His Gly Cys Gln Pro Val Thr Gln
        35                  40                  45

Glu Asp Gly Lys Glu Ser Arg Ile Ser Val Gln Glu Arg Gln
    50                  55                  60

<210> SEQ ID NO 9
<211> LENGTH: 330
<212> TYPE: DNA
<213> ORGANISM: Homo sapiens

<400> SEQUENCE: 9
aagaaggttg caaaaaaacc tactaataag gctcccccatc ctaagcaaga gccccaagaa      60
attaactttc ccgatgatct tccgggttct aacacggcag ccccggtgca ggagaccctg     120
catggttgtc aacccgtcac tcaggaggac gggaaagagt ctcgtatctc cgtccaggag     180
agacaggaca aggacgatag taaagcaggg atggaggagg accatacata cgagggactg     240
gatatcgatc agacagccac gtacgaagac attgtgacac tgagaactgg cgaggtgaag     300
tggtcagtgg gagaacatcc ggggcaggaa                                      330

<210> SEQ ID NO 10
<211> LENGTH: 110
<212> TYPE: PRT
<213> ORGANISM: Homo sapiens

<400> SEQUENCE: 10

Lys Lys Val Ala Lys Lys Pro Thr Asn Lys Ala Pro His Pro Lys Gln
1               5                   10                  15

Glu Pro Gln Glu Ile Asn Phe Pro Asp Asp Leu Pro Gly Ser Asn Thr
            20                  25                  30

Ala Ala Pro Val Gln Glu Thr Leu His Gly Cys Gln Pro Val Thr Gln
        35                  40                  45

Glu Asp Gly Lys Glu Ser Arg Ile Ser Val Gln Glu Arg Gln Asp Lys
    50                  55                  60

Asp Asp Ser Lys Ala Gly Met Glu Glu Asp His Thr Tyr Glu Gly Leu
65                  70                  75                  80

Asp Ile Asp Gln Thr Ala Thr Tyr Glu Asp Ile Val Thr Leu Arg Thr
                85                  90                  95

Gly Glu Val Lys Trp Ser Val Gly Glu His Pro Gly Gln Glu
            100                 105                 110

<210> SEQ ID NO 11
<211> LENGTH: 312
<212> TYPE: DNA
<213> ORGANISM: Homo sapiens

<400> SEQUENCE: 11
aagaaggttg caaaaaaacc tactaataag gctcccccatc ctaagcaaga gccccaagaa      60

-continued

```
attaactttc cgatgatct tccgggttct aacacggcag ccccggtgca ggagaccctg        120
catggttgtc aacccgtcac tcaggaggac gggaaagagt ctcgtatctc cgtccaggag        180
agacagaaaa gaggccgaaa aaagctgctg tacatcttca acaacccctt catgcgacct        240
gttcagacga cacaggagga ggacggctgc agctgtaggt ttcccgaaga agaggaggga        300
ggatgcgaac tt                                                            312
```

<210> SEQ ID NO 12
<211> LENGTH: 104
<212> TYPE: PRT
<213> ORGANISM: Homo sapiens

<400> SEQUENCE: 12

```
Lys Lys Val Ala Lys Lys Pro Thr Asn Lys Ala Pro His Pro Lys Gln
1               5                   10                  15

Glu Pro Gln Glu Ile Asn Phe Pro Asp Asp Leu Pro Gly Ser Asn Thr
            20                  25                  30

Ala Ala Pro Val Gln Glu Thr Leu His Gly Cys Gln Pro Val Thr Gln
        35                  40                  45

Glu Asp Gly Lys Glu Ser Arg Ile Ser Val Gln Glu Arg Gln Lys Arg
    50                  55                  60

Gly Arg Lys Lys Leu Leu Tyr Ile Phe Lys Gln Pro Phe Met Arg Pro
65                  70                  75                  80

Val Gln Thr Thr Gln Glu Glu Asp Gly Cys Ser Cys Arg Phe Pro Glu
                85                  90                  95

Glu Glu Glu Gly Gly Cys Glu Leu
            100
```

<210> SEQ ID NO 13
<211> LENGTH: 126
<212> TYPE: DNA
<213> ORGANISM: Homo sapiens

<400> SEQUENCE: 13

```
aaaagaggcc gaaaaaagct gctgtacatc ttcaaacaac ccttcatgcg acctgttcag        60
acgacacagg aggaggacgg ctgcagctgt aggtttcccg aagaagagga gggaggatgc       120
gaactt                                                                  126
```

<210> SEQ ID NO 14
<211> LENGTH: 42
<212> TYPE: PRT
<213> ORGANISM: Homo sapiens

<400> SEQUENCE: 14

```
Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40
```

<210> SEQ ID NO 15
<211> LENGTH: 414
<212> TYPE: DNA
<213> ORGANISM: Homo sapiens

<400> SEQUENCE: 15

```
aagaaggttg caaaaaaacc tactaataag gctccccatc ctaagcaaga gccccaagaa    60
attaactttc ccgatgatct tccgggttct aacacggcag ccccggtgca ggagaccctg   120
catggttgtc aacccgtcac tcaggaggac gggaaagagt ctcgtatctc cgtccaggag   180
agacagcgca aaaacgtat aagcgcaaac tctacagatc cagtaaaagc cgcgcaattc    240
gagcctcccg gccgccagat gattgcaata cggaaacgtc aactggagga aactaataat   300
gactatgaga cggccgacgg tggatacatg acccttaatc cccgcgcgcc aaccgacgat   360
gataagaaca tatatctgac gctccccct aacgatcacg ttaacagtaa taat          414
```

<210> SEQ ID NO 16
<211> LENGTH: 138
<212> TYPE: PRT
<213> ORGANISM: Homo sapiens
<400> SEQUENCE: 16

```
Lys Lys Val Ala Lys Lys Pro Thr Asn Lys Ala Pro His Pro Lys Gln
1               5                   10                  15

Glu Pro Gln Glu Ile Asn Phe Pro Asp Asp Leu Pro Gly Ser Asn Thr
                20                  25                  30

Ala Ala Pro Val Gln Glu Thr Leu His Gly Cys Gln Pro Val Thr Gln
            35                  40                  45

Glu Asp Gly Lys Glu Ser Arg Ile Ser Val Gln Glu Arg Gln Arg Lys
        50                  55                  60

Lys Arg Ile Ser Ala Asn Ser Thr Asp Pro Val Lys Ala Ala Gln Phe
65                  70                  75                  80

Glu Pro Pro Gly Arg Gln Met Ile Ala Ile Arg Lys Arg Gln Leu Glu
                85                  90                  95

Glu Thr Asn Asn Asp Tyr Glu Thr Ala Asp Gly Gly Tyr Met Thr Leu
                100                 105                 110

Asn Pro Arg Ala Pro Thr Asp Asp Lys Asn Ile Tyr Leu Thr Leu
            115                 120                 125

Pro Pro Asn Asp His Val Asn Ser Asn Asn
        130                 135
```

<210> SEQ ID NO 17
<211> LENGTH: 228
<212> TYPE: DNA
<213> ORGANISM: Homo sapiens
<400> SEQUENCE: 17

```
cgcaaaaaac gtataagcgc aaactctaca gatccagtaa aagccgcgca attcgagcct    60
cccggccgcc agatgattgc aatacggaaa cgtcaactgg aggaaactaa taatgactat   120
gagacggccg acggtggata catgacccct taatccccgcg cgccaaccga cgatgataag   180
aacatatatc tgacgctccc ccctaacgat cacgttaaca gtaataat                228
```

<210> SEQ ID NO 18
<211> LENGTH: 76
<212> TYPE: PRT
<213> ORGANISM: Homo sapiens
<400> SEQUENCE: 18

```
Arg Lys Lys Arg Ile Ser Ala Asn Ser Thr Asp Pro Val Lys Ala Ala
1               5                   10                  15

Gln Phe Glu Pro Pro Gly Arg Gln Met Ile Ala Ile Arg Lys Arg Gln
                20                  25                  30
```

```
Leu Glu Glu Thr Asn Asn Asp Tyr Glu Thr Ala Asp Gly Gly Tyr Met
         35                  40                  45

Thr Leu Asn Pro Arg Ala Pro Thr Asp Asp Lys Asn Ile Tyr Leu
 50                  55                  60

Thr Leu Pro Pro Asn Asp His Val Asn Ser Asn Asn
 65                  70                  75

<210> SEQ ID NO 19
<211> LENGTH: 681
<212> TYPE: DNA
<213> ORGANISM: Homo sapiens

<400> SEQUENCE: 19
atggcggcgg gcgggcccgg cgccggaagc gccgcgccag tctcatctac gtccagtctg      60
ccactggctg ccctgaacat gagagtgaga cgccgtttat ccctcttcct gaatgtgcgg     120
acccaggtcg ccgctgattg gaccgccctg ccgaagaga tggactttga atacttggaa      180
atcagacagc tggaaacaca ggcagaccca accgggagac tgcttgacgc ctggcaggga     240
cgcccagggg caagtgttgg tcggttactg gagcttttaa ctaagttggg ccgcgatgac     300
gtgctgttgg agttaggacc cagtatcgag gaggattgtc agaaatacat cttgaaacag     360
cagcaggagg aggcggaaaa gcccctgcag gtggcggccg ttgacagcag tgtacccaga     420
acagctgagc tggccggcat cacaaccctg gatgatcccc tgggccacat gcctgagagg     480
ttcgacgctt tcataaagaa ggttgcaaaa aaacctacta ataaggctcc ccatcctaag     540
caagagcccc aagaaattaa ctttcccgat gatcttccgg gttctaacac ggcagccccg     600
gtgcaggaga ccctgcatgg ttgtcaaccc gtcactcagg aggacgggaa agagtctcgt     660
atctccgtcc aggagagaca g                                               681

<210> SEQ ID NO 20
<211> LENGTH: 227
<212> TYPE: PRT
<213> ORGANISM: Homo sapiens

<400> SEQUENCE: 20

Met Ala Ala Gly Gly Pro Gly Ala Gly Ser Ala Ala Pro Val Ser Ser
 1               5                  10                  15

Thr Ser Ser Leu Pro Leu Ala Ala Leu Asn Met Arg Val Arg Arg Arg
             20                  25                  30

Leu Ser Leu Phe Leu Asn Val Arg Thr Gln Val Ala Ala Asp Trp Thr
         35                  40                  45

Ala Leu Ala Glu Glu Met Asp Phe Glu Tyr Leu Glu Ile Arg Gln Leu
 50                  55                  60

Glu Thr Gln Ala Asp Pro Thr Gly Arg Leu Leu Asp Ala Trp Gln Gly
 65                  70                  75                  80

Arg Pro Gly Ala Ser Val Gly Arg Leu Leu Glu Leu Leu Thr Lys Leu
                 85                  90                  95

Gly Arg Asp Asp Val Leu Leu Glu Leu Gly Pro Ser Ile Glu Glu Asp
                100                 105                 110

Cys Gln Lys Tyr Ile Leu Lys Gln Gln Gln Glu Glu Ala Glu Lys Pro
            115                 120                 125

Leu Gln Val Ala Ala Val Asp Ser Ser Val Pro Arg Thr Ala Glu Leu
        130                 135                 140

Ala Gly Ile Thr Thr Leu Asp Asp Pro Leu Gly His Met Pro Glu Arg
145                 150                 155                 160
```

```
Phe Asp Ala Phe Ile Lys Lys Val Ala Lys Lys Pro Thr Asn Lys Ala
                165                 170                 175

Pro His Pro Lys Gln Glu Pro Gln Glu Ile Asn Phe Pro Asp Asp Leu
            180                 185                 190

Pro Gly Ser Asn Thr Ala Ala Pro Val Gln Glu Thr Leu His Gly Cys
        195                 200                 205

Gln Pro Val Thr Gln Glu Asp Gly Lys Glu Ser Arg Ile Ser Val Gln
    210                 215                 220

Glu Arg Gln
225

<210> SEQ ID NO 21
<211> LENGTH: 495
<212> TYPE: DNA
<213> ORGANISM: Homo sapiens

<400> SEQUENCE: 21
atggcggcgg gcgggcccgg cgccggaagc gccgcgccag tctcatctac gtccagtctg      60
ccactggctg ccctgaacat gagagtgaga cgccgtttat ccctcttcct gaatgtgcgg     120
acccaggtcg ccgctgattg gaccgccctg gccgaagaga tggactttga atacttggaa     180
atcagacagc tggaaacaca ggcagaccca accgggagac tgcttgacgc ctggcaggga     240
cgcccagggg caagtgttgg tcggttactg gagcttttaa ctaagttggg ccgcgatgac     300
gtgctgttgg agttaggacc cagtatcgag gaggattgtc agaaatacat cttgaaacag     360
cagcaggagg aggcggaaaa gcccctgcag gtggcggccg ttgacagcag tgtacccaga     420
acagctgagc tggccggcat cacaaccctg gatgatcccc tgggccacat gcctgagagg     480
ttcgacgctt tcata                                                      495

<210> SEQ ID NO 22
<211> LENGTH: 165
<212> TYPE: PRT
<213> ORGANISM: Homo sapiens

<400> SEQUENCE: 22

Met Ala Ala Gly Gly Pro Gly Ala Gly Ser Ala Ala Pro Val Ser Ser
1               5                   10                  15

Thr Ser Ser Leu Pro Leu Ala Ala Leu Asn Met Arg Val Arg Arg Arg
            20                  25                  30

Leu Ser Leu Phe Leu Asn Val Arg Thr Gln Val Ala Ala Asp Trp Thr
        35                  40                  45

Ala Leu Ala Glu Glu Met Asp Phe Glu Tyr Leu Glu Ile Arg Gln Leu
    50                  55                  60

Glu Thr Gln Ala Asp Pro Thr Gly Arg Leu Leu Asp Ala Trp Gln Gly
65                  70                  75                  80

Arg Pro Gly Ala Ser Val Gly Arg Leu Leu Glu Leu Leu Thr Lys Leu
                85                  90                  95

Gly Arg Asp Asp Val Leu Leu Glu Leu Gly Pro Ser Ile Glu Glu Asp
            100                 105                 110

Cys Gln Lys Tyr Ile Leu Lys Gln Gln Gln Glu Glu Ala Glu Lys Pro
        115                 120                 125

Leu Gln Val Ala Ala Val Asp Ser Ser Val Pro Arg Thr Ala Glu Leu
    130                 135                 140

Ala Gly Ile Thr Thr Leu Asp Asp Pro Leu Gly His Met Pro Glu Arg
145                 150                 155                 160
```

Phe Asp Ala Phe Ile
                165

<210> SEQ ID NO 23
<211> LENGTH: 183
<212> TYPE: DNA
<213> ORGANISM: Homo sapiens

<400> SEQUENCE: 23
aggaaacgat ggcagaacga gaagctcggg ttggatgccg gggatgaata tgaagatgaa    60
aacctttatg aaggcctgaa cctggacgac tgctccatgt atgaggacat ctcccggggc   120
ctccagggca cctaccagga tgtgggcagc ctcaacatag agatgtcca gctggagaag   180 ccg                                                                 183

<210> SEQ ID NO 24
<211> LENGTH: 61
<212> TYPE: PRT
<213> ORGANISM: Homo sapiens

<400> SEQUENCE: 24

Arg Lys Arg Trp Gln Asn Glu Lys Leu Gly Leu Asp Ala Gly Asp Glu
1               5                   10                  15

Tyr Glu Asp Glu Asn Leu Tyr Glu Gly Leu Asn Leu Asp Asp Cys Ser
                20                  25                  30

Met Tyr Glu Asp Ile Ser Arg Gly Leu Gln Gly Thr Tyr Gln Asp Val
            35                  40                  45

Gly Ser Leu Asn Ile Gly Asp Val Gln Leu Glu Lys Pro
        50                  55                  60

<210> SEQ ID NO 25
<211> LENGTH: 147
<212> TYPE: DNA
<213> ORGANISM: Homo sapiens

<400> SEQUENCE: 25
ctggacaagg atgacagcaa ggctggcatg gaggaagatc acacctacga gggcctggac    60
attgaccaga cagccaccta tgaggacata gtgacgctgc ggacagggga agtgaagtgg   120
tctgtaggtg agcacccagg ccaggag                                       147

<210> SEQ ID NO 26
<211> LENGTH: 49
<212> TYPE: PRT
<213> ORGANISM: Homo sapiens

<400> SEQUENCE: 26

Leu Asp Lys Asp Asp Ser Lys Ala Gly Met Glu Glu Asp His Thr Tyr
1               5                   10                  15

Glu Gly Leu Asp Ile Asp Gln Thr Ala Thr Tyr Glu Asp Ile Val Thr
                20                  25                  30

Leu Arg Thr Gly Glu Val Lys Trp Ser Val Gly Glu His Pro Gly Gln
            35                  40                  45

Glu

<210> SEQ ID NO 27
<211> LENGTH: 165
<212> TYPE: DNA
<213> ORGANISM: Homo sapiens

<400> SEQUENCE: 27

-continued ttcgtgcctg tgttcctccc agctaagccc actaccaccc ccgctccaag gccgcccacg    60
cccgctccta ctattgctag tcagccttta agtttacgac ccgaagcttg caggcccgcc   120
gccggcggcg ctgtgcacac caggggggctt gatttttgcct gcgac                 165

<210> SEQ ID NO 28
<211> LENGTH: 55
<212> TYPE: PRT
<213> ORGANISM: Homo sapiens

<400> SEQUENCE: 28

Phe Val Pro Val Phe Leu Pro Ala Lys Pro Thr Thr Thr Pro Ala Pro
1               5                   10                  15

Arg Pro Pro Thr Pro Ala Pro Thr Ile Ala Ser Gln Pro Leu Ser Leu
            20                  25                  30

Arg Pro Glu Ala Cys Arg Pro Ala Ala Gly Gly Ala Val His Thr Arg
        35                  40                  45

Gly Leu Asp Phe Ala Cys Asp
    50                  55

<210> SEQ ID NO 29
<211> LENGTH: 189
<212> TYPE: DNA
<213> ORGANISM: Artificial Sequence
<220> FEATURE:
<223> OTHER INFORMATION: Synthetic

<400> SEQUENCE: 29
ggcgctggta gtggcggtaa ctggagccac cctcaatttg agaagggcgg gtcaggcgga    60
tcaggtggta gtggtgggtc caactggagc catccgcaat tgaaaaggg cggaagcggc   120 ggttccggcg gttcaggcgg tagcaactgg tcacatccgc aatttgagaa aggcgggtca   180
ggcggcggg                                                          189

<210> SEQ ID NO 30
<211> LENGTH: 63
<212> TYPE: PRT
<213> ORGANISM: Artificial Sequence
<220> FEATURE:
<223> OTHER INFORMATION: Synthetic

<400> SEQUENCE: 30

Gly Ala Gly Ser Gly Gly Asn Trp Ser His Pro Gln Phe Glu Lys Gly
1               5                   10                  15

Gly Ser Gly Gly Ser Gly Gly Ser Gly Ser Asn Trp Ser His Pro
            20                  25                  30

Gln Phe Glu Lys Gly Gly Ser Gly Gly Ser Gly Gly Ser Gly Gly Ser
        35                  40                  45

Asn Trp Ser His Pro Gln Phe Glu Lys Gly Gly Ser Gly Gly Gly
    50                  55                  60

<210> SEQ ID NO 31
<211> LENGTH: 903
<212> TYPE: DNA
<213> ORGANISM: Homo sapiens

<400> SEQUENCE: 31
cccaagagct gcgacaagac ccacacctgc cccccctgcc cagccccaga gctgctgggc    60
ggaccctccg tgttcctgtt ccccccaag cccaaggaca ccctgatgat cagcaggacc   120

```
cccgaggtga cctgcgtggt ggtggacgtg agccacgagg acccagaggt gaagttcaac    180
tggtacgtgg acggcgtgga ggtgcacaac gccaagacca gcccagaga ggagcagtac    240 aacagcacct acagggtggt gtccgtgctg accgtgctgc accaggactg gctgaacggc    300
aaggaataca agtgcaaggt ctccaacaag gccctgccag cccccatcga aaagaccatc    360
agcaaggcca agggccagcc acgggagccc caggtgtaca ccctgccccc ctcccgggag    420
gagatgacca gaaccaggt gtccctgacc tgtctggtga agggcttcta ccccagcgac     480
atcgccgtgg agtgggagag caacggccag cccgagaaca actacaagac cacccccca    540 gtgctggaca cgacggcag cttcttcctg tacagcaagc tgaccgtgga caagtccagg     600
tggcagcagg gcaacgtgtt cagctgcagc gtgatgcacg aggccctgca caaccactac    660
acccagaaga gcctgagcct gtcccccgag ctgcaactgg aggagagctg tgcggaggcg    720
caggacgggg agctggacgg gctgtggacg accatcacca tcttcatcac actcttcctg    780
ttaagcgtgt gctacagtgc caccgtcacc ttcttcaagg tgaagtggat cttctcctcg    840
gtggtggacc tgaagcagac catcatcccc gactacagga catgatcgg acaggggccc    900 tga                                                                  903

<210> SEQ ID NO 32
<211> LENGTH: 300
<212> TYPE: PRT
<213> ORGANISM: Homo sapiens

<400> SEQUENCE: 32

Pro Lys Ser Cys Asp Lys Thr His Thr Cys Pro Pro Cys Pro Ala Pro
1               5                   10                  15

Glu Leu Leu Gly Gly Pro Ser Val Phe Leu Phe Pro Pro Lys Pro Lys
            20                  25                  30

Asp Thr Leu Met Ile Ser Arg Thr Pro Glu Val Thr Cys Val Val Val
        35                  40                  45

Asp Val Ser His Glu Asp Pro Glu Val Lys Phe Asn Trp Tyr Val Asp
    50                  55                  60

Gly Val Glu Val His Asn Ala Lys Thr Lys Pro Arg Glu Glu Gln Tyr
65                  70                  75                  80

Asn Ser Thr Tyr Arg Val Val Ser Val Leu Thr Val Leu His Gln Asp
                85                  90                  95

Trp Leu Asn Gly Lys Glu Tyr Lys Cys Lys Val Ser Asn Lys Ala Leu
            100                 105                 110

Pro Ala Pro Ile Glu Lys Thr Ile Ser Lys Ala Lys Gly Gln Pro Arg
        115                 120                 125

Glu Pro Gln Val Tyr Thr Leu Pro Pro Ser Arg Glu Glu Met Thr Lys
    130                 135                 140

Asn Gln Val Ser Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175

Thr Thr Pro Pro Val Leu Asp Ser Asp Gly Ser Phe Phe Leu Tyr Ser
            180                 185                 190

Lys Leu Thr Val Asp Lys Ser Arg Trp Gln Gln Gly Asn Val Phe Ser
        195                 200                 205

Cys Ser Val Met His Glu Ala Leu His Asn His Tyr Thr Gln Lys Ser
    210                 215                 220

Leu Ser Leu Ser Pro Glu Leu Gln Leu Glu Glu Ser Cys Ala Glu Ala
```

```
                225                 230                 235                 240
Gln Asp Gly Glu Leu Asp Gly Leu Trp Thr Thr Ile Thr Ile Phe Ile
                    245                 250                 255

Thr Leu Phe Leu Leu Ser Val Cys Tyr Ser Ala Thr Val Thr Phe Phe
                260                 265                 270

Lys Val Lys Trp Ile Phe Ser Ser Val Val Asp Leu Lys Gln Thr Ile
                275                 280                 285

Ile Pro Asp Tyr Arg Asn Met Ile Gly Gln Gly Ala
                290                 295                 300
```

<210> SEQ ID NO 33  
<211> LENGTH: 726  
<212> TYPE: DNA  
<213> ORGANISM: Artificial Sequence  
<220> FEATURE:  
<223> OTHER INFORMATION: Synthetic

<400> SEQUENCE: 33

```
gaggttcaac ttgttcaatc tggggcagaa gtgaagaagc ccggggcatc tgtgaaagta      60
tcatgcaaaa catccggcta tacgtttacc gaatacacca ttcactgggt cagacaggct     120
cccgtcaaa gcctcgaatg gatgggaaat attaaccta caatggcgg aaccacatat       180
aatcagaaat tccaaggccg agtgacgata actgtcgata agagtacgtc cacagcttac     240
atggaactca gctcttgag atccgaagac actgcagttt attattgtgc agctggatgg      300
aacttcgact attggggaca agggactctt gttacggtgt ccagtggcaa accaggtagt     360
ggtaaacccg gaagcggcaa gcccgggagc ggtaaacctg gtagcgacat cgtcatgact     420
caaagccctg actcactcgc cgtgagcctg ggagagcgtg caacgctatc ttgtcgggcc     480
tctcaggatg tcggaactgc tgtagactgg tatcaacaga aacctgacca atcaccaaaa     540
ctcctgattt attgggcctc aacacgtcac acaggagtgc cagataggtt cacaggtagt     600
ggcagtggaa ctgatttta ctttgacaatt agcagcctgc aagccgaaga tgtagccgtt      660
tacttctgtc aacaatataa ctcatacccca ctaacgttcg gtgccgggac gaaggtagag     720
attaaa                                                                 726
```

<210> SEQ ID NO 34  
<211> LENGTH: 242  
<212> TYPE: PRT  
<213> ORGANISM: Artificial Sequence  
<220> FEATURE:  
<223> OTHER INFORMATION: Synthetic

<400> SEQUENCE: 34

```
Glu Val Gln Leu Val Gln Ser Gly Ala Glu Val Lys Lys Pro Gly Ala
1               5                   10                  15

Ser Val Lys Val Ser Cys Lys Thr Ser Gly Tyr Thr Phe Thr Glu Tyr
                20                  25                  30

Thr Ile His Trp Val Arg Gln Ala Pro Gly Gln Ser Leu Glu Trp Met
            35                  40                  45

Gly Asn Ile Asn Pro Asn Asn Gly Gly Thr Thr Tyr Asn Gln Lys Phe
        50                  55                  60

Gln Gly Arg Val Thr Ile Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ala Gly Trp Asn Phe Asp Tyr Trp Gly Gln Gly Thr Leu Val Thr
```

```
                    100                 105                 110
Val Ser Ser Gly Lys Pro Gly Ser Gly Lys Pro Gly Ser Gly Lys Pro
                115                 120                 125

Gly Ser Gly Lys Pro Gly Ser Asp Ile Val Met Thr Gln Ser Pro Asp
            130                 135                 140

Ser Leu Ala Val Ser Leu Gly Glu Arg Ala Thr Leu Ser Cys Arg Ala
145                 150                 155                 160

Ser Gln Asp Val Gly Thr Ala Val Asp Trp Tyr Gln Gln Lys Pro Asp
                165                 170                 175

Gln Ser Pro Lys Leu Leu Ile Tyr Trp Ala Ser Thr Arg His Thr Gly
            180                 185                 190

Val Pro Asp Arg Phe Thr Gly Ser Gly Ser Gly Thr Asp Phe Thr Leu
                195                 200                 205

Thr Ile Ser Ser Leu Gln Ala Glu Asp Val Ala Val Tyr Phe Cys Gln
            210                 215                 220

Gln Tyr Asn Ser Tyr Pro Leu Thr Phe Gly Ala Gly Thr Lys Val Glu
225                 230                 235                 240

Ile Lys

<210> SEQ ID NO 35
<211> LENGTH: 735
<212> TYPE: DNA
<213> ORGANISM: Artificial Sequence
<220> FEATURE:
<223> OTHER INFORMATION: Synthetic

<400> SEQUENCE: 35
gaagtccaat tggttgaaag cggtggtgga ctcgtcaaac ctggcggtag ccttaaactt      60
tcatgtgccg caagcggctt cacgtttagt aactatgcta tgagttgggt ccgccaaagt     120
ccagaaaagc gcctcgaatg ggtggcggag atctctggag gaggaacata tacatattat     180
ccagacacca tgaccggtag gtttacaatc tcaagagaca cgctaagaa caccctgtac      240 ctggaaatgt caagcctgag atcagaagat acggccatgt attattgtac gcgcctactc     300
gactattggg gtcaaggaac ttccgtgacg gtgtcaagcg gaggaggtgg agcggagga      360 ggcggaagtg gcggtggtgg ctctggtggc ggtggaagtg atatagtgat gacgcaagct     420 gcctttcaa accctgttac tttggggact agcgcatcaa tctcctgtag gtccagcaaa      480
tctttgctgc acagtaatgg aatcacctat ctttttctggt atttgcaaaa gcctgggcag    540
agcccgcaac tgctgatcta tcaaatgtca aatcttgctt ccggagttcc agaccgcttc     600
tcaagttccg ggtccggcac tgattttacc ttgagaattt ctagggtcga agctgaagac     660
gtcggtgtct attattgcgc gcaaaacctt gagcttccat acaccttcgg gggggcaca      720 aaacttgaga tcaag                                                      735

<210> SEQ ID NO 36
<211> LENGTH: 245
<212> TYPE: PRT
<213> ORGANISM: Artificial Sequence
<220> FEATURE:
<223> OTHER INFORMATION: Synthetic

<400> SEQUENCE: 36

Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Asn Tyr
                20                  25                  30
```

```
Ala Met Ser Trp Val Arg Gln Ser Pro Glu Lys Arg Leu Glu Trp Val
        35                  40                  45

Ala Glu Ile Ser Gly Gly Gly Thr Tyr Thr Tyr Tyr Pro Asp Thr Met
 50                  55                  60

Thr Gly Arg Phe Thr Ile Ser Arg Asp Asn Ala Lys Asn Thr Leu Tyr
 65                  70                  75                  80

Leu Glu Met Ser Ser Leu Arg Ser Glu Asp Thr Ala Met Tyr Tyr Cys
                 85                  90                  95

Thr Arg Leu Leu Asp Tyr Trp Gly Gln Gly Thr Ser Val Thr Val Ser
            100                 105                 110

Ser Gly Gly Gly Ser Gly Gly Gly Ser Gly Gly Gly Ser
            115                 120                 125

Gly Gly Gly Gly Ser Asp Ile Val Met Thr Gln Ala Ala Phe Ser Asn
        130                 135                 140

Pro Val Thr Leu Gly Thr Ser Ala Ser Ile Ser Cys Arg Ser Ser Lys
145                 150                 155                 160

Ser Leu Leu His Ser Asn Gly Ile Thr Tyr Leu Phe Trp Tyr Leu Gln
                165                 170                 175

Lys Pro Gly Gln Ser Pro Gln Leu Leu Ile Tyr Gln Met Ser Asn Leu
            180                 185                 190

Ala Ser Gly Val Pro Asp Arg Phe Ser Ser Gly Ser Gly Thr Asp
        195                 200                 205

Phe Thr Leu Arg Ile Ser Arg Val Glu Ala Glu Asp Val Gly Val Tyr
210                 215                 220

Tyr Cys Ala Gln Asn Leu Glu Leu Pro Tyr Thr Phe Gly Gly Gly Thr
225                 230                 235                 240

Lys Leu Glu Ile Lys
                245

<210> SEQ ID NO 37
<211> LENGTH: 759
<212> TYPE: DNA
<213> ORGANISM: Artificial Sequence
<220> FEATURE:
<223> OTHER INFORMATION: Synthetic

<400> SEQUENCE: 37
cagtctgtgt tgacgcagcc gccctcagtg tctgcggccc caggacagag ggtcaccatc      60
tcctgctctg gaaccaggtc caacattggg agtgattatg tttcctggta ccaacacctc     120
ccaggaacag cccccaaact cctcgtttat ggcgataatc tgcgaccctc agggattcct     180
gaccgattct ctgcctccaa gtctggcacg tcagccaccc tgggcatcac cggactccag     240
actggggacg aggccgatta ttactgcggc acatgggatt acaccctgaa tggtgtggtg     300
ttcggcggag ggaccaagct gaccgtccta ggttctagag gtggtggtgg tagcggcggc     360
ggcggctctg gtggtggtgg atccctcgag atggcccagg tgcagctggt ggagtctggg     420
ggaggcttgg tacagcctgg ggggtccctg agactctcct gtgcagcctc tggattcacc     480
tttagcagct atgccatgag ctgggtccgc caggctccag gaagggggct ggagtgggtc     540
tcagttattt atagcggtgg tagtagcaca tactatgcag actccgtgaa gggccggttc     600
accatctcca gagataattc caagaacacg ctgtatctgc aaatgaacag cctgagagcc     660
gaggacacgg ccgtatatta ctgtgcgcgc acttcttacc tgaaccatgg tgattactgg     720
ggtcaaggta ctctggtgac cgtgtctagc gccgctgca                            759
```

<210> SEQ ID NO 38
<211> LENGTH: 253
<212> TYPE: PRT
<213> ORGANISM: Artificial Sequence
<220> FEATURE:
<223> OTHER INFORMATION: Synthetic

<400> SEQUENCE: 38

```
Gln Ser Val Leu Thr Gln Pro Pro Ser Val Ser Ala Ala Pro Gly Gln
1               5                   10                  15
Arg Val Thr Ile Ser Cys Ser Gly Thr Arg Ser Asn Ile Gly Ser Asp
            20                  25                  30
Tyr Val Ser Trp Tyr Gln His Leu Pro Gly Thr Ala Pro Lys Leu Leu
        35                  40                  45
Val Tyr Gly Asp Asn Leu Arg Pro Ser Gly Ile Pro Asp Arg Phe Ser
    50                  55                  60
Ala Ser Lys Ser Gly Thr Ser Ala Thr Leu Gly Ile Thr Gly Leu Gln
65                  70                  75                  80
Thr Gly Asp Glu Ala Asp Tyr Tyr Cys Gly Thr Trp Asp Tyr Thr Leu
                85                  90                  95
Asn Gly Val Val Phe Gly Gly Gly Thr Lys Leu Thr Val Leu Gly Ser
            100                 105                 110
Arg Gly Gly Gly Ser Gly Gly Gly Ser Gly Gly Gly Gly Ser
        115                 120                 125
Leu Glu Met Ala Gln Val Gln Leu Val Glu Ser Gly Gly Gly Leu Val
    130                 135                 140
Gln Pro Gly Gly Ser Leu Arg Leu Ser Cys Ala Ala Ser Gly Phe Thr
145                 150                 155                 160
Phe Ser Ser Tyr Ala Met Ser Trp Val Arg Gln Ala Pro Gly Lys Gly
                165                 170                 175
Leu Glu Trp Val Ser Val Ile Tyr Ser Gly Gly Ser Ser Thr Tyr Tyr
            180                 185                 190
Ala Asp Ser Val Lys Gly Arg Phe Thr Ile Ser Arg Asp Asn Ser Lys
        195                 200                 205
Asn Thr Leu Tyr Leu Gln Met Asn Ser Leu Arg Ala Glu Asp Thr Ala
    210                 215                 220
Val Tyr Tyr Cys Ala Arg Thr Ser Tyr Leu Asn His Gly Asp Tyr Trp
225                 230                 235                 240
Gly Gln Gly Thr Leu Val Thr Val Ser Ser Ala Ala Ala
                245                 250
```

<210> SEQ ID NO 39
<211> LENGTH: 1704
<212> TYPE: DNA
<213> ORGANISM: Artificial Sequence
<220> FEATURE:
<223> OTHER INFORMATION: Synthetic

<400> SEQUENCE: 39

```
gaggttcaac ttgttcaatc tgggcagaa gtgaagaagc ccggggcatc tgtgaaagta      60
tcatgcaaaa catccggcta tacgtttacc gaatacacca ttcactgggt cagacaggct    120
cccggtcaaa gcctcgaatg gatgggaaat attaaccta caatggcgg aaccacatat      180 aatcagaaat ccaaggccg agtgacgata actgtcgata agagtacgtc cacagcttac    240 atgaactca gctctttgag atccgaagac actgcagttt attattgtgc agctggatgg    300
aacttcgact attggggaca aggactctt gttacggtgt ccagtggcaa accaggtagt    360
```

```
ggtaaacccg gaagcggcaa gcccgggagc ggtaaacctg gtagcgacat cgtcatgact    420
caaagccctg actcactcgc cgtgagcctg ggagagcgtg caacgctatc ttgtcgggcc    480
tctcaggatg tcggaactgc tgtagactgg tatcaacaga aacctgacca atcaccaaaa    540
ctcctgattt attgggcctc aacacgtcac acaggagtgc cagataggtt cacaggtagt    600
ggcagtggaa ctgattttac tttgacaatt agcagcctgc aagccgaaga tgtagccgtt    660
tacttctgtc aacaatataa ctcataccca ctaacgttcg gtgccgggac gaaggtagag    720
attaaattcg tgcctgtgtt cctcccagct aagcccacta ccaccccgc tccaaggccg      780 cccacgcccg ctcctactat tgctagtcag ccttttaagtt tacgacccga agcttgcagg    840
cccgccgccg gcggcgctgt gcacaccagg gggcttgatt ttgcctgcga cttttgggta    900
ttggtagtgg tgggcggagt tttagcctgc tacagcctcc tggtaacagt ggcttttatc     960
atcttttggg tgcagcgggc tttagtcttg cggcgtaaac gtaaaagaat gacagatcca   1020
actcgcaggt tcttcaaagt gaccccccca cctgggtccg gaccgcagaa ccaatatggg   1080
aatgtcctgt ctctgcctac gcctacaagt ggactgggta gggctcagag gtgggctgcc   1140
ggtctcggcg gaactgcgcc atcttacgga aatccctcct ccgacgttca ggcagacggg   1200
gccctggggt ctcgatcccc gcctggtgtt ggaccagaag aggaagaggg cgagggctac   1260
gaagagcccg actccgaaga ggacagtgag ttttacgaga acgacagcaa cctggggcag   1320
gatcagctgt cacaggatgg ctcaggatat gaaaaccctg aggacgagcc tttggggcct   1380
gaagatgagg actccttttc taatgcagag tcatatgaga atgaggacga agaattgact   1440
caacccgtgg caagaacaat ggatttcctc agtccacacg ggagtgcatg ggacccctcc   1500
agagaggcta ctagcctcgg ttctcaaagc tatgaggaca tgaggggtat tctgtacgca   1560
gcgcctcagt tgaggtccat ccgcggccag ccaggcccaa accatgagga agatgccgat   1620
tcttacgaaa acatggacaa ccccgatggt cctgaccccg catgggggg cggcgggagg    1680 atgggcacct ggtctactcg ctag                                          1704
```

<210> SEQ ID NO 40
<211> LENGTH: 567
<212> TYPE: PRT
<213> ORGANISM: Artificial Sequence
<220> FEATURE:
<223> OTHER INFORMATION: Synthetic

<400> SEQUENCE: 40

```
Glu Val Gln Leu Val Gln Ser Gly Ala Glu Val Lys Lys Pro Gly Ala
1               5                   10                  15

Ser Val Lys Val Ser Cys Lys Thr Ser Gly Tyr Thr Phe Thr Glu Tyr
            20                  25                  30

Thr Ile His Trp Val Arg Gln Ala Pro Gly Gln Ser Leu Glu Trp Met
        35                  40                  45

Gly Asn Ile Asn Pro Asn Asn Gly Gly Thr Thr Tyr Asn Gln Lys Phe
    50                  55                  60

Gln Gly Arg Val Thr Ile Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ala Gly Trp Asn Phe Asp Tyr Trp Gly Gln Gly Thr Leu Val Thr
            100                 105                 110

Val Ser Ser Gly Lys Pro Gly Ser Gly Lys Pro Gly Ser Gly Lys Pro
```

-continued

```
            115                 120                 125
Gly Ser Gly Lys Pro Gly Ser Asp Ile Val Met Thr Gln Ser Pro Asp
        130                 135                 140
Ser Leu Ala Val Ser Leu Gly Glu Arg Ala Thr Leu Ser Cys Arg Ala
145                 150                 155                 160
Ser Gln Asp Val Gly Thr Ala Val Asp Trp Tyr Gln Gln Lys Pro Asp
                165                 170                 175
Gln Ser Pro Lys Leu Leu Ile Tyr Trp Ala Ser Thr Arg His Thr Gly
            180                 185                 190
Val Pro Asp Arg Phe Thr Gly Ser Gly Ser Gly Thr Asp Phe Thr Leu
        195                 200                 205
Thr Ile Ser Ser Leu Gln Ala Glu Asp Val Ala Val Tyr Phe Cys Gln
210                 215                 220
Gln Tyr Asn Ser Tyr Pro Leu Thr Phe Gly Ala Gly Thr Lys Val Glu
225                 230                 235                 240
Ile Lys Phe Val Pro Val Phe Leu Pro Ala Lys Pro Thr Thr Thr Pro
                245                 250                 255
Ala Pro Arg Pro Pro Thr Pro Ala Pro Thr Ile Ala Ser Gln Pro Leu
            260                 265                 270
Ser Leu Arg Pro Glu Ala Cys Arg Pro Ala Ala Gly Gly Ala Val His
        275                 280                 285
Thr Arg Gly Leu Asp Phe Ala Cys Asp Phe Trp Val Leu Val Val Val
        290                 295                 300
Gly Gly Val Leu Ala Cys Tyr Ser Leu Leu Val Thr Val Ala Phe Ile
305                 310                 315                 320
Ile Phe Trp Val Gln Arg Ala Leu Val Leu Arg Arg Lys Arg Lys Arg
                325                 330                 335
Met Thr Asp Pro Thr Arg Arg Phe Phe Lys Val Thr Pro Pro Pro Gly
            340                 345                 350
Ser Gly Pro Gln Asn Gln Tyr Gly Asn Val Leu Ser Leu Pro Thr Pro
        355                 360                 365
Thr Ser Gly Leu Gly Arg Ala Gln Arg Trp Ala Ala Gly Leu Gly Gly
        370                 375                 380
Thr Ala Pro Ser Tyr Gly Asn Pro Ser Ser Asp Val Gln Ala Asp Gly
385                 390                 395                 400
Ala Leu Gly Ser Arg Ser Pro Pro Gly Val Gly Pro Glu Glu Glu Glu
                405                 410                 415
Gly Glu Gly Tyr Glu Glu Pro Asp Ser Glu Glu Asp Ser Glu Phe Tyr
            420                 425                 430
Glu Asn Asp Ser Asn Leu Gly Gln Asp Gln Leu Ser Gln Asp Gly Ser
        435                 440                 445
Gly Tyr Glu Asn Pro Glu Asp Glu Pro Leu Gly Pro Glu Asp Glu Asp
        450                 455                 460
Ser Phe Ser Asn Ala Glu Ser Tyr Glu Asn Glu Asp Glu Glu Leu Thr
465                 470                 475                 480
Gln Pro Val Ala Arg Thr Met Asp Phe Leu Ser Pro His Gly Ser Ala
                485                 490                 495
Trp Asp Pro Ser Arg Glu Ala Thr Ser Leu Gly Ser Gln Ser Tyr Glu
            500                 505                 510
Asp Met Arg Gly Ile Leu Tyr Ala Ala Pro Gln Leu Arg Ser Ile Arg
        515                 520                 525
Gly Gln Pro Gly Pro Asn His Glu Glu Asp Ala Asp Ser Tyr Glu Asn
        530                 535                 540
```

Met Asp Asn Pro Asp Gly Pro Asp Pro Ala Trp Gly Gly Gly Gly Arg
545                 550                 555                 560

Met Gly Thr Trp Ser Thr Arg
                565

<210> SEQ ID NO 41
<211> LENGTH: 1122
<212> TYPE: DNA
<213> ORGANISM: Artificial Sequence
<220> FEATURE:
<223> OTHER INFORMATION: Synthetic

<400> SEQUENCE: 41

| | | |
|---|---|---|
| gaggttcaac ttgttcaatc tggggcagaa gtgaagaagc ccggggcatc tgtgaaagta | 60 |
| tcatgcaaaa catccggcta tacgtttacc gaatacacca ttcactgggt cagacaggct | 120 |
| cccggtcaaa gcctcgaatg gatgggaaat attaaccta caatggcgg aaccacatat | 180 |
| aatcagaaat tccaaggccg agtgacgata actgtcgata gagtacgtc cacagcttac | 240 |
| atggaactca gctctttgag atccgaagac actgcagttt attattgtgc agctggatgg | 300 |
| aacttcgact attggggaca agggactctt gttacggtgt ccagtggcaa accaggtagt | 360 |
| ggtaaacccg gaagcggcaa gcccgggagc ggtaaacctg gtagcgacat cgtcatgact | 420 |
| caaagccctg actcactcgc cgtgagcctg gagagcgtg caacgctatc ttgtcgggcc | 480 |
| tctcaggatg tcggaactgc tgtagactgg tatcaacaga aacctgacca atcaccaaaa | 540 |
| ctcctgattt attgggcctc aacacgtcac acaggagtgc cagataggtt cacaggtagt | 600 |
| ggcagtggaa ctgattttac tttgacaatt agcagcctgc aagccgaaga tgtagccgtt | 660 |
| tacttctgtc aacaatataa ctcatacccca ctaacgttcg gtgccgggac gaaggtagag | 720 |
| attaaattcg tgcctgtgtt cctcccagct aagcccacta ccaccccgc tccaaggccg | 780 |
| cccacgcccg ctcctactat tgctagtcag ccttaagtt tacgaccga agcttgcagg | 840 |
| cccgccgccg gcggcgctgt gcacaccagg gggcttgatt ttgcctgcga cttttgggta | 900 |
| ttggtagtgg tgggcggagt tttagcctgc tacagcctcc tggtaacagt ggcttttatc | 960 |
| atcttttggg tgctggacaa ggatgacagc aaggctggca tggaggaaga tcacacctac | 1020 |
| gagggcctgg acattgacca gacagccacc tatgaggaca tagtgacgct gcggacaggg | 1080 |
| gaagtgaagt ggtctgtagg tgagcacca ggccaggagt ga | 1122 |

<210> SEQ ID NO 42
<211> LENGTH: 373
<212> TYPE: PRT
<213> ORGANISM: Artificial Sequence
<220> FEATURE:
<223> OTHER INFORMATION: Synthetic

<400> SEQUENCE: 42

Glu Val Gln Leu Val Gln Ser Gly Ala Glu Val Lys Lys Pro Gly Ala
1               5                   10                  15

Ser Val Lys Val Ser Cys Lys Thr Ser Gly Tyr Thr Phe Thr Glu Tyr
                20                  25                  30

Thr Ile His Trp Val Arg Gln Ala Pro Gly Gln Ser Leu Glu Trp Met
            35                  40                  45

Gly Asn Ile Asn Pro Asn Asn Gly Gly Thr Thr Tyr Asn Gln Lys Phe
        50                  55                  60

Gln Gly Arg Val Thr Ile Thr Val Asp Lys Ser Thr Ser Thr Ala Tyr
65                  70                  75                  80

```
Met Glu Leu Ser Ser Leu Arg Ser Glu Asp Thr Ala Val Tyr Tyr Cys
                85                  90                  95

Ala Ala Gly Trp Asn Phe Asp Tyr Trp Gly Gln Gly Thr Leu Val Thr
            100                 105                 110

Val Ser Ser Gly Lys Pro Gly Ser Gly Lys Pro Gly Ser Gly Lys Pro
        115                 120                 125

Gly Ser Gly Lys Pro Gly Ser Asp Ile Val Met Thr Gln Ser Pro Asp
130                 135                 140

Ser Leu Ala Val Ser Leu Gly Glu Arg Ala Thr Leu Ser Cys Arg Ala
145                 150                 155                 160

Ser Gln Asp Val Gly Thr Ala Val Asp Trp Tyr Gln Gln Lys Pro Asp
                165                 170                 175

Gln Ser Pro Lys Leu Leu Ile Tyr Trp Ala Ser Thr Arg His Thr Gly
            180                 185                 190

Val Pro Asp Arg Phe Thr Gly Ser Gly Ser Gly Thr Asp Phe Thr Leu
        195                 200                 205

Thr Ile Ser Ser Leu Gln Ala Glu Asp Val Ala Val Tyr Phe Cys Gln
210                 215                 220

Gln Tyr Asn Ser Tyr Pro Leu Thr Phe Gly Ala Gly Thr Lys Val Glu
225                 230                 235                 240

Ile Lys Phe Val Pro Val Phe Leu Pro Ala Lys Pro Thr Thr Thr Pro
                245                 250                 255

Ala Pro Arg Pro Pro Thr Pro Ala Pro Thr Ile Ala Ser Gln Pro Leu
            260                 265                 270

Ser Leu Arg Pro Glu Ala Cys Arg Pro Ala Ala Gly Gly Ala Val His
        275                 280                 285

Thr Arg Gly Leu Asp Phe Ala Cys Asp Phe Trp Val Leu Val Val Val
290                 295                 300

Gly Gly Val Leu Ala Cys Tyr Ser Leu Leu Val Thr Val Ala Phe Ile
305                 310                 315                 320

Ile Phe Trp Val Leu Asp Lys Asp Asp Ser Lys Ala Gly Met Glu Glu
                325                 330                 335

Asp His Thr Tyr Glu Gly Leu Asp Ile Asp Gln Thr Ala Thr Tyr Glu
            340                 345                 350

Asp Ile Val Thr Leu Arg Thr Gly Glu Val Lys Trp Ser Val Gly Glu
        355                 360                 365

His Pro Gly Gln Glu
    370

<210> SEQ ID NO 43
<211> LENGTH: 1305
<212> TYPE: DNA
<213> ORGANISM: Artificial Sequence
<220> FEATURE:
<223> OTHER INFORMATION: Synthetic

<400> SEQUENCE: 43
gaggttcaac ttgttcaatc tggggcagaa gtgaagaagc ccggggcatc tgtgaaagta      60
tcatgcaaaa catccggcta tacgtttacc gaatacacca ttcactgggt cagacaggct     120
cccggtcaaa gcctcgaatg gatgggaaat attaacccta caatggcgg aaccacatat      180 aatcagaaat ccaaggccg agtgacgata actgtcgata agagtacgtc cacagcttac      240
atggaactca gctctttgag atccgaagac actgcagttt attattgtgc agctggatgg     300
aacttcgact attggggaca aggactctt gttacggtgt ccagtggcaa accaggtagt      360
```

```
ggtaaacccg gaagcggcaa gcccgggagc ggtaaacctg gtagcgacat cgtcatgact    420
caaagccctg actcactcgc cgtgagcctg ggagagcgtg caacgctatc ttgtcgggcc    480
tctcaggatg tcggaactgc tgtagactgg tatcaacaga aacctgacca atcaccaaaa    540
ctcctgattt attgggcctc aacacgtcac acaggagtgc cagataggtt cacaggtagt    600
ggcagtggaa ctgattttac tttgacaatt agcagcctgc aagccgaaga tgtagccgtt    660
tacttctgtc aacaatataa ctcatacccc ctaacgttcg gtgccgggac gaaggtagag    720
attaaattcg tgcctgtgtt cctcccagct aagcccacta ccaccccgc tccaaggccg     780 cccacgcccg ctcctactat tgctagtcag cctttaagtt tacgacccga agcttgcagg    840
cccgccgccg gcggcgctgt gcacaccagg gggcttgatt ttgcctgcga cttttgggta    900
ttggtagtgg tgggcggagt tttagcctgc tacagcctcc tggtaacagt ggcttttatc    960
atcttttggg tgaagaaggt tgcaaaaaaa cctactaata aggctcccca tcctaagcaa   1020
gagccccaag aaattaactt tcccgatgat cttccgggtt ctaacacggc agccccggtg   1080
caggagaccc tgcatggttg tcaacccgtc actcaggagg acgggaaaga gtctcgtatc   1140
tccgtccagg agagacagga caaggacgat agtaaagcag ggatggagga ggaccataca   1200
tacgagggac tggatatcga tcagacagcc acgtacgaag acattgtgac actgagaact   1260
ggcgaggtga agtggtcagt gggagaacat ccggggcagg aataa                   1305
```

```
<210> SEQ ID NO 44
<211> LENGTH: 434
<212> TYPE: PRT
<213> ORGANISM: Artificial Sequence
<220> FEATURE:
<223> OTHER INFORMATION: Synthetic

<400> SEQUENCE: 44
```

Glu Val Gln Leu Val Gln Ser Gly Ala Glu Val Lys Lys Pro Gly Ala
1               5                   10                  15

Ser Val Lys Val Ser Cys Lys Thr Ser Gly Tyr Thr Phe Thr Glu Tyr
            20                  25                  30

Thr Ile His Trp Val Arg Gln Ala Pro Gly Gln Ser Leu Glu Trp Met
        35                  40                  45

Gly Asn Ile Asn Pro Asn Asn Gly Gly Thr Thr Tyr Asn Gln Lys Phe
    50                  55                  60

Gln Gly Arg Val Thr Ile Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ala Gly Trp Asn Phe Asp Tyr Trp Gly Gln Gly Thr Leu Val Thr
            100                 105                 110

Val Ser Ser Gly Lys Pro Gly Ser Gly Lys Pro Gly Ser Gly Lys Pro
        115                 120                 125

Gly Ser Gly Lys Pro Gly Ser Asp Ile Val Met Thr Gln Ser Pro Asp
    130                 135                 140

Ser Leu Ala Val Ser Leu Gly Glu Arg Ala Thr Leu Ser Cys Arg Ala
145                 150                 155                 160

Ser Gln Asp Val Gly Thr Ala Val Asp Trp Tyr Gln Gln Lys Pro Asp
                165                 170                 175

Gln Ser Pro Lys Leu Leu Ile Tyr Trp Ala Ser Thr Arg His Thr Gly
            180                 185                 190

```
Val Pro Asp Arg Phe Thr Gly Ser Gly Ser Gly Thr Asp Phe Thr Leu
            195                 200                 205

Thr Ile Ser Ser Leu Gln Ala Glu Asp Val Ala Val Tyr Phe Cys Gln
        210                 215                 220

Gln Tyr Asn Ser Tyr Pro Leu Thr Phe Gly Ala Gly Thr Lys Val Glu
225                 230                 235                 240

Ile Lys Phe Val Pro Val Phe Leu Pro Ala Lys Pro Thr Thr Thr Pro
                245                 250                 255

Ala Pro Arg Pro Pro Thr Pro Ala Pro Thr Ile Ala Ser Gln Pro Leu
            260                 265                 270

Ser Leu Arg Pro Glu Ala Cys Arg Pro Ala Ala Gly Gly Ala Val His
        275                 280                 285

Thr Arg Gly Leu Asp Phe Ala Cys Asp Phe Trp Val Leu Val Val Val
    290                 295                 300

Gly Gly Val Leu Ala Cys Tyr Ser Leu Leu Val Thr Val Ala Phe Ile
305                 310                 315                 320

Ile Phe Trp Val Lys Lys Val Ala Lys Lys Pro Thr Asn Lys Ala Pro
                325                 330                 335

His Pro Lys Gln Glu Pro Gln Glu Ile Asn Phe Pro Asp Asp Leu Pro
            340                 345                 350

Gly Ser Asn Thr Ala Ala Pro Val Gln Glu Thr Leu His Gly Cys Gln
        355                 360                 365

Pro Val Thr Gln Glu Asp Gly Lys Glu Ser Arg Ile Ser Val Gln Glu
    370                 375                 380

Arg Gln Asp Lys Asp Asp Ser Lys Ala Gly Met Glu Glu Asp His Thr
385                 390                 395                 400

Tyr Glu Gly Leu Asp Ile Asp Gln Thr Ala Thr Tyr Glu Asp Ile Val
                405                 410                 415

Thr Leu Arg Thr Gly Glu Val Lys Trp Ser Val Gly Glu His Pro Gly
            420                 425                 430

Gln Glu

<210> SEQ ID NO 45
<211> LENGTH: 1287
<212> TYPE: DNA
<213> ORGANISM: Artificial Sequence
<220> FEATURE:
<223> OTHER INFORMATION: Synthetic

<400> SEQUENCE: 45
gaggttcaac ttgttcaatc tggggcagaa gtgaagaagc cggggcatc tgtgaaagta      60 tcatgcaaaa catccggcta cgtttacc gaatacacca ttcactgggt cagacaggct     120
cccggtcaaa gcctcgaatg gatgggaaat attaaccta caatggcgg aaccacatat     180 aatcagaaat ccaaggccg agtgacgata actgtcgata agagtacgtc cacagcttac     240
atggaactca gctctttgag atccgaagac actgcagttt attattgtgc agctggatgg     300
aacttcgact attggggaca agggactctt gttacggtgt ccagtggcaa accaggtagt     360
ggtaaacccg aagcggcaa gcccgggagc ggtaaacctg gtagcgacat cgtcatgact     420
caaagccctg actcactcgc cgtgagcctg ggagagcgtg caacgctatc ttgtcgggcc     480
tctcaggatg tcggaactgc tgtagactgg tatcaacaga aacctgacca atcaccaaaa     540
ctcctgattt attgggcctc aacacgtcac acaggagtgc cagataggtt cacaggtagt     600
ggcagtggaa ctgattttac tttgacaatt agcagcctgc aagccgaaga tgtagccgtt     660
```

-continued

```
tacttctgtc aacaatataa ctcatacccca ctaacgttcg gtgccgggac gaaggtagag    720
attaaattcg tgcctgtgtt cctcccagct aagcccacta ccaccccgc tccaaggccg      780 cccacgcccg ctcctactat tgctagtcag cctttaagtt tacgacccga agcttgcagg    840
cccgccgccg gcggcgctgt gcacaccagg gggcttgatt ttgcctgcga cttttgggta    900
ttggtagtgg tgggcggagt tttagcctgc tacagcctcc tggtaacagt ggcttttatc    960
atcttttggg tgaagaaggt tgcaaaaaaa cctactaata aggctcccca tcctaagcaa   1020
gagccccaag aaattaactt tcccgatgat cttccgggtt ctaacacggc agccccggtg   1080
caggagaccc tgcatggttg tcaacccgtc actcaggagg acgggaaaga gtctcgtatc   1140
tccgtccagg agagacagaa aagaggccga aaaaagctgc tgtacatctt caaacaaccc   1200
ttcatgcgac ctgttcagac gacacaggag gaggacggct gcagctgtag gtttcccgaa   1260
gaagaggagg gaggatgcga actttaa                                       1287
```

<210> SEQ ID NO 46
<211> LENGTH: 428
<212> TYPE: PRT
<213> ORGANISM: Artificial Sequence
<220> FEATURE:
<223> OTHER INFORMATION: Synthetic

<400> SEQUENCE: 46

Glu Val Gln Leu Val Gln Ser Gly Ala Glu Val Lys Lys Pro Gly Ala
1               5                   10                  15

Ser Val Lys Val Ser Cys Lys Thr Ser Gly Tyr Thr Phe Thr Glu Tyr
            20                  25                  30

Thr Ile His Trp Val Arg Gln Ala Pro Gly Gln Ser Leu Glu Trp Met
        35                  40                  45

Gly Asn Ile Asn Pro Asn Asn Gly Gly Thr Thr Tyr Asn Gln Lys Phe
    50                  55                  60

Gln Gly Arg Val Thr Ile Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ala Gly Trp Asn Phe Asp Tyr Trp Gly Gln Gly Thr Leu Val Thr
            100                 105                 110

Val Ser Ser Gly Lys Pro Gly Ser Gly Lys Pro Gly Ser Gly Lys Pro
        115                 120                 125

Gly Ser Gly Lys Pro Gly Ser Asp Ile Val Met Thr Gln Ser Pro Asp
    130                 135                 140

Ser Leu Ala Val Ser Leu Gly Glu Arg Ala Thr Leu Ser Cys Arg Ala
145                 150                 155                 160

Ser Gln Asp Val Gly Thr Ala Val Asp Trp Tyr Gln Gln Lys Pro Asp
                165                 170                 175

Gln Ser Pro Lys Leu Leu Ile Tyr Trp Ala Ser Thr Arg His Thr Gly
            180                 185                 190

Val Pro Asp Arg Phe Thr Gly Ser Gly Ser Gly Thr Asp Phe Thr Leu
        195                 200                 205

Thr Ile Ser Ser Leu Gln Ala Glu Asp Val Ala Val Tyr Phe Cys Gln
    210                 215                 220

Gln Tyr Asn Ser Tyr Pro Leu Thr Phe Gly Ala Gly Thr Lys Val Glu
225                 230                 235                 240

Ile Lys Phe Val Pro Val Phe Leu Pro Ala Lys Pro Thr Thr Thr Pro
                245                 250                 255

-continued

```
Ala Pro Arg Pro Pro Thr Pro Ala Pro Thr Ile Ala Ser Gln Pro Leu
            260                 265                 270

Ser Leu Arg Pro Glu Ala Cys Arg Pro Ala Ala Gly Gly Ala Val His
        275                 280                 285

Thr Arg Gly Leu Asp Phe Ala Cys Asp Phe Trp Val Leu Val Val Val
    290                 295                 300

Gly Gly Val Leu Ala Cys Tyr Ser Leu Leu Val Thr Val Ala Phe Ile
305                 310                 315                 320

Ile Phe Trp Val Lys Lys Val Ala Lys Lys Pro Thr Asn Lys Ala Pro
            325                 330                 335

His Pro Lys Gln Glu Pro Gln Glu Ile Asn Phe Pro Asp Asp Leu Pro
        340                 345                 350

Gly Ser Asn Thr Ala Ala Pro Val Gln Glu Thr Leu His Gly Cys Gln
    355                 360                 365

Pro Val Thr Gln Glu Asp Gly Lys Glu Ser Arg Ile Ser Val Gln Glu
370                 375                 380

Arg Gln Lys Arg Gly Arg Lys Lys Leu Leu Tyr Ile Phe Lys Gln Pro
385                 390                 395                 400

Phe Met Arg Pro Val Gln Thr Thr Gln Glu Glu Asp Gly Cys Ser Cys
            405                 410                 415

Arg Phe Pro Glu Glu Glu Glu Gly Gly Cys Glu Leu
        420                 425

<210> SEQ ID NO 47
<211> LENGTH: 462
<212> TYPE: PRT
<213> ORGANISM: Artificial Sequence
<220> FEATURE:
<223> OTHER INFORMATION: Synthetic

<400> SEQUENCE: 47

Glu Val Gln Leu Val Gln Ser Gly Ala Glu Val Lys Lys Pro Gly Ala
1               5                   10                  15

Ser Val Lys Val Ser Cys Lys Thr Ser Gly Tyr Thr Phe Thr Glu Tyr
            20                  25                  30

Thr Ile His Trp Val Arg Gln Ala Pro Gly Gln Ser Leu Glu Trp Met
        35                  40                  45

Gly Asn Ile Asn Pro Asn Asn Gly Gly Thr Thr Tyr Asn Gln Lys Phe
    50                  55                  60

Gln Gly Arg Val Thr Ile Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ala Gly Trp Asn Phe Asp Tyr Trp Gly Gln Gly Thr Leu Val Thr
            100                 105                 110

Val Ser Ser Gly Lys Pro Gly Ser Gly Lys Pro Gly Ser Gly Lys Pro
        115                 120                 125

Gly Ser Gly Lys Pro Gly Ser Asp Ile Val Met Thr Gln Ser Pro Asp
    130                 135                 140

Ser Leu Ala Val Ser Leu Gly Glu Arg Ala Thr Leu Ser Cys Arg Ala
145                 150                 155                 160

Ser Gln Asp Val Gly Thr Ala Val Asp Trp Tyr Gln Gln Lys Pro Asp
                165                 170                 175

Gln Ser Pro Lys Leu Leu Ile Tyr Trp Ala Ser Thr Arg His Thr Gly
            180                 185                 190
```

Val Pro Asp Arg Phe Thr Gly Ser Gly Ser Gly Thr Asp Phe Thr Leu
        195                 200                 205

Thr Ile Ser Ser Leu Gln Ala Glu Asp Val Ala Val Tyr Phe Cys Gln
    210                 215                 220

Gln Tyr Asn Ser Tyr Pro Leu Thr Phe Gly Ala Gly Thr Lys Val Glu
225                 230                 235                 240

Ile Lys Phe Val Pro Val Phe Leu Pro Ala Lys Pro Thr Thr Thr Pro
                245                 250                 255

Ala Pro Arg Pro Pro Thr Pro Ala Pro Thr Ile Ala Ser Gln Pro Leu
            260                 265                 270

Ser Leu Arg Pro Glu Ala Cys Arg Pro Ala Ala Gly Gly Ala Val His
        275                 280                 285

Thr Arg Gly Leu Asp Phe Ala Cys Asp Phe Trp Val Leu Val Val Val
    290                 295                 300

Gly Gly Val Leu Ala Cys Tyr Ser Leu Leu Val Thr Val Ala Phe Ile
305                 310                 315                 320

Ile Phe Trp Val Lys Lys Val Ala Lys Lys Pro Thr Asn Lys Ala Pro
                325                 330                 335

His Pro Lys Gln Glu Pro Gln Glu Ile Asn Phe Pro Asp Asp Leu Pro
            340                 345                 350

Gly Ser Asn Thr Ala Ala Pro Val Gln Glu Thr Leu His Gly Cys Gln
        355                 360                 365

Pro Val Thr Gln Glu Asp Gly Lys Glu Ser Arg Ile Ser Val Gln Glu
    370                 375                 380

Arg Gln Arg Lys Lys Arg Ile Ser Ala Asn Ser Thr Asp Pro Val Lys
385                 390                 395                 400

Ala Ala Gln Phe Glu Pro Pro Gly Arg Gln Met Ile Ala Ile Arg Lys
                405                 410                 415

Arg Gln Leu Glu Glu Thr Asn Asn Asp Tyr Glu Thr Ala Asp Gly Gly
            420                 425                 430

Tyr Met Thr Leu Asn Pro Arg Ala Pro Thr Asp Asp Lys Asn Ile
        435                 440                 445

Tyr Leu Thr Leu Pro Pro Asn Asp His Val Asn Ser Asn Asn
    450                 455                 460

<210> SEQ ID NO 48
<211> LENGTH: 1656
<212> TYPE: DNA
<213> ORGANISM: Artificial Sequence
<220> FEATURE:
<223> OTHER INFORMATION: Synthetic

<400> SEQUENCE: 48
gaggttcaac ttgttcaatc tggggcagaa gtgaagaagc ccggggcatc tgtgaaagta      60
tcatgcaaaa catccggcta tacgtttacc gaatacacca ttcactgggt cagacaggct     120
cccggtcaaa gcctcgaatg gatgggaaat attaaccctc acaatggcgg aaccacatat     180
aatcagaaat tccaaggccg agtgacgata actgtcgata gagtacgtc cacagcttac      240 atggaactca gctcttttga gatccgaaga ctgcagttt attattgtgc agctggatgg      300
aacttcgact attggggaca agggactctt gttacggtgt ccagtggcaa accaggtagt     360
ggtaaacccg gaagcggcaa gcccgggagc ggtaaacctg gtagcgacat cgtcatgact     420
caaagccctg actcactcgc cgtgagcctg ggagagcgtg caacgctatc ttgtcgggcc     480
tctcaggatg tcggaactgc tgtagactgg tatcaacaga aacctgacca atcaccaaaa     540

-continued

```
ctcctgattt attgggcctc aacacgtcac acaggagtgc cagataggtt cacaggtagt      600
ggcagtggaa ctgattttac tttgacaatt agcagcctgc aagccgaaga tgtagccgtt      660
tacttctgtc aacaatataa ctcataccca ctaacgttcg gtgccgggac gaaggtagag      720
attaaattcg tgcctgtgtt cctcccagct aagcccacta ccaccccgc tccaaggccg       780 cccacgcccg ctcctactat tgctagtcag cctttaagtt tacgacccga agcttgcagg      840
cccgccgccg gcggcgctgt gcacaccagg gggcttgatt ttgcctgcga cttttgggta     900
ttggtagtgg tgggcggagt tttagcctgc tacagcctcc tggtaacagt ggcttttatc     960
atcttttggg tgatggcggc gggcgggccc ggcgccggaa gcgccgcgcc agtctcatct    1020
acgtccagtc tgccactggc tgccctgaac atgagagtga cgccgtttt atccctcttc      1080 ctgaatgtgc ggacccaggt cgccgctgat tggaccgccc tggccgaaga gatggacttt    1140
gaatacttgg aaatcagaca gctggaaaca caggcagacc caaccgggag actgcttgac    1200
gcctggcagg gacgcccagg ggcaagtgtt ggtcggttac tggagcttt aactaagttg      1260 ggccgcgatg acgtgctgtt ggagttagga cccagtatcg aggaggattg tcagaaatac    1320
atcttgaaac agcagcagga ggaggcgaaa agcccctgc aggtggcggc cgttgacagc     1380
agtgtaccca gaacagctga gctggccggc atcacaaccc tggatgatcc cctgggccac    1440
atgcctgaga ggttcgacgc tttcataaag aaggttgcaa aaaacctac taataaggct      1500 ccccatccta agcaagagcc ccaagaaatt aactttcccg atgatcttcc gggttctaac     1560
acggcagccc cggtgcagga gaccctgcat ggttgtcaac ccgtcactca ggaggacggg    1620
aaagagtctc gtatctccgt ccaggagaga cagtga                              1656
```

<210> SEQ ID NO 49
<211> LENGTH: 551
<212> TYPE: PRT
<213> ORGANISM: Artificial Sequence
<220> FEATURE:
<223> OTHER INFORMATION: Synthetic

<400> SEQUENCE: 49

```
Glu Val Gln Leu Val Gln Ser Gly Ala Glu Val Lys Lys Pro Gly Ala
1               5                   10                  15

Ser Val Lys Val Ser Cys Lys Thr Ser Gly Tyr Thr Phe Thr Glu Tyr
            20                  25                  30

Thr Ile His Trp Val Arg Gln Ala Pro Gly Gln Ser Leu Glu Trp Met
        35                  40                  45

Gly Asn Ile Asn Pro Asn Asn Gly Gly Thr Thr Tyr Asn Gln Lys Phe
    50                  55                  60

Gln Gly Arg Val Thr Ile Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ala Gly Trp Asn Phe Asp Tyr Trp Gly Gln Gly Thr Leu Val Thr
            100                 105                 110

Val Ser Ser Gly Lys Pro Gly Ser Gly Lys Pro Gly Ser Gly Lys Pro
        115                 120                 125

Gly Ser Gly Lys Pro Gly Ser Asp Ile Val Met Thr Gln Ser Pro Asp
    130                 135                 140

Ser Leu Ala Val Ser Leu Gly Glu Arg Ala Thr Leu Ser Cys Arg Ala
145                 150                 155                 160
```

Ser Gln Asp Val Gly Thr Ala Val Asp Trp Tyr Gln Lys Pro Asp
            165                 170                 175

Gln Ser Pro Lys Leu Leu Ile Tyr Trp Ala Ser Thr Arg His Thr Gly
        180                 185                 190

Val Pro Asp Arg Phe Thr Gly Ser Gly Ser Gly Thr Asp Phe Thr Leu
            195                 200                 205

Thr Ile Ser Ser Leu Gln Ala Glu Asp Val Ala Val Tyr Phe Cys Gln
            210                 215                 220

Gln Tyr Asn Ser Tyr Pro Leu Thr Phe Gly Ala Gly Thr Lys Val Glu
225                 230                 235                 240

Ile Lys Phe Val Pro Val Phe Leu Pro Ala Lys Pro Thr Thr Thr Pro
            245                 250                 255

Ala Pro Arg Pro Pro Thr Pro Ala Pro Thr Ile Ala Ser Gln Pro Leu
            260                 265                 270

Ser Leu Arg Pro Glu Ala Cys Arg Pro Ala Ala Gly Gly Ala Val His
        275                 280                 285

Thr Arg Gly Leu Asp Phe Ala Cys Asp Phe Trp Val Leu Val Val Val
        290                 295                 300

Gly Gly Val Leu Ala Cys Tyr Ser Leu Leu Val Thr Val Ala Phe Ile
305                 310                 315                 320

Ile Phe Trp Val Met Ala Ala Gly Gly Pro Gly Ala Gly Ser Ala Ala
            325                 330                 335

Pro Val Ser Ser Thr Ser Ser Leu Pro Leu Ala Ala Leu Asn Met Arg
            340                 345                 350

Val Arg Arg Arg Leu Ser Leu Phe Leu Asn Val Arg Thr Gln Val Ala
        355                 360                 365

Ala Asp Trp Thr Ala Leu Ala Glu Glu Met Asp Phe Glu Tyr Leu Glu
        370                 375                 380

Ile Arg Gln Leu Glu Thr Gln Ala Asp Pro Thr Gly Arg Leu Leu Asp
385                 390                 395                 400

Ala Trp Gln Gly Arg Pro Gly Ala Ser Val Gly Arg Leu Leu Glu Leu
            405                 410                 415

Leu Thr Lys Leu Gly Arg Asp Asp Val Leu Leu Glu Leu Gly Pro Ser
            420                 425                 430

Ile Glu Glu Asp Cys Gln Lys Tyr Ile Leu Lys Gln Gln Gln Glu Glu
        435                 440                 445

Ala Glu Lys Pro Leu Gln Val Ala Ala Val Asp Ser Ser Val Pro Arg
        450                 455                 460

Thr Ala Glu Leu Ala Gly Ile Thr Thr Leu Asp Asp Pro Leu Gly His
465                 470                 475                 480

Met Pro Glu Arg Phe Asp Ala Phe Ile Lys Lys Val Ala Lys Lys Pro
            485                 490                 495

Thr Asn Lys Ala Pro His Pro Lys Gln Glu Pro Gln Glu Ile Asn Phe
            500                 505                 510

Pro Asp Asp Leu Pro Gly Ser Asn Thr Ala Ala Pro Val Gln Glu Thr
        515                 520                 525

Leu His Gly Cys Gln Pro Val Thr Gln Glu Asp Gly Lys Glu Ser Arg
530                 535                 540

Ile Ser Val Gln Glu Arg Gln
545                 550

<210> SEQ ID NO 50
<211> LENGTH: 1158
<212> TYPE: DNA

<213> ORGANISM: Artificial Sequence
<220> FEATURE:
<223> OTHER INFORMATION: Synthetic

<400> SEQUENCE: 50

```
gaggttcaac ttgttcaatc tggggcagaa gtgaagaagc ccggggcatc tgtgaaagta      60
tcatgcaaaa catccggcta tacgtttacc gaatacacca ttcactgggt cagacaggct     120
cccggtcaaa gcctcgaatg gatgggaaat attaaccccta caatggcgg aaccacatat    180
aatcagaaat tccaaggccg agtgacgata actgtcgata agagtacgtc cacagcttac     240
atggaactca gctcttttgag atccgaagac actgcagttt attattgtgc agctggatgg     300
aacttcgact attggggaca agggactctt gttacggtgt ccagtggcaa accaggtagt     360
ggtaaacccg gaagcggcaa gcccgggagc ggtaaacctg gtagcgacat cgtcatgact     420
caaagccctg actcactcgc cgtgagcctg ggagagcgtg caacgctatc ttgtcgggcc     480
tctcaggatg tcggaactgc tgtagactgg tatcaacaga aacctgacca atcaccaaaa     540
ctcctgattt attgggcctc aacacgtcac acaggagtgc cagataggtt cacaggtagt     600
ggcagtggaa ctgattttac tttgacaatt agcagcctgc aagccgaaga tgtagccgtt     660
tacttctgtc aacaatataa ctcataccca ctaacgttcg gtgccgggac gaaggtagag     720
attaaattcg tgcctgtgtt cctcccagct aagcccacta ccacccccgc tccaaggccg     780
cccacgcccg ctcctactat tgctagtcag ccttttaagtt tacgaccccga agcttgcagg     840
cccgccgccg gcggcgctgt gcacaccagg gggcttgatt ttgcctgcga cttttgggta     900
ttggtagtgg tgggcggagt tttagcctgc tacagcctcc tggtaacagt ggcttttatc     960
atcttttggg tgaggaaacg atggcagaac gagaagctcg ggttggatgc cggggatgaa    1020
tatgaagatg aaaacccttta tgaaggcctg aacctggacg actgctccat gtatgaggac    1080
atctcccggg gcctccaggg cacctaccag gatgtgggca gcctcaacat aggagatgtc    1140
cagctggaga agccgtga                                                  1158
```

<210> SEQ ID NO 51
<211> LENGTH: 385
<212> TYPE: PRT
<213> ORGANISM: Artificial Sequence
<220> FEATURE:
<223> OTHER INFORMATION: Synthetic

<400> SEQUENCE: 51

```
Glu Val Gln Leu Val Gln Ser Gly Ala Glu Val Lys Lys Pro Gly Ala
1               5                   10                  15

Ser Val Lys Val Ser Cys Lys Thr Ser Gly Tyr Thr Phe Thr Glu Tyr
            20                  25                  30

Thr Ile His Trp Val Arg Gln Ala Pro Gly Gln Ser Leu Glu Trp Met
        35                  40                  45

Gly Asn Ile Asn Pro Asn Asn Gly Gly Thr Thr Tyr Asn Gln Lys Phe
    50                  55                  60

Gln Gly Arg Val Thr Ile Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ala Gly Trp Asn Phe Asp Tyr Trp Gly Gln Gly Thr Leu Val Thr
            100                 105                 110

Val Ser Ser Gly Lys Pro Gly Ser Gly Lys Pro Gly Ser Gly Lys Pro
        115                 120                 125
```

Gly Ser Gly Lys Pro Gly Ser Asp Ile Val Met Thr Gln Ser Pro Asp
          130                 135                 140

Ser Leu Ala Val Ser Leu Gly Glu Arg Ala Thr Leu Ser Cys Arg Ala
145                 150                 155                 160

Ser Gln Asp Val Gly Thr Ala Val Asp Trp Tyr Gln Gln Lys Pro Asp
                165                 170                 175

Gln Ser Pro Lys Leu Leu Ile Tyr Trp Ala Ser Thr Arg His Thr Gly
            180                 185                 190

Val Pro Asp Arg Phe Thr Gly Ser Gly Ser Gly Thr Asp Phe Thr Leu
        195                 200                 205

Thr Ile Ser Ser Leu Gln Ala Glu Asp Val Ala Val Tyr Phe Cys Gln
    210                 215                 220

Gln Tyr Asn Ser Tyr Pro Leu Thr Phe Gly Ala Gly Thr Lys Val Glu
225                 230                 235                 240

Ile Lys Phe Val Pro Val Phe Leu Pro Ala Lys Pro Thr Thr Thr Pro
                245                 250                 255

Ala Pro Arg Pro Pro Thr Pro Ala Pro Thr Ile Ala Ser Gln Pro Leu
            260                 265                 270

Ser Leu Arg Pro Glu Ala Cys Arg Pro Ala Ala Gly Gly Ala Val His
        275                 280                 285

Thr Arg Gly Leu Asp Phe Ala Cys Asp Phe Trp Val Leu Val Val Val
    290                 295                 300

Gly Gly Val Leu Ala Cys Tyr Ser Leu Leu Val Thr Val Ala Phe Ile
305                 310                 315                 320

Ile Phe Trp Val Arg Lys Arg Trp Gln Asn Glu Lys Leu Gly Leu Asp
                325                 330                 335

Ala Gly Asp Glu Tyr Glu Asp Glu Asn Leu Tyr Glu Gly Leu Asn Leu
            340                 345                 350

Asp Asp Cys Ser Met Tyr Glu Asp Ile Ser Arg Gly Leu Gln Gly Thr
        355                 360                 365

Tyr Gln Asp Val Gly Ser Leu Asn Ile Gly Asp Val Gln Leu Glu Lys
    370                 375                 380

Pro
385

<210> SEQ ID NO 52
<211> LENGTH: 1122
<212> TYPE: DNA
<213> ORGANISM: Artificial Sequence
<220> FEATURE:
<223> OTHER INFORMATION: Synthetic

<400> SEQUENCE: 52
gaggttcaac ttgttcaatc tggggcagaa gtgaagaagc cggggcatc tgtgaaagta      60 tcatgcaaaa catccggcta tcgtttacc gaatacacca ttcactgggt cagacaggct     120
cccggtcaaa gcctcgaatg gatgggaaat attaaccta caatggcgg aaccacatat     180 aatcagaaat tccaaggccg agtgacgata actgtcgata agagtacgtc cacagcttac     240
atggaactca gctctttgag atccgaagac actgcagttt attattgtgc agctggatgg     300
aacttcgact attggggaca agggactctt gttacggtgt ccagtggcaa accaggtagt     360 ggtaaaccg gaagcggcaa gcccgggagc ggtaaacctg gtagcgacat cgtcatgact     420
caaagccctg actcactcgc cgtgagcctg ggagagcgtg caacgctatc ttgtcgggcc     480
tctcaggatg tcggaactgc tgtagactgg tatcaacaga aacctgacca atcaccaaaa     540

-continued

```
ctcctgattt attgggcctc aacacgtcac acaggagtgc cagataggtt cacaggtagt    600
ggcagtggaa ctgattttac tttgacaatt agcagcctgc aagccgaaga tgtagccgtt    660
tacttctgtc aacaatataa ctcatacccca ctaacgttcg gtgccgggac gaaggtagag   720
attaaattcg tgcctgtgtt cctcccagct aagcccacta ccacccccgc tccaaggccg    780
cccacgcccg ctcctactat tgctagtcag cctttaagtt tacgacccga agcttgcagg    840
cccgccgccg gcggcgctgt gcacaccagg gggcttgatt ttgcctgcga cttttgggta    900
ttggtagtgg tgggcggagt tttagcctgc tacagcctcc tggtaacagt ggcttttatc    960
atcttttggg tgctggacaa ggatgacagc aaggctggca tggaggaaga tcacacctac   1020
gagggcctgg acattgacca gacagccacc tatgaggaca tagtgacgct gcggacaggg   1080
gaagtgaagt ggtctgtagg tgagcaccca ggccaggagt ga                      1122
```

<210> SEQ ID NO 53
<211> LENGTH: 373
<212> TYPE: PRT
<213> ORGANISM: Artificial Sequence
<220> FEATURE:
<223> OTHER INFORMATION: Synthetic

<400> SEQUENCE: 53

```
Glu Val Gln Leu Val Gln Ser Gly Ala Glu Val Lys Lys Pro Gly Ala
1               5                   10                  15

Ser Val Lys Val Ser Cys Lys Thr Ser Gly Tyr Thr Phe Thr Glu Tyr
            20                  25                  30

Thr Ile His Trp Val Arg Gln Ala Pro Gly Gln Ser Leu Glu Trp Met
        35                  40                  45

Gly Asn Ile Asn Pro Asn Asn Gly Gly Thr Thr Tyr Asn Gln Lys Phe
    50                  55                  60

Gln Gly Arg Val Thr Ile Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ala Gly Trp Asn Phe Asp Tyr Trp Gly Gln Gly Thr Leu Val Thr
            100                 105                 110

Val Ser Ser Gly Lys Pro Gly Ser Gly Lys Pro Gly Ser Gly Lys Pro
        115                 120                 125

Gly Ser Gly Lys Pro Gly Ser Asp Ile Val Met Thr Gln Ser Pro Asp
    130                 135                 140

Ser Leu Ala Val Ser Leu Gly Glu Arg Ala Thr Leu Ser Cys Arg Ala
145                 150                 155                 160

Ser Gln Asp Val Gly Thr Ala Val Asp Trp Tyr Gln Gln Lys Pro Asp
                165                 170                 175

Gln Ser Pro Lys Leu Leu Ile Tyr Trp Ala Ser Thr Arg His Thr Gly
            180                 185                 190

Val Pro Asp Arg Phe Thr Gly Ser Gly Ser Gly Thr Asp Phe Thr Leu
        195                 200                 205

Thr Ile Ser Ser Leu Gln Ala Glu Asp Val Ala Val Tyr Phe Cys Gln
    210                 215                 220

Gln Tyr Asn Ser Tyr Pro Leu Thr Phe Gly Ala Gly Thr Lys Val Glu
225                 230                 235                 240

Ile Lys Phe Val Pro Val Phe Leu Pro Ala Lys Pro Thr Thr Thr Pro
                245                 250                 255
```

```
Ala Pro Arg Pro Pro Thr Pro Ala Pro Thr Ile Ala Ser Gln Pro Leu
            260                 265                 270

Ser Leu Arg Pro Glu Ala Cys Arg Pro Ala Ala Gly Gly Ala Val His
        275                 280                 285

Thr Arg Gly Leu Asp Phe Ala Cys Asp Phe Trp Val Leu Val Val Val
    290                 295                 300

Gly Gly Val Leu Ala Cys Tyr Ser Leu Leu Val Thr Val Ala Phe Ile
305                 310                 315                 320

Ile Phe Trp Val Leu Asp Lys Asp Asp Ser Lys Ala Gly Met Glu Glu
                325                 330                 335

Asp His Thr Tyr Glu Gly Leu Asp Ile Asp Gln Thr Ala Thr Tyr Glu
            340                 345                 350

Asp Ile Val Thr Leu Arg Thr Gly Glu Val Lys Trp Ser Val Gly Glu
            355                 360                 365

His Pro Gly Gln Glu
    370
```

<210> SEQ ID NO 54
<211> LENGTH: 1143
<212> TYPE: DNA
<213> ORGANISM: Artificial Sequence
<220> FEATURE:
<223> OTHER INFORMATION: Synthetic

<400> SEQUENCE: 54

```
gaggttcaac ttgttcaatc tggggcagaa gtgaagaagc ccggggcatc tgtgaaagta      60
tcatgcaaaa catccggcta tacgtttacc gaatacacca ttcactgggt cagacaggct     120
cccggtcaaa gcctcgaatg gatgggaaat attaaccccta caatggcgg aaccacatat    180
aatcagaaat tccaaggccg agtgacgata actgtcgata gagtacgtc cacagcttac      240
atggaactca gctctttgag atccgaagac actgcagttt attattgtgc agctggatgg    300
aacttcgact attggggaca aggactcttg gttacggtgt ccagtggcaa ccaggtagt     360
ggtaaacccg gaagcggcaa gcccgggagc ggtaaacctg gtagcgacat cgtcatgact   420
caaagccctg actcactcgc cgtgagcctg gagagcgtg caacgctatc ttgtcgggcc    480
tctcaggatg tcggaactgc tgtagactgg tatcaacaga aacctgacca atcaccaaaa   540
ctcctgattt attgggcctc aacacgtcac acaggagtgc cagataggtt cacaggtagt   600
ggcagtggaa ctgatttac tttgacaatt agcagcctgc aagccgaaga tgtagccgtt   660
tacttctgtc aacaatataa ctcatacca ctaacgttcg gtgccgggac gaaggtagag  720
attaaaggcg ctggtagtgg cggtaactgg agccaccctc aatttgagaa gggcgggtca   780
ggcggatcag gtggtagtgg tgggtccaac tggagccatc cgcaatttga aaagggcgga   840
agcggcggtt ccggcggttc aggcggtagc aactggtcac atccgcaatt tgagaaaggc   900
gggtcaggcg gcgggttttg ggctctcgtg gtggtggctg gagtgctttt ctgctatggc   960
ctgctggtaa ccgtggccct ttgtgtaatc tggaccgata agacgatgg aaaagccggg  1020
atggaagaag accataccta cgaggggctc aatattgatc aaaccgccac gtatgaagac  1080
attgtaacac tgcgcacagg tgaggtcaag tggtccgtcg gtgaacaccc aggacaagaa  1140
taa                                                                 1143
```

<210> SEQ ID NO 55
<211> LENGTH: 380
<212> TYPE: PRT
<213> ORGANISM: Artificial Sequence
<220> FEATURE:
<223> OTHER INFORMATION: Synthetic

<400> SEQUENCE: 55

Glu Val Gln Leu Val Gln Ser Gly Ala Glu Val Lys Lys Pro Gly Ala
1               5                   10                  15

Ser Val Lys Val Ser Cys Lys Thr Ser Gly Tyr Thr Phe Thr Glu Tyr
            20                  25                  30

Thr Ile His Trp Val Arg Gln Ala Pro Gly Gln Ser Leu Glu Trp Met
        35                  40                  45

Gly Asn Ile Asn Pro Asn Asn Gly Gly Thr Thr Tyr Asn Gln Lys Phe
    50                  55                  60

Gln Gly Arg Val Thr Ile Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ala Gly Trp Asn Phe Asp Tyr Trp Gly Gln Gly Thr Leu Val Thr
            100                 105                 110

Val Ser Ser Gly Lys Pro Gly Ser Gly Lys Pro Gly Ser Gly Lys Pro
        115                 120                 125

Gly Ser Gly Lys Pro Gly Ser Asp Ile Val Met Thr Gln Ser Pro Asp
    130                 135                 140

Ser Leu Ala Val Ser Leu Gly Glu Arg Ala Thr Leu Ser Cys Arg Ala
145                 150                 155                 160

Ser Gln Asp Val Gly Thr Ala Val Asp Trp Tyr Gln Gln Lys Pro Asp
                165                 170                 175

Gln Ser Pro Lys Leu Leu Ile Tyr Trp Ala Ser Thr Arg His Thr Gly
            180                 185                 190

Val Pro Asp Arg Phe Thr Gly Ser Gly Ser Gly Thr Asp Phe Thr Leu
        195                 200                 205

Thr Ile Ser Ser Leu Gln Ala Glu Asp Val Ala Val Tyr Phe Cys Gln
    210                 215                 220

Gln Tyr Asn Ser Tyr Pro Leu Thr Phe Gly Ala Gly Thr Lys Val Glu
225                 230                 235                 240

Ile Lys Gly Ala Gly Ser Gly Gly Asn Trp Ser His Pro Gln Phe Glu
                245                 250                 255

Lys Gly Gly Ser Gly Gly Ser Gly Gly Ser Gly Gly Ser Asn Trp Ser
            260                 265                 270

His Pro Gln Phe Glu Lys Gly Gly Ser Gly Gly Ser Gly Gly Ser Gly
        275                 280                 285

Gly Ser Asn Trp Ser His Pro Gln Phe Glu Lys Gly Gly Ser Gly Gly
    290                 295                 300

Gly Phe Trp Ala Leu Val Val Ala Gly Val Leu Phe Cys Tyr Gly Leu
305                 310                 315                 320

Leu Leu Val Thr Val Ala Leu Cys Val Ile Trp Thr Asp Lys Asp Asp
                325                 330                 335

Gly Lys Ala Gly Met Glu Glu Asp His Thr Tyr Glu Gly Leu Asn Ile
            340                 345                 350

Asp Gln Thr Ala Thr Tyr Glu Asp Ile Val Thr Leu Arg Thr Gly Glu
        355                 360                 365

Val Lys Trp Ser Val Gly Glu His Pro Gly Gln Glu
    370                 375                 380

<210> SEQ ID NO 56

<211> LENGTH: 1152
<212> TYPE: DNA
<213> ORGANISM: Artificial Sequence
<220> FEATURE:
<223> OTHER INFORMATION: Synthetic

<400> SEQUENCE: 56

```
gaagtccaat tggttgaaag cggtggtgga ctcgtcaaac ctggcggtag ccttaaactt      60
tcatgtgccg caagcggctt cacgtttagt aactatgcta tgagttgggt ccgccaaagt     120
ccagaaaagc gcctcgaatg ggtggcggag atctctggag gaggaacata tacatattat     180
ccagacacca tgaccggtag gtttacaatc tcaagagaca acgctaagaa caccctgtac     240
ctggaaatgt caagcctgag atcagaagat acggccatgt attattgtac gcgcctactc     300
gactattggg gtcaaggaac ttccgtgacg gtgtcaagcg gaggaggtgg agcggagga     360
ggcggaagtg gcggtggtgg ctctggtggc ggtggaagtg atatagtgat gacgcaagct     420
gccttttcaa accctgttac tttggggact agcgcatcaa tctcctgtag gtccagcaaa     480
tctttgctgc acagtaatgg aatcacctat cttttctggt atttgcaaaa gcctgggcag     540
agcccgcaac tgctgatcta tcaaatgtca aatcttgctt ccggagttcc agaccgcttc     600
tcaagttccg ggtccggcac tgattttacc ttgagaattt ctagggtcga agctgaagac     660
gtcggtgtct attattgcgc gcaaaacctt gagcttccat acaccttcgg gggggcaca     720
aaacttgaga tcaagggcgc tgggagcggc gggaattgga gtcatccaca attcgaaaag     780
ggtgggtccg gcggcagtgg tggaagcggc gggagtaact ggtcacatcc ccagtttgag     840
aaaggcggta gtggtggcag cggcggtagt ggtggcagta attggagcca tccccaattc     900
gaaaagggcg gttccggcgg cggattttgg gctcttgttg tggtggccgg agtattgttt     960
tgctatggcc tgctcgttac agtggcattg tgcgtaattt ggactgataa agacgacggc    1020
aaagccggga tggaagaaga tcacacctat gaggggctta atatagatca aacagccaca    1080
tatgaagata ttgtgactct aaggactgga gaggttaaat ggagtgtggg tgagcatcca    1140
ggacaagaat aa                                                        1152
```

<210> SEQ ID NO 57
<211> LENGTH: 383
<212> TYPE: PRT
<213> ORGANISM: Artificial Sequence
<220> FEATURE:
<223> OTHER INFORMATION: Synthetic

<400> SEQUENCE: 57

```
Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Asn Tyr
            20                  25                  30

Ala Met Ser Trp Val Arg Gln Ser Pro Glu Lys Arg Leu Glu Trp Val
        35                  40                  45

Ala Glu Ile Ser Gly Gly Gly Thr Tyr Thr Tyr Tyr Pro Asp Thr Met
    50                  55                  60

Thr Gly Arg Phe Thr Ile Ser Arg Asp Asn Ala Lys Asn Thr Leu Tyr
65                  70                  75                  80

Leu Glu Met Ser Ser Leu Arg Ser Glu Asp Thr Ala Met Tyr Tyr Cys
                85                  90                  95

Thr Arg Leu Leu Asp Tyr Trp Gly Gln Gly Thr Ser Val Thr Val Ser
            100                 105                 110
```

Ser Gly Gly Gly Gly Ser Gly Gly Gly Ser Gly Gly Ser
    115             120             125

Gly Gly Gly Gly Ser Asp Ile Val Met Thr Gln Ala Ala Phe Ser Asn
    130             135             140

Pro Val Thr Leu Gly Thr Ser Ala Ser Ile Ser Cys Arg Ser Ser Lys
145             150             155             160

Ser Leu Leu His Ser Asn Gly Ile Thr Tyr Leu Phe Trp Tyr Leu Gln
                165             170             175

Lys Pro Gly Gln Ser Pro Gln Leu Leu Ile Tyr Gln Met Ser Asn Leu
            180             185             190

Ala Ser Gly Val Pro Asp Arg Phe Ser Ser Gly Ser Gly Thr Asp
    195             200             205

Phe Thr Leu Arg Ile Ser Arg Val Glu Ala Glu Asp Val Gly Val Tyr
    210             215             220

Tyr Cys Ala Gln Asn Leu Glu Leu Pro Tyr Thr Phe Gly Gly Gly Thr
225             230             235             240

Lys Leu Glu Ile Lys Gly Ala Gly Ser Gly Gly Asn Trp Ser His Pro
            245             250             255

Gln Phe Glu Lys Gly Gly Ser Gly Gly Ser Gly Gly Ser
        260             265             270

Asn Trp Ser His Pro Gln Phe Glu Lys Gly Gly Ser Gly Gly Ser Gly
        275             280             285

Gly Ser Gly Gly Ser Asn Trp Ser His Pro Gln Phe Glu Lys Gly Gly
    290             295             300

Ser Gly Gly Gly Phe Trp Ala Leu Val Val Ala Gly Val Leu Phe
305             310             315             320

Cys Tyr Gly Leu Leu Val Thr Val Ala Leu Cys Val Ile Trp Thr Asp
            325             330             335

Lys Asp Asp Gly Lys Ala Gly Met Glu Glu Asp His Thr Tyr Glu Gly
            340             345             350

Leu Asn Ile Asp Gln Thr Ala Thr Tyr Glu Asp Ile Val Thr Leu Arg
            355             360             365

Thr Gly Glu Val Lys Trp Ser Val Gly Glu His Pro Gly Gln Glu
    370             375             380

<210> SEQ ID NO 58
<211> LENGTH: 1191
<212> TYPE: DNA
<213> ORGANISM: Artificial Sequence
<220> FEATURE:
<223> OTHER INFORMATION: Synthetic

<400> SEQUENCE: 58
cagtctgtgt tgacgcagcc gccctcagtg tctgcggccc caggacagag ggtcaccatc      60
tcctgctctg gaaccaggtc aacattggga agtgattatg tttcctggta ccaacacctc     120
ccaggaacag cccccaaact cctcgtttat ggcgataatc tgcgaccctc agggattcct     180
gaccgattct ctgcctccaa gtctggcacg tcagccaccc tgggcatcac cggactccag     240
actggggacg aggccgatta ttactgcggc acatgggatt acaccctgaa tggtgtggtg     300
ttcggcggag ggaccaagct gaccgtccta ggttctagag tggtggtggt agcggcggc     360 ggcggctctg gtggtggtgg atccctcgag atggcccagg tgcagctggt ggagtctggg     420
ggaggcttgg tacagcctgg ggggtccctg agactctcct gtgcagcctc tggattcacc     480
tttagcagct atgccatgag ctgggtccgc caggctccag gaaggggct ggagtgggtc     540

```
tcagttattt atagcggtgg tagtagcaca tactatgcag actccgtgaa gggccggttc    600
accatctcca gagataattc aagaacacg ctgtatctgc aaatgaacag cctgagagcc     660
```

```
tcagttattt atagcggtgg tagtagcaca tactatgcag actccgtgaa gggccggttc    600
accatctcca gagataattc caagaacacg ctgtatctgc aaatgaacag cctgagagcc    660
gaggacacgg ccgtatatta ctgtgcgcgc acttcttacc tgaaccatgg tgattactgg    720
ggtcaaggta ctctggtgac cgtgtctagc gccgctgcat tcgtgcctgt gttcctccca    780
gctaagccca ctaccacccc cgctccaagg ccgcccacgc cgctcctac tattgctagt     840
cagcctttaa gtttacgacc cgaagcttgc aggcccgccg ccggcggcgc tgtgcacacc    900
aggggggcttg attttgcctg cgacttttgg gtattggtag tggtgggcgg agttttagcc   960
tgctacagcc tcctggtaac agtggctttt atcatctttt gggtgaggaa acgatggcag   1020
aacgagaagc tcgggttgga tgccggggat gaatatgaag atgaaaacct ttatgaaggc   1080
ctgaacctgg acgactgctc catgtatgag acatctccc gggcctcca gggcacctac     1140
caggatgtgg gcagcctcaa cataggagat gtccagctgg agaagccgtg a            1191
```

<210> SEQ ID NO 59
<211> LENGTH: 396
<212> TYPE: PRT
<213> ORGANISM: Artificial Sequence
<220> FEATURE:
<223> OTHER INFORMATION: Synthetic

<400> SEQUENCE: 59

```
Gln Ser Val Leu Thr Gln Pro Pro Ser Val Ser Ala Ala Pro Gly Gln
1               5                   10                  15

Arg Val Thr Ile Ser Cys Ser Gly Thr Arg Ser Asn Ile Gly Ser Asp
            20                  25                  30

Tyr Val Ser Trp Tyr Gln His Leu Pro Gly Thr Ala Pro Lys Leu Leu
        35                  40                  45

Val Tyr Gly Asp Asn Leu Arg Pro Ser Gly Ile Pro Asp Arg Phe Ser
    50                  55                  60

Ala Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Tyr Thr Leu
                85                  90                  95

Asn Gly Val Val Phe Gly Gly Gly Thr Lys Leu Thr Val Leu Gly Ser
            100                 105                 110

Arg Gly Gly Gly Ser Gly Gly Gly Ser Gly Gly Gly Ser
        115                 120                 125

Leu Glu Met Ala Gln Val Gln Leu Val Glu Ser Gly Gly Gly Leu Val
    130                 135                 140

Gln Pro Gly Gly Ser Leu Arg Leu Ser Cys Ala Ala Ser Gly Phe Thr
145                 150                 155                 160

Phe Ser Ser Tyr Ala Met Ser Trp Val Arg Gln Ala Pro Gly Lys Gly
                165                 170                 175

Leu Glu Trp Val Ser Val Ile Tyr Ser Gly Gly Ser Thr Tyr Tyr
            180                 185                 190

Ala Asp Ser Val Lys Gly Arg Phe Thr Ile Ser Arg Asp Asn Ser Lys
        195                 200                 205

Asn Thr Leu Tyr Leu Gln Met Asn Ser Leu Arg Ala Glu Asp Thr Ala
    210                 215                 220

Val Tyr Tyr Cys Ala Arg Thr Ser Tyr Leu Asn His Gly Asp Tyr Trp
225                 230                 235                 240

Gly Gln Gly Thr Leu Val Thr Val Ser Ser Ala Ala Ala Phe Val Pro
                245                 250                 255
```

```
Val Phe Leu Pro Ala Lys Pro Thr Thr Thr Pro Ala Pro Arg Pro Pro
            260                 265                 270

Thr Pro Ala Pro Thr Ile Ala Ser Gln Pro Leu Ser Leu Arg Pro Glu
        275                 280                 285

Ala Cys Arg Pro Ala Ala Gly Gly Ala Val His Thr Arg Gly Leu Asp
    290                 295                 300

Phe Ala Cys Asp Phe Trp Val Leu Val Val Gly Val Leu Ala
305                 310                 315                 320

Cys Tyr Ser Leu Leu Val Thr Val Ala Phe Ile Ile Phe Trp Val Arg
                325                 330                 335

Lys Arg Trp Gln Asn Glu Lys Leu Gly Leu Asp Ala Gly Asp Glu Tyr
            340                 345                 350

Glu Asp Glu Asn Leu Tyr Glu Gly Leu Asn Leu Asp Asp Cys Ser Met
                355                 360                 365

Tyr Glu Asp Ile Ser Arg Gly Leu Gln Gly Thr Tyr Gln Asp Val Gly
        370                 375                 380

Ser Leu Asn Ile Gly Asp Val Gln Leu Glu Lys Pro
385                 390                 395

<210> SEQ ID NO 60
<211> LENGTH: 1155
<212> TYPE: DNA
<213> ORGANISM: Artificial Sequence
<220> FEATURE:
<223> OTHER INFORMATION: Synthetic

<400> SEQUENCE: 60
cagtctgtgt tgacgcagcc gccctcagtg tctgcggccc caggacagag ggtcaccatc      60
tcctgctctg gaaccaggtc caacattggg agtgattatg tttcctggta ccaacacctc     120
ccaggaacag cccccaaact cctcgtttat ggcgataatc tgcgaccctc agggattcct     180
gaccgattct ctgcctccaa gtctggcacg tcagccaccc tgggcatcac cggactccag     240
actggggacg aggccgatta ttactgcggc acatgggatt acaccctgaa tggtgtggtg     300
ttcggcggag ggaccaagct gaccgtccta ggttctagag gtggtggtgg tagcggcggc     360
ggcggctctg gtggtggtgg atccctcgag atggcccagg tgcagctggt ggagtctggg     420
ggaggcttgg tacagcctgg ggggtccctg agactctcct gtgcagcctc tggattcacc     480
tttagcagct atgccatgag ctgggtccgc caggctccag ggaaggggct ggagtgggtc     540
tcagttattt atagcggtgg tagtagcaca tactatgcag actccgtgaa gggccggttc     600
accatctcca gagataattc caagaacacg ctgtatctgc aaatgaacag cctgagagcc     660
gaggacacgg ccgtatatta ctgtgcgcgc acttcttacc tgaaccatgg tgattactgg     720
ggtcaaggta ctctggtgac cgtgtctagc gccgctgcat tcgtgcctgt gttcctccca     780
gctaagccca ctaccacccc cgctccaagg ccgcccacgc cgctcctac tattgctagt     840
cagcctttaa gtttacgacc cgaagcttgc aggcccgccg ccggcggcgc tgtgcacacc     900
agggggcttg atttttgcct cgactttttgg gtattggtag tggtgggcgg agttttagcc     960
tgctacagcc tcctggtaac agtggctttt atcatctttt gggtgctgga caaggatgac    1020
agcaaggctg gcatggagga agatcacacc tacgagggcc tggacattga ccagacagcc    1080
acctatgagg acatagtgac gctgcggaca ggggaagtga agtggtctgt aggtgagcac    1140
ccaggccagg agtga                                                    1155
```

```
<210> SEQ ID NO 61
<211> LENGTH: 384
<212> TYPE: PRT
<213> ORGANISM: Artificial Sequence
<220> FEATURE:
<223> OTHER INFORMATION: Synthetic

<400> SEQUENCE: 61

Gln Ser Val Leu Thr Gln Pro Pro Ser Val Ser Ala Ala Pro Gly Gln
1               5                   10                  15

Arg Val Thr Ile Ser Cys Ser Gly Arg Ser Asn Ile Gly Ser Asp
            20                  25                  30

Tyr Val Ser Trp Tyr Gln His Leu Pro Gly Thr Ala Pro Lys Leu Leu
        35                  40                  45

Val Tyr Gly Asp Asn Leu Arg Pro Ser Gly Ile Pro Asp Arg Phe Ser
    50                  55                  60

Ala Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Tyr Thr Leu
                85                  90                  95

Asn Gly Val Val Phe Gly Gly Gly Thr Lys Leu Thr Val Leu Gly Ser
            100                 105                 110

Arg Gly Gly Gly Gly Ser Gly Gly Gly Ser Gly Gly Gly Gly Ser
        115                 120                 125

Leu Glu Met Ala Gln Val Gln Leu Val Glu Ser Gly Gly Gly Leu Val
    130                 135                 140

Gln Pro Gly Gly Ser Leu Arg Leu Ser Cys Ala Ala Ser Gly Phe Thr
145                 150                 155                 160

Phe Ser Ser Tyr Ala Met Ser Trp Val Arg Gln Ala Pro Gly Lys Gly
                165                 170                 175

Leu Glu Trp Val Ser Val Ile Tyr Ser Gly Gly Ser Ser Thr Tyr Tyr
            180                 185                 190

Ala Asp Ser Val Lys Gly Arg Phe Thr Ile Ser Arg Asp Asn Ser Lys
        195                 200                 205

Asn Thr Leu Tyr Leu Gln Met Asn Ser Leu Arg Ala Glu Asp Thr Ala
    210                 215                 220

Val Tyr Tyr Cys Ala Arg Thr Ser Tyr Leu Asn His Gly Asp Tyr Trp
225                 230                 235                 240

Gly Gln Gly Thr Leu Val Thr Val Ser Ser Ala Ala Phe Val Pro
                245                 250                 255

Val Phe Leu Pro Ala Lys Pro Thr Thr Thr Pro Ala Pro Arg Pro Pro
            260                 265                 270

Thr Pro Ala Pro Thr Ile Ala Ser Gln Pro Leu Ser Leu Arg Pro Glu
        275                 280                 285

Ala Cys Arg Pro Ala Ala Gly Gly Ala Val His Thr Arg Gly Leu Asp
    290                 295                 300

Phe Ala Cys Asp Phe Trp Val Leu Val Val Val Gly Gly Val Leu Ala
305                 310                 315                 320

Cys Tyr Ser Leu Leu Val Thr Val Ala Phe Ile Ile Phe Trp Val Leu
                325                 330                 335

Asp Lys Asp Asp Ser Lys Ala Gly Met Glu Glu Asp His Thr Tyr Glu
            340                 345                 350

Gly Leu Asp Ile Asp Gln Thr Ala Tyr Glu Asp Ile Val Thr Leu
        355                 360                 365

Arg Thr Gly Glu Val Lys Trp Ser Val Gly Glu His Pro Gly Gln Glu
```

```
                    370             375             380

<210> SEQ ID NO 62
<211> LENGTH: 1653
<212> TYPE: DNA
<213> ORGANISM: Artificial Sequence
<220> FEATURE:
<223> OTHER INFORMATION: Synthetic

<400> SEQUENCE: 62
cagtctgtgt tgacgcagcc gccctcagtg tctgcggccc caggacagag ggtcaccatc      60
tcctgctctg gaaccaggtc caacattggg agtgattatg tttcctggta ccaacacctc     120
ccaggaacag cccccaaact cctcgtttat ggcgataatc tgcgaccctc agggattcct     180
gaccgattct ctgcctccaa gtctggcacg tcagccaccc tgggcatcac cggactccag     240
actggggacg aggccgatta ttactgcggc acatgggatt acacccctga atggtgtggtg    300
ttcggcggag ggaccaagct gaccgtccta ggttctagag gtggtggtgg tagcggcggc     360
ggcggctctg gtggtggtgg atccctcgag atggcccagg tgcagctggt ggagtctggg     420
ggaggcttgg tacagcctgg ggggtccctg agactctcct gtgcagcctc tggattcacc     480
tttagcagct atgccatgag ctgggtccgc caggctccag gaaggggct ggagtgggtc      540
tcagttattt atagcggtgg tagtagcaca tactatgcag actccgtgaa gggccggttc     600
accatctcca gagataattc caagaacacg ctgtatctgc aaatgaacag cctgagagcc     660
gaggacacgg ccgtatatta ctgtgcgcgc acttcttacc tgaaccatgg tgattactgg     720
ggtcaaggta ctctggtgac cgtgtctagc cccaagagct cgacaagac ccacacctgc      780
cccccctgcc cagccccaga gctgctgggc ggaccctccg tgttcctgtt cccccccaag     840
cccaaggaca ccctgatgat cagcaggacc cccgaggtga cctgcgtggt ggtggacgtg     900
agccacgagg acccagaggt gaagttcaac tggtacgtgg acggcgtgga ggtgcacaac     960
gccaagacca gcccagaga ggagcagtac aacagcacct acaggtggt gtccgtgctg      1020
accgtgctgc accaggactg gctgaacggc aaggaatacc agtgcaaggt ctccaacaag    1080
gccctgccag cccccatcga aaagaccatc agcaaggcca agggcagcc acgggagccc     1140
caggtgtaca ccctgccccc ctcccgggag gagatgacca gaaccaggt gtccctgacc     1200
tgtctggtga agggcttcta ccccagcgac atcgccgtgg agtgggagag caacggccag    1260
cccgagaaca actacaagac caccccccca gtgctggaca gcgacggcag cttcttcctg    1320
tacagcaagc tgaccgtgga caagtccagg tggcagcagg gcaacgtgtt cagctgcagc    1380
gtgatgcacg aggccctgca caaccactac acccagaaga gcctgagcct gtcccccgag    1440
ctgcaactgg aggagagctg tgcggaggcg caggacgggg agctggacgg gctgtggacg    1500
accatcacca tcttcatcac actcttcctg ttaagcgtgt gctacagtgc caccgtcacc    1560
ttcttcaagg tgaagtggat cttctcctcg gtggtggacc tgaagcagac catcatcccc    1620
gactacagga acatgatcgg acaggggggcc tga                                1653

<210> SEQ ID NO 63
<211> LENGTH: 550
<212> TYPE: PRT
<213> ORGANISM: Artificial Sequence
<220> FEATURE:
<223> OTHER INFORMATION: Synthetic

<400> SEQUENCE: 63

Gln Ser Val Leu Thr Gln Pro Pro Ser Val Ser Ala Ala Pro Gly Gln
```

-continued

```
1               5                   10                  15
Arg Val Thr Ile Ser Cys Ser Gly Thr Arg Ser Asn Ile Gly Ser Asp
                20                  25                  30
Tyr Val Ser Trp Tyr Gln His Leu Pro Gly Thr Ala Pro Lys Leu Leu
                35                  40                  45
Val Tyr Gly Asp Asn Leu Arg Pro Ser Gly Ile Pro Asp Arg Phe Ser
                50                  55                  60
Ala Ser Lys Ser Gly Thr Ser Ala Thr Leu Gly Ile Thr Gly Leu Gln
65                  70                  75                  80
Thr Gly Asp Glu Ala Asp Tyr Tyr Cys Gly Thr Trp Asp Tyr Thr Leu
                85                  90                  95
Asn Gly Val Val Phe Gly Gly Gly Thr Lys Leu Thr Val Leu Gly Ser
                100                 105                 110
Arg Gly Gly Gly Gly Ser Gly Gly Gly Ser Gly Gly Gly Gly Ser
                115                 120                 125
Leu Glu Met Ala Gln Val Gln Leu Val Glu Ser Gly Gly Gly Leu Val
                130                 135                 140
Gln Pro Gly Gly Ser Leu Arg Leu Ser Cys Ala Ala Ser Gly Phe Thr
145                 150                 155                 160
Phe Ser Ser Tyr Ala Met Ser Trp Val Arg Gln Ala Pro Gly Lys Gly
                165                 170                 175
Leu Glu Trp Val Ser Val Ile Tyr Ser Gly Gly Ser Ser Thr Tyr Tyr
                180                 185                 190
Ala Asp Ser Val Lys Gly Arg Phe Thr Ile Ser Arg Asp Asn Ser Lys
                195                 200                 205
Asn Thr Leu Tyr Leu Gln Met Asn Ser Leu Arg Ala Glu Asp Thr Ala
210                 215                 220
Val Tyr Tyr Cys Ala Arg Thr Ser Tyr Leu Asn His Gly Asp Tyr Trp
225                 230                 235                 240
Gly Gln Gly Thr Leu Val Thr Val Ser Pro Lys Ser Cys Asp Lys
                245                 250                 255
Thr His Thr Cys Pro Pro Cys Pro Ala Pro Glu Leu Leu Gly Gly Pro
                260                 265                 270
Ser Val Phe Leu Phe Pro Pro Lys Pro Lys Asp Thr Leu Met Ile Ser
                275                 280                 285
Arg Thr Pro Glu Val Thr Cys Val Val Val Asp Val Ser His Glu Asp
                290                 295                 300
Pro Glu Val Lys Phe Asn Trp Tyr Val Asp Gly Val Glu Val His Asn
305                 310                 315                 320
Ala Lys Thr Lys Pro Arg Glu Glu Gln Tyr Asn Ser Thr Tyr Arg Val
                325                 330                 335
Val Ser Val Leu Thr Val Leu His Gln Asp Trp Leu Asn Gly Lys Glu
                340                 345                 350
Tyr Lys Cys Lys Val Ser Asn Lys Ala Leu Pro Ala Pro Ile Glu Lys
                355                 360                 365
Thr Ile Ser Lys Ala Lys Gly Gln Pro Arg Glu Pro Gln Val Tyr Thr
                370                 375                 380
Leu Pro Pro Ser Arg Glu Glu Met Thr Lys Asn Gln Val Ser Leu Thr
385                 390                 395                 400
Cys Leu Val Lys Gly Phe Tyr Pro Ser Asp Ile Ala Val Glu Trp Glu
                405                 410                 415
Ser Asn Gly Gln Pro Glu Asn Asn Tyr Lys Thr Thr Pro Pro Val Leu
                420                 425                 430
```

```
Asp Ser Asp Gly Ser Phe Phe Leu Tyr Ser Lys Leu Thr Val Asp Lys
            435                 440                 445

Ser Arg Trp Gln Gln Gly Asn Val Phe Ser Cys Ser Val Met His Glu
    450                 455                 460

Ala Leu His Asn His Tyr Thr Gln Lys Ser Leu Ser Leu Ser Pro Glu
465                 470                 475                 480

Leu Gln Leu Glu Glu Ser Cys Ala Glu Ala Gln Asp Gly Glu Leu Asp
                485                 490                 495

Gly Leu Trp Thr Thr Ile Thr Ile Phe Ile Thr Leu Phe Leu Leu Ser
            500                 505                 510

Val Cys Tyr Ser Ala Thr Val Thr Phe Phe Lys Val Lys Trp Ile Phe
            515                 520                 525

Ser Ser Val Val Asp Leu Lys Gln Thr Ile Ile Pro Asp Tyr Arg Asn
    530                 535                 540

Met Ile Gly Gln Gly Ala
545             550
```

<210> SEQ ID NO 64
<211> LENGTH: 648
<212> TYPE: DNA
<213> ORGANISM: Artificial Sequence
<220> FEATURE:
<223> OTHER INFORMATION: Synthetic

<400> SEQUENCE: 64

```
cagtctgtgt tgacgcagcc gccctcagtg tctgcggccc caggacagag ggtcaccatc      60
tcctgctctg gaaccaggtc caacattggg agtgattatg tttcctggta ccaacacctc     120
ccaggaacag cccccaaact cctcgtttat ggcgataatc tgcgacccct agggattcct     180
gaccgattct ctgcctccaa gtctggcacg tcagccaccc tgggcatcac cggactccag     240
actggggacg aggccgatta ttactgcggc acatggggtt acaccctgaa tggtgtggtg     300
ttcggcggag ggaccaagct gaccgtccta ggtcagccca aggccaaccc cactgtcact     360
ctgttcccgc cctcctctga ggagctccaa gccaacaagg ccacactagt gtgtctgatc     420
agtgacttct acccgggagc tgtgacagtg gcctggaagg cagatggcag ccccgtcaag     480
gcgggagtgg agaccaccaa accctccaaa cagagcaaca acaagtacgc ggccagcagc     540
tacctgagcc tgacgcccga gcagtggaag tcccacagaa gctacagctg ccaggtcacg     600
catgaaggga gcaccgtgga aagacagtg gcccctacag aatgttca                   648
```

<210> SEQ ID NO 65
<211> LENGTH: 216
<212> TYPE: PRT
<213> ORGANISM: Artificial Sequence
<220> FEATURE:
<223> OTHER INFORMATION: Synthetic

<400> SEQUENCE: 65

```
Gln Ser Val Leu Thr Gln Pro Pro Ser Val Ser Ala Ala Pro Gly Gln
1               5                   10                  15

Arg Val Thr Ile Ser Cys Ser Gly Thr Arg Ser Asn Ile Gly Ser Asp
            20                  25                  30

Tyr Val Ser Trp Tyr Gln His Leu Pro Gly Thr Ala Pro Lys Leu Leu
        35                  40                  45

Val Tyr Gly Asp Asn Leu Arg Pro Ser Gly Ile Pro Asp Arg Phe Ser
    50                  55                  60
```

Ala Ser Lys Ser Gly Thr Ser Ala Thr Leu Gly Ile Thr Gly Leu Gln
 65                  70                  75                  80

Thr Gly Asp Glu Ala Asp Tyr Tyr Cys Gly Thr Trp Asp Tyr Thr Leu
                 85                  90                  95

Asn Gly Val Val Phe Gly Gly Gly Thr Lys Leu Thr Val Leu Gly Gln
            100                 105                 110

Pro Lys Ala Asn Pro Thr Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Gly Ser Pro Val Lys
145                 150                 155                 160

Ala Gly Val Glu Thr Thr Lys Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215

<210> SEQ ID NO 66
<211> LENGTH: 1554
<212> TYPE: DNA
<213> ORGANISM: Artificial Sequence
<220> FEATURE:
<223> OTHER INFORMATION: Synthetic

<400> SEQUENCE: 66
caggtgcagc tggtggagtc tgggggaggc ttggtacagc ctgggggggtc cctgagactc        60 tcctgtgcag cctctggatt cacctttagc agctatgcca tgagctgggt ccgccaggct       120
ccagggaagg gctggagtg gtctcagtt atttatagcg gtggtagtag cacatactat        180
gcagactccg tgaagggccg gttcaccatc tccagagata attccaagaa cacgctgtat       240
ctgcaaatga acagcctgag agccgaggac acggccgtat attactgtgc gcgcacttct       300
tacctgaacc atggtgatta ctggggtcaa ggtactctgg tgaccgtgtc tagcgcctcc       360
accaagggcc catcggtctt ccccctggca ccctcctcca agagcacctc tgggggcaca       420
gcggccctgg gctgcctggt caaggactac ttccccgaac cggtgacggt gtcgtggaac       480
tcaggcgccc tgaccagcgg cgtgcacacc ttcccggctg tcctacagtc ctcaggactc       540
tactccctca gcagcgtggt gaccgtgccc tccagcagct gggcaccca gacctacatc       600 tgcaacgtga accacaagcc cagcaacacc aaggtggaca gagagtgga gcccaagagc       660 tgcgacaaga cccacacctg cccccctgc ccagcccag agctgctggg cggaccctcc       720
gtgttcctgt tccccccaa gcccaaggac accctgatga tcagcaggac ccccgaggtg       780
acctgcgtgg tggtggacgt gagccacgag gacccagagg tgaagttcaa ctggtacgtg       840
gacggcgtgg aggtgcacaa cgccaagacc aagcccagag aggagcagta caacagcacc       900
tacagggtgg tgtccgtgct gaccgtgctg caccaggact ggctgaacgg caaggaatac       960
aagtgcaagg tctccaacaa ggccctgcca gccccatcg aaaagaccat cagcaaggcc      1020
aagggccagc cacgggagcc ccaggtgtac accctgcccc cctcccggga ggagatgacc      1080
aagaaccagg tgtccctgac ctgtctggtg aagggcttct accccagcga catcgccgtg      1140
gagtgggaga gcaacggcca gccgagaac aactacaaga ccaccccccc agtgctggac      1200

```
agcgacggca gcttcttcct gtacagcaag ctgaccgtgg acaagtccag gtggcagcag    1260
ggcaacgtgt tcagctgcag cgtgatgcac gaggccctgc acaaccacta cacccagaag    1320
agcctgagcc tgtcccccga gctgcaactg aggagagct gtgcggaggc caggacggg     1380 gagctggacg gctgtggac gaccatcacc atcttcatca cactcttcct gttaagcgtg    1440
tgctacagtg ccaccgtcac cttcttcaag gtgaagtgga tcttctcctc ggtggtggac    1500
ctgaagcaga ccatcatccc cgactacagg aacatgatcg acagggggc ctga         1554
```

<210> SEQ ID NO 67
<211> LENGTH: 517
<212> TYPE: PRT
<213> ORGANISM: Artificial Sequence
<220> FEATURE:
<223> OTHER INFORMATION: Synthetic

<400> SEQUENCE: 67

```
Gln Val Gln Leu Val Glu Ser Gly Gly Gly Leu Val Gln Pro Gly Gly
1               5                  10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Val Ile Tyr Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Thr Ser Tyr Leu Asn His Gly Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300
```

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Ile Glu Lys Thr
            325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
            405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Glu Leu
            435                 440                 445

Gln Leu Glu Glu Ser Cys Ala Glu Ala Gln Asp Gly Glu Leu Asp Gly
    450                 455                 460

Leu Trp Thr Thr Ile Thr Ile Phe Ile Thr Leu Phe Leu Leu Ser Val
465                 470                 475                 480

Cys Tyr Ser Ala Thr Val Thr Phe Phe Lys Val Lys Trp Ile Phe Ser
            485                 490                 495

Ser Val Val Asp Leu Lys Gln Thr Ile Ile Pro Asp Tyr Arg Asn Met
            500                 505                 510

Ile Gly Gln Gly Ala
        515

<210> SEQ ID NO 68
<211> LENGTH: 327
<212> TYPE: DNA
<213> ORGANISM: Artificial Sequence
<220> FEATURE:
<223> OTHER INFORMATION: Synthetic

<400> SEQUENCE: 68
atgagacttt caacagcaac actcctcctg ttgctggctt catgtctgag ccctggtcat      60
ggtattttgg aggcccacta tacaaatctc aaatgtcggt gttcaggcgt aatatccacc     120
gtagtcggcc tgaacattat cgataggatt caggttacac cccccgggaa cggatgtcct     180
aagaccgagg tggtgatttg accaagatg aagaaggtca tttgtgtgaa cccacgggct      240
aaatggctgc agcgtctttt gcgacacgtg cagtccaaga gcttgtccag cacacctcag     300
gccccagtta gcaagcgacg tgcagcc                                         327

<210> SEQ ID NO 69
<211> LENGTH: 109
<212> TYPE: PRT
<213> ORGANISM: Artificial Sequence
<220> FEATURE:
<223> OTHER INFORMATION: Synthetic

<400> SEQUENCE: 69

Met Arg Leu Ser Thr Ala Thr Leu Leu Leu Leu Ala Ser Cys Leu
1               5                   10                  15

Ser Pro Gly His Gly Ile Leu Glu Ala His Tyr Thr Asn Leu Lys Cys

```
            20                  25                  30
Arg Cys Ser Gly Val Ile Ser Thr Val Val Gly Leu Asn Ile Ile Asp
            35                  40                  45

Arg Ile Gln Val Thr Pro Pro Gly Asn Gly Cys Pro Lys Thr Glu Val
        50                  55                  60

Val Ile Trp Thr Lys Met Lys Lys Val Ile Cys Val Asn Pro Arg Ala
65                  70                  75                  80

Lys Trp Leu Gln Arg Leu Leu Arg His Val Gln Ser Lys Ser Leu Ser
                85                  90                  95

Ser Thr Pro Gln Ala Pro Val Ser Lys Arg Arg Ala Ala
            100                 105

<210> SEQ ID NO 70
<211> LENGTH: 696
<212> TYPE: DNA
<213> ORGANISM: Artificial Sequence
<220> FEATURE:
<223> OTHER INFORMATION: Synthetic

<400> SEQUENCE: 70
atgacagtgc tggcccccgc gtggtctccc aatagctcac tcctcctctt gctgctactg      60
ctcagcccat gcctcagggg cacccccgat tgttacttca gccacagccc aatctcctcc     120
aacttcaaag tgaaatttag ggaactgacc gaccacctgc tgaaagatta tcctgtgact     180
gtggcagtga acctgcaaga cgaaaagcat tgtaaggcgc tatggagcct ctttcttgcc     240
caacgatgga ttgagcaact caaaactgta gccggaagca aaatgcagac gctactggag     300
gacgtgaata ctgagattca cttcgttacc agttgtactt tccagccact gccagagtgt     360
ctcaggtttg tgcagactaa tatcagccac tgctgaagg atacttgcac ccagctcctg     420
gctctcaagc cttgtatagg caaggcttgt caaaatttta gcaggtgtct cgaagtccag     480
tgccagccag attcatccac actgctgccg ccccgaagcc ctatcgcact cgaagcgaca     540
gagttgccag agcctcgtcc cagacagctt ctgctgctgc tacttctgct gctgccgcta     600
actctggtgc tacttgctgc cgcctggggc ctcagatggc aacgcgccag acgccgaggc     660
gaactccacc ctggggtgcc actgccatcc caccca                              696

<210> SEQ ID NO 71
<211> LENGTH: 232
<212> TYPE: PRT
<213> ORGANISM: Artificial Sequence
<220> FEATURE:
<223> OTHER INFORMATION: Synthetic

<400> SEQUENCE: 71

Met Thr Val Leu Ala Pro Ala Trp Ser Pro Asn Ser Ser Leu Leu Leu
1               5                   10                  15

Leu Leu Leu Leu Leu Ser Pro Cys Leu Arg Gly Thr Pro Asp Cys Tyr
            20                  25                  30

Phe Ser His Ser Pro Ile Ser Ser Asn Phe Lys Val Lys Phe Arg Glu
        35                  40                  45

Leu Thr Asp His Leu Leu Lys Asp Tyr Pro Val Thr Val Ala Val Asn
    50                  55                  60

Leu Gln Asp Glu Lys His Cys Lys Ala Leu Trp Ser Leu Phe Leu Ala
65                  70                  75                  80

Gln Arg Trp Ile Glu Gln Leu Lys Thr Val Ala Gly Ser Lys Met Gln
                85                  90                  95
```

```
Thr Leu Leu Glu Asp Val Asn Thr Glu Ile His Phe Val Thr Ser Cys
            100                 105                 110

Thr Phe Gln Pro Leu Pro Glu Cys Leu Arg Phe Val Gln Thr Asn Ile
        115                 120                 125

Ser His Leu Leu Lys Asp Thr Cys Thr Gln Leu Leu Ala Leu Lys Pro
    130                 135                 140

Cys Ile Gly Lys Ala Cys Gln Asn Phe Ser Arg Cys Leu Glu Val Gln
145                 150                 155                 160

Cys Gln Pro Asp Ser Ser Thr Leu Leu Pro Arg Ser Pro Ile Ala
                165                 170                 175

Leu Glu Ala Thr Glu Leu Pro Glu Pro Arg Pro Arg Gln Leu Leu Leu
                180                 185                 190

Leu Leu Leu Leu Leu Leu Pro Leu Thr Leu Val Leu Ala Ala Ala
            195                 200                 205

Trp Gly Leu Arg Trp Gln Arg Ala Arg Arg Gly Glu Leu His Pro
210                 215                 220

Gly Val Pro Leu Pro Ser His Pro
225                 230

<210> SEQ ID NO 72
<211> LENGTH: 342
<212> TYPE: DNA
<213> ORGANISM: Artificial Sequence
<220> FEATURE:
<223> OTHER INFORMATION: Synthetic

<400> SEQUENCE: 72
atgcgactct tgttgttgac ttttctcgga gtgtgctgcc tgacaccctg ggtcgtagag      60
ggagttggca ctgaagtact agaagagtcc tcctgcgtta acctgcagac acagcggctc     120
ccagtccaga aaattaagac ctacattata tgggaaggag caatgcgagc ggtgattttt     180
gtgaccaaga gggtctcaa gatttgcgcg gaccctgagg ccaagtgggt caaagcagct     240
attaagacag tagacggaag agcctccacc aggaagaata tggcagaaac tgtaccgacc     300
ggtgcgcagc ggtcaacatc taccgcaatc acactcaccg gc                       342

<210> SEQ ID NO 73
<211> LENGTH: 114
<212> TYPE: PRT
<213> ORGANISM: Artificial Sequence
<220> FEATURE:
<223> OTHER INFORMATION: Synthetic

<400> SEQUENCE: 73

Met Arg Leu Leu Leu Leu Thr Phe Leu Gly Val Cys Cys Leu Thr Pro
1               5                   10                  15

Trp Val Val Glu Gly Val Gly Thr Glu Val Leu Glu Glu Ser Ser Cys
            20                  25                  30

Val Asn Leu Gln Thr Gln Arg Leu Pro Val Gln Lys Ile Lys Thr Tyr
        35                  40                  45

Ile Ile Trp Glu Gly Ala Met Arg Ala Val Ile Phe Val Thr Lys Arg
    50                  55                  60

Gly Leu Lys Ile Cys Ala Asp Pro Glu Ala Lys Trp Val Lys Ala Ala
65                  70                  75                  80

Ile Lys Thr Val Asp Gly Arg Ala Ser Thr Arg Lys Asn Met Ala Glu
                85                  90                  95

Thr Val Pro Thr Gly Ala Gln Arg Ser Thr Ser Thr Ala Ile Thr Leu
            100                 105                 110
```

Thr Gly

<210> SEQ ID NO 74
<211> LENGTH: 1533
<212> TYPE: DNA
<213> ORGANISM: Artificial Sequence
<220> FEATURE:
<223> OTHER INFORMATION: Synthetic

<400> SEQUENCE: 74

```
atgagcaagg gccttctcct gctgtggcta gtaactgaat tgtggtggtt gtacctgaca      60
cctgccgcta gtgaggacac catcattggt ttccttgggc agcccgtcac cctcccttgc     120
cattacctaa gctggagcca gtcacggaac tctatgtgct ggggaaaggg gtcatgccct     180
aattccaagt gcaacgccga gctgttgcgc acggacggca ccagaataat ctcaagaaag     240
tccaccaagt atacgctgct cggcaaggtg caattcggtg aagtgagctt gaccataagt     300
aacaccaacc gcggtgactc cggagtttat tgttgcagga tcgaagtgcc aggctggttt     360
aacgacgtga agaaaaacgt gcggctggaa ctgaggaggg caactacgac caagaaacca     420
acaaccacga cgagacctac caccactcct tacgtgacaa ccacgacacc ggagctgttg     480
ccaactaccg tcatgacaac atctgtgttg ccaactacca cccccccca aacgctcgcg      540
acaactgcct tttccacagc cgttaccaca tgtccttcca ccaccccagg ctcttttct      600
caagaaacta ccaagggatc agcttttacc accgagtctg aaactctccc agcaagtaat     660
cactcacagc ggtcaatgat gaccatcagc acagacatcg ctgtcttgag acctactggc     720
agcaatccag gcattctgcc ctccacttca cagctgacta cccaaaagac tacactaacc     780
accagcgaaa gtctgcagaa aactacaaag agccatcaaa taaactcccg gcagactccc     840
agagggccca caatcaagcc ctgtcctcca tgcaaatgcc cagcacctaa cctcttgggt     900
ggaccatccg tcttcatctt ccctccaaag atcaaggatg tactcatgat ctccctgagc     960
cccatagtca catgtgtggt ggtggatgtg agcgaggatg acccagatgt ccagatcagc    1020
tggtttgtga acaacgtgga agtacacaca gctcagacac aaaccccatag agaggattac    1080
aacagtactc tccgggtggt cagtgccctc cccatccagc accaggactg gatgagtggc    1140
aaggagttca atgcaaggt caacaacaaa gacctcccag cgcccatcga gagaaccatc    1200
tcaaacccca agggtcagt aagagctcca caggtatatg tcttgcctcc accagaagaa    1260
gagatgacta gaaaacaggt cactctgacc tgcatggtca cagacttcat gcctgaagac    1320
atttacgtgg agtggaccaa caacgggaaa acagagctaa actacaagaa cactgaacca    1380
gtcctggact ctgatggttc ttacttcatg tacagcaagc tgagagtgga aaagaagaac    1440
tgggtggaaa gaaatagcta ctcctgttca gtggtccacg agggtctgca caatcaccac    1500
acgactaaga gcttctcccg gactccgggt aaa                                 1533
```

<210> SEQ ID NO 75
<211> LENGTH: 511
<212> TYPE: PRT
<213> ORGANISM: Artificial Sequence
<220> FEATURE:
<223> OTHER INFORMATION: Synthetic

<400> SEQUENCE: 75

Met Ser Lys Gly Leu Leu Leu Leu Trp Leu Val Thr Glu Leu Trp Trp
1               5                   10                  15

Leu Tyr Leu Thr Pro Ala Ala Ser Glu Asp Thr Ile Ile Gly Phe Leu

```
                   20                  25                  30
Gly Gln Pro Val Thr Leu Pro Cys His Tyr Leu Ser Trp Ser Gln Ser
           35                  40                  45
Arg Asn Ser Met Cys Trp Gly Lys Gly Ser Cys Pro Asn Ser Lys Cys
 50                  55                  60
Asn Ala Glu Leu Leu Arg Thr Asp Gly Thr Arg Ile Ile Ser Arg Lys
 65                  70                  75                  80
Ser Thr Lys Tyr Thr Leu Leu Gly Lys Val Gln Phe Gly Glu Val Ser
                     85                  90                  95
Leu Thr Ile Ser Asn Thr Asn Arg Gly Asp Ser Gly Val Tyr Cys Cys
                100                 105                 110
Arg Ile Glu Val Pro Gly Trp Phe Asn Asp Val Lys Lys Asn Val Arg
            115                 120                 125
Leu Glu Leu Arg Arg Ala Thr Thr Thr Lys Lys Pro Thr Thr Thr Thr
            130                 135                 140
Arg Pro Thr Thr Thr Pro Tyr Val Thr Thr Thr Pro Glu Leu Leu
145                 150                 155                 160
Pro Thr Thr Val Met Thr Thr Ser Val Leu Pro Thr Thr Pro Pro
                165                 170                 175
Gln Thr Leu Ala Thr Thr Ala Phe Ser Thr Ala Val Thr Thr Cys Pro
                180                 185                 190
Ser Thr Thr Pro Gly Ser Phe Ser Gln Glu Thr Thr Lys Gly Ser Ala
                195                 200                 205
Phe Thr Thr Glu Ser Glu Thr Leu Pro Ala Ser Asn His Ser Gln Arg
            210                 215                 220
Ser Met Met Thr Ile Ser Thr Asp Ile Ala Val Leu Arg Pro Thr Gly
225                 230                 235                 240
Ser Asn Pro Gly Ile Leu Pro Ser Thr Ser Gln Leu Thr Thr Gln Lys
                245                 250                 255
Thr Thr Leu Thr Thr Ser Glu Ser Leu Gln Lys Thr Thr Lys Ser His
                260                 265                 270
Gln Ile Asn Ser Arg Gln Thr Pro Arg Gly Pro Thr Ile Lys Pro Cys
            275                 280                 285
Pro Pro Cys Lys Cys Pro Ala Pro Asn Leu Leu Gly Gly Pro Ser Val
            290                 295                 300
Phe Ile Phe Pro Pro Lys Ile Lys Asp Val Leu Met Ile Ser Leu Ser
305                 310                 315                 320
Pro Ile Val Thr Cys Val Val Val Asp Val Ser Glu Asp Asp Pro Asp
                325                 330                 335
Val Gln Ile Ser Trp Phe Val Asn Asn Val Glu Val His Thr Ala Gln
                340                 345                 350
Thr Gln Thr His Arg Glu Asp Tyr Asn Ser Thr Leu Arg Val Val Ser
            355                 360                 365
Ala Leu Pro Ile Gln His Gln Asp Trp Met Ser Gly Lys Glu Phe Lys
            370                 375                 380
Cys Lys Val Asn Asn Lys Asp Leu Pro Ala Pro Ile Glu Arg Thr Ile
385                 390                 395                 400
Ser Lys Pro Lys Gly Ser Val Arg Ala Pro Gln Val Tyr Val Leu Pro
                405                 410                 415
Pro Pro Glu Glu Glu Met Thr Lys Lys Gln Val Thr Leu Thr Cys Met
                420                 425                 430
Val Thr Asp Phe Met Pro Glu Asp Ile Tyr Val Glu Trp Thr Asn Asn
            435                 440                 445
```

Gly Lys Thr Glu Leu Asn Tyr Lys Asn Thr Glu Pro Val Leu Asp Ser
    450                 455                 460

Asp Gly Ser Tyr Phe Met Tyr Ser Lys Leu Arg Val Glu Lys Lys Asn
465                 470                 475                 480

Trp Val Glu Arg Asn Ser Tyr Ser Cys Ser Val Val His Glu Gly Leu
                485                 490                 495

His Asn His His Thr Thr Lys Ser Phe Ser Arg Thr Pro Gly Lys
            500                 505                 510

<210> SEQ ID NO 76
<211> LENGTH: 927
<212> TYPE: DNA
<213> ORGANISM: Artificial Sequence
<220> FEATURE:
<223> OTHER INFORMATION: Synthetic

<400> SEQUENCE: 76
atggatcagc atacactgga cgtggaagat acagccgatg ccagacaccc tgctggaacg      60
tcctgtccca gcgacgctgc cctgctcaga gacaccgggc tgctcgcaga tgctgctctg     120
ctgagtgata ccgttcggcc aactaacgcg gccctaccca cagatgccgc atatcccgcg     180
gtaaatgtca gggaccggga agctgcctgg ccaccggccc tcaatttctg ctctagacat     240
ccgaaactgt acggtctggt cgcactggta ctgctgctac ttatagcagc ttgtgttccc     300
atatttaccc gcactgaacc cagacccgct ctcactatta caacttcacc aaacttgggc     360
acacgtgaaa acaatgcaga tcaggttacc cctgtaagtc atattggatg ccccaacacc     420
acacaacagg gaagtccggt gtttgcaaaa ctccttgcta agaatcaggc ttcactgtgt     480
aacactactc ttaattggca ctcacaagac ggggccggga gtagctatct cagccaaggt     540
ctccgctatg aagaagataa gaaagagttg gtggtggaca gcccaggact ctactacgtc     600
ttcctggagc taaaactaag ccccactttt actaacactg gacataaggt ccaaggttgg     660
gtgtccctcg tacttcaagc taaaccccag gtggacgact tcgataacct ggcgttgaca     720
gttgagctct tccttgctc tatggaaaat aagctcgtgg atcggagctg gtctcaactg     780
ttgctgctta aagccggtca tcgtctgtct gttggactac gcgcatactt gcatggagcc     840
caggacgcat atcgtgattg ggaactgagc tacccgaata ccactagctt tggactatt      900 cttgttaaac cagataatcc ttgggag                                         927

<210> SEQ ID NO 77
<211> LENGTH: 309
<212> TYPE: PRT
<213> ORGANISM: Artificial Sequence
<220> FEATURE:
<223> OTHER INFORMATION: Synthetic

<400> SEQUENCE: 77

Met Asp Gln His Thr Leu Asp Val Glu Asp Thr Ala Asp Ala Arg His
1               5                   10                  15

Pro Ala Gly Thr Ser Cys Pro Ser Asp Ala Ala Leu Leu Arg Asp Thr
            20                  25                  30

Gly Leu Leu Ala Asp Ala Ala Leu Leu Ser Asp Thr Val Arg Pro Thr
        35                  40                  45

Asn Ala Ala Leu Pro Thr Asp Ala Ala Tyr Pro Ala Val Asn Val Arg
    50                  55                  60

Asp Arg Glu Ala Ala Trp Pro Pro Ala Leu Asn Phe Cys Ser Arg His
65                  70                  75                  80

```
Pro Lys Leu Tyr Gly Leu Val Ala Leu Val Leu Leu Leu Ile Ala
                85                  90                  95

Ala Cys Val Pro Ile Phe Thr Arg Thr Glu Pro Arg Pro Ala Leu Thr
            100                 105                 110

Ile Thr Thr Ser Pro Asn Leu Gly Thr Arg Glu Asn Asn Ala Asp Gln
            115                 120                 125

Val Thr Pro Val Ser His Ile Gly Cys Pro Asn Thr Thr Gln Gln Gly
        130                 135                 140

Ser Pro Val Phe Ala Lys Leu Leu Ala Lys Asn Gln Ala Ser Leu Cys
145                 150                 155                 160

Asn Thr Thr Leu Asn Trp His Ser Gln Asp Gly Ala Gly Ser Ser Tyr
                165                 170                 175

Leu Ser Gln Gly Leu Arg Tyr Glu Glu Asp Lys Lys Glu Leu Val Val
            180                 185                 190

Asp Ser Pro Gly Leu Tyr Tyr Val Phe Leu Glu Leu Lys Leu Ser Pro
        195                 200                 205

Thr Phe Thr Asn Thr Gly His Lys Val Gln Gly Trp Val Ser Leu Val
    210                 215                 220

Leu Gln Ala Lys Pro Gln Val Asp Asp Phe Asp Asn Leu Ala Leu Thr
225                 230                 235                 240

Val Glu Leu Phe Pro Cys Ser Met Glu Asn Lys Leu Val Asp Arg Ser
                245                 250                 255

Trp Ser Gln Leu Leu Leu Leu Lys Ala Gly His Arg Leu Ser Val Gly
            260                 265                 270

Leu Arg Ala Tyr Leu His Gly Ala Gln Asp Ala Tyr Arg Asp Trp Glu
        275                 280                 285

Leu Ser Tyr Pro Asn Thr Thr Ser Phe Gly Leu Phe Leu Val Lys Pro
    290                 295                 300

Asp Asn Pro Trp Glu
305

<210> SEQ ID NO 78
<211> LENGTH: 705
<212> TYPE: DNA
<213> ORGANISM: Artificial Sequence
<220> FEATURE:
<223> OTHER INFORMATION: Synthetic

<400> SEQUENCE: 78
atggagagcg tagtgcaacc cagcgtattt gtggtggatg gacagaccga catcccattc      60
agacgcttgg aacagaacca ccgaagaagg cggtgcggca ccgtccaggt gtccctcgct     120
ctcgtgctgc tgcttggtgc tggcctcgca cacaagggt ggtttctttt gagactccat      180
caacgcttgg gagacatagt ggcccacctg cctgatggtg ggaagggctc ttggcaggac     240
cagcgatcac accaggctaa ccccgccgct cacctgacag gggcgaatgc cagcttgatc     300
ggaataggtg ggccgctgct gtgggaaact aggcttggac ttgcctttct gagagggctt     360
acataccatg acggagccct cgtaacaatg gagcctggtt attactacgt gtacagtaag     420
gtgcagcttt ctggagtcgg gtgtccccag gggctggcta acggactgcc catcactcat     480
ggactataca aacgcacatc cagatatcct aaagagctgg aactgttggt gtcccgtagg     540
agcccgtgtg gcagggccaa ctcttcccgt gtgtggtggg actcctcttt tctgggcggc     600
gtggtccatc tggaagctgg tgaggaagtc gtcgtaagag tacctggaaa ccgtctggtt     660
cgcccccgcg atggcaccag gtcctacttc ggagctttca tggta                     705
```

<210> SEQ ID NO 79
<211> LENGTH: 235
<212> TYPE: PRT
<213> ORGANISM: Artificial Sequence
<220> FEATURE:
<223> OTHER INFORMATION: Synthetic

<400> SEQUENCE: 79

```
Met Glu Ser Val Val Gln Pro Ser Val Phe Val Val Asp Gly Gln Thr
1               5                   10                  15

Asp Ile Pro Phe Arg Arg Leu Glu Gln Asn His Arg Arg Arg Arg Cys
            20                  25                  30

Gly Thr Val Gln Val Ser Leu Ala Leu Val Leu Leu Leu Gly Ala Gly
        35                  40                  45

Leu Ala Thr Gln Gly Trp Phe Leu Leu Arg Leu His Gln Arg Leu Gly
    50                  55                  60

Asp Ile Val Ala His Leu Pro Asp Gly Gly Lys Gly Ser Trp Gln Asp
65                  70                  75                  80

Gln Arg Ser His Gln Ala Asn Pro Ala Ala His Leu Thr Gly Ala Asn
                85                  90                  95

Ala Ser Leu Ile Gly Ile Gly Gly Pro Leu Leu Trp Glu Thr Arg Leu
            100                 105                 110

Gly Leu Ala Phe Leu Arg Gly Leu Thr Tyr His Asp Gly Ala Leu Val
        115                 120                 125

Thr Met Glu Pro Gly Tyr Tyr Tyr Val Tyr Ser Lys Val Gln Leu Ser
    130                 135                 140

Gly Val Gly Cys Pro Gln Gly Leu Ala Asn Gly Leu Pro Ile Thr His
145                 150                 155                 160

Gly Leu Tyr Lys Arg Thr Ser Arg Tyr Pro Lys Glu Leu Glu Leu Leu
                165                 170                 175

Val Ser Arg Arg Ser Pro Cys Gly Arg Ala Asn Ser Ser Arg Val Trp
            180                 185                 190

Trp Asp Ser Ser Phe Leu Gly Gly Val Val His Leu Glu Ala Gly Glu
        195                 200                 205

Glu Val Val Val Arg Val Pro Gly Asn Arg Leu Val Arg Pro Arg Asp
    210                 215                 220

Gly Thr Arg Ser Tyr Phe Gly Ala Phe Met Val
225                 230                 235
```

<210> SEQ ID NO 80
<211> LENGTH: 1821
<212> TYPE: DNA
<213> ORGANISM: Artificial Sequence
<220> FEATURE:
<223> OTHER INFORMATION: Synthetic

<400> SEQUENCE: 80

```
atgtgcccac agaaactcac aatttcttgg ttcgcaatcg tcctgctggt gtcaccctg      60 atggcaatgt gggagttgga aaaggatgta tacgtcgtcg aggtcgactg gacacctgac    120
gctccgggtg aaactgtcaa cctcacttgc gatactcctg aagaggacga catcacgtgg    180
acgagcgacc agcgacatgg agtgataggg tctggcaaga cgcttactat cacggttaag    240
gaatttctcg acgcagggca gtacacatgt cacaagggcg gcgagactct gagccactcc    300
catttgctgc tgcacaagaa ggagaatggt atctggtcta ccgaaatcct gaagaatttt    360
aagaacaaga cttttctgaa atgcgaggcc ccaaattatt ccggacgttt cacttgcagt    420
```

```
tggctcgttc aaagaaatat ggacttgaaa tttaacatta aatccagctc ttcatctcct    480
gacagcaggg ccgtaacttg tggaatggct tcattgtcag ctgagaaagt tacgcttgac    540
caaagggatt atgagaaata cagcgtgagt tgccaggaag atgtgacatg tccaacggca    600
gaggaaacgt tgccaattga gctcgctttg gaagctcgtc aacaaaacaa gtatgaaaac    660
tatagtacta gcttcttcat acgggacatc atcaaaccag atccacctaa gaatttgcag    720
atgaagcctc tgaagaattc acaagtcgag gtatcctggg aatacccaga ttcatggtcc    780
actcctcata gttactttag cctgaaattc tttgtacgca tacagcggaa gaaggagaaa    840
atgaaggaga cggaagaagg ctgcaatcag aaaggcgctt tcttgttga aaagacgagc     900 actgaggttc aatgcaaagg cgggaatgta tgtgttcaag cccaagatag gtattataat    960
agctcctgct ctaagtgggc ttgcgtacca tgcagagtta gaagtggctc aacctcaggc   1020
tccggaaaac ctggttccgg tgaaggttcc acaaagggc gtgtgattcc tgtgtccggc    1080
ccagctaggt gtctctccca gtcacggaat ctcctgaaaa ccacggatga catggtaaag   1140
acagctaggg agaaactcaa gcactactcc tgcacagctg aggatatcga tcatgaggac   1200
atcaccaggg accagacatc cactctgaaa acttgcctgc ctttggaact ccacaagaac   1260
gaatcttgtc tggcaacgcg tgaaacgagt tctactacaa gagggtcctg tcttcccct    1320 caaaagacaa gccttatgat gaccttgtgt ctcggtagca tttatgagga cctaaagatg   1380
tatcaaaccg agtttcaggc tatcaatgca gcgctccaga atcataacca tcagcagatc   1440
attcttgaca aaggaatgct cgtggccatt gatgaactaa tgcagagcct aaaccacaat   1500
ggcgagactc ttcgacagaa accgcctgtg ggcgaggccg atccatatag agtcaaaatg   1560
aaactgtgta ttctcctgca tgcatttagt actcgtgtag tgactattaa cagagtgatg   1620
ggttaccttt cctcagctaa tacacttgtc ctctttggcg ctgggttcgg cgccgtcata   1680
acggttgttg tcatcgtggt aataatcaag tgcttttgca agcacaggtc ttgttttcgc   1740
aggaatgaag cctctagaga aacaaataat tcactgacct ttggccccga agaagctctt   1800
gcagagcaaa cggtgtttct c                                             1821
```

<210> SEQ ID NO 81
<211> LENGTH: 607
<212> TYPE: PRT
<213> ORGANISM: Artificial Sequence
<220> FEATURE:
<223> OTHER INFORMATION: Synthetic

<400> SEQUENCE: 81

```
Met Cys Pro Gln Lys Leu Thr Ile Ser Trp Phe Ala Ile Val Leu Leu
1               5                   10                  15

Val Ser Pro Leu Met Ala Met Trp Glu Leu Glu Lys Asp Val Tyr Val
            20                  25                  30

Val Glu Val Asp Trp Thr Pro Asp Ala Pro Gly Glu Thr Val Asn Leu
        35                  40                  45

Thr Cys Asp Thr Pro Glu Glu Asp Ile Thr Trp Thr Ser Asp Gln
    50                  55                  60

Arg His Gly Val Ile Gly Ser Gly Lys Thr Leu Thr Ile Thr Val Lys
65                  70                  75                  80

Glu Phe Leu Asp Ala Gly Gln Tyr Thr Cys His Lys Gly Gly Glu Thr
                85                  90                  95

Leu Ser His Ser His Leu Leu Leu His Lys Lys Glu Asn Gly Ile Trp
            100                 105                 110
```

```
Ser Thr Glu Ile Leu Lys Asn Phe Lys Asn Lys Thr Phe Leu Lys Cys
            115                 120                 125

Glu Ala Pro Asn Tyr Ser Gly Arg Phe Thr Cys Ser Trp Leu Val Gln
130                 135                 140

Arg Asn Met Asp Leu Lys Phe Asn Ile Lys Ser Ser Ser Ser Ser Pro
145                 150                 155                 160

Asp Ser Arg Ala Val Thr Cys Gly Met Ala Ser Leu Ser Ala Glu Lys
                165                 170                 175

Val Thr Leu Asp Gln Arg Asp Tyr Glu Lys Tyr Ser Val Ser Cys Gln
            180                 185                 190

Glu Asp Val Thr Cys Pro Thr Ala Glu Glu Thr Leu Pro Ile Glu Leu
            195                 200                 205

Ala Leu Glu Ala Arg Gln Gln Asn Lys Tyr Glu Asn Tyr Ser Thr Ser
210                 215                 220

Phe Phe Ile Arg Asp Ile Ile Lys Pro Asp Pro Lys Asn Leu Gln
225                 230                 235                 240

Met Lys Pro Leu Lys Asn Ser Gln Val Glu Val Ser Trp Glu Tyr Pro
                245                 250                 255

Asp Ser Trp Ser Thr Pro His Ser Tyr Phe Ser Leu Lys Phe Phe Val
            260                 265                 270

Arg Ile Gln Arg Lys Lys Glu Lys Met Lys Glu Thr Glu Glu Gly Cys
            275                 280                 285

Asn Gln Lys Gly Ala Phe Leu Val Glu Lys Thr Ser Thr Glu Val Gln
290                 295                 300

Cys Lys Gly Gly Asn Val Cys Val Gln Ala Gln Asp Arg Tyr Tyr Asn
305                 310                 315                 320

Ser Ser Cys Ser Lys Trp Ala Cys Val Pro Cys Arg Val Arg Ser Gly
                325                 330                 335

Ser Thr Ser Gly Ser Gly Lys Pro Gly Ser Gly Glu Gly Ser Thr Lys
            340                 345                 350

Gly Arg Val Ile Pro Val Ser Gly Pro Ala Arg Cys Leu Ser Gln Ser
            355                 360                 365

Arg Asn Leu Leu Lys Thr Thr Asp Asp Met Val Lys Thr Ala Arg Glu
370                 375                 380

Lys Leu Lys His Tyr Ser Cys Thr Ala Glu Asp Ile Asp His Glu Asp
385                 390                 395                 400

Ile Thr Arg Asp Gln Thr Ser Thr Leu Lys Thr Cys Leu Pro Leu Glu
                405                 410                 415

Leu His Lys Asn Glu Ser Cys Leu Ala Thr Arg Glu Thr Ser Ser Thr
            420                 425                 430

Thr Arg Gly Ser Cys Leu Pro Pro Gln Lys Thr Ser Leu Met Met Thr
            435                 440                 445

Leu Cys Leu Gly Ser Ile Tyr Glu Asp Leu Lys Met Tyr Gln Thr Glu
450                 455                 460

Phe Gln Ala Ile Asn Ala Ala Leu Gln Asn His Asn His Gln Gln Ile
465                 470                 475                 480

Ile Leu Asp Lys Gly Met Leu Val Ala Ile Asp Glu Leu Met Gln Ser
                485                 490                 495

Leu Asn His Asn Gly Glu Thr Leu Arg Gln Lys Pro Pro Val Gly Glu
            500                 505                 510

Ala Asp Pro Tyr Arg Val Lys Met Lys Leu Cys Ile Leu Leu His Ala
            515                 520                 525
```

```
Phe Ser Thr Arg Val Val Thr Ile Asn Arg Val Met Gly Tyr Leu Ser
    530                 535                 540
Ser Ala Asn Thr Leu Val Leu Phe Gly Ala Gly Phe Gly Ala Val Ile
545                 550                 555                 560
Thr Val Val Val Ile Val Val Ile Ile Lys Cys Phe Cys Lys His Arg
                565                 570                 575
Ser Cys Phe Arg Arg Asn Glu Ala Ser Arg Glu Thr Asn Asn Ser Leu
            580                 585                 590
Thr Phe Gly Pro Glu Glu Ala Leu Ala Glu Gln Thr Val Phe Leu
            595                 600                 605

<210> SEQ ID NO 82
<211> LENGTH: 1716
<212> TYPE: DNA
<213> ORGANISM: Artificial Sequence
<220> FEATURE:
<223> OTHER INFORMATION: Synthetic

<400> SEQUENCE: 82
atgtgtcagt cacgctatct tctcttcctt gctactctgg ccttgctcaa tcacttgtcc      60
cttgctcgtg tgattcctgt gtccggccca gctaggtgtc tctcccagtc acggaatctc     120
ctgaaaacca cggatgacat ggtaaagaca gctagggaga aactcaagca ctactcctgc     180
acagctgagg atatcgatca tgaggacatc accaggacc agacatccac tctgaaaact      240
tgcctgcctt tggaactcca caagaacgaa tcttgtctgg caacgcgtga acgagttct      300 actacaagag ggtcctgtct tccccctcaa aagacaagcc ttatgatgac cttgtgtctc     360
ggtagcattt atgaggacct aaagatgtat caaaccgagt ttcaggctat caatgcagcg     420
ctccagaatc ataaccatca gcagatcatt cttgacaaag gaatgctcgt ggccattgat     480
gaactaatgc agagcctaaa ccacaatggc gagactcttc gacagaaacc gcctgtgggc     540
gaggccgatc catatagagt caaaatgaaa ctgtgtattc tcctgcatgc atttagtact     600
cgtgtagtga ctattaacag agtgatgggt tacctttcct cagctggaag cggcgccacc     660
aacttctccc tgctgaagca ggccggcgac gtggaggaga accccggccc catgtgccca     720
cagaaactca caatttcttg gttcgcaatc gtcctgctgg tgtcacccct gatggcaatg     780
tgggagttgg aaaaggatgt atacgtcgtc gaggtcgact ggacacctga cgctccgggt     840
gaaactgtca acctcacttg cgatactcct gaagaggacg acatcacgtg gacgagcgac     900
cagcgacatg gagtgatagg gtctggcaag acgcttacta tcacggttaa ggaatttctc     960
gacgcagggc agtacacatg tcacaagggc ggcgagactc tgagccactc ccatttgctg    1020
ctgcacaaga aggagaatgg tatctggtct accgaaatcc tgaagaattt taagaacaag    1080 actttctga atgcgaggc cccaaattat tccggacgtt tcacttgcag ttggctcgtt     1140
caaagaaata tggacttgaa atttaacatt aaatccagct cttcatctcc tgacagcagg    1200
gccgtaactt gtggaatggc ttcattgtca gctgagaaag ttacgcttga ccaaagggat    1260
tatgagaaat acagcgtgag ttgccaggaa gatgtgacat gtccaacggc agaggaaacg    1320
ttgccaattg agctcgcttt ggaagctcgt caacaaaaca gtatgaaaaa ctatagtact    1380
agcttcttca tacgggacat catcaaacca gatccaccta gaatttgca gatgaagcct     1440 ctgaagaatt cacaagtcga ggtatcctgg gaatacccag attcatggtc cactcctcat    1500
agttacttta gcctgaaatt cttttgtacgc atacagcgga agaaggagaa atgaaggag    1560 acggaagaag gctgcaatca gaaaggcgct tttcttgttg aaaagacgag cactgaggtt    1620
```

-continued

```
caatgcaaag gcgggaatgt atgtgttcaa gcccaagata ggtattataa tagctcctgc    1680
tctaagtggg cttgcgtacc atgcagagtt agaagt                              1716
```

<210> SEQ ID NO 83
<211> LENGTH: 572
<212> TYPE: PRT
<213> ORGANISM: Artificial Sequence
<220> FEATURE:
<223> OTHER INFORMATION: Synthetic

<400> SEQUENCE: 83

```
Met Cys Gln Ser Arg Tyr Leu Leu Phe Leu Ala Thr Leu Ala Leu Leu
1               5                   10                  15

Asn His Leu Ser Leu Ala Arg Val Ile Pro Val Ser Gly Pro Ala Arg
            20                  25                  30

Cys Leu Ser Gln Ser Arg Asn Leu Leu Lys Thr Thr Asp Asp Met Val
        35                  40                  45

Lys Thr Ala Arg Glu Lys Leu Lys His Tyr Ser Cys Thr Ala Glu Asp
    50                  55                  60

Ile Asp His Glu Asp Ile Thr Arg Asp Gln Thr Ser Thr Leu Lys Thr
65                  70                  75                  80

Cys Leu Pro Leu Glu Leu His Lys Asn Glu Ser Cys Leu Ala Thr Arg
                85                  90                  95

Glu Thr Ser Ser Thr Thr Arg Gly Ser Cys Leu Pro Pro Gln Lys Thr
            100                 105                 110

Ser Leu Met Met Thr Leu Cys Leu Gly Ser Ile Tyr Glu Asp Leu Lys
        115                 120                 125

Met Tyr Gln Thr Glu Phe Gln Ala Ile Asn Ala Ala Leu Gln Asn His
    130                 135                 140

Asn His Gln Gln Ile Ile Leu Asp Lys Gly Met Leu Val Ala Ile Asp
145                 150                 155                 160

Glu Leu Met Gln Ser Leu Asn His Asn Gly Glu Thr Leu Arg Gln Lys
                165                 170                 175

Pro Pro Val Gly Glu Ala Asp Pro Tyr Arg Val Lys Met Lys Leu Cys
            180                 185                 190

Ile Leu Leu His Ala Phe Ser Thr Arg Val Val Thr Ile Asn Arg Val
        195                 200                 205

Met Gly Tyr Leu Ser Ser Ala Gly Ser Gly Ala Thr Asn Phe Ser Leu
    210                 215                 220

Leu Lys Gln Ala Gly Asp Val Glu Glu Asn Pro Gly Pro Met Cys Pro
225                 230                 235                 240

Gln Lys Leu Thr Ile Ser Trp Phe Ala Ile Val Leu Leu Val Ser Pro
                245                 250                 255

Leu Met Ala Met Trp Glu Leu Glu Lys Asp Val Tyr Val Val Glu Val
            260                 265                 270

Asp Trp Thr Pro Asp Ala Pro Gly Glu Thr Val Asn Leu Thr Cys Asp
        275                 280                 285

Thr Pro Glu Glu Asp Asp Ile Thr Trp Thr Ser Asp Gln Arg His Gly
    290                 295                 300

Val Ile Gly Ser Gly Lys Thr Leu Thr Ile Thr Val Lys Glu Phe Leu
305                 310                 315                 320

Asp Ala Gly Gln Tyr Thr Cys His Lys Gly Gly Glu Thr Leu Ser His
                325                 330                 335

Ser His Leu Leu Leu His Lys Lys Glu Asn Gly Ile Trp Ser Thr Glu
            340                 345                 350
```

```
Ile Leu Lys Asn Phe Lys Asn Lys Thr Phe Leu Lys Cys Glu Ala Pro
        355                 360                 365

Asn Tyr Ser Gly Arg Phe Thr Cys Ser Trp Leu Val Gln Arg Asn Met
    370                 375                 380

Asp Leu Lys Phe Asn Ile Lys Ser Ser Ser Ser Pro Asp Ser Arg
385                 390                 395                 400

Ala Val Thr Cys Gly Met Ala Ser Leu Ser Ala Glu Lys Val Thr Leu
                405                 410                 415

Asp Gln Arg Asp Tyr Glu Lys Tyr Ser Val Ser Cys Gln Glu Asp Val
            420                 425                 430

Thr Cys Pro Thr Ala Glu Glu Thr Leu Pro Ile Glu Leu Ala Leu Glu
        435                 440                 445

Ala Arg Gln Gln Asn Lys Tyr Glu Asn Tyr Ser Thr Ser Phe Phe Ile
    450                 455                 460

Arg Asp Ile Ile Lys Pro Asp Pro Lys Asn Leu Gln Met Lys Pro
465                 470                 475                 480

Leu Lys Asn Ser Gln Val Glu Val Ser Trp Glu Tyr Pro Asp Ser Trp
                485                 490                 495

Ser Thr Pro His Ser Tyr Phe Ser Leu Lys Phe Phe Val Arg Ile Gln
            500                 505                 510

Arg Lys Lys Glu Lys Met Lys Glu Thr Glu Glu Gly Cys Asn Gln Lys
        515                 520                 525

Gly Ala Phe Leu Val Glu Lys Thr Ser Thr Glu Val Gln Cys Lys Gly
    530                 535                 540

Gly Asn Val Cys Val Gln Ala Gln Asp Arg Tyr Tyr Asn Ser Ser Cys
545                 550                 555                 560

Ser Lys Trp Ala Cys Val Pro Cys Arg Val Arg Ser
                565                 570

<210> SEQ ID NO 84
<211> LENGTH: 570
<212> TYPE: DNA
<213> ORGANISM: Artificial Sequence
<220> FEATURE:
<223> OTHER INFORMATION: Synthetic

<400> SEQUENCE: 84
atggccaggc tttgcgcttt tctcgtcatg ctgatcgtca tgagttactg gtccatttgc      60
agcctcggat gtgatctgcc ccacacctac aacctgcgca caaacgagc tctcaaagtg     120 ttggcccaaa tgaggcggtt gcccttcctt tcctgtctca agacaggca agattttgga     180 tttccactag agaaagtaga caatcaacag atacagaaag ctcaagctat ccccgtgttg     240
agggacttga ctcaacagac gttgaatcta tttactagca aggccagctc tgctgcttgg     300
aatgccaccc ttcttgactc attttgcaat gacctacatc aacaactgaa tgatctccaa     360
acatgtttga tgcagcaggt aggtgtccaa gaaccccgc ttactcagga agacgccctt     420
ctggctgtcc gcaagtactt tcacagaatc acagtgtacc tgcgcgaaaa gaaacactcc     480
ccctgcgctt gggaagtggt cagggccgag gtttggcgag ccctgagtag ctccgtcaat     540
ctccttcctc ggttgtccga ggagaaagag                                     570

<210> SEQ ID NO 85
<211> LENGTH: 190
<212> TYPE: PRT
<213> ORGANISM: Artificial Sequence
<220> FEATURE:
```

<223> OTHER INFORMATION: Synthetic

<400> SEQUENCE: 85

```
Met Ala Arg Leu Cys Ala Phe Leu Val Met Leu Ile Val Met Ser Tyr
1               5                   10                  15
Trp Ser Ile Cys Ser Leu Gly Cys Asp Leu Pro His Thr Tyr Asn Leu
            20                  25                  30
Arg Asn Lys Arg Ala Leu Lys Val Leu Ala Gln Met Arg Arg Leu Pro
        35                  40                  45
Phe Leu Ser Cys Leu Lys Asp Arg Gln Asp Phe Gly Phe Pro Leu Glu
    50                  55                  60
Lys Val Asp Asn Gln Gln Ile Gln Lys Ala Gln Ala Ile Pro Val Leu
65                  70                  75                  80
Arg Asp Leu Thr Gln Gln Thr Leu Asn Leu Phe Thr Ser Lys Ala Ser
                85                  90                  95
Ser Ala Ala Trp Asn Ala Thr Leu Leu Asp Ser Phe Cys Asn Asp Leu
            100                 105                 110
His Gln Gln Leu Asn Asp Leu Gln Thr Cys Leu Met Gln Gln Val Gly
        115                 120                 125
Val Gln Glu Pro Pro Leu Thr Gln Glu Asp Ala Leu Leu Ala Val Arg
    130                 135                 140
Lys Tyr Phe His Arg Ile Thr Val Tyr Leu Arg Glu Lys Lys His Ser
145                 150                 155                 160
Pro Cys Ala Trp Glu Val Val Arg Ala Glu Val Trp Arg Ala Leu Ser
                165                 170                 175
Ser Ser Val Asn Leu Leu Pro Arg Leu Ser Glu Glu Lys Glu
            180                 185                 190
```

<210> SEQ ID NO 86
<211> LENGTH: 918
<212> TYPE: DNA
<213> ORGANISM: Artificial Sequence
<220> FEATURE:
<223> OTHER INFORMATION: Synthetic

<400> SEQUENCE: 86

| | | |
|---|---|---|
| atggcttgca actgtcagct catgcaagat actcccctgc ttaagtttcc ctgccctaga | 60 |
| ctcattctcc tcttcgtcct tctcattcgc ctaagccagg tgagttccga tgtggatgaa | 120 |
| caactgagta atctgtcaa ggataaagtt ctgctcccat gccgctacaa tagcccccat | 180 |
| gaggacgagt ccgaagatag gatttactgg cagaaacatg ataaggtggt gctatccgtc | 240 |
| attgccggta aattgaaggt gtggcccgaa tataagaata gaaccctgta tgacaacaca | 300 |
| acttatagcc taatcatcct cggtctcgta ctgagcgacc gaggtactta ctcatgcgtt | 360 |
| gtgcagaaga aggagcgcgg aacatacgaa gtcaagcacc ttgcattggt gaaattgtca | 420 |
| ataaaagctg acttttcaac tcctaatatt actgaatcag gtaaccctcc cgcagacact | 480 |
| aaaagaatta catgcttcgc ctctggcggg tttcccaaac cacggttctc ttggctagag | 540 |
| aatgggagag aacttccagg tatcaataca accatctctc aagacccaga atcagaactg | 600 |
| tacaccatct ccagccaact cgatttcaat accacaagaa atcatacaat aaaatgtctg | 660 |
| ataaagtacg gagatgcaca tgtctctgaa gatttcacat gggagaaacc accagaggac | 720 |
| ccgccagaca gcaagaatac acttgtcctc tttggcgctg ggttcggcgc cgtcataacg | 780 |
| gttgttgtca tcgtggtaat aatcaagtgc ttttgcaagc acaggtcttg ttttcgcagg | 840 |
| aatgaagcct ctagagaaac aaataattca ctgacctttg gccccgaaga agctcttgca | 900 | gagcaaacgg tgtttctc            918

<210> SEQ ID NO 87
<211> LENGTH: 306
<212> TYPE: PRT
<213> ORGANISM: Artificial Sequence
<220> FEATURE:
<223> OTHER INFORMATION: Synthetic

<400> SEQUENCE: 87

Met Ala Cys Asn Cys Gln Leu Met Gln Asp Thr Pro Leu Leu Lys Phe
1               5                   10                  15

Pro Cys Pro Arg Leu Ile Leu Leu Phe Val Leu Leu Ile Arg Leu Ser
                20                  25                  30

Gln Val Ser Ser Asp Val Asp Glu Gln Leu Ser Lys Ser Val Lys Asp
            35                  40                  45

Lys Val Leu Leu Pro Cys Arg Tyr Asn Ser Pro His Glu Asp Glu Ser
    50                  55                  60

Glu Asp Arg Ile Tyr Trp Gln Lys His Asp Lys Val Val Leu Ser Val
65                  70                  75                  80

Ile Ala Gly Lys Leu Lys Val Trp Pro Glu Tyr Lys Asn Arg Thr Leu
                85                  90                  95

Tyr Asp Asn Thr Thr Tyr Ser Leu Ile Ile Leu Gly Leu Val Leu Ser
                100                 105                 110

Asp Arg Gly Thr Tyr Ser Cys Val Val Gln Lys Lys Glu Arg Gly Thr
            115                 120                 125

Tyr Glu Val Lys His Leu Ala Leu Val Lys Leu Ser Ile Lys Ala Asp
    130                 135                 140

Phe Ser Thr Pro Asn Ile Thr Glu Ser Gly Asn Pro Ser Ala Asp Thr
145                 150                 155                 160

Lys Arg Ile Thr Cys Phe Ala Ser Gly Gly Phe Pro Lys Pro Arg Phe
                165                 170                 175

Ser Trp Leu Glu Asn Gly Arg Glu Leu Pro Gly Ile Asn Thr Thr Ile
                180                 185                 190

Ser Gln Asp Pro Glu Ser Glu Leu Tyr Thr Ile Ser Ser Gln Leu Asp
            195                 200                 205

Phe Asn Thr Thr Arg Asn His Thr Ile Lys Cys Leu Ile Lys Tyr Gly
    210                 215                 220

Asp Ala His Val Ser Glu Asp Phe Thr Trp Glu Lys Pro Pro Glu Asp
225                 230                 235                 240

Pro Pro Asp Ser Lys Asn Thr Leu Val Leu Phe Gly Ala Gly Phe Gly
                245                 250                 255

Ala Val Ile Thr Val Val Val Ile Val Val Ile Ile Lys Cys Phe Cys
                260                 265                 270

Lys His Arg Ser Cys Phe Arg Arg Asn Glu Ala Ser Arg Glu Thr Asn
            275                 280                 285

Asn Ser Leu Thr Phe Gly Pro Glu Glu Ala Leu Ala Glu Gln Thr Val
    290                 295                 300

Phe Leu
305

<210> SEQ ID NO 88
<211> LENGTH: 780
<212> TYPE: DNA
<213> ORGANISM: Artificial Sequence
<220> FEATURE:

<223> OTHER INFORMATION: Synthetic

<400> SEQUENCE: 88

```
atgatcgaaa cttattccca accctcaccg cgctcagtag caactggcct accagccagc    60
atgaagatat tcatgtacct cttgactgta ttcttgatca cgcaaatgat tggtagtgtt   120
ttgttcgccg tttatctcca caggcgcctg gataaagttg aagaagaggt taatctccat   180
gaagacttcg tgttcattaa gaaactcaaa agatgtaaca aaggtgaggg atctctgtct   240
cttctgaact gtgaggagat gcgacggcaa ttcgaggacc tcgtaaaaga cataactctc   300
aacaaagaag agaagaaaga aaactctttc gagatgcaac ggggcgacga ggaccctcaa   360
attgccgcac atgtcgtttc tgaagcgaat tccaatgccg cgtccgtgct ccagtgggcg   420
aagaagggat actacacgat gaagagcaac cttgtgatgc ttgaaaatgg caagcagctc   480
acagttaaac gcgagggact ctactatgta tacacccaag tgaccttttg ttccaaccgg   540
gagccaagta gccaacgccc gttcatcgtt gggctgtggc tcaagccttc ttcagggagt   600
gaacgaatcc ttctcaaggc agccaacacg cattccagca gccaactgtg tgagcaacaa   660
tccgtgcatc ttggcggggt ctttgagctg caagcgggcg cctctgtgtt cgtgaatgtt   720
accgaagcca gccaggttat ccaccgcgtg ggtttcagta gttttggcct gctcaagctg   780
```

<210> SEQ ID NO 89
<211> LENGTH: 260
<212> TYPE: PRT
<213> ORGANISM: Artificial Sequence
<220> FEATURE:
<223> OTHER INFORMATION: Synthetic

<400> SEQUENCE: 89

```
Met Ile Glu Thr Tyr Ser Gln Pro Ser Pro Arg Ser Val Ala Thr Gly
1               5                   10                  15

Leu Pro Ala Ser Met Lys Ile Phe Met Tyr Leu Leu Thr Val Phe Leu
            20                  25                  30

Ile Thr Gln Met Ile Gly Ser Val Leu Phe Ala Val Tyr Leu His Arg
        35                  40                  45

Arg Leu Asp Lys Val Glu Glu Val Asn Leu His Glu Asp Phe Val
    50                  55                  60

Phe Ile Lys Lys Leu Lys Arg Cys Asn Lys Gly Glu Gly Ser Leu Ser
65                  70                  75                  80

Leu Leu Asn Cys Glu Glu Met Arg Arg Gln Phe Glu Asp Leu Val Lys
                85                  90                  95

Asp Ile Thr Leu Asn Lys Glu Glu Lys Lys Glu Asn Ser Phe Glu Met
            100                 105                 110

Gln Arg Gly Asp Glu Asp Pro Gln Ile Ala Ala His Val Val Ser Glu
        115                 120                 125

Ala Asn Ser Asn Ala Ala Ser Val Leu Gln Trp Ala Lys Lys Gly Tyr
    130                 135                 140

Tyr Thr Met Lys Ser Asn Leu Val Met Leu Glu Asn Gly Lys Gln Leu
145                 150                 155                 160

Thr Val Lys Arg Glu Gly Leu Tyr Tyr Val Tyr Thr Gln Val Thr Phe
                165                 170                 175

Cys Ser Asn Arg Glu Pro Ser Ser Gln Arg Pro Phe Ile Val Gly Leu
            180                 185                 190

Trp Leu Lys Pro Ser Ser Gly Ser Glu Arg Ile Leu Leu Lys Ala Ala
        195                 200                 205
```

Asn Thr His Ser Ser Ser Gln Leu Cys Glu Gln Gln Ser Val His Leu
    210                 215                 220

Gly Gly Val Phe Glu Leu Gln Ala Gly Ala Ser Val Phe Val Asn Val
225                 230                 235                 240

Thr Glu Ala Ser Gln Val Ile His Arg Val Gly Phe Ser Ser Phe Gly
                245                 250                 255

Leu Leu Lys Leu
            260

<210> SEQ ID NO 90
<211> LENGTH: 438
<212> TYPE: DNA
<213> ORGANISM: Artificial Sequence
<220> FEATURE:
<223> OTHER INFORMATION: Synthetic

<400> SEQUENCE: 90
atggagcgta ctctggtctg ccttgttgtg atattcttgg ggacagttgc acacaaatca      60
tcaccccaag gaccggatag actcctcata cgcctgcgcc atctgattga cattgtcgag     120
cagttgaaga tttatgagaa cgacctggac cctgaactat tgagcgcgcc tcaagacgtc     180
aaagggcatt gcgagcatgc tgcatttgca tgttttcaga agctaagct caaaccaagt      240 aatcccggta acaataaaac attcatcatc gacctggtgg cccaactaag acgccggttg     300
ccggcgcgcc ggggtggtaa gaaacagaaa catattgcta atgcccctc ttgcgactct      360 tacgagaaaa ggacacctaa ggaattcctc gaacgattga atggttgtt gcagaagatg      420 atccatcaac atctgagc                                                   438

<210> SEQ ID NO 91
<211> LENGTH: 146
<212> TYPE: PRT
<213> ORGANISM: Artificial Sequence
<220> FEATURE:
<223> OTHER INFORMATION: Synthetic

<400> SEQUENCE: 91

Met Glu Arg Thr Leu Val Cys Leu Val Val Ile Phe Leu Gly Thr Val
1               5                   10                  15

Ala His Lys Ser Ser Pro Gln Gly Pro Asp Arg Leu Leu Ile Arg Leu
            20                  25                  30

Arg His Leu Ile Asp Ile Val Glu Gln Leu Lys Ile Tyr Glu Asn Asp
        35                  40                  45

Leu Asp Pro Glu Leu Leu Ser Ala Pro Gln Asp Val Lys Gly His Cys
    50                  55                  60

Glu His Ala Ala Phe Ala Cys Phe Gln Lys Ala Lys Leu Lys Pro Ser
65                  70                  75                  80

Asn Pro Gly Asn Asn Lys Thr Phe Ile Ile Asp Leu Val Ala Gln Leu
                85                  90                  95

Arg Arg Arg Leu Pro Ala Arg Arg Gly Gly Lys Gln Lys His Ile
            100                 105                 110

Ala Lys Cys Pro Ser Cys Asp Ser Tyr Glu Lys Arg Thr Pro Lys Glu
        115                 120                 125

Phe Leu Glu Arg Leu Lys Trp Leu Leu Gln Lys Met Ile His Gln His
    130                 135                 140

Leu Ser
145

```
<210> SEQ ID NO 92
<211> LENGTH: 399
<212> TYPE: DNA
<213> ORGANISM: Artificial Sequence
<220> FEATURE:
<223> OTHER INFORMATION: Synthetic

<400> SEQUENCE: 92
atggcacaaa tgatgacact gtccctactt agtctagttc tagctttgtg tattccctgg      60
actcaaggca gtgacggagg aggacaagac tgctgcctca aatattctca aaagaaaatc     120
ccttattcta tagtccgagg ttaccgtaag caagaaccga gtctaggttg tcctatcccc     180
gcaatcctct ttctaccacg gaaacatagc aaaccagaat tgtgcgccaa cccagaagag     240
ggttgggtcc aaaatttgat gaggcgcctt gaccaaccac cggccccggg taaacaatca     300
ccggggtgtc ggaagaatag ggtacatcc aaatccggga agaaagggaa ggggagtaag      360
ggctgtaaga gaacggaaca aactcaacct agcagaggt                            399

<210> SEQ ID NO 93
<211> LENGTH: 133
<212> TYPE: PRT
<213> ORGANISM: Artificial Sequence
<220> FEATURE:
<223> OTHER INFORMATION: Synthetic

<400> SEQUENCE: 93

Met Ala Gln Met Met Thr Leu Ser Leu Leu Ser Leu Val Leu Ala Leu
1               5                   10                  15

Cys Ile Pro Trp Thr Gln Gly Ser Asp Gly Gly Gly Gln Asp Cys Cys
            20                  25                  30

Leu Lys Tyr Ser Gln Lys Lys Ile Pro Tyr Ser Ile Val Arg Gly Tyr
        35                  40                  45

Arg Lys Gln Glu Pro Ser Leu Gly Cys Pro Ile Pro Ala Ile Leu Phe
    50                  55                  60

Leu Pro Arg Lys His Ser Lys Pro Glu Leu Cys Ala Asn Pro Glu Glu
65                  70                  75                  80

Gly Trp Val Gln Asn Leu Met Arg Arg Leu Asp Gln Pro Pro Ala Pro
                85                  90                  95

Gly Lys Gln Ser Pro Gly Cys Arg Lys Asn Arg Gly Thr Ser Lys Ser
            100                 105                 110

Gly Lys Lys Gly Lys Gly Ser Lys Gly Cys Lys Arg Thr Glu Gln Thr
        115                 120                 125

Gln Pro Ser Arg Gly
    130

<210> SEQ ID NO 94
<211> LENGTH: 1224
<212> TYPE: DNA
<213> ORGANISM: Artificial Sequence
<220> FEATURE:
<223> OTHER INFORMATION: Synthetic

<400> SEQUENCE: 94
atggaaaccg acacattgct cctctgggtt ctccttctat gggtccccgg ttccaccgga      60
gatatccaaa tgacacaatc acccagcagc ctgcctgcct ctctgggcga ccgcgttacc     120
atcaattgtc aagcttccca agatataagt aattatctca ctggtacca gcaaaagccc     180
ggtaaagcgc ctaaattgct gatttattat actaataaac tcgcagatgg agttcctagt     240
agattttctg gttcagggag tggacgggac tccagtttta ccatatcaag tctggaatcc     300
```

```
gaggatatcg gcagctacta ttgccagcaa tattataatt acccttggac ttttggaccc    360
gggactaaac ttgagatcaa aagaggcgga ggaggcagtg gtggtggtgg atcaggcggc    420
ggtggtagtg aggtacaact cgtggaatca ggcggcggac tggtccaacc cggcaagagc    480
cttaaactct cttgtgaggc cagtggattt acattcagcg ttatggaat gcactgggtg     540
agacaagctc ccggcagggg cctagaatca gtggcgtaca tcaccagctc atcaataaac    600
attaaatacg ctgatgcagt caagggccgg tttactgtat cccgcgacaa cgctaagaat    660
cttctctttc tgcaaatgaa catacttaag agcgaggata ctgccatgta ttattgtgcc    720
cgcttcgatt gggataagaa ttattgggga caaggcacca tggttaccgt tagtagtcca    780
aacatcacat caaataatag caaccccgtg aaggggacg actctgtttc actcacctgt    840
gattcctata ccgatcctga taatatcaac tatctatggt ctcgtaacgg tgaaagtctc    900
agcgaaggcg accggttgaa actctccgaa ggtaacagaa cccttacgct tctgaacgtc    960
acccggaacg ataccgggcc ctatgtttgc gaaactagga accctgttag cgtgaatcgt   1020
agcgacccct tctccctaaa taatactcta gtgctattcg gagcgggatt cggtgccgtc   1080
atcacagtag tcgttattgt agtcattatt aaatgctttt gtaaacatag gtcttgcttc   1140
agaagaaatg aggccagccg tgaaactaat aattccctga cctttgggcc cgaagaagct   1200
ttggctgaac agactgtgtt tctc                                          1224
```

<210> SEQ ID NO 95
<211> LENGTH: 408
<212> TYPE: PRT
<213> ORGANISM: Artificial Sequence
<220> FEATURE:
<223> OTHER INFORMATION: Synthetic

<400> SEQUENCE: 95

Met Glu Thr Asp Thr Leu Leu Leu Trp Val Leu Leu Leu Trp Val Pro
1               5                   10                  15

Gly Ser Thr Gly Asp Ile Gln Met Thr Gln Ser Pro Ser Ser Leu Pro
            20                  25                  30

Ala Ser Leu Gly Asp Arg Val Thr Ile Asn Cys Gln Ala Ser Gln Asp
        35                  40                  45

Ile Ser Asn Tyr Leu Asn Trp Tyr Gln Gln Lys Pro Gly Lys Ala Pro
    50                  55                  60

Lys Leu Leu Ile Tyr Tyr Thr Asn Lys Leu Ala Asp Gly Val Pro Ser
65                  70                  75                  80

Arg Phe Ser Gly Ser Gly Ser Gly Arg Asp Ser Ser Phe Thr Ile Ser
                85                  90                  95

Ser Leu Glu Ser Glu Asp Ile Gly Ser Tyr Tyr Cys Gln Gln Tyr Tyr
            100                 105                 110

Asn Tyr Pro Trp Thr Phe Gly Pro Gly Thr Lys Leu Glu Ile Lys Arg
        115                 120                 125

Gly Gly Gly Gly Ser Gly Gly Gly Ser Gly Gly Gly Ser Glu
    130                 135                 140

Val Gln Leu Val Glu Ser Gly Gly Gly Leu Val Gln Pro Gly Lys Ser
145                 150                 155                 160

Leu Lys Leu Ser Cys Glu Ala Ser Gly Phe Thr Phe Ser Gly Tyr Gly
                165                 170                 175

Met His Trp Val Arg Gln Ala Pro Gly Arg Gly Leu Glu Ser Val Ala
            180                 185                 190

Tyr Ile Thr Ser Ser Ile Asn Ile Lys Tyr Ala Asp Ala Val Lys
            195                 200                 205

Gly Arg Phe Thr Val Ser Arg Asp Asn Ala Lys Asn Leu Leu Phe Leu
210                 215                 220

Gln Met Asn Ile Leu Lys Ser Glu Asp Thr Ala Met Tyr Tyr Cys Ala
225                 230                 235                 240

Arg Phe Asp Trp Asp Lys Asn Tyr Trp Gly Gln Gly Thr Met Val Thr
                245                 250                 255

Val Ser Ser Pro Asn Ile Thr Ser Asn Ser Asn Pro Val Glu Gly
            260                 265                 270

Asp Asp Ser Val Ser Leu Thr Cys Asp Ser Tyr Thr Asp Pro Asp Asn
            275                 280                 285

Ile Asn Tyr Leu Trp Ser Arg Asn Gly Glu Ser Leu Ser Glu Gly Asp
290                 295                 300

Arg Leu Lys Leu Ser Glu Gly Asn Arg Thr Leu Thr Leu Leu Asn Val
305                 310                 315                 320

Thr Arg Asn Asp Thr Gly Pro Tyr Val Cys Glu Thr Arg Asn Pro Val
                325                 330                 335

Ser Val Asn Arg Ser Asp Pro Phe Ser Leu Asn Asn Thr Leu Val Leu
            340                 345                 350

Phe Gly Ala Gly Phe Gly Ala Val Ile Thr Val Val Ile Val Val
            355                 360                 365

Ile Ile Lys Cys Phe Cys Lys His Arg Ser Cys Phe Arg Arg Asn Glu
370                 375                 380

Ala Ser Arg Glu Thr Asn Asn Ser Leu Thr Phe Gly Pro Glu Glu Ala
385                 390                 395                 400

Leu Ala Glu Gln Thr Val Phe Leu
                405

<210> SEQ ID NO 96
<211> LENGTH: 420
<212> TYPE: DNA
<213> ORGANISM: Artificial Sequence
<220> FEATURE:
<223> OTHER INFORMATION: Synthetic

<400> SEQUENCE: 96
atggttcttc tcaggagcct cttcatcctg caagtactag tacgatgggg gctaacttac      60
aacttttcta actgcaactt cacgtcaatt acgaaaatat attgtaacat aattttttcat    120 gacctgactg agatttgaa aggggctaag ttcgagcaaa tcgaggactg tgagagcaag      180
ccagcttgtc tcctgaaaat cgagtactat actctcaatc ctatccctgg ctgcccttca    240
ctccccgaca aaacatttgc ccggagaaca agagaagccc tcaatgacca ctgcccaggc    300
taccctgaaa ctgagagaaa tgacggtact caggaaatgg cacaagaagt ccaaaacatc    360
tgcctgaatc aaacctcaca aattctaaga ttgtggtatt ccttcatgca atctccagaa    420

<210> SEQ ID NO 97
<211> LENGTH: 140
<212> TYPE: PRT
<213> ORGANISM: Artificial Sequence
<220> FEATURE:
<223> OTHER INFORMATION: Synthetic

<400> SEQUENCE: 97

Met Val Leu Leu Arg Ser Leu Phe Ile Leu Gln Val Leu Val Arg Met
1               5                   10                  15

Gly Leu Thr Tyr Asn Phe Ser Asn Cys Asn Phe Thr Ser Ile Thr Lys
            20                  25                  30

Ile Tyr Cys Asn Ile Ile Phe His Asp Leu Thr Gly Asp Leu Lys Gly
            35                  40                  45

Ala Lys Phe Glu Gln Ile Glu Asp Cys Glu Ser Lys Pro Ala Cys Leu
        50                  55                  60

Leu Lys Ile Glu Tyr Tyr Thr Leu Asn Pro Ile Pro Gly Cys Pro Ser
65                  70                  75                  80

Leu Pro Asp Lys Thr Phe Ala Arg Arg Thr Arg Glu Ala Leu Asn Asp
                85                  90                  95

His Cys Pro Gly Tyr Pro Glu Thr Glu Arg Asn Asp Gly Thr Gln Glu
            100                 105                 110

Met Ala Gln Glu Val Gln Asn Ile Cys Leu Asn Gln Thr Ser Gln Ile
        115                 120                 125

Leu Arg Leu Trp Tyr Ser Phe Met Gln Ser Pro Glu
        130                 135                 140

<210> SEQ ID NO 98
<211> LENGTH: 423
<212> TYPE: DNA
<213> ORGANISM: Artificial Sequence
<220> FEATURE:
<223> OTHER INFORMATION: Synthetic

<400> SEQUENCE: 98
atgtggctgc agaatttact tttcctgggc attgtggtct acagcctctc agcacccacc    60
cgctcaccca tcactgtcac ccggccttgg aagcatgtag aggccatcaa agaagccctg   120
aacctcctgg atgacatgcc tgtcacgttg aatgaagagg tagaagtcgt ctctaacgag   180
ttctccttca gaagctaac atgtgtgcag acccgcctga agatattcga gcagggtcta   240
cggggcaatt tcaccaaact caagggcgcc ttgaacatga cagccagcta ctaccagaca   300
tactgccccc caactccgga aacggactgt gaaacacaag ttaccaccta tgcggatttc   360
atagacagcc ttaaaaacctt tctgactgat atccccttg aatgcaaaaa accaggccaa   420
aaa                                                                  423

<210> SEQ ID NO 99
<211> LENGTH: 141
<212> TYPE: PRT
<213> ORGANISM: Artificial Sequence
<220> FEATURE:
<223> OTHER INFORMATION: Synthetic

<400> SEQUENCE: 99

Met Trp Leu Gln Asn Leu Leu Phe Leu Gly Ile Val Val Tyr Ser Leu
1               5                   10                  15

Ser Ala Pro Thr Arg Ser Pro Ile Thr Val Thr Arg Pro Trp Lys His
            20                  25                  30

Val Glu Ala Ile Lys Glu Ala Leu Asn Leu Leu Asp Asp Met Pro Val
        35                  40                  45

Thr Leu Asn Glu Glu Val Glu Val Val Ser Asn Glu Phe Ser Phe Lys
    50                  55                  60

Lys Leu Thr Cys Val Gln Thr Arg Leu Lys Ile Phe Glu Gln Gly Leu
65                  70                  75                  80

Arg Gly Asn Phe Thr Lys Leu Lys Gly Ala Leu Asn Met Thr Ala Ser
                85                  90                  95

Tyr Tyr Gln Thr Tyr Cys Pro Pro Thr Pro Glu Thr Asp Cys Glu Thr

```
              100                 105                 110
Gln Val Thr Thr Tyr Ala Asp Phe Ile Asp Ser Leu Lys Thr Phe Leu
        115                 120                 125

Thr Asp Ile Pro Phe Glu Cys Lys Lys Pro Gly Gln Lys
    130                 135                 140
```

<210> SEQ ID NO 100
<211> LENGTH: 465
<212> TYPE: DNA
<213> ORGANISM: Artificial Sequence
<220> FEATURE:
<223> OTHER INFORMATION: Synthetic

<400> SEQUENCE: 100

```
atgaacgcta cacactgcat cttggctttg cagctcttcc tcatggctgt ttctggctgt      60
tactgccacg gcacagtcat tgaaagccta gaaagtctga ataactattt taactcaagt     120
ggcatagatg tggaagaaaa gagtctcttc ttggatatct ggaggaactg gcaaaaggat     180
ggtgacatga aaatcctgca gagccagatt atctctttct acctcagact ctttgaagtc     240
ttgaaagaca atcaggccat cagcaacaac ataagcgtca ttgaatcaca cctgattact     300
accttcttca gcaacagcaa ggcgaaaaag gatgcattca tgagtattgc caagtttgag     360
gtcaacaacc cacaggtcca gcgccaagca ttcaatgagc tcatccgagt ggtccaccag     420
ctgttgccgg aatccagcct caggaagcgg aaaaggagtc gctgc                     465
```

<210> SEQ ID NO 101
<211> LENGTH: 155
<212> TYPE: PRT
<213> ORGANISM: Artificial Sequence
<220> FEATURE:
<223> OTHER INFORMATION: Synthetic

<400> SEQUENCE: 101

```
Met Asn Ala Thr His Cys Ile Leu Ala Leu Gln Leu Phe Leu Met Ala
1               5                   10                  15

Val Ser Gly Cys Tyr Cys His Gly Thr Val Ile Glu Ser Leu Glu Ser
            20                  25                  30

Leu Asn Asn Tyr Phe Asn Ser Ser Gly Ile Asp Val Glu Glu Lys Ser
        35                  40                  45

Leu Phe Leu Asp Ile Trp Arg Asn Trp Gln Lys Asp Gly Asp Met Lys
    50                  55                  60

Ile Leu Gln Ser Gln Ile Ile Ser Phe Tyr Leu Arg Leu Phe Glu Val
65                  70                  75                  80

Leu Lys Asp Asn Gln Ala Ile Ser Asn Asn Ile Ser Val Ile Glu Ser
                85                  90                  95

His Leu Ile Thr Thr Phe Phe Ser Asn Ser Lys Ala Lys Lys Asp Ala
            100                 105                 110

Phe Met Ser Ile Ala Lys Phe Glu Val Asn Asn Pro Gln Val Gln Arg
        115                 120                 125

Gln Ala Phe Asn Glu Leu Ile Arg Val Val His Gln Leu Leu Pro Glu
    130                 135                 140

Ser Ser Leu Arg Lys Arg Lys Arg Ser Arg Cys
145                 150                 155
```

<210> SEQ ID NO 102
<211> LENGTH: 462
<212> TYPE: DNA
<213> ORGANISM: Artificial Sequence
<220> FEATURE:
<223> OTHER INFORMATION: Synthetic

<400> SEQUENCE: 102

```
atgttccatg tttcttttag atatatcttt ggaattcctc cactgatcct tgttctgctg        60
cctgtcacat catctgagtg ccacattaaa gacaaagaag gtaaagcata tgagagtgta       120
ctgatgatca gcatcgatga attggacaaa atgacaggaa ctgatagtaa ttgcccgaat       180
aatgaaccaa actttttag aaaacatgta tgtgatgata caaggaagc tgcttttcta        240
aatcgtgctg ctcgcaagtt gaagcaattt cttaaaatga atatcagtga agaattcaat       300
gtccacttac taacagtatc acaaggcaca caaacactgg tgaactgcac aagtaaggaa       360
gaaaaaaacg taaggaaca gaaaaagaat gatgcatgtt tcctaaagag actactgaga       420
gaaataaaaa cttgttggaa taaaattttg aagggcagta ta                         462
```

<210> SEQ ID NO 103
<211> LENGTH: 154
<212> TYPE: PRT
<213> ORGANISM: Artificial Sequence
<220> FEATURE:
<223> OTHER INFORMATION: Synthetic

<400> SEQUENCE: 103

```
Met Phe His Val Ser Phe Arg Tyr Ile Phe Gly Ile Pro Pro Leu Ile
1               5                   10                  15

Leu Val Leu Leu Pro Val Thr Ser Ser Glu Cys His Ile Lys Asp Lys
            20                  25                  30

Glu Gly Lys Ala Tyr Glu Ser Val Leu Met Ile Ser Ile Asp Glu Leu
        35                  40                  45

Asp Lys Met Thr Gly Thr Asp Ser Asn Cys Pro Asn Asn Glu Pro Asn
    50                  55                  60

Phe Phe Arg Lys His Val Cys Asp Asp Thr Lys Glu Ala Ala Phe Leu
65                  70                  75                  80

Asn Arg Ala Ala Arg Lys Leu Lys Gln Phe Leu Lys Met Asn Ile Ser
                85                  90                  95

Glu Glu Phe Asn Val His Leu Leu Thr Val Ser Gln Gly Thr Gln Thr
            100                 105                 110

Leu Val Asn Cys Thr Ser Lys Glu Glu Lys Asn Val Lys Glu Gln Lys
        115                 120                 125

Lys Asn Asp Ala Cys Phe Leu Lys Arg Leu Leu Arg Glu Ile Lys Thr
    130                 135                 140

Cys Trp Asn Lys Ile Leu Lys Gly Ser Ile
145                 150
```

<210> SEQ ID NO 104
<211> LENGTH: 966
<212> TYPE: DNA
<213> ORGANISM: Artificial Sequence
<220> FEATURE:
<223> OTHER INFORMATION: Synthetic

<400> SEQUENCE: 104

```
atgcagctaa agtgtccctg ttttgtgtcc ttgggaacca ggcagcctgt ttggaagaag        60
ctccatgttt ctagcgggtt ctttttctggt cttggtctgt tcttgctgct gttgagcagc      120
ctctgtgctg cctctgcaga gactgaagtc ggtgcaatgg tgggcagcaa tgtggtgctc      180
agctgcattg accccacag acgccatttc aacttgagtg gtctgtatgt ctattggcaa      240
```

```
atcgaaaacc cagaagtttc ggtgacttac tacctgcctt acaagtctcc agggatcaat    300
gtggacagtt cctacaagaa caggggccat ctgtccctgg actccatgaa gcagggtaac    360
ttctctctgt acctgaagaa tgtcacccct caggatacc aggagttcac atgccgggta     420
tttatgaata cagccacaga gttagtcaag atcttggaag aggtggtcag gctgcgtgtg    480
gcagcaaact tcagtacacc tgtcatcagc acctctgata gctccaaccc gggccaggaa    540
cgtacctaca cctgcatgtc caagaatggc tacccagagc ccaacctgta ttggatcaac    600
acaacggaca atagcctaat agacacggct ctgcagaata cactgtcta cttgaacaag     660 ttgggcctgt atgatgtaat cagcacatta aggctcccctt ggacatctcg tggggatgtt   720
ctgtgctgcg tagagaatgt ggctctccac cagaacatca ctagcattag ccaggcagaa    780
agtttcactg gaataacac aaagaaccca caggaaccc acaataatga gttaaaagtc      840
cttgtccccg tccttgctgt actggcggca gcggcattcg tttccttcat catatacaga    900
cgcacgcgtc cccaccgaag ctatacagga cccaagactg tacagcttga acttacagac    960
cacgcc                                                               966
```

<210> SEQ ID NO 105
<211> LENGTH: 322
<212> TYPE: PRT
<213> ORGANISM: Artificial Sequence
<220> FEATURE:
<223> OTHER INFORMATION: Synthetic

<400> SEQUENCE: 105

```
Met Gln Leu Lys Cys Pro Cys Phe Val Ser Leu Gly Thr Arg Gln Pro
1               5                   10                  15

Val Trp Lys Lys Leu His Val Ser Ser Gly Phe Phe Ser Gly Leu Gly
                20                  25                  30

Leu Phe Leu Leu Leu Leu Ser Ser Leu Cys Ala Ala Ser Ala Glu Thr
            35                  40                  45

Glu Val Gly Ala Met Val Gly Ser Asn Val Val Leu Ser Cys Ile Asp
        50                  55                  60

Pro His Arg Arg His Phe Asn Leu Ser Gly Leu Tyr Val Tyr Trp Gln
65                  70                  75                  80

Ile Glu Asn Pro Glu Val Ser Val Thr Tyr Tyr Leu Pro Tyr Lys Ser
                85                  90                  95

Pro Gly Ile Asn Val Asp Ser Ser Tyr Lys Asn Arg Gly His Leu Ser
            100                 105                 110

Leu Asp Ser Met Lys Gln Gly Asn Phe Ser Leu Tyr Leu Lys Asn Val
        115                 120                 125

Thr Pro Gln Asp Thr Gln Glu Phe Thr Cys Arg Val Phe Met Asn Thr
    130                 135                 140

Ala Thr Glu Leu Val Lys Ile Leu Glu Glu Val Val Arg Leu Arg Val
145                 150                 155                 160

Ala Ala Asn Phe Ser Thr Pro Val Ile Ser Thr Ser Asp Ser Ser Asn
                165                 170                 175

Pro Gly Gln Glu Arg Thr Tyr Thr Cys Met Ser Lys Asn Gly Tyr Pro
            180                 185                 190

Glu Pro Asn Leu Tyr Trp Ile Asn Thr Thr Asp Asn Ser Leu Ile Asp
        195                 200                 205

Thr Ala Leu Gln Asn Asn Thr Val Tyr Leu Asn Lys Leu Gly Leu Tyr
    210                 215                 220

Asp Val Ile Ser Thr Leu Arg Leu Pro Trp Thr Ser Arg Gly Asp Val
```

```
            225                 230                 235                 240
Leu Cys Cys Val Glu Asn Val Ala Leu His Gln Asn Ile Thr Ser Ile
                245                 250                 255

Ser Gln Ala Glu Ser Phe Thr Gly Asn Asn Thr Lys Asn Pro Gln Glu
            260                 265                 270

Thr His Asn Asn Glu Leu Lys Val Leu Val Pro Val Leu Ala Val Leu
        275                 280                 285

Ala Ala Ala Ala Phe Val Ser Phe Ile Ile Tyr Arg Arg Thr Arg Pro
    290                 295                 300

His Arg Ser Tyr Thr Gly Pro Lys Thr Val Gln Leu Glu Leu Thr Asp
305                 310                 315                 320

His Ala
```

<210> SEQ ID NO 106
<211> LENGTH: 909
<212> TYPE: DNA
<213> ORGANISM: Artificial Sequence
<220> FEATURE:
<223> OTHER INFORMATION: Synthetic

<400> SEQUENCE: 106

```
atgtggccct tggcggcggc gctgttgctg ggctcctgct gctgcggttc agctcaacta      60
ctgtttagta acgtcaactc catagagttc acttcatgca atgaaactgt ggtcatccct     120
tgcatcgtcc gtaatgtgga ggcgcaaagc accgaagaaa tgtttgtgaa gtggaagttg     180
aacaaatcgt atattttcat ctatgatgga aataaaaata gcactactac agatcaaaac     240
tttaccagtg caaaaatctc agtctcagac ttaatcaatg gcattgcctc tttgaaaatg     300
gataagcgcg atgccatggt gggaaactac acttgcgaag tgacagagtt atccagagaa     360
ggcaaaacag ttatagagct gaaaaaccgc acggtttcgt ggttttctcc aaatgaaaag     420
atcctcattg ttattttccc aattttggct atactcctgt tctggggaaa gtttggtatt     480
ttaacactca aatataaatc cagccatacg aataagagaa tcattctgct gctcgttgcc     540
gggctggtgc tcacagtcat cgtggttgtt ggagccatcc ttctcatccc aggagaaaag     600
cccgtgaaga atgcttctgg acttggcctc attgtaatct ctacgggdat attaatacta     660
cttcagtaca atgtgtttat gacagctttt ggaatgacct cttcaccat tgccatattg     720
atcactcaag tgctgggcta cgtccttgct ttggtcgggc tgtgtctctg catcatggca     780
tgtgagccag tgcacggccc cctttgatt tcaggtttgg ggatcatagc tctagcagaa     840
ctacttggat tagtttatat gaagtttgtc gcttccaacc agaggactat ccaacctcct     900
aggaatagg                                                              909
```

<210> SEQ ID NO 107
<211> LENGTH: 303
<212> TYPE: PRT
<213> ORGANISM: Artificial Sequence
<220> FEATURE:
<223> OTHER INFORMATION: Synthetic

<400> SEQUENCE: 107

```
Met Trp Pro Leu Ala Ala Ala Leu Leu Leu Gly Ser Cys Cys Cys Gly
1               5                   10                  15

Ser Ala Gln Leu Leu Phe Ser Asn Val Asn Ser Ile Glu Phe Thr Ser
            20                  25                  30

Cys Asn Glu Thr Val Val Ile Pro Cys Ile Val Arg Asn Val Glu Ala
        35                  40                  45
```

Gln Ser Thr Glu Glu Met Phe Val Lys Trp Lys Leu Asn Lys Ser Tyr
    50                  55                  60

Ile Phe Ile Tyr Asp Gly Asn Lys Asn Ser Thr Thr Asp Gln Asn
65                  70                  75                  80

Phe Thr Ser Ala Lys Ile Ser Val Ser Asp Leu Ile Asn Gly Ile Ala
                85                  90                  95

Ser Leu Lys Met Asp Lys Arg Asp Ala Met Val Gly Asn Tyr Thr Cys
            100                 105                 110

Glu Val Thr Glu Leu Ser Arg Glu Gly Lys Thr Val Ile Glu Leu Lys
        115                 120                 125

Asn Arg Thr Val Ser Trp Phe Ser Pro Asn Glu Lys Ile Leu Ile Val
    130                 135                 140

Ile Phe Pro Ile Leu Ala Ile Leu Leu Phe Trp Gly Lys Phe Gly Ile
145                 150                 155                 160

Leu Thr Leu Lys Tyr Lys Ser Ser His Thr Asn Lys Arg Ile Ile Leu
                165                 170                 175

Leu Leu Val Ala Gly Leu Val Leu Thr Val Ile Val Val Gly Ala
            180                 185                 190

Ile Leu Leu Ile Pro Gly Glu Lys Pro Val Lys Asn Ala Ser Gly Leu
        195                 200                 205

Gly Leu Ile Val Ile Ser Thr Gly Ile Leu Ile Leu Gln Tyr Asn
    210                 215                 220

Val Phe Met Thr Ala Phe Gly Met Thr Ser Phe Thr Ile Ala Ile Leu
225                 230                 235                 240

Ile Thr Gln Val Leu Gly Tyr Val Leu Ala Leu Val Gly Leu Cys Leu
                245                 250                 255

Cys Ile Met Ala Cys Glu Pro Val His Gly Pro Leu Leu Ile Ser Gly
            260                 265                 270

Leu Gly Ile Ile Ala Leu Ala Glu Leu Leu Gly Leu Val Tyr Met Lys
        275                 280                 285

Phe Val Ala Ser Asn Gln Arg Thr Ile Gln Pro Pro Arg Asn Arg
    290                 295                 300

<210> SEQ ID NO 108
<211> LENGTH: 1161
<212> TYPE: DNA
<213> ORGANISM: Artificial Sequence
<220> FEATURE:
<223> OTHER INFORMATION: Synthetic

<400> SEQUENCE: 108
atggcagcag cagtaacttg gatacctctc ctggcaggtc tcctggcagg actgagggac      60
accaaggccc agcagacaac tttacaccta cttgtgggtc gtgtgtttgt gcatcctttg     120
gaacatgcca ccttcctgcg ccttccagaa cacgttgcgg tgccacccac tgtccgactc     180
acctaccacg ctcacctcca gggacatcca gacctgccca ggtggctgca ctacacacag     240
cgcagtccct ataaccctgg cttcctctac ggctccccca ctccagaaga tcgtgggtac     300
caagtcatcg aggtcacagc ctacaatcga gacagttttg acaccactag acagaggctg     360
ctgctgctga ttggggaccc cgaaggtccc ggttgccat accaagctga gttcctggtg      420
cgcagccatg atgtggagga ggtgctgccc accacacctg ccaaccgctt cctcaccgcc     480 ttgggggac tgtgggagcc aggagagctt cagctgctca acatcacttc cgccttggac     540
cggggaggcc gagtccctct tcctattgag ggacggaagg aagggggtata cattaaggta     600

```
ggctctgcca caccctnctc cacctgcctg aagatggtgg cgtcgcccga cagctatgcc    660
cgttgtgccc agggacagcc tccactactg tcctgctacg acactttggc accccacttc    720
cgcgttgact ggtgcaatgt gtctctggta gacaagtcag tacccgagcc cctggatgag    780
gtacctactc caggcgatgg gatcttggag cacgacccgt tcttctgccc acccactgaa    840
gccacagacc gagacttcct gacagatgcc ttggtgaccc tcttggtgcc tttgttggtg    900
gctctgctgc ttactctgtt gctggcttac atcatgtgct tcggcgtga aggacggctg    960 aagagagaca tggccacctc tgacatccag atgtttcacc actgttccat ccatgggaat   1020
acagaagagc ttcggcagat ggcagccagc cgagaggtgc cccggcctct ttccaccttg   1080
cccatgttta atgttcgtac aggagagcgg ttacctcccc gagtagacag cgcacagatg   1140
cctcttatcc tggaccagca c                                              1161
```

<210> SEQ ID NO 109
<211> LENGTH: 387
<212> TYPE: PRT
<213> ORGANISM: Artificial Sequence
<220> FEATURE:
<223> OTHER INFORMATION: Synthetic

<400> SEQUENCE: 109

```
Met Ala Ala Ala Val Thr Trp Ile Pro Leu Leu Ala Gly Leu Leu Ala
1               5                   10                  15

Gly Leu Arg Asp Thr Lys Ala Gln Gln Thr Thr Leu His Leu Val
            20                  25                  30

Gly Arg Val Phe Val His Pro Leu Glu His Ala Thr Phe Leu Arg Leu
        35                  40                  45

Pro Glu His Val Ala Val Pro Pro Thr Val Arg Leu Thr Tyr His Ala
    50                  55                  60

His Leu Gln Gly His Pro Asp Leu Pro Arg Trp Leu His Tyr Thr Gln
65                  70                  75                  80

Arg Ser Pro Tyr Asn Pro Gly Phe Leu Tyr Gly Ser Pro Thr Pro Glu
                85                  90                  95

Asp Arg Gly Tyr Gln Val Ile Glu Val Thr Ala Tyr Asn Arg Asp Ser
            100                 105                 110

Phe Asp Thr Thr Arg Gln Arg Leu Leu Leu Ile Gly Asp Pro Glu
        115                 120                 125

Gly Pro Arg Leu Pro Tyr Gln Ala Glu Phe Leu Val Arg Ser His Asp
    130                 135                 140

Val Glu Glu Val Leu Pro Thr Thr Pro Ala Asn Arg Phe Leu Thr Ala
145                 150                 155                 160

Leu Gly Gly Leu Trp Glu Pro Gly Glu Leu Gln Leu Leu Asn Ile Thr
                165                 170                 175

Ser Ala Leu Asp Arg Gly Gly Arg Val Pro Leu Pro Ile Glu Gly Arg
            180                 185                 190

Lys Glu Gly Val Tyr Ile Lys Val Gly Ser Ala Thr Pro Phe Ser Thr
        195                 200                 205

Cys Leu Lys Met Val Ala Ser Pro Asp Ser Tyr Ala Arg Cys Ala Gln
    210                 215                 220

Gly Gln Pro Pro Leu Leu Ser Cys Tyr Asp Thr Leu Ala Pro His Phe
225                 230                 235                 240

Arg Val Asp Trp Cys Asn Val Ser Leu Val Asp Lys Ser Val Pro Glu
                245                 250                 255

Pro Leu Asp Glu Val Pro Thr Pro Gly Asp Gly Ile Leu Glu His Asp
```

```
            260                 265                 270
Pro Phe Phe Cys Pro Pro Thr Glu Ala Thr Asp Arg Asp Phe Leu Thr
            275                 280                 285

Asp Ala Leu Val Thr Leu Leu Val Pro Leu Leu Val Ala Leu Leu Leu
        290                 295                 300

Thr Leu Leu Leu Ala Tyr Ile Met Cys Phe Arg Arg Glu Gly Arg Leu
305                 310                 315                 320

Lys Arg Asp Met Ala Thr Ser Asp Ile Gln Met Phe His His Cys Ser
                325                 330                 335

Ile His Gly Asn Thr Glu Glu Leu Arg Gln Met Ala Ala Ser Arg Glu
            340                 345                 350

Val Pro Arg Pro Leu Ser Thr Leu Pro Met Phe Asn Val Arg Thr Gly
        355                 360                 365

Glu Arg Leu Pro Pro Arg Val Asp Ser Ala Gln Met Pro Leu Ile Leu
    370                 375                 380

Asp Gln His
385

<210> SEQ ID NO 110
<211> LENGTH: 627
<212> TYPE: DNA
<213> ORGANISM: Artificial Sequence
<220> FEATURE:
<223> OTHER INFORMATION: Synthetic

<400> SEQUENCE: 110
atgtggaaat ggatactgac acattgtgcc tcagcctttc cccacctgcc gggctgctgt      60
tgctgcttct tgttgctctt tttggtgtct tcgttccctg tcacctgcca agctcttggt     120
caggacatgg tgtcacagga ggccaccaac tgctcttctt cctcctcgtc cttctccctct    180 ccttccagtg cgggaaggca tgtgcggagc tacaatcacc tccaaggaga gtgtccgctgg    240 agaaggctgt tctccttcac caagtacttt ctcacgattg agaagaacgg caaggtcagc    300
gggaccaaga atgaagactg tccgtacagt gtcctggaga taacatcagt ggaaatcgga    360
gttgttgccg tcaaagccat caacagcaac tattacttag ccatgaacaa gaaggggaaa    420
ctctatggct caaagagtt taacaacgac tgtaagctga agagagaat agaggaaaat     480 ggatacaaca cctatgcatc ttttaactgg cagcacaatg gcaggcaaat gtatgtggca    540
ttgaatggaa aaggagctcc caggagagga caaaaaacaa gaaggaaaaa cacctctgct    600
cacttcctcc ccatgacgat ccaaaca                                        627

<210> SEQ ID NO 111
<211> LENGTH: 209
<212> TYPE: PRT
<213> ORGANISM: Artificial Sequence
<220> FEATURE:
<223> OTHER INFORMATION: Synthetic

<400> SEQUENCE: 111

Met Trp Lys Trp Ile Leu Thr His Cys Ala Ser Ala Phe Pro His Leu
1               5                   10                  15

Pro Gly Cys Cys Cys Cys Phe Leu Leu Leu Phe Leu Val Ser Ser Phe
            20                  25                  30

Pro Val Thr Cys Gln Ala Leu Gly Gln Asp Met Val Ser Gln Glu Ala
        35                  40                  45

Thr Asn Cys Ser Ser Ser Ser Ser Phe Ser Ser Pro Ser Ser Ala
    50                  55                  60
```

Gly Arg His Val Arg Ser Tyr Asn His Leu Gln Gly Asp Val Arg Trp
65                  70                  75                  80

Arg Arg Leu Phe Ser Phe Thr Lys Tyr Phe Leu Thr Ile Glu Lys Asn
                85                  90                  95

Gly Lys Val Ser Gly Thr Lys Asn Glu Asp Cys Pro Tyr Ser Val Leu
            100                 105                 110

Glu Ile Thr Ser Val Glu Ile Gly Val Val Ala Val Lys Ala Ile Asn
            115                 120                 125

Ser Asn Tyr Tyr Leu Ala Met Asn Lys Lys Gly Lys Leu Tyr Gly Ser
130                 135                 140

Lys Glu Phe Asn Asn Asp Cys Lys Leu Lys Glu Arg Ile Glu Glu Asn
145                 150                 155                 160

Gly Tyr Asn Thr Tyr Ala Ser Phe Asn Trp Gln His Asn Gly Arg Gln
                165                 170                 175

Met Tyr Val Ala Leu Asn Gly Lys Gly Ala Pro Arg Arg Gly Gln Lys
            180                 185                 190

Thr Arg Arg Lys Asn Thr Ser Ala His Phe Leu Pro Met Thr Ile Gln
            195                 200                 205

Thr

<210> SEQ ID NO 112
<211> LENGTH: 5853
<212> TYPE: DNA
<213> ORGANISM: Artificial Sequence
<220> FEATURE:
<223> OTHER INFORMATION: Synthetic

<400> SEQUENCE: 112

```
atgcctcctc tgccactgga acacagaccc aggcagcagc ctggtgcctc cgtgctggtt      60
cggtacttca tgatcccctg caacatctgc ttgatcctct ggctacttca tacgttgggc     120
tttgcggtgc tgcttttcct cagcaactac aaacctggga tccacttcac agcagcgcct     180
tctatgcctc ctgatgtgtg caggggaatg ttatgtggct ttggtgctgt gtgtgaacct     240
agtgttgagg atccaggccg ggcctcctgt gtgtgcaaga gaatgtctg ccctgctatg      300
gtagctcctg tgtgtggctc agatgcttcc acctatagca acgagtgtga gctacagcgt     360
gcacagtgca accagcaacg cgcatccgc tactccgcc aagggccatg tgggtcccgg       420
gaccctgtg ccaatgtgac ctgcagtttc ggtagtacct gtgtaccttc agccgatgga      480
cagaccgcct cgtgtctgtg tcctacaacc tgctttgggg ccctgatgg cacagtgtgt      540
ggcagtgatg tgttgactg cctagtgag tgccagctgc tccgtcatgc ctgtgccaac       600
caggagcaca tctttaagaa gttcgatggt ccttgtgacc cctgccaggg cagcatgtca     660
gacctgaatc atatttgccg ggtgaaccca cgtacacggc acccagaaat gcttctgcgg     720
cctgagaact gccccgccca acacacacct atctgtggag atgatggggt cacctatgaa     780
aacgactgtg tcatgagccg tataggtgca gcccgtggcc tgcttctcca gaaagtgcgc     840
tctggtcaat gccagactcg agaccagtgc ccggagacct gccagtttaa ctctgtatgc     900
ctgtcccgcc gcggccgtcc ccactgttcc tgcgatcgcg tcacctgtga tgggcttac     960
aggccagtgt gtgcccagga tgggcacacg tatgacaatg actgttggcg ccaacaggcc    1020
gagtgtcgac aacagcagac cattccccc aagcaccagg gccgtgtga ccagacccca      1080
tccccgtgcc gtggagcgca gtgtgcattt ggggcaacat gcacagtgaa gaatgggaaa    1140
gctgtgtgcg agtgccagcg ggtgtgctcg ggcggctacg atcctgtgtg cggcagtgat    1200
```

```
ggtgtcactt acggcagtgt gtgcgagctg gaatccatgg cctgtaccct tgggcgggaa   1260
atccgagtgg cccgcagagg accgtgtgac cgatgtgggc agtgccggtt tggatccttg   1320
tgcgaggtgg agactggacg ctgtgtgtgc ccctctgagt gtgtggagtc agcccagccc   1380
gtatgtggct ctgacggaca cacatatgct agtgaatgtg agctgcatgt ccacgcctgt   1440
acacaccaga tcagcctata cgtggcctca gccggacact gccagacctg tggagaaaca   1500
gtttgtacct tggggctgt gtgctcagct ggacagtgtg tatgtccccg ttgtgagcac   1560
cccccacctg ccctgtgtg cggcagtgat ggcgtcacct acctcagtgc ctgtgagctc   1620
cgagaggctg cctgtcagca gcaggtacaa attgaggagg cccgtgcagg gccgtgtgag   1680
ccggctgagt gtggctcagg gggctctggg tctggggaag acaatgcgtg tgagcaggag   1740
ctgtgtcggc agcatggtgg tgtctgggat gaggactcag aagacgggcc gtgtgtctgt   1800
gactttagtt gccagagtgt ccttaaaagc ccagtgtgtg gctcagatgg agtcacctat   1860
agcacggagt gccatctgaa gaaggccaga tgtgaagcgc ggcaagagct gtacgtcgct   1920
gctcagggag cctgccgggg ccctaccttg gctccactgc tacctatggc ctccccacac   1980
tgtgcccaaa cccctatgg ctgctgccag gacaatgtca ctgctgccca gggtgtgggc   2040
ttggctggct gtcccagcac ctgccattgc aacccacacg gctcctatag cggcacttgt   2100
gacccagtca cagggcagtg ctcctgccga ccaggtgtag gaggcctcag gtgtgatcgc   2160
tgtgagcctg gcttctggaa cttccgtggc attgtcaccg atggacatag tggttgcact   2220
ccctgcagct gtgaccctcg gggtgctgta agagatgact gtgagcagat gactggattg   2280
tgttcctgta gacctggtgt ggctggtccc aagtgtgggc agtgtccaga tggtcaagcc   2340
ctgggccatc ttggctgtga agcagatccc acaacaccag tgacttgtgt ggaaatgcac   2400
tgtgagtttg gcgcctcctg cgtagaggag gctggttttg cccagtgtgt ctgcccaact   2460
ctcacatgtc cagaggctaa ctctaccaag gtctgtggat cagatggtgt cacatacggc   2520
aatgaatgcc agctgaagac cattgcctgc cgccagcgtc tggacatctc cattcagagt   2580
cttggtccat gccgggagag tgttgctcct ggggtttccc ctacatctgc atctatgacc   2640
accccaaggc atatcctgag caggacactg gcgtctcccc acagcagcct tcctctgtct   2700
cccagcacta ctgcccatga ttggcccacc ccattaccca catcacctca gaccgtagtc   2760
ggcaccccca ggagcactgc agccacaccc tctgatgtgg ccagtcttgc tacagcgatc   2820
ttcagggaat ctggcagcac caacggcagt ggcgatgagg agctcagtgg cgatgaggag   2880
gccagtgggg gcgggtctgg gggacttgag ccccggtgg gcagcgttgt ggtgacccac   2940
gggccaccca tcgagagggc ttcctgttac aactcacctt tgggctgctg ctcagatggc   3000 aagcaccct cactggactc agaaggctcc aactgtccag ctaccaaggc attccagggc   3060
gtgctggagc ttgagggggt cgagggacag gaactgttct acacaccaga tggctgac   3120 cccaagtcag agttgtttgg ggagactgca aggagcattg agagcacgct ggacgacctg   3180
ttccggaatt cggatgttaa gaaggacttc tggagcatcc gcctacggga actggggcct   3240
ggcaaattag tccgtgccat tgtggatgtt cactttgacc ccaccacagc cttccaggca   3300
ccagatgtgg tcaggccttt gctccaacag atccaggtat ccaggcgtg ggccctggca   3360 gtgaggaggc ctctgcggga gcatgtgcga ttcttggact ttgactggtt tcccactttt   3420
tttacgggag ctgcaacagg aaccacagct gctgtggcca cagccagagc caccactgtg   3480
agccgactgt ctgcctcttc tgtcacccca cgagtctacc ccagttacac cagccggcct   3540
```

```
gttggcagaa ctacggcacc gctaaccact cgccggccac caaccactac cgccagtatt   3600
gaccgacctc ggactccagg ccccgcaacgg cccccaaagt cctgtgattc ccagccttgc   3660
ctccacggag gtacctgcca ggacctggat tctggcaagg gtttcagctg cagctgtact   3720
gcaggcaggg ctggcactgt ctgtgagaaa gtgcagctcc cctctgtgcc agcttttaag   3780
ggccactcct tcttggcctt ccccacccctc cgagcctacc acacgctgcg tctggcacta   3840
gaattccggg cgctggagac agagggactg ctgctctaca atggcaatgc acgtggcaaa   3900
gatttcctgg ctctggctct gttggatggt catgtacagt tcaggttcga cacgggctca   3960
gggccggcgg tgctaacaag cttagtgcca gtggaaccgg gacggtggca ccgcctcgag   4020
ttgtcacggc attggcggca gggcacactt tctgtggatg gcgaggctcc tgttgtaggt   4080
gaaagtccga gtggcactga tggcctcaac ttggacacga agctctatgt gggtggtctc   4140
ccagaagaac aagttgccac ggtgcttgat cggacctctg tgggcatcgg cctgaaagga   4200
tgcattcgta tgttggacat caacaaccag cagctggagc tgagcgattg cagagggct   4260 gtggttcaaa gctctggtgt gggggaatgc ggagaccatc cctgctcacc taacccctgc   4320
catggcgggg ccctctgcca ggccctggag gctggcgtgt tcctctgtca gtgcccacct   4380
ggccgctttg gcccaacttg tgcagatgaa aagaaccccct gccaaccgaa ccctgccac   4440 gggtcagccc cctgccatgt gctttccagg ggtggggcca agtgtgcgtg ccccctggga   4500
cgcagtggtt cctctgtga cagtcctg gagaatgctg ctcccggcc ttcctggct   4560 gactttaatg gcttctccta cctggaactg aaaggcttgc acaccttcga gagagaccta   4620
ggggagaaga tggcgctgga gatggtgttc ttggctcgtg ggcccagtgg cttactcctc   4680
tacaatgggc agaagacgga tgcaagggg gactttgtat ccctggccct gcataaccgg   4740
cacctagagt tccgctatga ccttggcaag ggggctgcaa tcatcaggag caaagagccc   4800
atagccctgg gcacctgggt tagggtattc ctggaacgaa atggccgcaa gggtgccctt   4860 caagtggggta tgggccccg tgtgctaggg aatctccga aatcccgcaa ggtcccgcac   4920
accatgctca acctcaagga gcccctctat gtgggggggag ctcctgactt cagcaagctg   4980
gctcggggcg ctgcagtggc ctccggcttt gatggtgcca tccagctggt gtctctaaga   5040
ggccatcagc tgctgactca ggagcatgtg ttgcgggcag tagatgtagc gcctttttgca   5100 ggccacccctt gtacccaggc cgtggacaac ccctgcctta tgggggctc ctgtatcccg   5160 agggaagcca cttatgagtg cctgtgtcct gggggcttct ctgggctgca ctgcgagaag   5220
gggatagttg agaagtcagt gggggaccta gaaacactgg cctttgatgg gcggacctac   5280
atcgagtacc tcaatgctgt gactgagagc gagctgacca atgagatccc agcccccgaa   5340
actctggatt cccgggccct tttcagtgag aaagcgctgc agagcaacca ctttgagctg   5400
agcttacgca ctgaggccac gcaggggctg gtgctgtgga ttggaaaggt tggagaacgt   5460
gcagactaca tggctctggc cattgtggat gggcacctac aactgagcta tgacctaggc   5520
tcccagccag ttgtgctgcg ctccactgtg aaggtcaaca ccaaccgctg gcttcgagtc   5580
agggctcaca gggagcacag ggaaggttcc cttcaggtgg gcaatgaagc ccctgtgact   5640
ggctcttccc cgctggggtgc cacacaattg gacacagatg gagccctgtg gcttggaggc   5700
ctacagaagc ttcctgtggg gcaggctctc cccaaggcct atggcacggg ttttgtgggc   5760
tgtctgcggg acgtggtagt gggccatcgc cagctgcatc tgctggagga cgctgtcacc   5820
aaaccagagc taagaccctg cccccactctc tga                               5853
```

<210> SEQ ID NO 113
<211> LENGTH: 1949
<212> TYPE: PRT
<213> ORGANISM: Artificial Sequence
<220> FEATURE:
<223> OTHER INFORMATION: Synthetic

<400> SEQUENCE: 113

```
Met Pro Pro Leu Pro Leu Glu His Arg Pro Arg Gln Gln Pro Gly Ala
1               5                   10                  15

Ser Val Leu Val Arg Tyr Phe Met Ile Pro Cys Asn Ile Cys Leu Ile
            20                  25                  30

Leu Leu Ala Thr Ser Thr Leu Gly Phe Ala Val Leu Leu Phe Leu Ser
        35                  40                  45

Asn Tyr Lys Pro Gly Ile His Phe Thr Ala Ala Pro Ser Met Pro Pro
    50                  55                  60

Asp Val Cys Arg Gly Met Leu Cys Gly Phe Gly Ala Val Cys Glu Pro
65                  70                  75                  80

Ser Val Glu Asp Pro Gly Arg Ala Ser Cys Val Cys Lys Lys Asn Val
                85                  90                  95

Cys Pro Ala Met Val Ala Pro Val Cys Gly Ser Asp Ala Ser Thr Tyr
            100                 105                 110

Ser Asn Glu Cys Glu Leu Gln Arg Ala Gln Cys Asn Gln Gln Arg Arg
        115                 120                 125

Ile Arg Leu Leu Arg Gln Gly Pro Cys Gly Ser Arg Asp Pro Cys Ala
    130                 135                 140

Asn Val Thr Cys Ser Phe Gly Ser Thr Cys Val Pro Ser Ala Asp Gly
145                 150                 155                 160

Gln Thr Ala Ser Cys Leu Cys Pro Thr Thr Cys Phe Gly Ala Pro Asp
                165                 170                 175

Gly Thr Val Cys Gly Ser Asp Gly Val Asp Tyr Pro Ser Glu Cys Gln
            180                 185                 190

Leu Leu Arg His Ala Cys Ala Asn Gln Glu His Ile Phe Lys Lys Phe
        195                 200                 205

Asp Gly Pro Cys Asp Pro Cys Gln Gly Ser Met Ser Asp Leu Asn His
    210                 215                 220

Ile Cys Arg Val Asn Pro Arg Thr Arg His Pro Glu Met Leu Leu Arg
225                 230                 235                 240

Pro Glu Asn Cys Pro Ala Gln His Thr Pro Ile Cys Gly Asp Asp Gly
                245                 250                 255

Val Thr Tyr Glu Asn Asp Cys Val Met Ser Arg Ile Gly Ala Ala Arg
            260                 265                 270

Gly Leu Leu Leu Gln Lys Val Arg Ser Gly Gln Cys Gln Thr Arg Asp
        275                 280                 285

Gln Cys Pro Glu Thr Cys Gln Phe Asn Ser Val Cys Leu Ser Arg Arg
    290                 295                 300

Gly Arg Pro His Cys Ser Cys Asp Arg Val Thr Cys Asp Gly Ala Tyr
305                 310                 315                 320

Arg Pro Val Cys Ala Gln Asp Gly His Thr Tyr Asp Asn Asp Cys Trp
                325                 330                 335

Arg Gln Gln Ala Glu Cys Arg Gln Gln Thr Ile Pro Pro Lys His
            340                 345                 350

Gln Gly Pro Cys Asp Gln Thr Pro Ser Pro Cys Arg Gly Ala Gln Cys
        355                 360                 365

Ala Phe Gly Ala Thr Cys Thr Val Lys Asn Gly Lys Ala Val Cys Glu
```

```
                370              375              380
Cys Gln Arg Val Cys Ser Gly Gly Tyr Asp Pro Val Cys Gly Ser Asp
385              390              395              400

Gly Val Thr Tyr Gly Ser Val Cys Glu Leu Glu Ser Met Ala Cys Thr
                405              410              415

Leu Gly Arg Glu Ile Arg Val Ala Arg Arg Gly Pro Cys Asp Arg Cys
                420              425              430

Gly Gln Cys Arg Phe Gly Ser Leu Cys Glu Val Glu Thr Gly Arg Cys
            435              440              445

Val Cys Pro Ser Glu Cys Val Glu Ser Ala Gln Pro Val Cys Gly Ser
        450              455              460

Asp Gly His Thr Tyr Ala Ser Glu Cys Glu Leu His Val His Ala Cys
465              470              475              480

Thr His Gln Ile Ser Leu Tyr Val Ala Ser Ala Gly His Cys Gln Thr
                485              490              495

Cys Gly Glu Thr Val Cys Thr Phe Gly Ala Val Cys Ser Ala Gly Gln
            500              505              510

Cys Val Cys Pro Arg Cys Glu His Pro Pro Gly Pro Val Cys Gly
        515              520              525

Ser Asp Gly Val Thr Tyr Leu Ser Ala Cys Glu Leu Arg Glu Ala Ala
530              535              540

Cys Gln Gln Val Gln Ile Glu Glu Ala Arg Ala Gly Pro Cys Glu
545              550              555              560

Pro Ala Glu Cys Gly Ser Gly Ser Gly Ser Gly Glu Asp Asn Ala
            565              570              575

Cys Glu Gln Glu Leu Cys Arg Gln His Gly Gly Val Trp Asp Glu Asp
            580              585              590

Ser Glu Asp Gly Pro Cys Val Cys Asp Phe Ser Cys Gln Ser Val Leu
        595              600              605

Lys Ser Pro Val Cys Gly Ser Asp Gly Val Thr Tyr Ser Thr Glu Cys
        610              615              620

His Leu Lys Lys Ala Arg Cys Glu Ala Arg Gln Glu Leu Tyr Val Ala
625              630              635              640

Ala Gln Gly Ala Cys Arg Gly Pro Thr Leu Ala Pro Leu Pro Met
                645              650              655

Ala Ser Pro His Cys Ala Gln Thr Pro Tyr Gly Cys Cys Gln Asp Asn
            660              665              670

Val Thr Ala Ala Gln Gly Val Gly Leu Ala Gly Cys Pro Ser Thr Cys
        675              680              685

His Cys Asn Pro His Gly Ser Tyr Ser Gly Thr Cys Asp Pro Val Thr
    690              695              700

Gly Gln Cys Ser Cys Arg Pro Gly Val Gly Leu Arg Cys Asp Arg
705              710              715              720

Cys Glu Pro Gly Phe Trp Asn Phe Arg Gly Ile Val Thr Asp Gly His
                725              730              735

Ser Gly Cys Thr Pro Cys Ser Cys Asp Pro Arg Gly Ala Val Arg Asp
            740              745              750

Asp Cys Glu Gln Met Thr Gly Leu Cys Ser Cys Arg Pro Gly Val Ala
            755              760              765

Gly Pro Lys Cys Gly Gln Cys Pro Asp Gly Gln Ala Leu Gly His Leu
        770              775              780

Gly Cys Glu Ala Asp Pro Thr Thr Pro Val Thr Cys Val Glu Met His
785              790              795              800
```

-continued

```
Cys Glu Phe Gly Ala Ser Cys Val Glu Glu Ala Gly Phe Ala Gln Cys
                805                 810                 815
Val Cys Pro Thr Leu Thr Cys Pro Glu Ala Asn Ser Thr Lys Val Cys
                820                 825                 830
Gly Ser Asp Gly Val Thr Tyr Gly Asn Glu Cys Gln Leu Lys Thr Ile
                835                 840                 845
Ala Cys Arg Gln Arg Leu Asp Ile Ser Ile Gln Ser Leu Gly Pro Cys
                850                 855                 860
Arg Glu Ser Val Ala Pro Gly Val Ser Pro Thr Ser Ala Ser Met Thr
865                 870                 875                 880
Thr Pro Arg His Ile Leu Ser Arg Thr Leu Ala Ser Pro His Ser Ser
                885                 890                 895
Leu Pro Leu Ser Pro Ser Thr Thr Ala His Asp Trp Pro Thr Pro Leu
                900                 905                 910
Pro Thr Ser Pro Gln Thr Val Val Gly Thr Pro Arg Ser Thr Ala Ala
                915                 920                 925
Thr Pro Ser Asp Val Ala Ser Leu Ala Thr Ala Ile Phe Arg Glu Ser
                930                 935                 940
Gly Ser Thr Asn Gly Ser Gly Asp Glu Glu Leu Ser Gly Asp Glu Glu
945                 950                 955                 960
Ala Ser Gly Gly Gly Ser Gly Gly Leu Glu Pro Pro Val Gly Ser Val
                965                 970                 975
Val Val Thr His Gly Pro Pro Ile Glu Arg Ala Ser Cys Tyr Asn Ser
                980                 985                 990
Pro Leu Gly Cys Cys Ser Asp Gly Lys Thr Pro Ser Leu Asp Ser Glu
                995                 1000                1005
Gly Ser Asn Cys Pro Ala Thr Lys Ala Phe Gln Gly Val Leu Glu
                1010                1015                1020
Leu Glu Gly Val Glu Gly Gln Glu Leu Phe Tyr Thr Pro Glu Met
                1025                1030                1035
Ala Asp Pro Lys Ser Glu Leu Phe Gly Glu Thr Ala Arg Ser Ile
                1040                1045                1050
Glu Ser Thr Leu Asp Asp Leu Phe Arg Asn Ser Asp Val Lys Lys
                1055                1060                1065
Asp Phe Trp Ser Ile Arg Leu Arg Glu Leu Gly Pro Gly Lys Leu
                1070                1075                1080
Val Arg Ala Ile Val Asp Val His Phe Asp Pro Thr Thr Ala Phe
                1085                1090                1095
Gln Ala Pro Asp Val Gly Gln Ala Leu Leu Gln Gln Ile Gln Val
                1100                1105                1110
Ser Arg Pro Trp Ala Leu Ala Val Arg Arg Pro Leu Arg Glu His
                1115                1120                1125
Val Arg Phe Leu Asp Phe Asp Trp Phe Pro Thr Phe Phe Thr Gly
                1130                1135                1140
Ala Ala Thr Gly Thr Thr Ala Ala Val Ala Thr Ala Arg Ala Thr
                1145                1150                1155
Thr Val Ser Arg Leu Ser Ala Ser Ser Val Thr Pro Arg Val Tyr
                1160                1165                1170
Pro Ser Tyr Thr Ser Arg Pro Val Gly Arg Thr Ala Pro Leu
                1175                1180                1185
Thr Thr Arg Arg Pro Pro Thr Thr Thr Ala Ser Ile Asp Arg Pro
                1190                1195                1200
```

```
Arg Thr Pro Gly Pro Gln Arg Pro Pro Lys Ser Cys Asp Ser Gln
    1205                1210                1215

Pro Cys Leu His Gly Gly Thr Cys Gln Asp Leu Asp Ser Gly Lys
    1220                1225                1230

Gly Phe Ser Cys Ser Cys Thr Ala Gly Arg Ala Gly Thr Val Cys
    1235                1240                1245

Glu Lys Val Gln Leu Pro Ser Val Pro Ala Phe Lys Gly His Ser
    1250                1255                1260

Phe Leu Ala Phe Pro Thr Leu Arg Ala Tyr His Thr Leu Arg Leu
    1265                1270                1275

Ala Leu Glu Phe Arg Ala Leu Glu Thr Glu Gly Leu Leu Leu Tyr
    1280                1285                1290

Asn Gly Asn Ala Arg Gly Lys Asp Phe Leu Ala Leu Ala Leu Leu
    1295                1300                1305

Asp Gly His Val Gln Phe Arg Phe Asp Thr Gly Ser Gly Pro Ala
    1310                1315                1320

Val Leu Thr Ser Leu Val Pro Val Glu Pro Gly Arg Trp His Arg
    1325                1330                1335

Leu Glu Leu Ser Arg His Trp Arg Gln Gly Thr Leu Ser Val Asp
    1340                1345                1350

Gly Glu Ala Pro Val Val Gly Glu Ser Pro Ser Gly Thr Asp Gly
    1355                1360                1365

Leu Asn Leu Asp Thr Lys Leu Tyr Val Gly Gly Leu Pro Glu Glu
    1370                1375                1380

Gln Val Ala Thr Val Leu Asp Arg Thr Ser Val Gly Ile Gly Leu
    1385                1390                1395

Lys Gly Cys Ile Arg Met Leu Asp Ile Asn Asn Gln Gln Leu Glu
    1400                1405                1410

Leu Ser Asp Trp Gln Arg Ala Val Val Gln Ser Ser Gly Val Gly
    1415                1420                1425

Glu Cys Gly Asp His Pro Cys Ser Pro Asn Pro Cys His Gly Gly
    1430                1435                1440

Ala Leu Cys Gln Ala Leu Glu Ala Gly Val Phe Leu Cys Gln Cys
    1445                1450                1455

Pro Pro Gly Arg Phe Gly Pro Thr Cys Ala Asp Glu Lys Asn Pro
    1460                1465                1470

Cys Gln Pro Asn Pro Cys His Gly Ser Ala Pro Cys His Val Leu
    1475                1480                1485

Ser Arg Gly Gly Ala Lys Cys Ala Cys Pro Leu Gly Arg Ser Gly
    1490                1495                1500

Ser Phe Cys Glu Thr Val Leu Glu Asn Ala Gly Ser Arg Pro Phe
    1505                1510                1515

Ala Asp Phe Asn Gly Phe Ser Tyr Leu Glu Leu Lys Gly Leu His
    1520                1525                1530

Thr Phe Glu Arg Asp Leu Gly Glu Lys Met Ala Leu Glu Met Val
    1535                1540                1545

Phe Leu Ala Arg Gly Pro Ser Gly Leu Leu Leu Tyr Asn Gly Gln
    1550                1555                1560

Lys Thr Asp Gly Lys Gly Asp Phe Val Ser Leu Ala Leu His Asn
    1565                1570                1575

Arg His Leu Glu Phe Arg Tyr Asp Leu Gly Lys Gly Ala Ala Ile
    1580                1585                1590

Ile Arg Ser Lys Glu Pro Ile Ala Leu Gly Thr Trp Val Arg Val
```

```
                    1595                1600                1605
Phe Leu Glu Arg Asn Gly Arg Lys Gly Ala Leu Gln Val Gly Asp
    1610                1615                1620
Gly Pro Arg Val Leu Gly Glu Ser Pro Lys Ser Arg Lys Val Pro
    1625                1630                1635
His Thr Met Leu Asn Leu Lys Glu Pro Leu Tyr Val Gly Gly Ala
    1640                1645                1650
Pro Asp Phe Ser Lys Leu Ala Arg Gly Ala Ala Val Ala Ser Gly
    1655                1660                1665
Phe Asp Gly Ala Ile Gln Leu Val Ser Leu Arg Gly His Gln Leu
    1670                1675                1680
Leu Thr Gln Glu His Val Leu Arg Ala Val Asp Val Ala Pro Phe
    1685                1690                1695
Ala Gly His Pro Cys Thr Gln Ala Val Asp Asn Pro Cys Leu Asn
    1700                1705                1710
Gly Gly Ser Cys Ile Pro Arg Glu Ala Thr Tyr Glu Cys Leu Cys
    1715                1720                1725
Pro Gly Gly Phe Ser Gly Leu His Cys Glu Lys Gly Ile Val Glu
    1730                1735                1740
Lys Ser Val Gly Asp Leu Glu Thr Leu Ala Phe Asp Gly Arg Thr
    1745                1750                1755
Tyr Ile Glu Tyr Leu Asn Ala Val Thr Glu Ser Glu Leu Thr Asn
    1760                1765                1770
Glu Ile Pro Ala Pro Glu Thr Leu Asp Ser Arg Ala Leu Phe Ser
    1775                1780                1785
Glu Lys Ala Leu Gln Ser Asn His Phe Glu Leu Ser Leu Arg Thr
    1790                1795                1800
Glu Ala Thr Gln Gly Leu Val Leu Trp Ile Gly Lys Val Gly Glu
    1805                1810                1815
Arg Ala Asp Tyr Met Ala Leu Ala Ile Val Asp Gly His Leu Gln
    1820                1825                1830
Leu Ser Tyr Asp Leu Gly Ser Gln Pro Val Val Leu Arg Ser Thr
    1835                1840                1845
Val Lys Val Asn Thr Asn Arg Trp Leu Arg Val Arg Ala His Arg
    1850                1855                1860
Glu His Arg Glu Gly Ser Leu Gln Val Gly Asn Glu Ala Pro Val
    1865                1870                1875
Thr Gly Ser Ser Pro Leu Gly Ala Thr Gln Leu Asp Thr Asp Gly
    1880                1885                1890
Ala Leu Trp Leu Gly Gly Leu Gln Lys Leu Pro Val Gly Gln Ala
    1895                1900                1905
Leu Pro Lys Ala Tyr Gly Thr Gly Phe Val Gly Cys Leu Arg Asp
    1910                1915                1920
Val Val Val Gly His Arg Gln Leu His Leu Leu Glu Asp Ala Val
    1925                1930                1935
Thr Lys Pro Glu Leu Arg Pro Cys Pro Thr Leu
    1940                1945

<210> SEQ ID NO 114
<211> LENGTH: 537
<212> TYPE: DNA
<213> ORGANISM: Artificial Sequence
<220> FEATURE:
<223> OTHER INFORMATION: Synthetic
```

<400> SEQUENCE: 114

```
atgcctggct cagcactgct atgctgcctg ctcttactga ctggcatgag gatcagcagg      60
ggccagtaca gccgggaaga caataactgc acccacttcc cagtcggcca gagccacatg     120
ctcctagagc tgcggactgc cttcagccag gtgaagactt tctttcaaac aaaggaccag     180
ctggacaaca tactgctaac cgactcctta atgcaggact ttaagggtta cttgggttgc     240
caagccttat cggaaatgat ccagttttac ctggtagaag tgatgcccca ggcagagaag     300
catggcccag aaatcaagga gcatttgaat tccctgggtg agaagctgaa gaccctcagg     360
atgcggctga gcgctgtca tcgatttctc ccctgtgaaa ataagagcaa ggcagtggag     420
caggtgaaga gtgattttaa taagctccaa gaccaaggtg tctacaaggc catgaatgaa     480
tttgacatct tcatcaactg catagaagca tacatgatga tcaaaatgaa aagctaa       537
```

<210> SEQ ID NO 115
<211> LENGTH: 178
<212> TYPE: PRT
<213> ORGANISM: Artificial Sequence
<220> FEATURE:
<223> OTHER INFORMATION: Synthetic

<400> SEQUENCE: 115

```
Met Pro Gly Ser Ala Leu Leu Cys Cys Leu Leu Leu Thr Gly Met
1               5                   10                  15

Arg Ile Ser Arg Gly Gln Tyr Ser Arg Glu Asp Asn Asn Cys Thr His
            20                  25                  30

Phe Pro Val Gly Gln Ser His Met Leu Leu Glu Leu Arg Thr Ala Phe
        35                  40                  45

Ser Gln Val Lys Thr Phe Phe Gln Thr Lys Asp Gln Leu Asp Asn Ile
    50                  55                  60

Leu Leu Thr Asp Ser Leu Met Gln Asp Phe Lys Gly Tyr Leu Gly Cys
65                  70                  75                  80

Gln Ala Leu Ser Glu Met Ile Gln Phe Tyr Leu Val Glu Val Met Pro
                85                  90                  95

Gln Ala Glu Lys His Gly Pro Glu Ile Lys Glu His Leu Asn Ser Leu
            100                 105                 110

Gly Glu Lys Leu Lys Thr Leu Arg Met Arg Leu Arg Arg Cys His Arg
        115                 120                 125

Phe Leu Pro Cys Glu Asn Lys Ser Lys Ala Val Glu Gln Val Lys Ser
    130                 135                 140

Asp Phe Asn Lys Leu Gln Asp Gln Gly Val Tyr Lys Ala Met Asn Glu
145                 150                 155                 160

Phe Asp Ile Phe Ile Asn Cys Ile Glu Ala Tyr Met Met Ile Lys Met
                165                 170                 175

Lys Ser
```

<210> SEQ ID NO 116
<211> LENGTH: 501
<212> TYPE: DNA
<213> ORGANISM: Artificial Sequence
<220> FEATURE:
<223> OTHER INFORMATION: Synthetic

<400> SEQUENCE: 116

```
atggcagccc ccagcggagg cttctggact gcggtggtcc tggcggccgc agcgctgaaa      60
ttggccgccg ctgtgtccga gcccaccacc gtgccatttg acgtgaggcc cggagggggtc    120
```

```
gtgcattcgt tctcccagga cgtaggaccc gggaacaagt ttacatgtac attcacctac    180
gcttcccaag gagggaccaa cgagcaatgg cagatgagcc tggggacaag tgaagacagc    240 cagcactta cctgtaccat ctggaggccc caggggaaat cctacctcta cttcacacag     300
ttcaaggctg agttgcgagg tgctgagatc gagtatgcca tggcctactc caaagccgca    360
tttgagagag agagtgatgt ccccctgaaa agtgaggagt ttgaagtgac caagacagca    420
gtgtctcaca ggcctggggc cttcaaagct gagctctcca agctggtgat cgtagccaag    480
gcggcacgct cggagctgtg a                                              501
```

<210> SEQ ID NO 117
<211> LENGTH: 166
<212> TYPE: PRT
<213> ORGANISM: Artificial Sequence
<220> FEATURE:
<223> OTHER INFORMATION: Synthetic

<400> SEQUENCE: 117

```
Met Ala Ala Pro Ser Gly Gly Phe Trp Thr Ala Val Val Leu Ala Ala
1               5                   10                  15

Ala Ala Leu Lys Leu Ala Ala Ala Val Ser Glu Pro Thr Thr Val Pro
            20                  25                  30

Phe Asp Val Arg Pro Gly Gly Val Val His Ser Phe Ser Gln Asp Val
        35                  40                  45

Gly Pro Gly Asn Lys Phe Thr Cys Thr Phe Thr Tyr Ala Ser Gln Gly
    50                  55                  60

Gly Thr Asn Glu Gln Trp Gln Met Ser Leu Gly Thr Ser Glu Asp Ser
65                  70                  75                  80

Gln His Phe Thr Cys Thr Ile Trp Arg Pro Gln Gly Lys Ser Tyr Leu
                85                  90                  95

Tyr Phe Thr Gln Phe Lys Ala Glu Leu Arg Gly Ala Glu Ile Glu Tyr
            100                 105                 110

Ala Met Ala Tyr Ser Lys Ala Ala Phe Glu Arg Glu Ser Asp Val Pro
        115                 120                 125

Leu Lys Ser Glu Glu Phe Glu Val Thr Lys Thr Ala Val Ser His Arg
    130                 135                 140

Pro Gly Ala Phe Lys Ala Glu Leu Ser Lys Leu Val Ile Val Ala Lys
145                 150                 155                 160

Ala Ala Arg Ser Glu Leu
                165
```

<210> SEQ ID NO 118
<211> LENGTH: 2412
<212> TYPE: DNA
<213> ORGANISM: Artificial Sequence
<220> FEATURE:
<223> OTHER INFORMATION: Synthetic

<400> SEQUENCE: 118

```
cagtctgtgt tgacgcagcc gccctcagtg tctgcggccc caggacagag ggtcaccatc    60
tcctgctctg gaaccaggtc caacattggg agtgattatg tttcctggta ccaacacctc    120
ccaggaacag cccccaaact cctcgtttat ggcgataatc tgcgaccctc agggattcct    180
gaccgattct ctgcctccaa gtctggcacg tcagccaccc tgggcatcac cggactccag    240
actggggacg aggccgatta ttactgcggc acatgggatt acaccctgaa tggtgtggtg    300
ttcggcggag ggaccaagct gaccgtccta ggtcagccca aggccaaccc cactgtcact    360
```

```
ctgttcccgc ctcctctga ggagctccaa gccaacaagg ccacactagt gtgtctgatc     420
agtgacttct acccgggagc tgtgacagtg gcctggaagg cagatggcag ccccgtcaag    480
gcgggagtgg agaccaccaa accctccaaa cagagcaaca caagtacgc ggccagcagc     540 tacctgagcc tgacgcccga gcagtggaag tcccacagaa gctacagctg ccaggtcacg    600
catgaaggga gcaccgtgga aagacagtg gcccctacag aatgttcagg cgccggatct     660
ggtgaaaact ggagtcatcc ccaattcgag aagggcggaa gcgtgggag tggcgggtcc     720 ggtggaagca actggtcaca cccacaattc gagaaaggcg gttctggcgg atctggtgga    780
tctggcggaa gtaactggtc tcatcctcaa ttcgaaaagg gcggaagcgg tggcggcagg    840
ctaggtggag gctcagtgca ggtgcagctg gtggagtctg ggggaggctt ggtacagcct    900
ggggggtccc tgagactctc ctgtgcagcc tctggattca cctttagcag ctatgccatg    960
agctgggtcc gccaggctcc agggaagggg ctggagtggg tctcagttat ttatagcggt   1020
ggtagtagca catactatgc agactccgtg aagggccggt tcaccatctc cagagataat   1080
tccaagaaca cgctgtatct gcaaatgaac agcctgagag ccgaggacac ggccgtatat   1140
tactgtgcgc gcacttctta cctgaaccat ggtgattact ggggtcaagg tactctggtg   1200
accgtgtcta gcgcctccac caagggccca tcggtcttcc ccctggcacc ctcctccaag   1260
agcacctctg gggcacagc ggccctgggc tgcctggtca aggactactt ccccgaaccg    1320
gtgacggtgt cgtggaactc aggcgccctg accagcggcg tgcacacctt cccggctgtc   1380
ctacagtcct caggactcta ctccctcagc agcgtggtga ccgtgccctc agcagcttg    1440 ggcacccaga cctacatctg caacgtgaac cacaagccca gcaacaccaa ggtggacaag   1500
agagtggagc ccaagagctg cgacaagacc cacacctgcc cccctgccc agccccagag    1560 ctgctgggcg gaccctccgt gttcctgttc cccccaagc caaggacac cctgatgatc     1620 agcaggaccc ccgaggtgac ctgcgtggtg gtggacgtga gccacgagga cccagaggtg   1680
aagttcaact ggtacgtgga cggcgtggag gtgcacaacg ccaagaccaa gccagagag    1740 gagcagtaca acagcaccta cagggtggtg tccgtgctga ccgtgctgca ccaggactgg   1800
ctgaacggca aggaatacaa gtgcaaggtc tccaacaagg ccctgccagc ccccatcgaa   1860
aagaccatca gcaaggccaa gggccagcca cgggagcccc aggtgtacac cctgccccc    1920 tcccgggagg agatgaccaa gaaccaggtg tccctgacct gtctggtgaa gggcttctac   1980
cccagcgaca tcgccgtgga gtgggagagc aacggccagc ccgagaacaa ctacaagacc   2040 accccccag tgctggacag cgacggcagc ttcttcctgt acagcaagct gaccgtggac    2100
aagtccaggt ggcagcaggg caacgtgttc agctgcagcg tgatgcacga ggccctgcac   2160
aaccactaca cccagaagag cctgagcctg tcccccgagc tgcaactgga ggagagctgt   2220
gcggaggcgc aggacgggga gctggacggg ctgtggacga ccatcaccat cttcatcaca   2280
ctcttcctgt taagcgtgtg ctacagtgcc accgtcacct tcttcaaggt gaagtggatc   2340
ttctcctcgg tggtggacct gaagcagacc atcatccccg actacaggaa catgatcgga   2400
cagggggcct ga                                                       2412
```

<210> SEQ ID NO 119
<211> LENGTH: 803
<212> TYPE: PRT
<213> ORGANISM: Artificial Sequence
<220> FEATURE:
<223> OTHER INFORMATION: Synthetic

<400> SEQUENCE: 119

```
Gln Ser Val Leu Thr Gln Pro Pro Ser Val Ala Ala Pro Gly Gln
1               5                   10                  15

Arg Val Thr Ile Ser Cys Ser Gly Thr Arg Ser Asn Ile Gly Ser Asp
                20                  25                  30

Tyr Val Ser Trp Tyr Gln His Leu Pro Gly Thr Ala Pro Lys Leu Leu
            35                  40                  45

Val Tyr Gly Asp Asn Leu Arg Pro Ser Gly Ile Pro Asp Arg Phe Ser
        50                  55                  60

Ala Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Tyr Thr Leu
                85                  90                  95

Asn Gly Val Val Phe Gly Gly Gly Thr Lys Leu Thr Val Leu Gly Gln
            100                 105                 110

Pro Lys Ala Asn Pro Thr Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Gly Ser Pro Val Lys
145                 150                 155                 160

Ala Gly Val Glu Thr Thr Lys Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser Gly Ala Gly Ser Gly Gly Asn Trp
210                 215                 220

Ser His Pro Gln Phe Glu Lys Gly Gly Ser Gly Gly Ser Gly Gly Ser
225                 230                 235                 240

Gly Gly Ser Asn Trp Ser His Pro Gln Phe Glu Lys Gly Gly Ser Gly
            245                 250                 255

Gly Ser Gly Gly Ser Gly Gly Ser Asn Trp Ser His Pro Gln Phe Glu
        260                 265                 270

Lys Gly Gly Ser Gly Gly Gly Arg Leu Gly Gly Gly Ser Val Gln Val
    275                 280                 285

Gln Leu Val Glu Ser Gly Gly Gly Leu Val Gln Pro Gly Gly Ser Leu
    290                 295                 300

Arg Leu Ser Cys Ala Ala Ser Gly Phe Thr Phe Ser Ser Tyr Ala Met
305                 310                 315                 320

Ser Trp Val Arg Gln Ala Pro Gly Lys Gly Leu Glu Trp Val Ser Val
                325                 330                 335

Ile Tyr Ser Gly Gly Ser Ser Thr Tyr Tyr Ala Asp Ser Val Lys Gly
            340                 345                 350

Arg Phe Thr Ile Ser Arg Asp Asn Ser Lys Asn Thr Leu Tyr Leu Gln
        355                 360                 365

Met Asn Ser Leu Arg Ala Glu Asp Thr Ala Val Tyr Tyr Cys Ala Arg
    370                 375                 380

Thr Ser Tyr Leu Asn His Gly Asp Tyr Trp Gly Gln Gly Thr Leu Val
385                 390                 395                 400

Thr Val Ser Ser Ala Ser Thr Lys Gly Pro Ser Val Phe Pro Leu Ala
                405                 410                 415
```

-continued

Pro Ser Ser Lys Ser Thr Ser Gly Gly Thr Ala Ala Leu Gly Cys Leu
                420                 425                 430

Val Lys Asp Tyr Phe Pro Glu Pro Val Thr Val Ser Trp Asn Ser Gly
            435                 440                 445

Ala Leu Thr Ser Gly Val His Thr Phe Pro Ala Val Leu Gln Ser Ser
        450                 455                 460

Gly Leu Tyr Ser Leu Ser Ser Val Val Thr Val Pro Ser Ser Ser Leu
465                 470                 475                 480

Gly Thr Gln Thr Tyr Ile Cys Asn Val Asn His Lys Pro Ser Asn Thr
                485                 490                 495

Lys Val Asp Lys Arg Val Glu Pro Lys Ser Cys Asp Lys Thr His Thr
            500                 505                 510

Cys Pro Pro Cys Pro Ala Pro Glu Leu Leu Gly Gly Pro Ser Val Phe
        515                 520                 525

Leu Phe Pro Pro Lys Pro Lys Asp Thr Leu Met Ile Ser Arg Thr Pro
        530                 535                 540

Glu Val Thr Cys Val Val Val Asp Val Ser His Glu Asp Pro Glu Val
545                 550                 555                 560

Lys Phe Asn Trp Tyr Val Asp Gly Val Glu Val His Asn Ala Lys Thr
                565                 570                 575

Lys Pro Arg Glu Glu Gln Tyr Asn Ser Thr Tyr Arg Val Val Ser Val
            580                 585                 590

Leu Thr Val Leu His Gln Asp Trp Leu Asn Gly Lys Glu Tyr Lys Cys
        595                 600                 605

Lys Val Ser Asn Lys Ala Leu Pro Ala Pro Ile Glu Lys Thr Ile Ser
610                 615                 620

Lys Ala Lys Gly Gln Pro Arg Glu Pro Gln Val Tyr Thr Leu Pro Pro
625                 630                 635                 640

Ser Arg Glu Glu Met Thr Lys Asn Gln Val Ser Leu Thr Cys Leu Val
                645                 650                 655

Lys Gly Phe Tyr Pro Ser Asp Ile Ala Val Glu Trp Glu Ser Asn Gly
            660                 665                 670

Gln Pro Glu Asn Asn Tyr Lys Thr Thr Pro Pro Val Leu Asp Ser Asp
        675                 680                 685

Gly Ser Phe Phe Leu Tyr Ser Lys Leu Thr Val Asp Lys Ser Arg Trp
690                 695                 700

Gln Gln Gly Asn Val Phe Ser Cys Ser Val Met His Glu Ala Leu His
705                 710                 715                 720

Asn His Tyr Thr Gln Lys Ser Leu Ser Leu Ser Pro Glu Leu Gln Leu
                725                 730                 735

Glu Glu Ser Cys Ala Glu Ala Gln Asp Gly Glu Leu Asp Gly Leu Trp
            740                 745                 750

Thr Thr Ile Thr Ile Phe Ile Thr Leu Phe Leu Leu Ser Val Cys Tyr
        755                 760                 765

Ser Ala Thr Val Thr Phe Phe Lys Val Lys Trp Ile Phe Ser Ser Val
        770                 775                 780

Val Asp Leu Lys Gln Thr Ile Ile Pro Asp Tyr Arg Asn Met Ile Gly
785                 790                 795                 800

Gln Gly Ala

<210> SEQ ID NO 120
<211> LENGTH: 645
<212> TYPE: DNA
<213> ORGANISM: Artificial Sequence
<220> FEATURE:
<223> OTHER INFORMATION: Synthetic

<400> SEQUENCE: 120

```
cagtctgtgt tgacgcagcc gccctcagtg tctgcggccc caggacagag ggtcaccatc    60
tcctgctctg gaaccaggtc caacattggg agtgattatg tttcctggta ccaacacctc   120
ccaggaacag cccccaaact cctcgtttat ggcgataatc tgcgaccctc agggattcct   180
gaccgattct ctgcctccaa gtctggcacg tcagccaccc tgggcatcac cggactccag   240
actggggacg aggccgatta ttactgcggc acatgggatt acaccctgaa tggtgtggtg   300
ttcggcggag ggaccaagct gaccgtccta tcttcagcct ccaccaaggg cccatcggtc   360
ttccccctgg caccctcctc caagagcacc tctgggggca cagcggccct gggctgcctg   420
gtcaaggact acttccccga accggtgacg gtgtcgtgga actcaggcgc cctgaccagc   480
ggcgtgcaca ccttcccggc tgtcctacag tcctcaggac tctactccct cagcagcgtg   540
gtgaccgtgc cctccagcag cttgggcacc cagacctaca tctgcaacgt gaaccacaag   600
cccagcaaca ccaaggtgga caagagagtg gagcccaaga gctgc                   645
```

<210> SEQ ID NO 121
<211> LENGTH: 215
<212> TYPE: PRT
<213> ORGANISM: Artificial Sequence
<220> FEATURE:
<223> OTHER INFORMATION: Synthetic

<400> SEQUENCE: 121

```
Gln Ser Val Leu Thr Gln Pro Pro Ser Val Ser Ala Ala Pro Gly Gln
1               5                   10                  15
Arg Val Thr Ile Ser Cys Ser Gly Thr Arg Ser Asn Ile Gly Ser Asp
            20                  25                  30
Tyr Val Ser Trp Tyr Gln His Leu Pro Gly Thr Ala Pro Lys Leu Leu
        35                  40                  45
Val Tyr Gly Asp Asn Leu Arg Pro Ser Gly Ile Pro Asp Arg Phe Ser
    50                  55                  60
Ala Ser Lys Ser Gly Thr Ser Ala Thr Leu Gly Ile Thr Gly Leu Gln
65                  70                  75                  80
Thr Gly Asp Glu Ala Asp Tyr Tyr Cys Gly Thr Trp Asp Tyr Thr Leu
                85                  90                  95
Asn Gly Val Val Phe Gly Gly Gly Thr Lys Leu Thr Val Leu Ser Ser
            100                 105                 110
Ala Ser Thr Lys Gly Pro Ser Val Phe Pro Leu Ala Pro Ser Ser Lys
        115                 120                 125
Ser Thr Ser Gly Gly Thr Ala Ala Leu Gly Cys Leu Val Lys Asp Tyr
    130                 135                 140
Phe Pro Glu Pro Val Thr Val Ser Trp Asn Ser Gly Ala Leu Thr Ser
145                 150                 155                 160
Gly Val His Thr Phe Pro Ala Val Leu Gln Ser Ser Gly Leu Tyr Ser
                165                 170                 175
Leu Ser Ser Val Val Thr Val Pro Ser Ser Ser Leu Gly Thr Gln Thr
            180                 185                 190
Tyr Ile Cys Asn Val Asn His Lys Pro Ser Asn Thr Lys Val Asp Lys
        195                 200                 205
Arg Val Glu Pro Lys Ser Cys
    210                 215
```

<210> SEQ ID NO 122
<211> LENGTH: 1566
<212> TYPE: DNA
<213> ORGANISM: Artificial Sequence
<220> FEATURE:
<223> OTHER INFORMATION: Synthetic

<400> SEQUENCE: 122

```
caggtgcagc tggtggagtc tgggggaggc ttggtacagc ctgggggtc cctgagactc        60
tcctgtgcag cctctggatt caccttagc agctatgcca tgagctgggt ccgccaggct       120
ccagggaagg gctggagtg gtctcagtt atttatagcg gtggtagtag cacatactat       180
gcagactccg tgaagggccg gttcaccatc tccagagata attccaagaa cacgctgtat     240
ctgcaaatga acagcctgag agccgaggac acggccgtat attactgtgc gcgcacttct     300
tacctgaacc atggtgatta ctggggtcaa ggtactctgg tgaccgtgtc tagcgcctcc     360
gtggctgcac catctgtctt catcttcccg ccatctgatg agcagttgaa atctggaact     420
gcctctgttg tgtgcctgct gaataacttc tatcccagag aggccaaagt acagtggaag     480
gtggataacg ccctccaatc gggtaactcc caggagagtg tcacagagca ggacagcaag     540
gacagcacct acagcctcag cagcaccctg acgctgagca agcagactac gagaaacac     600
aaagtctacg cctgcgaagt cacccatcag ggcctgagct cgcccgtcac aaagagcttc     660
aacaggggag agtgtgacaa gacccacacc tgccccccct gcccagcccc agagctgctg     720
ggcggacccct ccgtgttcct gttccccccc aagcccaagg acaccctgat gatcagcagg     780
accccccgagg tgacctgcgt ggtggtggac gtgagccacg aggacccaga ggtgaagttc     840
aactggtacg tggacggcgt ggaggtgcac aacgccaaga ccaagcccag agaggagcag     900
tacaacagca cctacagggt ggtgtccgtg ctgaccgtgc tgcaccagga ctggctgaac     960
ggcaaggaat acaagtgcaa ggtctccaac aaggccctgc cagcccccat cgaaaagacc    1020
atcagcaagg ccaagggcca gccacgggag ccccaggtgt acaccctgcc ccctcccgg    1080
gaggagatga ccaagaacca ggtgtccctg acctgtctgg tgaagggctt ctaccccagc    1140
gacatcgccg tggagtggga gagcaacggc cagcccgaga caactacaa gaccacccc    1200
ccagtgctgg acagcgacgg cagcttcttc ctgtacagca agctgaccgt ggacaagtcc    1260
aggtggcagc agggcaacgt gttcagctgc agcgtgatgc acgaggccct gcacaaccac    1320
tacacccaga gagcctgag cctgtccccc gagctgcaac tggaggagag ctgtgcggag    1380
gcgcaggacg gggagctgga cgggctgtgg acgaccatca ccatcttcat cacactcttc    1440
ctgttaagcg tgtgctacag tgccaccgtc accttcttca aggtgaagtg gatcttctcc    1500
tcggtggtgg acctgaagca gaccatcatc cccgactaca ggaacatgat cggacagggg    1560
gcctga                                                                  1566
```

<210> SEQ ID NO 123
<211> LENGTH: 521
<212> TYPE: PRT
<213> ORGANISM: Artificial Sequence
<220> FEATURE:
<223> OTHER INFORMATION: Synthetic

<400> SEQUENCE: 123

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30
```

```
Ala Met Ser Trp Val Arg Gln Ala Pro Gly Lys Gly Leu Glu Trp Val
         35                  40                  45

Ser Val Ile Tyr Ser Gly Gly Ser Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Thr Ser Tyr Leu Asn His Gly Asp Tyr Trp Gly Gln Gly Thr
             100                 105                 110

Leu Val Thr Val Ser Ser Ala Ser Val Ala Ala Pro Ser Val Phe Ile
         115                 120                 125

Phe Pro Pro Ser Asp Glu Gln Leu Lys Ser Gly Thr Ala Ser Val Val
 130                 135                 140

Cys Leu Leu Asn Asn Phe Tyr Pro Arg Glu Ala Lys Val Gln Trp Lys
 145                 150                 155                 160

Val Asp Asn Ala Leu Gln Ser Gly Asn Ser Gln Glu Ser Val Thr Glu
                 165                 170                 175

Gln Asp Ser Lys Asp Ser Thr Tyr Ser Leu Ser Ser Thr Leu Thr Leu
             180                 185                 190

Ser Lys Ala Asp Tyr Glu Lys His Lys Val Tyr Ala Cys Glu Val Thr
         195                 200                 205

His Gln Gly Leu Ser Ser Pro Val Thr Lys Ser Phe Asn Arg Gly Glu
 210                 215                 220

Cys Asp Lys Thr His Thr Cys Pro Pro Cys Pro Ala Pro Glu Leu Leu
 225                 230                 235                 240

Gly Gly Pro Ser Val Phe Leu Phe Pro Pro Lys Pro Lys Asp Thr Leu
                 245                 250                 255

Met Ile Ser Arg Thr Pro Glu Val Thr Cys Val Val Val Asp Val Ser
             260                 265                 270

His Glu Asp Pro Glu Val Lys Phe Asn Trp Tyr Val Asp Gly Val Glu
         275                 280                 285

Val His Asn Ala Lys Thr Lys Pro Arg Glu Glu Gln Tyr Asn Ser Thr
 290                 295                 300

Tyr Arg Val Val Ser Val Leu Thr Val Leu His Gln Asp Trp Leu Asn
 305                 310                 315                 320

Gly Lys Glu Tyr Lys Cys Lys Val Ser Asn Lys Ala Leu Pro Ala Pro
                 325                 330                 335

Ile Glu Lys Thr Ile Ser Lys Ala Lys Gly Gln Pro Arg Glu Pro Gln
             340                 345                 350

Val Tyr Thr Leu Pro Pro Ser Arg Glu Glu Met Thr Lys Asn Gln Val
         355                 360                 365

Ser Leu Thr Cys Leu Val Lys Gly Phe Tyr Pro Ser Asp Ile Ala Val
 370                 375                 380

Glu Trp Glu Ser Asn Gly Gln Pro Glu Asn Asn Tyr Lys Thr Thr Pro
 385                 390                 395                 400

Pro Val Leu Asp Ser Asp Gly Ser Phe Phe Leu Tyr Ser Lys Leu Thr
                 405                 410                 415

Val Asp Lys Ser Arg Trp Gln Gln Gly Asn Val Phe Ser Cys Ser Val
             420                 425                 430

Met His Glu Ala Leu His Asn His Tyr Thr Gln Lys Ser Leu Ser Leu
         435                 440                 445
```

```
Ser Pro Glu Leu Gln Leu Glu Glu Ser Cys Ala Glu Ala Gln Asp Gly
    450                 455                 460

Glu Leu Asp Gly Leu Trp Thr Thr Ile Thr Ile Phe Ile Thr Leu Phe
465                 470                 475                 480

Leu Leu Ser Val Cys Tyr Ser Ala Thr Val Thr Phe Phe Lys Val Lys
                485                 490                 495

Trp Ile Phe Ser Ser Val Val Asp Leu Lys Gln Thr Ile Ile Pro Asp
                500                 505                 510

Tyr Arg Asn Met Ile Gly Gln Gly Ala
            515                 520
```

<210> SEQ ID NO 124
<211> LENGTH: 486
<212> TYPE: DNA
<213> ORGANISM: Artificial Sequence
<220> FEATURE:
<223> OTHER INFORMATION: Synthetic

<400> SEQUENCE: 124

```
atgaaaattt tgaaaccata tatgaggaat acatccatct cgtgctactt gtgtttcctt      60
ctaaacagtc acttttaac tgaggctggc attcatgtct tcattttggg ctgtgtcagt     120
gtaggtctcc ctaaaacaga ggccaactgg atagatgtaa gatatgacct ggagaaaatt    180
gaaagcctta ttcaatctat tcatattgac accactttat acactgacag tgactttcat    240
cccagttgca agttactgc aatgaactgc tttctcctgg aattgcaggt tattttacat     300
gagtacagta acatgactct taatgaaaca gtaagaaacg tgctctacct tgcaaacagc    360
actctgtctt ctaacaagaa tgtagcagaa tctggctgca aggaatgtga ggagctggag    420
gagaaaacct tcacagagtt tttgcaaagc tttatacgca ttgtccaaat gttcatcaac    480
acgtcc                                                               486
```

<210> SEQ ID NO 125
<211> LENGTH: 162
<212> TYPE: PRT
<213> ORGANISM: Artificial Sequence
<220> FEATURE:
<223> OTHER INFORMATION: Synthetic

<400> SEQUENCE: 125

```
Met Lys Ile Leu Lys Pro Tyr Met Arg Asn Thr Ser Ile Ser Cys Tyr
1               5                   10                  15

Leu Cys Phe Leu Leu Asn Ser His Phe Leu Thr Glu Ala Gly Ile His
                20                  25                  30

Val Phe Ile Leu Gly Cys Val Ser Val Gly Leu Pro Lys Thr Glu Ala
            35                  40                  45

Asn Trp Ile Asp Val Arg Tyr Asp Leu Glu Lys Ile Glu Ser Leu Ile
    50                  55                  60

Gln Ser Ile His Ile Asp Thr Thr Leu Tyr Thr Asp Ser Asp Phe His
65                  70                  75                  80

Pro Ser Cys Lys Val Thr Ala Met Asn Cys Phe Leu Leu Glu Leu Gln
                85                  90                  95

Val Ile Leu His Glu Tyr Ser Asn Met Thr Leu Asn Glu Thr Val Arg
            100                 105                 110

Asn Val Leu Tyr Leu Ala Asn Ser Thr Leu Ser Ser Asn Lys Asn Val
        115                 120                 125

Ala Glu Ser Gly Cys Lys Glu Cys Glu Glu Leu Glu Glu Lys Thr Phe
    130                 135                 140
```

Thr Glu Phe Leu Gln Ser Phe Ile Arg Ile Val Gln Met Phe Ile Asn
145                 150                 155                 160

Thr Ser

<210> SEQ ID NO 126
<211> LENGTH: 1185
<212> TYPE: DNA
<213> ORGANISM: Artificial Sequence
<220> FEATURE:
<223> OTHER INFORMATION: Synthetic

<400> SEQUENCE: 126

```
cagtctgtgt tgacgcagcc gccctcagtg tctgcggccc caggacagag ggtcaccatc        60
tcctgctctg gaaccaggtc caacattggg agtgattatg tttcctggta ccaacacctc       120
ccaggaacag cccccaaact cctcgtttat ggcgataatc tgcgaccctc agggattcct       180
gaccgattct ctgcctccaa gtctggcacg tcagccaccc tgggcatcac cggactccag       240
actgggacg aggccgatta ttactgcggc acatgggatt acaccctgaa tggtgtggtg        300
ttcggcggag ggaccaagct gaccgtccta ggttctagag gtggtggtgg tagcggcggc       360
ggcggctctg gtggtggtgg atccctcgag atggcccagg tgcagctggt ggagtctggg       420
ggaggcttgg tacagcctgg ggggtccctg agactctcct gtgcagcctc tggattcacc       480
tttagcagct atgccatgag ctgggtccgc caggctccag gaaggggct ggagtgggtc        540
tcagttattt atagcggtgg tagtagcaca tactatgcag actccgtgaa gggccggttc       600
accatctcca gagataattc caagaacacg ctgtatctgc aaatgaacag cctgagagcc       660
gaggacacgg ccgtatatta ctgtgcgcgc acttcttacc tgaaccatgg tgattactgg       720
ggtcaaggta ctctggtgac cgtgtctagc gccgctgcag tggtcccgt gctgcagaaa        780
gttaatagca ccaccactaa acctgtcctg aggactccta gtccagtgca cccaacaggg       840
accagtcagc cacagagacc ggaagactgc agaccaagag gttcagtgaa gggaaccggc       900
ctggatttcg cctgcgattt ttgggccctg gtcgtcgtcg caggagtttt gttttgctat       960
ggactgctcg tcacagttgc tttgtgtgtt atctggacaa ggaaacggtg gcaaaatgag      1020
aagtttgggg tggacatgcc agatgactat gaagatgaaa atctctatga gggcctgaac      1080
cttgatgact gttctatgta tgaggacatc tccaggggac tccagggcac ctaccaggat      1140
gtgggcaacc tccacattgg agatgcccag ctggaaaagc catga                     1185
```

<210> SEQ ID NO 127
<211> LENGTH: 394
<212> TYPE: PRT
<213> ORGANISM: Artificial Sequence
<220> FEATURE:
<223> OTHER INFORMATION: Synthetic

<400> SEQUENCE: 127

Gln Ser Val Leu Thr Gln Pro Pro Ser Val Ser Ala Ala Pro Gly Gln
1               5                   10                  15

Arg Val Thr Ile Ser Cys Ser Gly Thr Arg Ser Asn Ile Gly Ser Asp
            20                  25                  30

Tyr Val Ser Trp Tyr Gln His Leu Pro Gly Thr Ala Pro Lys Leu Leu
        35                  40                  45

Val Tyr Gly Asp Asn Leu Arg Pro Ser Gly Ile Pro Asp Arg Phe Ser
    50                  55                  60

Ala Ser Lys Ser Gly Thr Ser Ala Thr Leu Gly Ile Thr Gly Leu Gln

```
                65                  70                  75                  80
Thr Gly Asp Glu Ala Asp Tyr Tyr Cys Gly Thr Trp Asp Tyr Thr Leu
                    85                  90                  95

Asn Gly Val Val Phe Gly Gly Thr Lys Leu Thr Val Leu Gly Ser
                100                 105                 110

Arg Gly Gly Gly Ser Gly Gly Gly Ser Gly Gly Gly Ser
                115                 120                 125

Leu Glu Met Ala Gln Val Gln Leu Val Glu Ser Gly Gly Gly Leu Val
    130                 135                 140

Gln Pro Gly Gly Ser Leu Arg Leu Ser Cys Ala Ala Ser Gly Phe Thr
145                 150                 155                 160

Phe Ser Ser Tyr Ala Met Ser Trp Val Arg Gln Ala Pro Gly Lys Gly
                165                 170                 175

Leu Glu Trp Val Ser Val Ile Tyr Ser Gly Gly Ser Ser Thr Tyr Tyr
                180                 185                 190

Ala Asp Ser Val Lys Gly Arg Phe Thr Ile Ser Arg Asp Asn Ser Lys
                195                 200                 205

Asn Thr Leu Tyr Leu Gln Met Asn Ser Leu Arg Ala Glu Asp Thr Ala
    210                 215                 220

Val Tyr Tyr Cys Ala Arg Thr Ser Tyr Leu Asn His Gly Asp Tyr Trp
225                 230                 235                 240

Gly Gln Gly Thr Leu Val Thr Val Ser Ala Ala Val Val Pro
                245                 250                 255

Val Leu Gln Lys Val Asn Ser Thr Thr Thr Lys Pro Val Leu Arg Thr
                260                 265                 270

Pro Ser Pro Val His Pro Thr Gly Thr Ser Gln Pro Gln Arg Pro Glu
                275                 280                 285

Asp Cys Arg Pro Arg Gly Ser Val Lys Gly Thr Gly Leu Asp Phe Ala
                290                 295                 300

Cys Asp Phe Trp Ala Leu Val Val Val Ala Gly Val Leu Phe Cys Tyr
305                 310                 315                 320

Gly Leu Leu Val Thr Val Ala Leu Cys Val Ile Trp Thr Arg Lys Arg
                325                 330                 335

Trp Gln Asn Glu Lys Phe Gly Val Asp Met Pro Asp Tyr Glu Asp
                340                 345                 350

Glu Asn Leu Tyr Glu Gly Leu Asn Leu Asp Asp Cys Ser Met Tyr Glu
                355                 360                 365

Asp Ile Ser Arg Gly Leu Gln Gly Thr Tyr Gln Asp Val Gly Asn Leu
                370                 375                 380

His Ile Gly Asp Ala Gln Leu Glu Lys Pro
385                 390
```

<210> SEQ ID NO 128
<211> LENGTH: 1152
<212> TYPE: DNA
<213> ORGANISM: Artificial Sequence
<220> FEATURE:
<223> OTHER INFORMATION: Synthetic

<400> SEQUENCE: 128

```
gaggttcaac ttgttcaatc tggggcagaa gtgaagaagc cgggggcatc tgtgaaagta      60
tcatgcaaaa catccggcta tacgtttacc gaatacacca ttcactgggt cagacaggct     120
cccggtcaaa gcctcgaatg gatgggaaat attaacccta caatggcgg aaccacatat     180 aatcagaaat tccaaggccg agtgacgata actgtcgata agagtacgtc cacagcttac     240
```

```
atggaactca gctctttgag atccgaagac actgcagttt attattgtgc agctggatgg    300
aacttcgact attggggaca agggactctt gttacggtgt ccagtggcaa accaggtagt    360
ggtaaacccg gaagcggcaa gcccgggagc ggtaaacctg gtagcgacat cgtcatgact    420
caaagccctg actcactcgc cgtgagcctg ggagagcgtg caacgctatc ttgtcgggcc    480
tctcaggatg tcggaactgc tgtagactgg tatcaacaga aacctgacca atcaccaaaa    540
ctcctgattt attgggcctc aacacgtcac acaggagtgc cagataggtt cacaggtagt    600
ggcagtggaa ctgattttac tttgacaatt agcagcctgc aagccgaaga tgtagccgtt    660
tacttctgtc aacaatataa ctcatacccc ctaacgttcg gtgccgggac gaaggtagag    720
attaaagtgg tccccgtgct gcagaaagtt aatagcacca ccactaaacc tgtcctgagg    780
actcctagtc cagtgcaccc aacagggacc agtcagccac agagaccgga agactgcaga    840
ccaagaggtt cagtgaaggg aaccggcctg gatttcgcct gcgattttg gggccctggtc    900 gtcgtcgcag gagttttgtt ttgctatgga ctgctcgtca cagttgcttt gtgtgttatc    960
tggacaagga aacggtggca aaatgagaag tttggggtgg acatgccaga tgactatgaa   1020
gatgaaaatc tctatgaggg cctgaacctt gatgactgtt ctatgtatga ggacatctcc   1080
aggggactcc agggcaccta ccaggatgtg ggcaacctcc acattggaga tgcccagctg   1140
gaaaagccat ga                                                        1152

<210> SEQ ID NO 129
<211> LENGTH: 383
<212> TYPE: PRT
<213> ORGANISM: Artificial Sequence
<220> FEATURE:
<223> OTHER INFORMATION: Synthetic

<400> SEQUENCE: 129

Glu Val Gln Leu Val Gln Ser Gly Ala Glu Val Lys Lys Pro Gly Ala
1               5                   10                  15

Ser Val Lys Val Ser Cys Lys Thr Ser Gly Tyr Thr Phe Thr Glu Tyr
            20                  25                  30

Thr Ile His Trp Val Arg Gln Ala Pro Gly Gln Ser Leu Glu Trp Met
        35                  40                  45

Gly Asn Ile Asn Pro Asn Asn Gly Gly Thr Thr Tyr Asn Gln Lys Phe
    50                  55                  60

Gln Gly Arg Val Thr Ile Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ala Gly Trp Asn Phe Asp Tyr Trp Gly Gln Gly Thr Leu Val Thr
            100                 105                 110

Val Ser Ser Gly Lys Pro Gly Ser Gly Lys Pro Gly Ser Gly Lys Pro
        115                 120                 125

Gly Ser Gly Lys Pro Gly Ser Asp Ile Val Met Thr Gln Ser Pro Asp
    130                 135                 140

Ser Leu Ala Val Ser Leu Gly Glu Arg Ala Thr Leu Ser Cys Arg Ala
145                 150                 155                 160

Ser Gln Asp Val Gly Thr Ala Val Asp Trp Tyr Gln Gln Lys Pro Asp
                165                 170                 175

Gln Ser Pro Lys Leu Leu Ile Tyr Trp Ala Ser Thr Arg His Thr Gly
            180                 185                 190
```

```
Val Pro Asp Arg Phe Thr Gly Ser Gly Ser Gly Thr Asp Phe Thr Leu
            195                 200                 205

Thr Ile Ser Ser Leu Gln Ala Glu Asp Val Ala Val Tyr Phe Cys Gln
        210                 215                 220

Gln Tyr Asn Ser Tyr Pro Leu Thr Phe Gly Ala Gly Thr Lys Val Glu
225                 230                 235                 240

Ile Lys Val Val Pro Val Leu Gln Lys Val Asn Ser Thr Thr Thr Lys
                245                 250                 255

Pro Val Leu Arg Thr Pro Ser Pro Val His Pro Thr Gly Thr Ser Gln
            260                 265                 270

Pro Gln Arg Pro Glu Asp Cys Arg Pro Arg Gly Ser Val Lys Gly Thr
        275                 280                 285

Gly Leu Asp Phe Ala Cys Asp Phe Trp Ala Leu Val Val Val Ala Gly
        290                 295                 300

Val Leu Phe Cys Tyr Gly Leu Leu Val Thr Val Ala Leu Cys Val Ile
305                 310                 315                 320

Trp Thr Arg Lys Arg Trp Gln Asn Glu Lys Phe Gly Val Asp Met Pro
                325                 330                 335

Asp Asp Tyr Glu Asp Glu Asn Leu Tyr Glu Gly Leu Asn Leu Asp Asp
            340                 345                 350

Cys Ser Met Tyr Glu Asp Ile Ser Arg Gly Leu Gln Gly Thr Tyr Gln
        355                 360                 365

Asp Val Gly Asn Leu His Ile Gly Asp Ala Gln Leu Glu Lys Pro
        370                 375                 380

<210> SEQ ID NO 130
<211> LENGTH: 1344
<212> TYPE: DNA
<213> ORGANISM: Mus musculus

<400> SEQUENCE: 130
atgtgtcagt cacgctatct tctcttcctt gctactctgg ccttgctcaa tcacttgtcc      60
cttgctcgtg tgattcctgt gtccggccca gctaggtgtc tctcccagtc acggaatctc     120
ctgaaaacca cggatgacat ggtaaagaca gctaggggaga aactcaagca ctactcctgc     180
acagctgagg atatcgatca tgaggacatc accagggacc agacatccac tctgaaaact     240
tgcctgcctt tggaactcca caagaacgaa tcttgtctgg caacgcgtga aacgagttct     300
actacaagag ggtcctgtct tcccctcaa aagacaagcc ttatgatgac cttgtgtctc     360
ggtagcattt atgaggacct aaagatgtat caaaccgagt ttcaggctat caatgcagcg     420
ctccagaatc ataaccatca gcagatcatt cttgacaaag gaatgctcgt ggccattgat     480
gaactaatgc agagcctaaa ccacaatggc gagactcttc gacagaaacc gcctgtgggc     540
gaggccgatc catatagagt caaaatgaaa ctgtgtattc tcctgcatgc atttagtact     600
cgtgtagtga ctattaacag agtgatgggt tacctttcct cagctcccag agggcccaca     660
atcaagccct gtcctccatg caaatgccca gcacctaacc tcttgggtgg accatccgtc     720
ttcatcttcc ctccaaagat caaggatgta ctcatgatct ccctgagccc catagtcaca     780
tgtgtggtgg tggatgtgag cgaggatgac ccagatgtcc agatcagctg gtttgtgaac     840
aacgtggaag tacacacagc tcagacacaa acccatagag aggattacaa cagtactctc     900
cgggtggtca gtgccctccc catccagcac caggactgga tgagtggcaa ggagttcaaa     960
tgcaaggtca caacaagaga cctcccagcg cccatcgaga gaaccatctc aaaacccaaa    1020
gggtcagtaa gagctccaca ggtatatgtc ttgcctccac cagaagaaga gatgactaag    1080
```

```
aaacaggtca ctctgacctg catggtcaca gacttcatgc ctgaagacat ttacgtggag    1140
tggaccaaca acgggaaaac agagctaaac tacaagaaca ctgaaccagt cctggactct    1200
gatggttctt acttcatgta cagcaagctg agagtggaaa agaagaactg ggtggaaaga    1260
aatagctact cctgttcagt ggtccacgag ggtctgcaca atcaccacac gactaagagc    1320
ttctcccgga ctccgggtaa atag                                           1344
```

```
<210> SEQ ID NO 131
<211> LENGTH: 447
<212> TYPE: PRT
<213> ORGANISM: Mus musculus

<400> SEQUENCE: 131
```

| | | | | | | | | | | | | | | |
|---|---|---|---|---|---|---|---|---|---|---|---|---|---|---|
| Met | Cys | Gln | Ser | Arg | Tyr | Leu | Leu | Phe | Leu | Ala | Thr | Leu | Ala | Leu | Leu |
| 1 | | | | 5 | | | | | 10 | | | | | 15 | |
| Asn | His | Leu | Ser | Leu | Ala | Arg | Val | Ile | Pro | Val | Ser | Gly | Pro | Ala | Arg |
| | | | 20 | | | | | 25 | | | | | 30 | | |
| Cys | Leu | Ser | Gln | Ser | Arg | Asn | Leu | Leu | Lys | Thr | Thr | Asp | Asp | Met | Val |
| | | | 35 | | | | | 40 | | | | | 45 | | |
| Lys | Thr | Ala | Arg | Glu | Lys | Leu | Lys | His | Tyr | Ser | Cys | Thr | Ala | Glu | Asp |
| 50 | | | | | 55 | | | | | 60 | | | | | |
| Ile | Asp | His | Glu | Asp | Ile | Thr | Arg | Asp | Gln | Thr | Ser | Thr | Leu | Lys | Thr |
| 65 | | | | | 70 | | | | | 75 | | | | | 80 |
| Cys | Leu | Pro | Leu | Glu | Leu | His | Lys | Asn | Glu | Ser | Cys | Leu | Ala | Thr | Arg |
| | | | | 85 | | | | | 90 | | | | | 95 | |
| Glu | Thr | Ser | Ser | Thr | Thr | Arg | Gly | Ser | Cys | Leu | Pro | Pro | Gln | Lys | Thr |
| | | | 100 | | | | | 105 | | | | | 110 | | |
| Ser | Leu | Met | Met | Thr | Leu | Cys | Leu | Gly | Ser | Ile | Tyr | Glu | Asp | Leu | Lys |
| | | | 115 | | | | | 120 | | | | | 125 | | |
| Met | Tyr | Gln | Thr | Glu | Phe | Gln | Ala | Ile | Asn | Ala | Ala | Leu | Gln | Asn | His |
| | 130 | | | | | 135 | | | | | 140 | | | | |
| Asn | His | Gln | Gln | Ile | Ile | Leu | Asp | Lys | Gly | Met | Leu | Val | Ala | Ile | Asp |
| 145 | | | | | 150 | | | | | 155 | | | | | 160 |
| Glu | Leu | Met | Gln | Ser | Leu | Asn | His | Asn | Gly | Glu | Thr | Leu | Arg | Gln | Lys |
| | | | | 165 | | | | | 170 | | | | | 175 | |
| Pro | Pro | Val | Gly | Glu | Ala | Asp | Pro | Tyr | Arg | Val | Lys | Met | Lys | Leu | Cys |
| | | | 180 | | | | | 185 | | | | | 190 | | |
| Ile | Leu | Leu | His | Ala | Phe | Ser | Thr | Arg | Val | Val | Thr | Ile | Asn | Arg | Val |
| | | | 195 | | | | | 200 | | | | | 205 | | |
| Met | Gly | Tyr | Leu | Ser | Ser | Ala | Pro | Arg | Gly | Pro | Thr | Ile | Lys | Pro | Cys |
| | 210 | | | | | 215 | | | | | 220 | | | | |
| Pro | Pro | Cys | Lys | Cys | Pro | Ala | Pro | Asn | Leu | Leu | Gly | Gly | Pro | Ser | Val |
| 225 | | | | | 230 | | | | | 235 | | | | | 240 |
| Phe | Ile | Phe | Pro | Pro | Lys | Ile | Lys | Asp | Val | Leu | Met | Ile | Ser | Leu | Ser |
| | | | | 245 | | | | | 250 | | | | | 255 | |
| Pro | Ile | Val | Thr | Cys | Val | Val | Val | Asp | Val | Ser | Glu | Asp | Asp | Pro | Asp |
| | | | 260 | | | | | 265 | | | | | 270 | | |
| Val | Gln | Ile | Ser | Trp | Phe | Val | Asn | Asn | Val | Glu | Val | His | Thr | Ala | Gln |
| | | | 275 | | | | | 280 | | | | | 285 | | |
| Thr | Gln | Thr | His | Arg | Glu | Asp | Tyr | Asn | Ser | Thr | Leu | Arg | Val | Val | Ser |
| | 290 | | | | | 295 | | | | | 300 | | | | |
| Ala | Leu | Pro | Ile | Gln | His | Gln | Asp | Trp | Met | Ser | Gly | Lys | Glu | Phe | Lys |
| 305 | | | | | 310 | | | | | 315 | | | | | 320 |

Cys Lys Val Asn Asn Lys Asp Leu Pro Ala Pro Ile Glu Arg Thr Ile
            325                 330                 335

Ser Lys Pro Lys Gly Ser Val Arg Ala Pro Gln Val Tyr Val Leu Pro
        340                 345                 350

Pro Pro Glu Glu Glu Met Thr Lys Lys Gln Val Thr Leu Thr Cys Met
        355                 360                 365

Val Thr Asp Phe Met Pro Glu Asp Ile Tyr Val Glu Trp Thr Asn Asn
    370                 375                 380

Gly Lys Thr Glu Leu Asn Tyr Lys Asn Thr Glu Pro Val Leu Asp Ser
385                 390                 395                 400

Asp Gly Ser Tyr Phe Met Tyr Ser Lys Leu Arg Val Glu Lys Lys Asn
                405                 410                 415

Trp Val Glu Arg Asn Ser Tyr Ser Cys Ser Val Val His Glu Gly Leu
            420                 425                 430

His Asn His His Thr Thr Lys Ser Phe Ser Arg Thr Pro Gly Lys
        435                 440                 445

<210> SEQ ID NO 132
<211> LENGTH: 1704
<212> TYPE: DNA
<213> ORGANISM: Mus musculus

<400> SEQUENCE: 132

| | |
|---|---|
| atgtgcccac agaaactcac aatttcttgg ttcgcaatcg tcctgctggt gtcacccctg | 60 |
| atggcaatgt gggagttgga aaaggatgta tacgtcgtcg aggtcgactg gacacctgac | 120 |
| gctccgggtg aaactgtcaa cctcacttgc gatactcctg aagaggacga catcacgtgg | 180 |
| acgagcgacc agcgacatgg agtgataggg tctggcaaga cgcttactat cacggttaag | 240 |
| gaatttctcg acgcagggca gtacacatgt cacaagggcg cgagactct gagccactcc | 300 |
| catttgctgc tgcacaagaa ggagaatggt atctggtcta ccgaaatcct gaagaatttt | 360 |
| aagaacaaga cttttctgaa atgcgaggcc ccaaattatt ccggacgttt cacttgcagt | 420 |
| tggctcgttc aaagaaatat ggacttgaaa tttaacatta atccagctc ttcatctcct | 480 |
| gacagcaggg ccgtaacttg tggaatggct tcattgtcag ctgagaaagt tacgcttgac | 540 |
| caaagggatt atgagaaata cagcgtgagt tgccaggaag atgtgacatg ccaacggca | 600 |
| gaggaaacgt tgccaattga gctcgctttg gaagctcgtc aacaaaacaa gtatgaaaac | 660 |
| tatagtacta gcttcttcat acgggacatc atcaaaccag atccacctaa gaatttgcag | 720 |
| atgaagcctc tgaagaattc acaagtcgag gtatcctggg aatacccaga ttcatggtcc | 780 |
| actcctcata gttactttag cctgaaattc tttgtacgca tacagcggaa gaaggagaaa | 840 |
| atgaaggaga cggaagaagg ctgcaatcag aaaggcgctt ttcttgttga aaagacgagc | 900 |
| actgaggttc aatgcaaagg cgggaatgta tgtgttcaag cccaagatag gtattataat | 960 |
| agctcctgct ctaagtgggc ttgcgtacca tgcagagtta gaagtccag agggcccaca | 1020 |
| atcaagccc gtcctccatg caaatgccca gcacctaacc tcttgggtgg accatccgtc | 1080 |
| ttcatcttcc ctccaaagat caaggatgta ctcatgatct ccctgagccc catagtcaca | 1140 |
| tgtgtggtgg tggatgtgag cgaggatgac ccagatgtcc agatcagctg gtttgtgaac | 1200 |
| aacgtggaag tacacacagc tcagacacaa acccatagag aggattacaa cagtactctc | 1260 |
| cgggtggtca gtgccctccc catccagcac caggactgga tgagtggcaa ggagttcaaa | 1320 |
| tgcaaggtca acaacaaaga cctcccagcg cccatcgaga gaaccatctc aaaacccaaa | 1380 |
| gggtcagtaa gagctccaca ggtatatgtc ttgcctccac cagaagaaga gatgactaag | 1440 |

```
aaacaggtca ctctgacctg catggtcaca gacttcatgc ctgaagacat ttacgtggag    1500
tggaccaaca acgggaaaac agagctaaac tacaagaaca ctgaaccagt cctggactct    1560
gatggttctt acttcatgta cagcaagctg agagtggaaa agaagaactg ggtggaaaga    1620
aatagctact cctgttcagt ggtccacgag ggtctgcaca atcaccacac gactaagagc    1680
ttctcccgga ctccgggtaa atag                                          1704
```

<210> SEQ ID NO 133
<211> LENGTH: 567
<212> TYPE: PRT
<213> ORGANISM: Mus musculus

<400> SEQUENCE: 133

| | | | | | | | | | | | | | | |
|---|---|---|---|---|---|---|---|---|---|---|---|---|---|---|
| Met | Cys | Pro | Gln | Lys | Leu | Thr | Ile | Ser | Trp | Phe | Ala | Ile | Val | Leu | Leu |
| 1 | | | | 5 | | | | | 10 | | | | | 15 | |
| Val | Ser | Pro | Leu | Met | Ala | Met | Trp | Glu | Leu | Glu | Lys | Asp | Val | Tyr | Val |
| | | | 20 | | | | | 25 | | | | | 30 | | |
| Val | Glu | Val | Asp | Trp | Thr | Pro | Asp | Ala | Pro | Gly | Glu | Thr | Val | Asn | Leu |
| | | 35 | | | | | 40 | | | | | 45 | | | |
| Thr | Cys | Asp | Thr | Pro | Glu | Glu | Asp | Asp | Ile | Thr | Trp | Thr | Ser | Asp | Gln |
| | 50 | | | | | 55 | | | | | 60 | | | | |
| Arg | His | Gly | Val | Ile | Gly | Ser | Gly | Lys | Thr | Leu | Thr | Ile | Thr | Val | Lys |
| 65 | | | | | 70 | | | | | 75 | | | | | 80 |
| Glu | Phe | Leu | Asp | Ala | Gly | Gln | Tyr | Thr | Cys | His | Lys | Gly | Gly | Glu | Thr |
| | | | | 85 | | | | | 90 | | | | | 95 | |
| Leu | Ser | His | Ser | His | Leu | Leu | Leu | His | Lys | Lys | Glu | Asn | Gly | Ile | Trp |
| | | | 100 | | | | | 105 | | | | | 110 | | |
| Ser | Thr | Glu | Ile | Leu | Lys | Asn | Phe | Lys | Asn | Lys | Thr | Phe | Leu | Lys | Cys |
| | | 115 | | | | | 120 | | | | | 125 | | | |
| Glu | Ala | Pro | Asn | Tyr | Ser | Gly | Arg | Phe | Thr | Cys | Ser | Trp | Leu | Val | Gln |
| | 130 | | | | | 135 | | | | | 140 | | | | |
| Arg | Asn | Met | Asp | Leu | Lys | Phe | Asn | Ile | Lys | Ser | Ser | Ser | Ser | Ser | Pro |
| 145 | | | | | 150 | | | | | 155 | | | | | 160 |
| Asp | Ser | Arg | Ala | Val | Thr | Cys | Gly | Met | Ala | Ser | Leu | Ser | Ala | Glu | Lys |
| | | | | 165 | | | | | 170 | | | | | 175 | |
| Val | Thr | Leu | Asp | Gln | Arg | Asp | Tyr | Glu | Lys | Tyr | Ser | Val | Ser | Cys | Gln |
| | | | 180 | | | | | 185 | | | | | 190 | | |
| Glu | Asp | Val | Thr | Cys | Pro | Thr | Ala | Glu | Glu | Thr | Leu | Pro | Ile | Glu | Leu |
| | | 195 | | | | | 200 | | | | | 205 | | | |
| Ala | Leu | Glu | Ala | Arg | Gln | Gln | Asn | Lys | Tyr | Glu | Asn | Tyr | Ser | Thr | Ser |
| | 210 | | | | | 215 | | | | | 220 | | | | |
| Phe | Phe | Ile | Arg | Asp | Ile | Ile | Lys | Pro | Asp | Pro | Pro | Lys | Asn | Leu | Gln |
| 225 | | | | | 230 | | | | | 235 | | | | | 240 |
| Met | Lys | Pro | Leu | Lys | Asn | Ser | Gln | Val | Glu | Val | Ser | Trp | Glu | Tyr | Pro |
| | | | | 245 | | | | | 250 | | | | | 255 | |
| Asp | Ser | Trp | Ser | Thr | Pro | His | Ser | Tyr | Phe | Ser | Leu | Lys | Phe | Phe | Val |
| | | | 260 | | | | | 265 | | | | | 270 | | |
| Arg | Ile | Gln | Arg | Lys | Lys | Glu | Lys | Met | Lys | Glu | Thr | Glu | Glu | Gly | Cys |
| | | 275 | | | | | 280 | | | | | 285 | | | |
| Asn | Gln | Lys | Gly | Ala | Phe | Leu | Val | Glu | Lys | Thr | Ser | Thr | Glu | Val | Gln |
| | 290 | | | | | 295 | | | | | 300 | | | | |
| Cys | Lys | Gly | Gly | Asn | Val | Cys | Val | Gln | Ala | Gln | Asp | Arg | Tyr | Tyr | Asn |
| 305 | | | | | 310 | | | | | 315 | | | | | 320 |

| | | | | | | | | | | | | |
|---|---|---|---|---|---|---|---|---|---|---|---|---|
|Ser|Ser|Cys|Ser|Lys|Trp|Ala|Cys|Val|Pro|Cys|Arg|Val|Arg|Ser|Pro|
| | | | |325| | | |330| | | |335| | | |

Ser Ser Cys Ser Lys Trp Ala Cys Val Pro Cys Arg Val Arg Ser Pro
            325                 330                 335

Arg Gly Pro Thr Ile Lys Pro Cys Pro Pro Cys Lys Cys Pro Ala Pro
            340                 345                 350

Asn Leu Leu Gly Gly Pro Ser Val Phe Ile Phe Pro Pro Lys Ile Lys
            355                 360                 365

Asp Val Leu Met Ile Ser Leu Ser Pro Ile Val Thr Cys Val Val Val
            370                 375                 380

Asp Val Ser Glu Asp Asp Pro Asp Val Gln Ile Ser Trp Phe Val Asn
385                 390                 395                 400

Asn Val Glu Val His Thr Ala Gln Thr Gln Thr His Arg Glu Asp Tyr
            405                 410                 415

Asn Ser Thr Leu Arg Val Val Ser Ala Leu Pro Ile Gln His Gln Asp
            420                 425                 430

Trp Met Ser Gly Lys Glu Phe Lys Cys Lys Val Asn Asn Lys Asp Leu
            435                 440                 445

Pro Ala Pro Ile Glu Arg Thr Ile Ser Lys Pro Lys Gly Ser Val Arg
            450                 455                 460

Ala Pro Gln Val Tyr Val Leu Pro Pro Glu Glu Glu Met Thr Lys
465                 470                 475                 480

Lys Gln Val Thr Leu Thr Cys Met Val Thr Asp Phe Met Pro Glu Asp
            485                 490                 495

Ile Tyr Val Glu Trp Thr Asn Asn Gly Lys Thr Glu Leu Asn Tyr Lys
            500                 505                 510

Asn Thr Glu Pro Val Leu Asp Ser Asp Gly Ser Tyr Phe Met Tyr Ser
            515                 520                 525

Lys Leu Arg Val Glu Lys Lys Asn Trp Val Glu Arg Asn Ser Tyr Ser
            530                 535                 540

Cys Ser Val Val His Glu Gly Leu His Asn His His Thr Thr Lys Ser
545                 550                 555                 560

Phe Ser Arg Thr Pro Gly Lys
            565

<210> SEQ ID NO 134
<211> LENGTH: 1344
<212> TYPE: DNA
<213> ORGANISM: Mus musculus

<400> SEQUENCE: 134

```
atgtgtcagt cacgctatct tctcttcctt gctactctgg ccttgctcaa tcacttgtcc     60
cttgctcgtg tgattcctgt gtccggccca gctaggtgtc tctcccagtc acggaatctc    120
ctgaaaacca cggatgacat ggtaaagaca gctagggaga aactcaagca ctactcctgc    180
acagctgagg atatcgatca tgaggacatc accagggacc agacatccac tctgaaaact    240
tgcctgcctt tggaactcca caagaacgaa tcttgtctgg aacgcgtgaa acgagttct    300 actacaagag ggtcctgtct tccccctcaa aagacaagcc ttatgatgac cttgtgtctc    360
ggtagcattt atgaggacct aaagatgtat caaaccgagt ttcaggctat caatgcagcg    420
ctccagaatc ataaccatca gcagatcatt cttgacaaag gaatgctcgt ggccattgat    480
gaactaatgc agagcctaaa ccacaatggc gagactcttc gacagaaacc gcctgtgggc    540
gaggccgatc catatagagt caaaatgaaa ctgtgtattc tcctgcatgc atttagtact    600
cgtgtagtga ctattaacag agtgatgggt taccttttcct cagctcccag agggcccaca    660
atcaagccct gtcctccatg caaatgccca gcacctaacg ctgccggtgg accatccgtc    720
```

```
ttcatcttcc ctccaaagat caaggatgta ctcatgatct ccctgagccc catagtcaca    780
tgtgtggtgg tggatgtgag cgaggatgac ccagatgtcc agatcagctg gtttgtgaac    840
aacgtggaag tacacacagc tcagacacaa acccatagag aggattacaa cagtactctc    900
cgggtggtca gtgccctccc catccagcac caggactgga tgagtggcaa ggagttcaaa    960
tgcaaggtca acaacaaaga cctcggagcg cccatcgaga gaaccatctc aaaacccaaa   1020
gggtcagtaa gagctccaca ggtatatgtc ttgcctccac cagaagaaga gatgactaag   1080
aaacaggtca ctctgacctg catggtcaca gacttcatgc ctgaagacat ttacgtggag   1140
tggaccaaca acgggaaaac agagctaaac tacaagaaca ctgaaccagt cctggactct   1200
gatggttctt acttcatgta cagcaagctg agagtggaaa agaagaactg ggtggaaaga   1260
aatagctact cctgttcagt ggtccacgag ggtctgcaca atcaccacac gactaagagc   1320
ttctcccgga ctccgggtaa atga                                          1344

<210> SEQ ID NO 135
<211> LENGTH: 447
<212> TYPE: PRT
<213> ORGANISM: Mus musculus

<400> SEQUENCE: 135

Met Cys Gln Ser Arg Tyr Leu Leu Phe Leu Ala Thr Leu Ala Leu Leu
1               5                   10                  15

Asn His Leu Ser Leu Ala Arg Val Ile Pro Val Ser Gly Pro Ala Arg
                20                  25                  30

Cys Leu Ser Gln Ser Arg Asn Leu Leu Lys Thr Thr Asp Asp Met Val
            35                  40                  45

Lys Thr Ala Arg Glu Lys Leu Lys His Tyr Ser Cys Thr Ala Glu Asp
        50                  55                  60

Ile Asp His Glu Asp Ile Thr Arg Asp Gln Thr Ser Thr Leu Lys Thr
65                  70                  75                  80

Cys Leu Pro Leu Glu Leu His Lys Asn Glu Ser Cys Leu Ala Thr Arg
                85                  90                  95

Glu Thr Ser Ser Thr Thr Arg Gly Ser Cys Leu Pro Pro Gln Lys Thr
            100                 105                 110

Ser Leu Met Met Thr Leu Cys Leu Gly Ser Ile Tyr Glu Asp Leu Lys
        115                 120                 125

Met Tyr Gln Thr Glu Phe Gln Ala Ile Asn Ala Ala Leu Gln Asn His
    130                 135                 140

Asn His Gln Gln Ile Ile Leu Asp Lys Gly Met Leu Val Ala Ile Asp
145                 150                 155                 160

Glu Leu Met Gln Ser Leu Asn His Asn Gly Glu Thr Leu Arg Gln Lys
                165                 170                 175

Pro Pro Val Gly Glu Ala Asp Pro Tyr Arg Val Lys Met Lys Leu Cys
            180                 185                 190

Ile Leu Leu His Ala Phe Ser Thr Arg Val Val Thr Ile Asn Arg Val
        195                 200                 205

Met Gly Tyr Leu Ser Ser Ala Pro Arg Gly Pro Thr Ile Lys Pro Cys
    210                 215                 220

Pro Pro Cys Lys Cys Pro Ala Pro Asn Ala Ala Gly Gly Pro Ser Val
225                 230                 235                 240

Phe Ile Phe Pro Pro Lys Ile Lys Asp Val Leu Met Ile Ser Leu Ser
                245                 250                 255
```

```
Pro Ile Val Thr Cys Val Val Asp Val Ser Glu Asp Pro Asp
            260             265             270

Val Gln Ile Ser Trp Phe Val Asn Asn Val Glu Val His Thr Ala Gln
        275                 280                 285

Thr Gln Thr His Arg Glu Asp Tyr Asn Ser Thr Leu Arg Val Val Ser
    290                 295                 300

Ala Leu Pro Ile Gln His Gln Asp Trp Met Ser Gly Lys Glu Phe Lys
305                 310                 315                 320

Cys Lys Val Asn Asn Lys Asp Leu Gly Ala Pro Ile Glu Arg Thr Ile
                325                 330                 335

Ser Lys Pro Lys Gly Ser Val Arg Ala Pro Gln Val Tyr Val Leu Pro
            340                 345                 350

Pro Pro Glu Glu Glu Met Thr Lys Lys Gln Val Thr Leu Thr Cys Met
        355                 360                 365

Val Thr Asp Phe Met Pro Glu Asp Ile Tyr Val Glu Trp Thr Asn Asn
    370                 375                 380

Gly Lys Thr Glu Leu Asn Tyr Lys Asn Thr Glu Pro Val Leu Asp Ser
385                 390                 395                 400

Asp Gly Ser Tyr Phe Met Tyr Ser Lys Leu Arg Val Glu Lys Lys Asn
                405                 410                 415

Trp Val Glu Arg Asn Ser Tyr Ser Cys Ser Val Val His Glu Gly Leu
            420                 425                 430

His Asn His His Thr Thr Lys Ser Phe Ser Arg Thr Pro Gly Lys
        435                 440                 445

<210> SEQ ID NO 136
<211> LENGTH: 1704
<212> TYPE: DNA
<213> ORGANISM: Mus musculus

<400> SEQUENCE: 136
atgtgcccac agaaactcac aatttcttgg ttcgcaatcg tcctgctggt gtcacccctg        60
atggcaatgt gggagttgga aaaggatgta tacgtcgtcg aggtcgactg gacacctgac       120
gctccgggtg aaactgtcaa cctcacttgc gatactcctg aagaggacga catcacgtgg       180
acgagcgacc agcgacatgg agtgataggg tctggcaaga cgcttactat cacggttaag       240
gaatttctcg acgcagggca gtacacatgt cacaagggcg gcgagactct gagccactcc       300
catttgctgc tgcacaagaa ggagaatggt atctggtcta ccgaaatcct gaagaatttt       360
aagaacaaga cttttctgaa atgcgaggcc ccaaattatt ccggacgttt cacttgcagt       420
tggctcgttc aaagaaatat ggacttgaaa tttaacatta atccagctc ttcatctcct        480 gacagcaggg ccgtaacttg tggaatggct tcattgtcag ctgagaaagt tacgcttgac       540
caaagggatt atgagaaata cagcgtgagt tgccaggaag atgtgacatg ccaacggca        600 gaggaaacgt tgccaattga gctcgctttg gaagctcgtc aacaaaacaa gtatgaaaac       660
tatagtacta gcttcttcat acgggacatc atcaaaccag atccacctaa gaatttgcag       720
atgaagcctc tgaagaattc acaagtcgag gtatcctggg aatacccaga ttcatggtcc       780
actcctcata gttactttag cctgaaattc tttgtacgca tacagcggaa gaggagaaa        840 atgaaggaga cggaagaagg ctgcaatcag aaaggcgctt ttcttgttga aaagacgagc       900
actgaggttc aatgcaaagg cgggaatgta tgtgttcaag cccaagatag gtattataat       960
agctcctgct ctaagtgggc ttgcgtacca tgcagagtta gaagtccag agggcccaca       1020 atcaagccct gtcctccatg caaatgccca gcacctaacg ctgccggtgg accatccgtc      1080
```

```
ttcatcttcc ctccaaagat caaggatgta ctcatgatct ccctgagccc catagtcaca   1140
tgtgtggtgg tggatgtgag cgaggatgac ccagatgtcc agatcagctg gtttgtgaac   1200
aacgtggaag tacacacagc tcagacacaa acccatagag aggattacaa cagtactctc   1260
cgggtggtca gtgccctccc catccagcac caggactgga tgagtggcaa ggagttcaaa   1320
tgcaaggtca caacaaaga cctcggagcg cccatcgaga gaaccatctc aaaacccaaa   1380
gggtcagtaa gagctccaca ggtatatgtc ttgcctccac cagaagaaga gatgactaag   1440
aaacaggtca ctctgacctg catggtcaca gacttcatgc ctgaagacat ttacgtggag   1500
tggaccaaca acgggaaaac agagctaaac tacaagaaca ctgaaccagt cctggactct   1560
gatggttctt acttcatgta cagcaagctg agagtggaaa agaagaactg ggtggaaaga   1620
aatagctact cctgttcagt ggtccacgag ggtctgcaca atcaccacac gactaagagc   1680
ttctcccgga ctccgggtaa atga                                          1704
```

<210> SEQ ID NO 137
<211> LENGTH: 567
<212> TYPE: PRT
<213> ORGANISM: Mus musculus

<400> SEQUENCE: 137

```
Met Cys Pro Gln Lys Leu Thr Ile Ser Trp Phe Ala Ile Val Leu Leu
1               5                   10                  15

Val Ser Pro Leu Met Ala Met Trp Glu Leu Glu Lys Asp Val Tyr Val
                20                  25                  30

Val Glu Val Asp Trp Thr Pro Asp Ala Pro Gly Glu Thr Val Asn Leu
            35                  40                  45

Thr Cys Asp Thr Pro Glu Glu Asp Asp Ile Thr Trp Thr Ser Asp Gln
        50                  55                  60

Arg His Gly Val Ile Gly Ser Gly Lys Thr Leu Thr Ile Thr Val Lys
65                  70                  75                  80

Glu Phe Leu Asp Ala Gly Gln Tyr Thr Cys His Lys Gly Gly Glu Thr
                85                  90                  95

Leu Ser His Ser His Leu Leu Leu His Lys Lys Glu Asn Gly Ile Trp
            100                 105                 110

Ser Thr Glu Ile Leu Lys Asn Phe Lys Asn Lys Thr Phe Leu Lys Cys
        115                 120                 125

Glu Ala Pro Asn Tyr Ser Gly Arg Phe Thr Cys Ser Trp Leu Val Gln
    130                 135                 140

Arg Asn Met Asp Leu Lys Phe Asn Ile Lys Ser Ser Ser Ser Ser Pro
145                 150                 155                 160

Asp Ser Arg Ala Val Thr Cys Gly Met Ala Ser Leu Ser Ala Glu Lys
                165                 170                 175

Val Thr Leu Asp Gln Arg Asp Tyr Glu Lys Tyr Ser Val Ser Cys Gln
            180                 185                 190

Glu Asp Val Thr Cys Pro Thr Ala Glu Glu Thr Leu Pro Ile Glu Leu
        195                 200                 205

Ala Leu Glu Ala Arg Gln Gln Asn Lys Tyr Glu Asn Tyr Ser Thr Ser
    210                 215                 220

Phe Phe Ile Arg Asp Ile Ile Lys Pro Asp Pro Lys Asn Leu Gln
225                 230                 235                 240

Met Lys Pro Leu Lys Asn Ser Gln Val Glu Val Ser Trp Glu Tyr Pro
                245                 250                 255
```

Asp Ser Trp Ser Thr Pro His Ser Tyr Phe Ser Leu Lys Phe Val
            260                 265                 270

Arg Ile Gln Arg Lys Lys Glu Lys Met Lys Glu Thr Glu Glu Gly Cys
        275                 280                 285

Asn Gln Lys Gly Ala Phe Leu Val Glu Lys Thr Ser Thr Glu Val Gln
    290                 295                 300

Cys Lys Gly Gly Asn Val Cys Val Gln Ala Gln Asp Arg Tyr Tyr Asn
305                 310                 315                 320

Ser Ser Cys Ser Lys Trp Ala Cys Val Pro Cys Arg Val Arg Ser Pro
                325                 330                 335

Arg Gly Pro Thr Ile Lys Pro Cys Pro Pro Cys Lys Cys Pro Ala Pro
            340                 345                 350

Asn Ala Ala Gly Gly Pro Ser Val Phe Ile Phe Pro Pro Lys Ile Lys
        355                 360                 365

Asp Val Leu Met Ile Ser Leu Ser Pro Ile Val Thr Cys Val Val Val
    370                 375                 380

Asp Val Ser Glu Asp Asp Pro Asp Val Gln Ile Ser Trp Phe Val Asn
385                 390                 395                 400

Asn Val Glu Val His Thr Ala Gln Thr Gln Thr His Arg Glu Asp Tyr
                405                 410                 415

Asn Ser Thr Leu Arg Val Val Ser Ala Leu Pro Ile Gln His Gln Asp
            420                 425                 430

Trp Met Ser Gly Lys Glu Phe Lys Cys Lys Val Asn Asn Lys Asp Leu
        435                 440                 445

Gly Ala Pro Ile Glu Arg Thr Ile Ser Lys Pro Lys Gly Ser Val Arg
    450                 455                 460

Ala Pro Gln Val Tyr Val Leu Pro Pro Glu Glu Glu Met Thr Lys
465                 470                 475                 480

Lys Gln Val Thr Leu Thr Cys Met Val Thr Asp Phe Met Pro Glu Asp
                485                 490                 495

Ile Tyr Val Glu Trp Thr Asn Asn Gly Lys Thr Glu Leu Asn Tyr Lys
            500                 505                 510

Asn Thr Glu Pro Val Leu Asp Ser Asp Gly Ser Tyr Phe Met Tyr Ser
        515                 520                 525

Lys Leu Arg Val Glu Lys Lys Asn Trp Val Glu Arg Asn Ser Tyr Ser
    530                 535                 540

Cys Ser Val Val His Glu Gly Leu His Asn His His Thr Thr Lys Ser
545                 550                 555                 560

Phe Ser Arg Thr Pro Gly Lys
                565

<210> SEQ ID NO 138
<211> LENGTH: 113
<212> TYPE: PRT
<213> ORGANISM: Homo sapiens

<400> SEQUENCE: 138

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Gln Arg Arg Lys Asn Pro Gln Glu Gly Leu Tyr Asn Glu Leu Gln
    50                  55                  60

```
Lys Asp Lys Met Ala Glu Ala Tyr Ser Glu Ile Gly Met Lys Gly Glu
 65                  70                  75                  80

Arg Arg Arg Gly Lys Gly His Asp Gly Leu Tyr Gln Gly Leu Ser Thr
                 85                  90                  95

Ala Thr Lys Asp Thr Tyr Asp Ala Leu His Met Gln Ala Leu Pro Pro
            100                 105                 110

Arg

<210> SEQ ID NO 139
<211> LENGTH: 342
<212> TYPE: DNA
<213> ORGANISM: Homo sapiens

<400> SEQUENCE: 139
agagtgaagt tcagcaggag cgcagacgcc cccgcgtacc agcagggcca gaaccagctc      60
tataacgagc tcaatctagg acgaagagag gagtacgatg ttttggacaa gagacgtggc     120
cgggaccctg agatggggggg aaagccgcag agaaggaaga accctcagga aggcctgtac    180
aatgaactgc agaaagataa gatggcggag gcctacagtg agattgggat gaaaggcgag     240
cgccggaggg gcaaggggca cgatggcctt taccagggtc tcagtacagc caccaaggac     300
acctacgacg cccttcacat gcaggccctg cccctcgct aa                        342

<210> SEQ ID NO 140
<211> LENGTH: 570
<212> TYPE: PRT
<213> ORGANISM: Artificial Sequence
<220> FEATURE:
<223> OTHER INFORMATION: Synthetic

<400> SEQUENCE: 140

Met Glu Thr Asp Thr Leu Leu Leu Trp Val Leu Leu Leu Trp Val Pro
  1               5                  10                  15

Gly Ser Thr Gly Gln Ser Val Leu Thr Gln Pro Pro Ser Val Ser Ala
                 20                  25                  30

Ala Pro Gly Gln Arg Val Thr Ile Ser Cys Ser Gly Thr Arg Ser Asn
             35                  40                  45

Ile Gly Ser Asp Tyr Val Ser Trp Tyr Gln His Leu Pro Gly Thr Ala
 50                  55                  60

Pro Lys Leu Leu Val Tyr Gly Asp Asn Leu Arg Pro Ser Gly Ile Pro
 65                  70                  75                  80

Asp Arg Phe Ser Ala Ser Lys Ser Gly Thr Ser Ala Thr Leu Gly Ile
                 85                  90                  95

Thr Gly Leu Gln Thr Gly Asp Glu Ala Asp Tyr Tyr Cys Gly Thr Trp
            100                 105                 110

Asp Tyr Thr Leu Asn Gly Val Val Phe Gly Gly Gly Thr Lys Leu Thr
            115                 120                 125

Val Leu Gly Ser Arg Gly Gly Gly Ser Gly Gly Gly Gly Ser Gly
        130                 135                 140

Gly Gly Gly Ser Leu Glu Met Ala Gln Val Gln Leu Val Glu Ser Gly
145                 150                 155                 160

Gly Gly Leu Val Gln Pro Gly Gly Ser Leu Arg Leu Ser Cys Ala Ala
                165                 170                 175

Ser Gly Phe Thr Phe Ser Ser Tyr Ala Met Ser Trp Val Arg Gln Ala
            180                 185                 190

Pro Gly Lys Gly Leu Glu Trp Val Ser Val Ile Tyr Ser Gly Gly Ser
```

195                 200                 205

Ser Thr Tyr Tyr Ala Asp Ser Val Lys Gly Arg Phe Thr Ile Ser Arg
210                 215                 220

Asp Asn Ser Lys Asn Thr Leu Tyr Leu Gln Met Asn Ser Leu Arg Ala
225                 230                 235                 240

Glu Asp Thr Ala Val Tyr Tyr Cys Ala Arg Thr Ser Tyr Leu Asn His
                245                 250                 255

Gly Asp Tyr Trp Gly Gln Gly Thr Leu Val Thr Val Ser Ser Pro Lys
                260                 265                 270

Ser Cys Asp Lys Thr His Thr Cys Pro Pro Cys Pro Ala Pro Glu Leu
            275                 280                 285

Leu Gly Gly Pro Ser Val Phe Leu Phe Pro Pro Lys Pro Lys Asp Thr
290                 295                 300

Leu Met Ile Ser Arg Thr Pro Glu Val Thr Cys Val Val Val Asp Val
305                 310                 315                 320

Ser His Glu Asp Pro Glu Val Lys Phe Asn Trp Tyr Val Asp Gly Val
                325                 330                 335

Glu Val His Asn Ala Lys Thr Lys Pro Arg Glu Glu Gln Tyr Asn Ser
            340                 345                 350

Thr Tyr Arg Val Val Ser Val Leu Thr Val Leu His Gln Asp Trp Leu
        355                 360                 365

Asn Gly Lys Glu Tyr Lys Cys Lys Val Ser Asn Lys Ala Leu Pro Ala
370                 375                 380

Pro Ile Glu Lys Thr Ile Ser Lys Ala Lys Gly Gln Pro Arg Glu Pro
385                 390                 395                 400

Gln Val Tyr Thr Leu Pro Pro Ser Arg Glu Glu Met Thr Lys Asn Gln
                405                 410                 415

Val Ser Leu Thr Cys Leu Val Lys Gly Phe Tyr Pro Ser Asp Ile Ala
            420                 425                 430

Val Glu Trp Glu Ser Asn Gly Gln Pro Glu Asn Asn Tyr Lys Thr Thr
        435                 440                 445

Pro Pro Val Leu Asp Ser Asp Gly Ser Phe Phe Leu Tyr Ser Lys Leu
450                 455                 460

Thr Val Asp Lys Ser Arg Trp Gln Gln Gly Asn Val Phe Ser Cys Ser
465                 470                 475                 480

Val Met His Glu Ala Leu His Asn His Tyr Thr Gln Lys Ser Leu Ser
                485                 490                 495

Leu Ser Pro Glu Leu Gln Leu Glu Glu Ser Cys Ala Glu Ala Gln Asp
            500                 505                 510

Gly Glu Leu Asp Gly Leu Trp Thr Thr Ile Thr Ile Phe Ile Thr Leu
        515                 520                 525

Phe Leu Leu Ser Val Cys Tyr Ser Ala Thr Val Thr Phe Phe Lys Val
530                 535                 540

Lys Trp Ile Phe Ser Ser Val Val Asp Leu Lys Gln Thr Ile Ile Pro
545                 550                 555                 560

Asp Tyr Arg Asn Met Ile Gly Gln Gly Ala
                565                 570

<210> SEQ ID NO 141
<211> LENGTH: 1713
<212> TYPE: DNA
<213> ORGANISM: Artificial Sequence
<220> FEATURE:
<223> OTHER INFORMATION: Synthetic

<400> SEQUENCE: 141

```
atggaaaccg atacactgct gctgtgggtg ctgctgctgt gggtgccagg atctaccggt    60
cagtctgtgt tgacgcagcc gccctcagtg tctgcggccc caggacagag ggtcaccatc   120
tcctgctctg gaaccaggtc caacattggg agtgattatg tttcctggta ccaacacctc   180
ccaggaacag cccccaaact cctcgtttat ggcgataatc tgcgaccctc agggattcct   240
gaccgattct ctgcctccaa gtctggcacg tcagccaccc tgggcatcac cggactccag   300
actggggacg aggccgatta ttactgcggc acatgggatt acaccctgaa tggtgtggtg   360
ttcggcggag ggaccaagct gaccgtccta ggttctagag gtggtggtgg tagcggcggc   420
ggcggctctg gtggtggtgg atccctcgag atggcccagg tgcagctggt ggagtctggg   480
ggaggcttgg tacagcctgg ggggtccctg agactctcct gtgcagcctc tggattcacc   540
tttagcagct atgccatgag ctgggtccgc caggctccag gaaggggct ggagtgggtc   600
tcagttattt atagcggtgg tagtagcaca tactatgcag actccgtgaa gggccggttc   660
accatctcca gagataattc caagaacacg ctgtatctgc aaatgaacag cctgagagcc   720
gaggacacgg ccgtatatta ctgtgcgcgc acttcttacc tgaaccatgg tgattactgg   780
ggtcaaggta ctctggtgac cgtgtctagc cccaagagct cgacaagac ccacacctgc   840
cccccctgcc cagccccaga gctgctgggc ggaccctccg tgttcctgtt ccccccaag   900
cccaaggaca ccctgatgat cagcaggacc cccgaggtga cctgcgtggt ggtggacgtg   960
agccacgagg acccagaggt gaagttcaac tggtacgtgg acggcgtgga ggtgcacaac  1020
gccaagacca agcccagaga ggagcagtac aacagcacct acagggtggt gtccgtgctg  1080
accgtgctgc accaggactg gctgaacggc aaggaataca gtgcaaggt ctccaacaag  1140
gccctgccag ccccatcga aaagaccatc agcaaggcca agggccagcc acgggagccc  1200
caggtgtaca ccctgccccc ctcccgggag gagatgacca gaaccaggt gccctgacc  1260
tgtctggtga agggcttcta ccccagcgac atcgccgtgg agtgggagag caacggccag  1320
cccgagaaca actacaagac cacccccca gtgctggaca gcgacggcag cttcttcctg  1380
tacagcaagc tgaccgtgga caagtccagg tggcagcagg gcaacgtgtt cagctgcagc  1440
gtgatgcacg aggccctgca caaccactac acccagaaga gcctgagcct gtcccccgag  1500
ctgcaactgg aggagagctg tgcggaggcg caggacgggg agctggacgg gctgtggacg  1560
accatcacca tcttcatcac actcttcctg ttaagcgtgt gctacagtgc caccgtcacc  1620
ttcttcaagg tgaagtggat cttctcctcg gtggtggacc tgaagcagac catcatcccc  1680
gactacagga acatgatcgg acagggggcc tga                               1713
```

<210> SEQ ID NO 142
<211> LENGTH: 236
<212> TYPE: PRT
<213> ORGANISM: Artificial Sequence
<220> FEATURE:
<223> OTHER INFORMATION: Synthetic

<400> SEQUENCE: 142

```
Met Glu Thr Asp Thr Leu Leu Leu Trp Val Leu Leu Leu Trp Val Pro
1               5                   10                  15

Gly Ser Thr Gly Gln Ser Val Leu Thr Gln Pro Pro Ser Val Ser Ala
            20                  25                  30

Ala Pro Gly Gln Arg Val Thr Ile Ser Cys Ser Gly Thr Arg Ser Asn
        35                  40                  45
```

```
Ile Gly Ser Asp Tyr Val Ser Trp Tyr Gln His Leu Pro Gly Thr Ala
 50                  55                  60
Pro Lys Leu Leu Val Tyr Gly Asp Asn Leu Arg Pro Ser Gly Ile Pro
 65                  70                  75                  80
Asp Arg Phe Ser Ala Ser Lys Ser Gly Thr Ser Ala Thr Leu Gly Ile
                 85                  90                  95
Thr Gly Leu Gln Thr Gly Asp Glu Ala Asp Tyr Tyr Cys Gly Thr Trp
            100                 105                 110
Asp Tyr Thr Leu Asn Gly Val Val Phe Gly Gly Gly Thr Lys Leu Thr
        115                 120                 125
Val Leu Gly Gln Pro Lys Ala Asn Pro Thr Val Thr Leu Phe Pro Pro
130                 135                 140
Ser Ser Glu Glu Leu Gln Ala Asn Lys Ala Thr Leu Val Cys Leu Ile
145                 150                 155                 160
Ser Asp Phe Tyr Pro Gly Ala Val Thr Val Ala Trp Lys Ala Asp Gly
                165                 170                 175
Ser Pro Val Lys Ala Gly Val Glu Thr Thr Lys Pro Ser Lys Gln Ser
            180                 185                 190
Asn Asn Lys Tyr Ala Ala Ser Ser Tyr Leu Ser Leu Thr Pro Glu Gln
        195                 200                 205
Trp Lys Ser His Arg Ser Tyr Ser Cys Gln Val Thr His Glu Gly Ser
210                 215                 220
Thr Val Glu Lys Thr Val Ala Pro Thr Glu Cys Ser
225                 230                 235

<210> SEQ ID NO 143
<211> LENGTH: 711
<212> TYPE: DNA
<213> ORGANISM: Artificial Sequence
<220> FEATURE:
<223> OTHER INFORMATION: Synthetic

<400> SEQUENCE: 143
atggaaaccg atacactgct gctgtgggtg ctgctgctgt gggtgccagg atctaccggt      60
cagtctgtgt tgacgcagcc gccctcagtg tctgcggccc caggacagag ggtcaccatc     120
tcctgctctg gaaccaggtc caacattggg agtgattatg tttcctggta ccaacacctc     180
ccaggaacag cccccaaact cctcgtttat ggcgataatc tgcgaccctc agggattcct     240
gaccgattct ctgcctccaa gtctggcacg tcagccaccc tgggcatcac cggactccag     300
actggggacg aggccgatta ttactgcggc acatgggatt acaccctgaa tggtgtggtg     360
ttcggcggag ggaccaagct gaccgtccta ggtcagccca aggccaaccc cactgtcact     420
ctgttcccgc cctcctctga ggagctccaa gccaacaagg ccacactagt gtgtctgatc     480
agtgacttct acccgggagc tgtgacagtg gcctggaagg cagatggcag ccccgtcaag     540
gcgggagtgg agaccaccaa accctccaaa cagagcaaca acaagtacgc ggccagcagc     600
tacctgagcc tgacgcccga gcagtggaag tcccacagaa gctacagctg ccaggtcacg     660
catgaaggga gcaccgtgga agacagtg gccccctacag aatgttcata g              711

<210> SEQ ID NO 144
<211> LENGTH: 537
<212> TYPE: PRT
<213> ORGANISM: Artificial Sequence
<220> FEATURE:
<223> OTHER INFORMATION: Synthetic

<400> SEQUENCE: 144
```

-continued

```
Met Val Phe Thr Pro Gln Ile Leu Gly Leu Met Leu Phe Trp Ile Ser
1               5                   10                  15

Ala Ser Arg Gly Gln Val Gln Leu Val Glu Ser Gly Gly Gly Leu Val
            20                  25                  30

Gln Pro Gly Gly Ser Leu Arg Leu Ser Cys Ala Ala Ser Gly Phe Thr
            35                  40                  45

Phe Ser Ser Tyr Ala Met Ser Trp Val Arg Gln Ala Pro Gly Lys Gly
50                  55                  60

Leu Glu Trp Val Ser Val Ile Tyr Ser Gly Gly Ser Thr Tyr Tyr
65                  70                  75                  80

Ala Asp Ser Val Lys Gly Arg Phe Thr Ile Ser Arg Asp Asn Ser Lys
                85                  90                  95

Asn Thr Leu Tyr Leu Gln Met Asn Ser Leu Arg Ala Glu Asp Thr Ala
            100                 105                 110

Val Tyr Tyr Cys Ala Arg Thr Ser Tyr Leu Asn His Gly Asp Tyr Trp
        115                 120                 125

Gly Gln Gly Thr Leu Val Thr Val Ser Ser Ala Ser Thr Lys Gly Pro
    130                 135                 140

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Ser Leu Gly Thr Gln Thr Tyr Ile Cys Asn Val Asn
    210                 215                 220

His Lys Pro Ser Asn Thr Lys Val Asp Lys Arg Val Glu Pro Lys Ser
225                 230                 235                 240

Cys Asp Lys Thr His Thr Cys Pro Pro Cys Pro Ala Pro Glu Leu Leu
                245                 250                 255

Gly Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
        275                 280                 285

His Glu Asp Pro Glu Val Lys Phe Asn Trp Tyr Val Asp Gly Val Glu
    290                 295                 300

Val His Asn Ala Lys Thr Lys Pro Arg Glu Glu Gln Tyr Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Ala Leu Pro Ala Pro
            340                 345                 350

Ile Glu Lys Thr Ile Ser Lys Ala Lys Gly Gln Pro Arg Glu Pro Gln
        355                 360                 365

Val Tyr Thr Leu Pro Pro Ser Arg Glu Glu Met Thr Lys Asn Gln Val
    370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415
```

```
Pro Val Leu Asp Ser Asp Gly Ser Phe Phe Leu Tyr Ser Lys Leu Thr
            420                 425                 430

Val Asp Lys Ser Arg Trp Gln Gln Gly Asn Val Phe Ser Cys Ser Val
        435                 440                 445

Met His Glu Ala Leu His Asn His Tyr Thr Gln Lys Ser Leu Ser Leu
    450                 455                 460

Ser Pro Glu Leu Gln Leu Glu Glu Ser Cys Ala Glu Ala Gln Asp Gly
465                 470                 475                 480

Glu Leu Asp Gly Leu Trp Thr Thr Ile Thr Ile Phe Ile Thr Leu Phe
                485                 490                 495

Leu Leu Ser Val Cys Tyr Ser Ala Thr Val Thr Phe Phe Lys Val Lys
            500                 505                 510

Trp Ile Phe Ser Ser Val Val Asp Leu Lys Gln Thr Ile Ile Pro Asp
        515                 520                 525

Tyr Arg Asn Met Ile Gly Gln Gly Ala
    530                 535
```

<210> SEQ ID NO 145
<211> LENGTH: 1614
<212> TYPE: DNA
<213> ORGANISM: Artificial Sequence
<220> FEATURE:
<223> OTHER INFORMATION: Synthetic

<400> SEQUENCE: 145

| | | | | | |
|---|---|---|---|---|---|
| atggtgttta | caccgcaaat | attggggctc | atgcttttct | ggatcagtgc | aagcagggga | 60 |
| caggtgcagc | tggtggagtc | tgggggaggc | ttggtacagc | ctgggggtc | cctgagactc | 120 |
| tcctgtgcag | cctctggatt | cacctttagc | agctatgcca | tgagctgggt | ccgccaggct | 180 |
| ccagggaagg | ggctggagtg | ggtctcagtt | atttatagcg | gtggtagtag | cacatactat | 240 |
| gcagactccg | tgaagggccg | gttcaccatc | tccagagata | attccaagaa | cacgctgtat | 300 |
| ctgcaaatga | acagcctgag | agccgaggac | acggccgtat | attactgtgc | gcgcacttct | 360 |
| tacctgaacc | atggtgatta | ctggggtcaa | ggtactctgg | tgaccgtgtc | tagcgcctcc | 420 |
| accaagggcc | catcggtctt | ccccctggca | ccctcctcca | agagcacctc | tgggggcaca | 480 |
| gcggccctgg | gctgcctggt | caaggactac | ttccccgaac | cggtgacggt | gtcgtggaac | 540 |
| tcaggcgccc | tgaccagcgg | cgtgcacacc | ttcccggctg | tcctacagtc | ctcaggactc | 600 |
| tactccctca | gcagcgtggt | gaccgtgccc | tccagcagct | gggcaccca | gacctacatc | 660 |
| tgcaacgtga | accacaagcc | cagcaacacc | aaggtggaca | agagagtgga | gcccaagagc | 720 |
| tgcgacaaga | cccacacctg | ccccccctgc | ccagcccag | agctgctggg | cggaccctcc | 780 |
| gtgttcctgt | tccccccaa | gcccaaggac | accctgatga | tcagcaggac | ccccgaggtg | 840 |
| acctgcgtgg | tggtggacgt | gagccacgag | gacccagagg | tgaagttcaa | ctggtacgtg | 900 |
| gacggcgtgg | aggtgcacaa | cgccaagacc | aagcccagag | aggagcagta | caacagcacc | 960 |
| tacagggtgg | tgtccgtgct | gaccgtgctg | caccaggact | ggctgaacgg | caaggaatac | 1020 |
| aagtgcaagg | tctccaacaa | ggccctgcca | gcccccatcg | aaaagaccat | cagcaaggcc | 1080 |
| aagggccagc | cacgggagcc | ccaggtgtac | accctgcccc | cctcccggga | ggagatgacc | 1140 |
| aagaaccagg | tgtccctgac | ctgtctggtg | aagggcttct | accccagcga | catcgccgtg | 1200 |
| gagtgggaga | gcaacggcca | gcccgagaac | aactacaaga | ccaccccccc | agtgctggac | 1260 |
| agcgacggca | gcttcttcct | gtacagcaag | ctgaccgtgg | acaagtccag | gtggcagcag | 1320 |
| ggcaacgtgt | tcagctgcag | cgtgatgcac | gaggccctgc | acaaccacta | cacccagaag | 1380 |

```
agcctgagcc tgtcccccga gctgcaactg gaggagagct gtgcggaggc gcaggacggg    1440
gagctggacg ggctgtggac gaccatcacc atcttcatca cactcttcct gttaagcgtg    1500
tgctacagtg ccaccgtcac cttcttcaag gtgaagtgga tcttctcctc ggtggtggac    1560
ctgaagcaga ccatcatccc cgactacagg aacatgatcg acagggggc ctga           1614
```

<210> SEQ ID NO 146
<211> LENGTH: 404
<212> TYPE: PRT
<213> ORGANISM: Artificial Sequence
<220> FEATURE:
<223> OTHER INFORMATION: Synthetic

<400> SEQUENCE: 146

```
Met Glu Thr Asp Thr Leu Leu Leu Trp Val Leu Leu Leu Trp Val Pro
1               5                   10                  15

Gly Ser Thr Gly Gln Ser Val Leu Thr Gln Pro Pro Ser Val Ser Ala
            20                  25                  30

Ala Pro Gly Gln Arg Val Thr Ile Ser Cys Ser Gly Thr Arg Ser Asn
        35                  40                  45

Ile Gly Ser Asp Tyr Val Ser Trp Tyr Gln His Leu Pro Gly Thr Ala
    50                  55                  60

Pro Lys Leu Leu Val Tyr Gly Asp Asn Leu Arg Pro Ser Gly Ile Pro
65                  70                  75                  80

Asp Arg Phe Ser Ala Ser Lys Ser Gly Thr Ser Ala Thr Leu Gly Ile
                85                  90                  95

Thr Gly Leu Gln Thr Gly Asp Glu Ala Asp Tyr Tyr Cys Gly Thr Trp
            100                 105                 110

Asp Tyr Thr Leu Asn Gly Val Val Phe Gly Gly Gly Thr Lys Leu Thr
        115                 120                 125

Val Leu Gly Ser Arg Gly Gly Gly Ser Gly Gly Gly Gly Ser Gly
    130                 135                 140

Gly Gly Gly Ser Leu Glu Met Ala Gln Val Gln Leu Val Glu Ser Gly
145                 150                 155                 160

Gly Gly Leu Val Gln Pro Gly Gly Ser Leu Arg Leu Ser Cys Ala Ala
                165                 170                 175

Ser Gly Phe Thr Phe Ser Ser Tyr Ala Met Ser Trp Val Arg Gln Ala
            180                 185                 190

Pro Gly Lys Gly Leu Glu Trp Val Ser Val Ile Tyr Ser Gly Gly Ser
        195                 200                 205

Ser Thr Tyr Tyr Ala Asp Ser Val Lys Gly Arg Phe Thr Ile Ser Arg
    210                 215                 220

Asp Asn Ser Lys Asn Thr Leu Tyr Leu Gln Met Asn Ser Leu Arg Ala
225                 230                 235                 240

Glu Asp Thr Ala Val Tyr Tyr Cys Ala Arg Thr Ser Tyr Leu Asn His
                245                 250                 255

Gly Asp Tyr Trp Gly Gln Gly Thr Leu Val Thr Val Ser Ser Ala Ala
            260                 265                 270

Ala Phe Val Pro Val Phe Leu Pro Ala Lys Pro Thr Thr Thr Pro Ala
        275                 280                 285

Pro Arg Pro Pro Thr Pro Ala Pro Thr Ile Ala Ser Gln Pro Leu Ser
    290                 295                 300

Leu Arg Pro Glu Ala Cys Arg Pro Ala Ala Gly Gly Ala Val His Thr
305                 310                 315                 320
```

Arg Gly Leu Asp Phe Ala Cys Asp Phe Trp Val Leu Val Val Val Gly
                            325                 330                 335

Gly Val Leu Ala Cys Tyr Ser Leu Leu Val Thr Val Ala Phe Ile Ile
                        340                 345                 350

Phe Trp Val Leu Asp Lys Asp Asp Ser Lys Ala Gly Met Glu Glu Asp
                        355                 360                 365

His Thr Tyr Glu Gly Leu Asp Ile Asp Gln Thr Ala Thr Tyr Glu Asp
                370                 375                 380

Ile Val Thr Leu Arg Thr Gly Glu Val Lys Trp Ser Val Gly Glu His
        385                 390                 395                 400

Pro Gly Gln Glu

<210> SEQ ID NO 147
<211> LENGTH: 1215
<212> TYPE: DNA
<213> ORGANISM: Artificial Sequence
<220> FEATURE:
<223> OTHER INFORMATION: Synthetic

<400> SEQUENCE: 147

| | | | | | |
|---|---|---|---|---|---|
| atggaaaccg | atacactgct | gctgtgggtg | ctgctgctgt | gggtgccagg | atctaccggt | 60 |
| cagtctgtgt | tgacgcagcc | gccctcagtg | tctgcggccc | caggacagag | ggtcaccatc | 120 |
| tcctgctctg | gaaccaggtc | caacattggg | agtgattatg | tttcctggta | ccaacacctc | 180 |
| ccaggaacag | cccccaaact | cctcgtttat | ggcgataatc | tgcgaccctc | agggattcct | 240 |
| gaccgattct | ctgcctccaa | gtctggcacg | tcagccaccc | tgggcatcac | cggactccag | 300 |
| actggggacg | aggccgatta | ttactgcggc | acatgggatt | acaccctgaa | tggtgtgggg | 360 |
| ttcggcggag | ggaccaagct | gaccgtccta | ggttctagag | gtggtggtgg | tagcggcggc | 420 |
| ggcggctctg | gtggtggtgg | atccctcgag | atggcccagg | tgcagctggt | ggagtctggg | 480 |
| ggaggcttgg | tacagcctgg | ggggtccctg | agactctcct | gtgcagcctc | tggattcacc | 540 |
| tttagcagct | atgccatgag | ctgggtccgc | caggctccag | ggaaggggct | ggagtgggtc | 600 |
| tcagttattt | atagcggtgg | tagtagcaca | tactatgcag | actccgtgaa | gggccggttc | 660 |
| accatctcca | gagataattc | caagaacacg | ctgtatctgc | aaatgaacag | cctgagagcc | 720 |
| gaggacacgg | ccgtatatta | ctgtgcgcgc | acttcttacc | tgaaccatgg | tgattactgg | 780 |
| ggtcaaggta | ctctggtgac | cgtgtctagc | gccgctgcat | cgtgcctgt | gttcctccca | 840 |
| gctaagccca | ctaccacccc | cgctccaagg | ccgcccacgc | cgctcctac | tattgctagt | 900 |
| cagcctttaa | gtttacgacc | cgaagcttgc | aggcccgccg | ccggcggcgc | tgtgcacacc | 960 |
| agggggcttg | attttgcctg | cgactttcgg | gtattggtag | tggtgggcgg | agttttagcc | 1020 |
| tgctacagcc | tcctggtaac | agtggctttt | atcatctttt | gggtgctgga | caaggatgac | 1080 |
| agcaaggctg | gcatggagga | agatcacacc | tacgagggcc | tggacattga | ccagacagcc | 1140 |
| acctatgagg | acatagtgac | gctgcggaca | ggggaagtga | agtggtctgt | aggtgagcac | 1200 |
| ccaggccagg | agtga | | | | | 1215 |

<210> SEQ ID NO 148
<211> LENGTH: 416
<212> TYPE: PRT
<213> ORGANISM: Artificial Sequence
<220> FEATURE:
<223> OTHER INFORMATION: Synthetic

<400> SEQUENCE: 148

```
Met Glu Thr Asp Thr Leu Leu Leu Trp Val Leu Leu Leu Trp Val Pro
1               5                   10                  15

Gly Ser Thr Gly Gln Ser Val Leu Thr Gln Pro Pro Ser Val Ser Ala
            20                  25                  30

Ala Pro Gly Gln Arg Val Thr Ile Ser Cys Ser Gly Thr Arg Ser Asn
            35                  40                  45

Ile Gly Ser Asp Tyr Val Ser Trp Tyr Gln His Leu Pro Gly Thr Ala
50                  55                  60

Pro Lys Leu Leu Val Tyr Gly Asp Asn Leu Arg Pro Ser Gly Ile Pro
65                  70                  75                  80

Asp Arg Phe Ser Ala Ser Lys Ser Gly Thr Ser Ala Thr Leu Gly Ile
                85                  90                  95

Thr Gly Leu Gln Thr Gly Asp Glu Ala Asp Tyr Tyr Cys Gly Thr Trp
            100                 105                 110

Asp Tyr Thr Leu Asn Gly Val Val Phe Gly Gly Gly Thr Lys Leu Thr
            115                 120                 125

Val Leu Gly Ser Arg Gly Gly Gly Ser Gly Gly Gly Gly Ser Gly
    130                 135                 140

Gly Gly Gly Ser Leu Glu Met Ala Gln Val Gln Leu Val Glu Ser Gly
145                 150                 155                 160

Gly Gly Leu Val Gln Pro Gly Gly Ser Leu Arg Leu Ser Cys Ala Ala
                165                 170                 175

Ser Gly Phe Thr Phe Ser Ser Tyr Ala Met Ser Trp Val Arg Gln Ala
            180                 185                 190

Pro Gly Lys Gly Leu Glu Trp Val Ser Val Ile Tyr Ser Gly Gly Ser
            195                 200                 205

Ser Thr Tyr Tyr Ala Asp Ser Val Lys Gly Arg Phe Thr Ile Ser Arg
210                 215                 220

Asp Asn Ser Lys Asn Thr Leu Tyr Leu Gln Met Asn Ser Leu Arg Ala
225                 230                 235                 240

Glu Asp Thr Ala Val Tyr Tyr Cys Ala Arg Thr Ser Tyr Leu Asn His
                245                 250                 255

Gly Asp Tyr Trp Gly Gln Gly Thr Leu Val Thr Val Ser Ser Ala Ala
            260                 265                 270

Ala Phe Val Pro Val Phe Leu Pro Ala Lys Pro Thr Thr Thr Pro Ala
            275                 280                 285

Pro Arg Pro Pro Thr Pro Ala Pro Thr Ile Ala Ser Gln Pro Leu Ser
            290                 295                 300

Leu Arg Pro Glu Ala Cys Arg Pro Ala Ala Gly Gly Ala Val His Thr
305                 310                 315                 320

Arg Gly Leu Asp Phe Ala Cys Asp Phe Trp Val Leu Val Val Val Gly
                325                 330                 335

Gly Val Leu Ala Cys Tyr Ser Leu Leu Val Thr Val Ala Phe Ile Ile
            340                 345                 350

Phe Trp Val Arg Lys Arg Trp Gln Asn Glu Lys Leu Gly Leu Asp Ala
            355                 360                 365

Gly Asp Glu Tyr Glu Asp Glu Asn Leu Tyr Glu Gly Leu Asn Leu Asp
370                 375                 380

Asp Cys Ser Met Tyr Glu Asp Ile Ser Arg Gly Leu Gln Gly Thr Tyr
385                 390                 395                 400

Gln Asp Val Gly Ser Leu Asn Ile Gly Asp Val Gln Leu Glu Lys Pro
                405                 410                 415
```

<210> SEQ ID NO 149
<211> LENGTH: 1251
<212> TYPE: DNA
<213> ORGANISM: Artificial Sequence
<220> FEATURE:
<223> OTHER INFORMATION: Synthetic

<400> SEQUENCE: 149

| | |
|---|---|
| atggaaaccg atacactgct gctgtgggtg ctgctgctgt gggtgccagg atctaccggt | 60 |
| cagtctgtgt tgacgcagcc gccctcagtg tctgcggccc aggacagag ggtcaccatc | 120 |
| tcctgctctg gaaccaggtc aacattggg agtgattatg tttcctggta ccaacacctc | 180 |
| ccaggaacag cccccaaact cctcgtttat ggcgataatc tgcgaccctc agggattcct | 240 |
| gaccgattct ctgcctccaa gtctggcacg tcagccaccc tgggcatcac cggactccag | 300 |
| actggggacg aggccgatta ttactgcggc acatgggatt acaccctgaa tggtgtggtg | 360 |
| ttcggcggag ggaccaagct gaccgtccta ggttctagag gtggtggtgg tagcggcggc | 420 |
| ggcggctctg gtggtggtgg atccctcgag atggcccagg tgcagctggt ggagtctggg | 480 |
| ggaggcttgg tacagcctgg ggggtccctg agactctcct gtgcagcctc tggattcacc | 540 |
| tttagcagct atgccatgag ctgggtccgc caggctccag gaaggggct ggagtgggtc | 600 |
| tcagttattt atagcggtgg tagtagcaca tactatgcag actccgtgaa gggccggttc | 660 |
| accatctcca gagataattc caagaacacg ctgtatctgc aaatgaacag cctgagagcc | 720 |
| gaggacacgg ccgtatatta ctgtgcgcgc acttcttacc tgaaccatgg tgattactgg | 780 |
| ggtcaaggta ctctggtgac cgtgtctagc gccgctgcat cgtgcctgt gttcctccca | 840 |
| gctaagccca ctaccacccc cgctccaagg ccgcccacgc ccgctcctac tattgctagt | 900 |
| cagcctttaa gtttacgacc cgaagcttgc aggcccgccg ccggcggcgc tgtgcacacc | 960 |
| agggggcttg attttgcctg cgacttttgg gtattggtag tggtgggcgg agttttagcc | 1020 |
| tgctacagcc tcctggtaac agtggctttt atcatctttt gggtgaggaa cgatggcag | 1080 |
| aacgagaagc tcgggttgga tgccggggat gaatatgaag atgaaaacct ttatgaaggc | 1140 |
| ctgaacctgg acgactgctc catgtatgag gacatctccc ggggcctcca gggcacctac | 1200 |
| caggatgtgg gcagcctcaa cataggagat gtccagctgg agaagccgtg a | 1251 |

<210> SEQ ID NO 150
<211> LENGTH: 1389
<212> TYPE: DNA
<213> ORGANISM: Artificial Sequence
<220> FEATURE:
<223> OTHER INFORMATION: Synthetic

<400> SEQUENCE: 150

| | |
|---|---|
| gaggttcaac ttgttcaatc tggggcagaa gtgaagaagc cggggcatc tgtgaaagta | 60 |
| tcatgcaaaa catccggcta tacgtttacc gaatacacca ttcactgggt cagacaggct | 120 |
| cccgtcaaa gcctcgaatg gatgggaaat attaaccta acaatggcgg aaccacatat | 180 |
| aatcagaaat tccaaggccg agtgacgata actgtcgata gagtacgtc cacagcttac | 240 |
| atggaactca gctctttgag atccgaagac actgcagttt attattgtgc agctggatgg | 300 |
| aacttcgact attggggaca agggactctt gttacggtgt ccagtggcaa accaggtagt | 360 |
| ggtaaacccg gaagcggcaa gcccgggagc ggtaaacctg gtagcgacat cgtcatgact | 420 |
| caaagccctg actcactcgc cgtgagcctg ggagagcgtg caacgctatc ttgtcgggcc | 480 |
| tctcaggatg tcggaactgc tgtagactgg tatcaacaga aacctgacca atcaccaaaa | 540 |

-continued

```
ctcctgattt attgggcctc aacacgtcac acaggagtgc cagataggtt cacaggtagt    600
ggcagtggaa ctgattttac tttgacaatt agcagcctgc aagccgaaga tgtagccgtt    660
tacttctgtc aacaatataa ctcataccca ctaacgttcg gtgccgggac gaaggtagag    720
attaaattcg tgcctgtgtt cctcccagct aagcccacta ccaccccgc tccaaggccg    780 cccacgcccg ctcctactat tgctagtcag cctttaagtt tacgacccga agcttgcagg    840
cccgccgccg gcggcgctgt gcacaccagg gggcttgatt ttgcctgcga cttttgggta    900
ttggtagtgg tgggcggagt tttagcctgc tacagcctcc tggtaacagt ggcttttatc    960
atcttttggg tgaagaaggt tgcaaaaaaa cctactaata aggctcccca tcctaagcaa   1020 gagcccaag aaattaactt tcccgatgat cttccgggtt ctaacacggc agccccggtg    1080
caggagaccc tgcatggttg tcaacccgtc actcaggagg acgggaaaga gtctcgtatc   1140
tccgtccagg agagacagcg caaaaaacgt ataagcgcaa actctacaga tccagtaaaa   1200
gccgcgcaat tcgagcctcc cggccgccag atgattgcaa tacggaaacg tcaactggag   1260
gaaactaata atgactatga gacggccgac ggtggataca tgacccttaa tccccgcgcg   1320
ccaaccgacg atgataagaa catatatctg acgctccccc ctaacgatca cgttaacagt   1380
aataattaa                                                           1389
```

MODIFIED B CELLS AND METHODS OF USE THEREOF

RELATED APPLICATIONS

The present application is a continuation of International Patent Application No. PCT/US2021/025273, filed Mar. 31, 2021, which claims the benefit of priority to U.S. Provisional Patent Application No. 63/003,120, filed Mar. 31, 2020, and the present application also claims priority to U.S. Provisional Patent Application No. 63/073,799, filed Sep. 2, 2020. Each of the priority applications is hereby incorporated by reference in its entirety.

SEQUENCE LISTING

The instant application contains a Sequence Listing, which has been submitted electronically in ASCII format and is hereby incorporated by reference in its entirety. Said ASCII copy, created on Sep. 2, 2021, is named "109036-0046_SEQ.txt" and is 315,176 bytes in size.

BACKGROUND OF THE INVENTION

Most cellular immunotherapies to date have focused in T cells. For example, cancer immunotherapies are primarily focused on modification and administration of T cells—enhancing the killer T cell response to a tumor. Modifying B cells for the treatment of various disease, however, is a technique that has not been extensively studied, despite the critical role of B cells in immune responses.

B cells, also known as B lymphocytes, are a type of white blood cell responsible for, among other things, helping the body resist infection and diseases. They are part of our adaptive immune system, and are capable of various immune responses, for example, secreting antibodies in response to a recognized antigen. Additionally, B cells are capable of presenting antigens, and can also secret cytokines.

Many B cells mature into plasma cells that produce antibodies (proteins) capable of fighting off infections. Other B cells mature into memory B cells. All plasma cells descended from a single B cell produce the same antibody that is directed against the antigen that stimulated it to mature. The same principle holds with memory B cells. Thus, all plasma cells and memory cells "remember" the stimulus that led to their formation. The B cell, or B lymphocyte, is not thymus-dependent, has a short lifespan, and is responsible for the production of immunoglobulins. See e.g., https://www.medicinenet.com/script/main/art.asp?articlekey=2413. The B cell is thus an immunologically important cell.

B cells appear to be associated with patient outcomes in the treatment of cancer. For example, the presence of tertiary lymphoid structures (TLSs) is associated with better patient outcomes. See, e.g., Helmink, B. A., et al., Nature, 2020, 577(7791), 549-555; Petitprez F et al., Nature, 2020, 577 (7791), 556-560. TLSs are aggregates of immune cells (mostly T and B cells) that arise in response to immunological stimuli. While TLSs that surround tumor cells include B cells, the role of B cells in antitumor responses have been unclear. B cells found in tumors can produce inhibitory factors that hinder the function of immune cells. See, e.g., Kessel, A., et al., Autoimmun Rev., 2012, 11(9), 670-677; Khan, A. R., et al., Nature Commun., 2015, 6, 5997. Further, current evidence indicates that B cells impede antitumor responses in most mouse models of cancer. Affara, N. I., et al. Cancer Cell, 2014, 25(6), 809-821; Shalapour, S., et al., Nature, 2017, 551, 340-345; Ammirante, M. et al., Nature, 2010, 464, 302-305. Yet, the presence of B cells in TLS structures is correlated with positive clinical outcomes to cancer immunotherapy. Petitprez 2020. Intratumoral injection of LPS-activated spleen cells, which include B cells, in combination with checkpoint inhibitors has been shown to produce anti-tumor responses. Soldevilla et al., Oncoimmunology, 2018, 7:8, e1450711.

CD79 (also termed "Cluster of Differentiation 79") is a transmembrane protein that forms a complex with the B-cell receptor and is capable of generating a signal following recognition of an antigen by the B-cell receptor.[1] CD79 is comprised of two different chains known as CD79A and CD79B (also termed Igα and Igβ). CD79a and CD79b are both members of the immunoglobulin superfamily. These form a heterodimer on the surface of B cells stabilized by disulfide bonding. Both CD79 chains contain an immunoreceptor tyrosine-based activation motif ("ITAM") in their intracellular tail regions that propagate a signal in a B cell.[2]

[1] See Chu P G, Arber D A (June 2001); CD79: a review; Applied Immunohistochemistry & Molecular Morphology. 9 (2): 97-106. doi:10.1097/00022744-200106000-00001. PMID 11396639. See also https://en.wikipedia.org/wiki/CD79.

[2] See Müller B, Cooper L, Terhorst C (January 1995), Interplay between the human TCR/CD3 epsilon and the B-cell antigen receptor associated Ig-beta (B29); Immunology Letters. 44 (2-3): 97-103. doi:10.1016/0165-2478(94)00199-2. PMID 7541024.

Given the natural ability of B cells to present antigens and secrete proteins, there is great potential as a cellular therapy for targeting certain diseased cell types and secreting therapeutic payloads. There thus exists a need for alternative treatments beyond T cell therapies, such as engineered B cells, for the treatment of a variety of diseases and disorders, including cancer, heart disease, inflammatory disease, muscle wasting disease, neurological disease, and the like.

SUMMARY OF THE INVENTION

It has now been found that engineered B cells can be efficacious in the treatment of various diseases and disorders as recited herein. The invention therefore relates to modified B cells.

It has also been found that CD79a (Immunoglobulin α) when incorporated into the intracellular signaling domain of the CAR-B constructs of the invention exhibits superior qualities over CD79b (Immunoglobulin β). Further, it has further been found that when used in the CAR-B constructs described herein, intracellular CD79b (Immunoglobulin β) displays no (or even a negative effect) on efficacy. The invention thus relates to, inter alia, CAR-B constructs comprising the CD79a intracellular signaling domain.

In certain embodiments, the invention relates to an isolated modified B cell ("CAR-B cell), capable of expressing a chimeric receptor ("CAR-B receptor"), wherein said chimeric receptor comprises (a) an extracellular domain; (b) a transmembrane domain; and (c) a cytoplasmic domain that comprises at least one signaling domain. The cytoplasmic domain preferably comprises CD79a. In various embodiments, the extracellular domain comprises an extracellular binding domain and a hinge domain. In various embodiments, the extracellular binding domain(s) recognizes at least one antigen or protein expressed on the surface of a target cell. In various embodiments, the target cell is selected from the group consisting of a tumor cell, cardiac muscle cell, a skeletal muscle cell, a bone cell, a blood cell, a nerve cell, a fat cell, a skin cell, and an endothelial cell. In various embodiments, the B cell expresses more than one CAR-B receptor construct. In various embodiments, the CAR-B receptor comprises more than one extracellular binding domain. In various embodiments, the extracellular binding domain is a single chain variable fragment (scFv), or a full-length antibody, or the extracellular domain of a receptor or ligand. In various embodiments, the extracellular binding domain is capable of binding to an antigen or protein selected from the group consisting of: PSMA, GPC3, ASGR1, ASGR2, Sarcoglycan, Corin, FAP (fibroblast activation protein) and Her2. In various embodiments, the hinge domain is derived from the group consisting of IgG, CD28 and CD8. In various embodiments, the hinge domain is comprised of a nucleic acid sequence selected from the group consisting of SEQ ID Nos. 27, 29, 31. In various embodiments, the cytoplasmic domain comprises at least one signaling domain native to B cell receptors. In various embodiments, the cytoplasmic domain comprises a domain that is selected from the group consisting of: CD79a (Immunoglobulin α), CD79b (Immunoglobulin β), CD40, CD19, CD137, Fcγr2a, MyD88, CD21, Syk, FYN, LYN, PI3K, BTK, PLCγ2, CD3ζ and BLNK. In various embodiments, the cytoplasmic domain further comprises a costimulatory domain.

In various embodiments, the invention comprises an isolated modified B cell, wherein said B cell is capable of expressing and secreting a payload, wherein the payload is not naturally expressed in a B cell or is expressed at higher levels than is naturally expressed in a B cell. In various embodiments, the payload is an antibody or fragment thereof. In various embodiments, the antibody is a secreted antibody and can include blocking antibodies (eg anti-PD-1) or agonist antibodies (anti-CD137, GITR, OX40) engineered to contain native or engineered Fc regions and can be soluble or membrane-bound In various embodiments, the payload(s) can be immune modifiers such as chemokines or cytokines. In various embodiments, the payload is selected from the group consisting of: IL-1, IL-7, IL-8, IL-10, IL-12, IL-13, IL-17, IL18, IL-21, interferon α, interferon β, interferon γ, TSLP, CCL21, FLT3L, XCL1, LIGHT(TNFSF14), OX40L, CD137L, CD40L, ICOSL, anti-CD3 antibody, CD47, TIM4-FC, CXCL13, CCL21, CD80, CD40L, IFNα A2, LIGHT, 4-1BBL, MDGF (C19orf10), FGF10, PDGF, agrin, TNF-α, GM-CSF, an anti-FAP antibody, an anti-TGF-β antibody; a TGF-β trap, decoy or other inhibitory molecule; an anti-BMP antibody; a BMP trap, decoy or other inhibitory molecule. In various embodiments, the B cell is capable of expressing more than one payload. In various embodiments, the B cell is capable of expressing more than 1, 2, 3, 4, 5, 6, 7, 8, 9, 10, 11, or 12 payloads.

In various embodiments, the invention relates to a method of treating a patient comprising administering the modified B cell of the present invention. In various embodiments, the modified B cell is administered intra-tumorally, intravenously, subcutaneously, or intradermally. In various embodiments, the method further comprises administering a checkpoint inhibitor. In various embodiments, the checkpoint inhibitor to a checkpoint molecule that is selected from the group consisting of PD-1, PD-L1, CTLA-4, LAG3, TIM-3 and NKG2A proteins. In various embodiments, the checkpoint inhibitor is a monoclonal antibody.

In various embodiments, the invention relates to an isolated modified B cell, capable of expressing a chimeric receptor, wherein said chimeric receptor comprises (a) an extracellular domain, wherein the extracellular domain comprises an extracellular binding domain and a hinge domain; (b) a transmembrane domain; and (c) a cytoplasmic domain that comprises at least one signaling domain, wherein said modified B cell is further capable of expressing a payload, wherein the payload is not naturally expressed on the surface of a cell. In various embodiments, the extracellular binding domain recognizes an antigen or protein expressed on the surface of a target cell. In various embodiments, the target cell is selected from the group consisting of a tumor cell, a cardiac muscle cell, a skeletal muscle cell, a bone cell, a blood cell, a nerve cell, a fat cell, a skin cell and an endothelial cell. In various embodiments, the B cell expresses more than one CAR-B receptor construct. In various embodiments, the CAR-B receptor comprises more than one extracellular binding domain. In various embodiments, the extracellular binding domain is a single chain variable fragment (scFv), an antibody, or the extracellular domain of a receptor or ligand. In various embodiments, the extracellular binding domain is capable of binding to an antigen or protein selected from the group consisting of PSMA, GP3, ASGR1, ASGR2, Sarcoglycan, Corin, FAP and Her2. In various embodiments, the hinge domain is derived from the group consisting of IgG, CD28 and CD8. In various embodiments, the hinge domain is comprised of a nucleic acid sequence selected from the group consisting of SEQ ID Nos. 27, 29, and 31. In various embodiments, the cytoplasmic domain comprises at least one signaling domain native to B cells. In various embodiments, the cytoplasmic domain comprises a domain selected from the group consisting of: CD79a (Immunoglobulin α), CD79b (Immunoglobulin β), CD40, CD19, CD137, Fcγr2a, MyD88, CD21, Syk, FYN, LYN, PI3K, BTK, PLCγ2, CD3ζ and BLNK. In various embodiments, the cytoplasmic domain further comprises a costimulatory domain. In various embodiments, the payload is a secreted or membrane bound antibody or fragment thereof. In various embodiments, the payload is selected from the group consisting of: IL-1, IL-7, IL-8, IL-10, IL-12, IL-13, IL-17, IL-18, IL-21, interferon α, interferon β, interferon γ, TSLP, CCL21, FLT3L, XCL1, LIGHT(TNFSF14), OX40L, CD137L, CD40L, ICOSL, anti-CD3 antibody, CD47, TIM4-FC, CXCL13, CCL21, CD80, CD40L, IFNα A2, LIGHT, 4-1BBL, MDGF (C19orf10), FGF10, PDGF, agrin, TNF-α, GM-CSF, an anti-FAP antibody, an anti-TGF-β antibody; a TGF-β trap, decoy or other inhibitory molecule; an anti-BMP antibody; a BMP trap, decoy or other inhibitory molecule. In various embodiments, the B cell is capable of expressing more than one payload. In various embodiments, the B cell is capable of expressing more than 1, 2, 3, 4, 5, 6, 7, 8, 9, 10, 11, or 12 payloads. In various embodiments, the modified B cell further encodes at least one protein selected from the group consisting of: the cytoplasmic domains of CD79a, CD79b, CD40, CD19, CD137, Fcγr2a, CD3ζ and MyD88. In various embodiments, the intention relates to a method of treating a patient comprising administering the modified B cell. In various embodiments, the method further comprises administering a checkpoint inhibitor. In various embodiments, the checkpoint inhibitor is selected from inhibitors to one or more checkpoint molecules from the group consisting of: PD-1, PD-L1, CTLA-4, LAG3, TIM-3 and NKG2A. In various embodiments, the checkpoint inhibitor is a monoclonal antibody. In various embodiments, the present invention relates to an isolated modified B cell, capable of expressing a chimeric receptor, wherein said chimeric receptor comprises an extracellular domain, wherein said extracellular domain comprises a hinge domain and an extracellular binding domain, wherein said extracellular binding domain is not naturally expressed on a B cell; and wherein said extracellular binding domain is capable of recognizing a target of interest. In various embodiments, the binding domain is a single chain variable fragment (scFv), antibody, ligand or receptor. In various embodiments, the binding domain is an scFv. In various embodiments, the binding domain is a receptor, a ligand, or a fragment thereof. In various embodiments, the B cell is further capable of expressing a payload. In various embodiments, the invention comprises a method of treating a patient comprising administering the modified B cell to a patient.

In various embodiments, the present invention comprises a nucleic acid capable of expressing a chimeric B cell receptor, wherein said chimeric receptor comprises: (a) an extracellular domain, wherein said extracellular domain comprises an extracellular binding domain and a hinge domain; (b) a transmembrane domain; and (c) a cytoplasmic domain that comprises at least one signaling domain. In various embodiments, the extracellular binding domain, recognizes an antigen or protein expressed on the surface of a target cell. In various embodiments, the extracellular binding domain is a single chain variable fragment (scFv), antibody, receptor or ligand. In various embodiments, the target cell is selected from the group consisting of a tumor cell, a cardiac muscle cell, a skeletal muscle cell, a bone cell, a blood cell, a nerve cell, a fat cell, a skin cell and an endothelial cell. In various embodiments, the vector expresses more than one CAR-B receptor. In various embodiments, the CAR-B receptor expresses more than one extracellular binding domain. In various embodiments, the extracellular binding domain is capable of binding to an antigen or protein selected from the group consisting of: PSMA, GP3, ASGR1, ASGR2, Sarcoglycan, Corin, Her2, FAP, MUC1, CEA153, JAM-1, and LFA-1. In various embodiments, the hinge domain is derived from the group consisting of IgG, CD28 and CD8. In various embodiments, the hinge domain is comprised of a nucleic acid sequence selected from the group consisting of SEQ ID Nos. 27, 29, and 31. In various embodiments, the cytoplasmic domain comprises at least one signaling domain native to B cell receptors. In various embodiments, the cytoplasmic domain comprises a domain selected from the group consisting of: CD79a (Immunoglobulin α), CD79b (Immunoglobulin β), CD40, CD19, CD137, Fcγr2a, MyD88, CD21, Syk, FYN, LYN, PI3K, BTK, PLCγ2, CD3ζ and BLNK. In various embodiments, the cytoplasmic domain further comprises a costimulatory domain.

In various embodiments, the invention relates to a vector comprising a nucleic acid capable of expressing a chimeric B cell receptor, wherein said chimeric receptor comprises: (a) an extracellular domain, wherein said extracellular domain comprises an extracellular binding domain and a hinge domain; (b) a transmembrane domain; and (c) a cytoplasmic domain that comprises at least one signaling domain. In various embodiments, the extracellular binding domain recognizes an antigen or protein. In various embodiments, the target cell is selected from the group consisting of a tumor cell, a cardiac muscle cell, a skeletal muscle cell, a bone cell, a blood cell, a nerve cell, a fat cell, a skin cell and an endothelial cell. In various embodiments, the vector expresses more than one CAR-B receptor. In various embodiments, the CAR-B expresses more than one extracellular binding domain. In various embodiments, the extracellular binding domain is a single chain variable fragment (scFv), antibody, receptor or ligand. In various embodiments, the extracellular binding domain is capable of binding to an antigen or protein selected from the group consisting of: PSMA, GPC3, ASGR1, AGSR2, Sarcoglycan, Corin, Her2, FAP, MUC1, CEA153, JAM-1, and LFA-1. In various embodiments, the hinge domain is derived from the group consisting of IgG, CD28 and CD8. In various embodiments, the hinge domain is comprised of a nucleic acid sequence selected from the group consisting of SEQ ID Nos. 27, 29, and 31. In various embodiments, the cytoplasmic domain comprises at least one signaling domain native to B cells. In various embodiments, the cytoplasmic domain comprises a signaling domain selected from the group consisting of: CD79a (Immunoglobulin α), CD79b (Immunoglobulin β), CD40, CD19, CD137, Fcγr2a, MyD88, CD21, Syk, FYN, LYN, PI3K, BTK, PLCγ2, CD3ζ and BLNK. In various embodiments, the cytoplasmic domain further comprises a costimulatory domain. The various embodiments, the cytoplasmic region is comprised of multiple, 2 or more, domains, being either identical or unique.

In various embodiments, the invention relates to an isolated modified B cell, capable of expressing an integrin, a homing antibody, protein, a receptor, or combinations thereof, wherein said integrin, homing antibody, protein, or receptor is not naturally expressed in a B cell or is expressed at higher levels than is naturally expressed in a B cell; and wherein said integrin, homing antibody, protein, receptor, or combinations thereof is attracted to a site or target of interest. In various embodiments, the integrin, homing antibody, protein, and receptor is selected from CLA (PSGL-1 glycoform), CLA (PSGL-1 glycoform), CCR10, CCR3, CCR4, CCR5, CCR6, CCR9, CD43E, CD44, c-Met, CXCR3, CXCR4, LFA-1, LFA-1 (αLβ2), selectin ligands, VLA-4, VLA-4 (α4β1), and α4β7, or combinations thereof. In various embodiments, the site of interest is a homing or target tissue, an inflammatory site in a specific location or tissue, or a tumor or tumor microenvironment, where delivery of payloads is desirable. In various embodiments, the homing or target tissue is selected from skin, gut (intestine, colon, mesenteric lymph nodes (mLN), Peyer's Patch (PP), small intestine), liver, lung, bone marrow, heart, peripheral lymph node (LN), CNS, thymus, and bone marrow. In various embodiments, the target of interest is selected from CXCL16, CCL17, CCL17(22), CCL20 (MIP-3α), CCL21, CCL25, CCL27, CCL28, CCL4, CCL5, CD62E, CD62P, CXCL10, CXCL12, CXCL13, CXCL16, CXCL9/CXCL10, CXCR3, E/P-selectin, E-selectin, GPR15L, HGF, Hyaluronate, ICAM-1, ligands for CCR1, 2, 5, MAdCAM, MAdCAM-1, PNAd, VAP-1, VCAM, and VCAM-1, or combinations thereof. In various embodiments, the method comprises treating a patient by administering the isolated modified B cell. In various embodiments, the method involves further administering a compound or a derivative thereof, wherein the compound or derivative thereof is capable of increasing the expression of the integrin, homing antibody, protein, and receptor, or combinations thereof. In various embodiments, the compound or a derivative thereof is capable of altering trafficking of B cells to a site or target of interest in the patient. In various embodiments, the compound is all-trans-retinoic acid (ATRA) or a derivative thereof.

In various embodiments, the invention relates to an isolated modified B cell, capable of expressing an immune inhibitory molecule, wherein said immune inhibitory molecule is not naturally expressed in a B cell or is expressed at higher levels than is naturally expressed in a B cell. In various embodiments, said immune inhibitory molecule is selected from IL-10, TGF-β, PD-L1, PD-L2, LAG-3, and TIM-3, or combinations thereof. In various embodiments, said immune inhibitory molecule is capable of decreasing inflammation and autoimmune activity of B cells at a site or target of interest in a patient. In various embodiments, the invention relates to a method of treating a patient comprising administering said isolated modified B cell. In various embodiments, said immune inhibitory molecule is selected from IL-10, TGF-β, PD-L1, PD-L2, LAG-3, and TIM-3, or combinations thereof. In various embodiments, said immune inhibitory molecule is capable of decreasing inflammation and autoimmune activity of B cells at a site or target of interest in the patient. In various embodiments, the invention relates to further administering a compound or a derivative thereof capable of increasing the expression of an integrin, a homing antibody, a protein, a receptor, or combinations thereof in the B cell. In various embodiments, said compound or derivative thereof is capable of altering trafficking of B cells to a site or target of interest in the patient. In various embodiments, said compound is all-trans-retinoic acid (ATRA) or a derivative thereof. In various embodiments, the invention relates to an isolated modified B cell, wherein the isolated modified B cell is treated with a compound or a derivative thereof, wherein said compound or derivative thereof is capable of increasing the expression of an integrin, a homing antibody, a protein, a receptor, or combinations thereof in B cells. In various embodiments, said compound or derivative thereof is capable of altering trafficking of B cells to a site or target of interest in the patient. In various embodiments, said compound is all-trans-retinoic acid (ATRA) or a derivative thereof. In various embodiments, said compound or derivative thereof is capable of (i) increasing the expression of an integrin, a homing antibody, a protein, a receptor, or combinations thereof in B cells, and (ii) altering trafficking of B cells to a site or target of interest in the patient. In various embodiments, said compound is all-trans-retinoic acid (ATRA) or a derivative thereof.

In various embodiments, the invention relates to an isolated modified B cell, capable of expressing at least one or more of a constitutively active Toll-like receptor (TLR), wherein said TLR is not naturally expressed in a B cell or is expressed at higher levels than is naturally expressed in a B cell. In various embodiments, said TLR is selected from TLR1, TLR2, TLR3, TLR4, TLR5, TLR6, TLR7, TLR8, TLR9, TLR10, TLR11, TLR12, and TLR13, or combinations thereof. In various embodiments, said TLR is capable of potentiating B cells for increasing immune responses in a patient. In various embodiments, said TLR is capable of producing potent effector B cells for increasing immune responses in a patient. In various embodiments, said immune inhibitory molecule is capable of decreasing inflammation and autoimmune activity of B cells at a site or target of interest in a patient. In various embodiments, said TLR is selected from TLR1, TLR2, TLR3, TLR4, TLR5, TLR6, TLR7, TLR8, TLR9, TLR10, TLR11, TLR12, and TLR13, or combinations thereof. In various embodiments, said TLR is capable of (i) potentiating B cells, and (ii) producing potent effector B cells, for increasing immune responses in a patient. In various embodiments, at least one or more of a TLR agonist is administered to the patient. In various embodiments, the isolated modified B cell is treated with at least one or more of a TLR agonist. In various embodiments, said TLR agonist is capable of (i) potentiating B cells, and (ii) producing potent effector B cells, for increasing immune responses in a patient. In various embodiments, said TLR agonist binds to one or more TLRs selected from TLR1, TLR2, TLR3, TLR4, TLR5, TLR6, TLR7, TLR8, TLR9, TLR10, TLR11, TLR12, and TLR13, or combinations thereof. In various embodiments, said TLR agonist is selected from CpG-rich oligonucleotides, double-stranded RNA mimic, polyinosinic acid:polycytidylic acid (poly-I:C). In various embodiments, said TLR agonist comprises CpG oligonucleotides. In various embodiments, said TLR agonist is capable of is capable of (i) potentiating B cells, and (ii) producing potent effector B cells, for increasing immune responses in the patient. In various embodiments, said TLR agonist binds to one or more TLRs selected from TLR1, TLR2, TLR3, TLR4, TLR5, TLR6, TLR7, TLR8, TLR9, TLR10, TLR11, TLR12, and TLR13, or combinations thereof. In various embodiments, said TLR agonist is selected from CpG-rich oligonucleotides, double-stranded RNA mimic, polyinosinic acid:polycytidylic acid (poly-I:C). In various embodiments, said TLR agonist comprises CpG oligonucleotides.

In various embodiments, the invention relates to an isolated modified B cell, wherein said B cell is electroporated with an mRNA encoding at least one or more of an antigen fused to a targeting signal. In various embodiments, said antigen is (i) not naturally presented by a B cell, (ii) not presented by a B cell simultaneously in both HLA class I and class II molecules naturally, or (iii) not presented by a B cell with high efficiencies in both HLA class I and class II molecules naturally. In various embodiments, said targeting signal is targeting signal of a lysosomal protein. In various embodiments, said targeting signal is a targeting signal of lysosome-associated membrane protein-1 (LAMP1). In various embodiments, said antigen is capable of being targeted to the lysosomes and presented simultaneously and efficiently in both HLA class I and class II molecules. In various embodiments, said B cells is capable of increasing antigen-specific immune responses in a patient. In various embodiments, said antigen is (i) not naturally presented by a B cell, (ii) not presented by a B cell simultaneously in both HLA class I and class II molecules naturally, or (iii) not presented by a B cell with high efficiencies in both HLA class I and class II molecules naturally. In various embodiments, said targeting signal is targeting signal of a lysosomal protein. In various embodiments, said targeting signal is a targeting signal of lysosome-associated membrane protein-1 (LAMP1). In various embodiments, said antigen is capable of being targeted to the lysosomes and presented simultaneously and efficiently in both HLA class I and class II molecules. In various embodiments, said B cells is capable of increasing antigen-specific immune responses in the patient.

BRIEF DESCRIPTION OF THE FIGURES

FIG. 3 shows examples of certain CAR-B constructs of the present invention. (A) CAR-B that binds GPC3. (B) CAR-B that binds PSMA.

DETAILED DESCRIPTION

Figure 1:
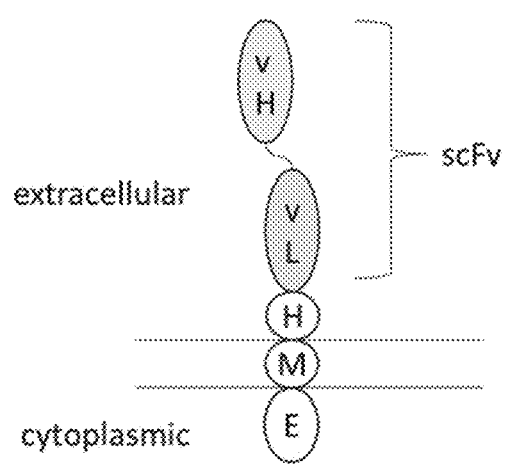
FIG. 1 sets forth an example of a chimeric B Cell Receptor (CAR-B) of the present invention. In certain embodiments, the CAR-B construct will comprise an extracellular domain, a transmembrane domain, and a cytoplasmic domain. As depicted in FIG. 1, the extracellular domain may in certain embodiments comprise a binding domain and a hinge region. In certain embodiments, the binding region may be an scFv. CAR-B constructs are cloned into a vector for expression.

The invention disclosed herein relates to several embodiments of engineered or modified B cells:
1. B cells that have been modified to home to a site/target of interest, using, e.g., a binding domain such as an scFv, antibody, ligand, receptor, or fragments thereof;
2. B cells that have been modified with a homing domain, further comprising an activation, and optionally a costimulatory domain, such that the B cells can home and activate upon interaction with a desired target;
3. B cells engineered to be capable of making a desired protein payload, such as an antibody, therapeutic protein, polypeptide, nucleic acid sequence (such as RNAi) or the like;
4. Engineered B cells comprising a homing/binding domain, an activating domain, an optional costimulatory domain, and further engineered to express a desire protein payload, such as an antibody, therapeutic protein, polypeptide, nucleic acid sequence (such as RNAi) or the like;
5. B cells that have been modified to express an integrin, a homing antibody, protein, or a receptor, such that the B cells are attracted to specific ligands, chemokines, or attractants at a specific site/target of interest (e.g., a homing tissue) and can thereby home to the site/target of interest, for example, to deliver a desired payload;
6. B cells that have been modified to express an immune inhibitory molecule, such that the inflammation and autoimmune activity of B cells localized to a site/target of interest is decreased, thereby leading to a positive therapeutic response;
7. B cells that have been treated with a compound or derivatives thereof, such that trafficking of the B cells is altered by expression of specific B cell integrins and/or homing receptors;
8. B cells that have been (i) treated with a Toll-like receptor (TLR) agonist, and/or (ii) engineered to express a constitutively active TLR, for potentiating B cells and/or producing potent effector B cells for increasing immune responses in a subject;
9. B cells that have been electroporated with an mRNA encoding specific antigens of interest fused to a targeting signal of a lysosomal protein, such that the B cells can simultaneously and efficiently present the specific antigens and/or antigen-derived epitopes of interest in both HLA class I and class II molecules.
10. B cells that have been electroporated with a self-amplifying RNA that encodes any items noted heretofore in 1-9.

It is understood that the various embodiments of engineered or modified B cells of the present application are not mutually exclusive and can be combined with each other in any way and without any restriction unless explicitly indicated, for achieving of facilitating any of the results and/or therapeutic responses contemplated herein.

Tumor Antigen. In certain embodiments, the site/target of interest is a tumor antigen. The selection of the antigen-binding domain (moiety) of the invention will depend on the particular type of cancer to be treated. Some tumor antigens may be membrane bound, whereas other may be secreted. For example, a tumor antigen may be secreted and accumulate in the extracellular matrix, or the tumor antigen may be expressed as part of the MHC complex. Tumor antigens are well known in the art and may include, for example, CD19, KRAS, HGF, CLL, a glioma-associated antigen, carcinoembryonic antigen (CEA); β-human chorionic gonadotropin, alphafetoprotein (AFP), lectin-reactive AFP, thyroglobulin, RAGE-1, MN-CA IX, human telomerase reverse transcriptase, RU1, RU2 (AS), intestinal carboxyl esterase, mut hsp70-2, M-CSF, prostase, prostate-specific antigen (PSA), PAP, NY-ESO-1, LAGE-1a, p53, protein, PSMA, Her2/neu, survivin and telomerase, prostate-carcinoma tumor antigen-1 (PCTA-1), MAGE, ELF2M, neutrophil elastase, ephrinB2, CD22, insulin growth factor (IGF)-I, IGF-II, IGF-I receptor, mesothelin, EGFR, BCMA, KIT and IL-13.

Infectious Disease Antigen. In certain embodiments, the site/target of interest is an infectious disease antigen against which an immune response may be desired. Infectious disease antigens are well known in the art and may include, but are not limited to, viruses, bacteria, protists, and parasitic antigens, such as parasites, fungi, yeasts, mycoplasma, viral proteins, bacterial proteins and carbohydrates, and fungal proteins and carbohydrates. In addition, the type of infectious disease of the infectious disease antigen is not particularly limited, and may include, but are not limited to, intractable diseases among viral infectious diseases such as AIDS, hepatitis B, Epstein Barr Virus (EBV) infection, HPV infection, HCV infection, SARS, SARS-CoV2, etc. Parasitic antigens may include, but are not limited to, the malaria parasite sporozoide protein.

In certain embodiments the modified B cells express an engineered B cell receptor (CAR-B) comprising an extracellular domain, a transmembrane domain and an intracellular domain. In certain embodiments, the extracellular domain comprises a binding domain and a hinge domain. In certain embodiments, the extracellular domain comprises a binding domain, such as an scFv, ligand, antibody, receptor, or fragment thereof which allows the modified B cell to target specific target cells by binding to proteins expressed on the surface of those cells. In certain embodiments, the modified tumor cells target and bind to proteins/antigens expressed on the surface of tumor cells. In certain embodiments, the modified B cell further expresses a payload. In certain embodiments, the payload is capable of increasing the number of cross-presenting antigen or antigenic fragments to dendritic cells (DC) in tumors or in lymph nodes. In certain embodiments, the payload is capable of activating and attracting T cells into tumors. In certain embodiments, the payload is capable of fomenting the formation of tertiary lymphoid structures (TLS) in tumors. In certain embodiments of the invention, the modified B cell expresses both a CAR-B and a payload. In certain embodiments, the CAR-B comprises stimulatory domains that activate expression of the payload when bound to an antigen or protein expressed on the surface of a tumor cell.

1. Design and Domain Orientation of Chimeric Antigen Receptors in B Cells (CAR-Bs)

In various embodiments, the invention provides a chimeric B Cell Receptor (CAR-B). It will be appreciated that chimeric B cell receptors (CAR-Bs) are genetically engineered receptors. These engineered receptors can be readily inserted into and expressed by B cells in accordance with techniques known in the art. With a CAR-B, a single receptor can be programmed to both recognize a specific protein or antigen expressed on a tumor cell, and when bound to said protein or antigen elicit an anti-tumor response. In various embodiments, the CAR-Bs serve in part as a homing mechanism to deliver B cells to target tissue.

It will be appreciated that relative to the cell bearing the receptor, the chimeric B cell receptor of the invention will comprise an extracellular domain (which will comprise an antigen-binding domain and may comprise an extracellular signaling domain and/or a hinge domain), a transmembrane domain, and an intracellular domain. The intracellular domain comprises at least an activating domain, preferably comprised of CD79a (Immunoglobulin α), CD79b (Immunoglobulin β), CD40, CD19, CD137, CD3ζ Fcγr2a and/or MyD88. It will further be appreciated that the antigen-binding domain is engineered such that it is located in the extracellular portion of the molecule/construct, such that it is capable of recognizing and binding to its target or targets.

Structurally it will be appreciated that these domains correspond to locations relative to the immune cell. Exemplary CAR-B constructs in accordance with the invention are set forth in Table 1:

TABLE 1

| Construct Name | Extracellular Domain | Hinge | TM | Signal 1 | Signal 2 |
|---|---|---|---|---|---|
| pWF-82 | anti-PSMA | CD8 | CD28 | hCD19 | |
| pWF-83 | anti-PSMA | CD8 | CD28 | hCD40 | |
| pWF-84 | anti-PSMA | CD8 | CD28 | hCD40 | CD79b |
| pWF-85 | anti-PSMA | CD8 | CD28 | hCD40 | CD137 |
| pWF-86 | anti-PSMA | CD8 | CD28 | hCD40 | Fcγr2a |
| pWF-87 | anti-PSMA | CD8 | CD28 | hMyd88 | hCD40 |
| pWF-88 | anti-PSMA | CD8 | CD28 | CD79a | |
| pWF-89 | anti-PSMA | CD8 | CD28 | CD79b | |
| pWF-391 | anti-PSMA | 3x strep II tag | CD28 | CD79b | |
| pWF-394 | anti-Sarcoglycan | 3x strep II tag | CD28 | CD79b | |
| pWF-396 | anti-GPC-3 | CD8 | CD28 | CD79a | |
| pWF-397 | anti-GPC-3 | CD8 | CD28 | CD79b | |
| pWF-460 | anti-GPC-3 | Human IgG1 Fc | CD28 | CD79a | |
| pWF428 | anti-GPC-3 | Human Lambda Constant region | Human Lambda Constant region | | |
| pWF429 | anti-GPC-3 | Human IgG1 Fc | Human IgG1 Fc | | |
| pWF-521 | Anti-GPC3 vL-hclambda constant region-linker-vH-hcH1-cH2-cH3 | Human IgG1 Fc | Human IgG1 | Endogenous BCR complex | |

TABLE 1-continued

| Construct Name | Extracellular Domain | Hinge | TM | Signal 1 | Signal 2 |
|---|---|---|---|---|---|
| pWF-533 | Anti-GPC3-vL-hcH1 | | Human IgG1 (complex with pWF534) | Endogenous BCR complex | |
| pWF-534 | Anti-GPC3-vH-hcKappa-hcH2-cH3 | Human IgG1 Fc | Human IgG1 | Endogenous BCR complex | |

In various embodiments, chimeric B cell receptors are comprised of an extracellular domain, a transmembrane domain and a cytoplasmic domain. In various embodiments, the cytoplasmic domain comprises an activating domain. In various embodiments, the cytoplasmic domain may also comprise a co-stimulatory domain. In various embodiments, the extracellular domain comprises an antigen-binding domain. In various embodiments, the extracellular domain further comprises a hinge region between the antigen-binding domain and the transmembrane domain. FIG. 1 provides a schematic representation of a chimeric B cell receptor of various embodiments of the present invention.

Extracellular Domain. A number of extracellular domains may be used with the present invention. In various embodiments, the extracellular domain comprises an antigen-binding domain. In various embodiments, the extracellular domain may also comprise a hinge region and/or a signaling domain. In various embodiments, the extracellular domains containing IgG1 constant domain may also comprise either IgG1 (hole) or IgG1 (knob) to facilitate directed CAR-B formation.

Antigen-Binding Domain and Binding Domain. As used herein, an "antigen binding domain," "antigen-binding domain" or "binding domain" refers to a portion of the CAR-B capable of binding an antigen or protein expressed on the surface of a cell. In some embodiments, the antigen-binding domain binds to an antigen or protein on a cell involved in a hyperproliferative disease. In preferred embodiments, the antigen-binding domain binds to an antigen or protein expressed on the surface of a tumor cell. The antigen-binding molecules will be further understood in view of the definitions and descriptions below.

An antigen-binding domain is said to "specifically bind" its target antigen or protein when the dissociation constant ($K_d$) is $1 \times 10^{-7}$ M. The antigen-binding domain specifically binds antigen with "high affinity" when the $K_d$ is $1$-$5 \times 10^{-9}$ M, and with "very high affinity" when the $K_d$ is $1$-$5 \times 10^{-10}$ M. In one embodiment, the antigen-binding domain has a $K_d$ of $10^{-9}$ M. In one embodiment, the off-rate is $<1 \times 10^{-5}$. In other embodiments, the antigen-binding domain will bind to antigen or protein with a $K_d$ of between about $10^{-7}$ M and $10^{-13}$ M, and in yet another embodiment the antigen-binding domain will bind with a $K_d$ $1.0$-$5.0 \times 10^{10}$.

An antigen-binding domain is said to be "selective" when it binds to one target more tightly than it binds to a second target.

The term "neutralizing" refers to an antigen-binding domain that binds to a ligand and prevents or reduces the biological effect of that ligand. This can be done, for example, by directly blocking a binding site on the ligand or by binding to the ligand and altering the ligand's ability to bind through indirect means (such as structural or energetic alterations in the ligand). In some embodiments, the term can also denote an antigen-binding domain that prevents the protein to which it is bound from performing a biological function.

The term "target" or "antigen" refers to a molecule or a portion of a molecule capable of being bound by an antigen-binding molecule. In certain embodiments, a target can have one or more epitopes.

The term "antibody" refers to what are known as immunoglobulins, Y-shaped proteins that are produced by the immune system to recognize a particular antigen. The term "antibody fragment" refers to antigen-binding fragments and Fc fragments of antibodies. Types of antigen-binding fragments include: F(ab')2, Fab, Fab' and scFv molecules. Fc fragments are generated entirely from the heavy chain constant region of an immunoglobulin.

Extracellular Signaling Domains. The extracellular domain is beneficial for signaling and for an efficient response of lymphocytes to an antigen. Extracellular domains of particular use in this invention may be derived from (i.e., comprise) CD28, CD28T (See e.g., U.S. Patent Application US2017/0283500A1), OX40, 4-1BB/CD137, CD2, CD7, CD27, CD30, CD40, programmed death-1 (PD-1), inducible T cell costimulator (ICOS), lymphocyte function-associated antigen-1 (LFA-1, CD1-1a/CD18), CD3 gamma, CD3 delta, CD3 epsilon, CD247, CD276 (B7-H3), LIGHT, (TNFSF14), NKG2C, CD79a (Immunoglobulin α), CD79b (Immunoglobulin β), DAP-10, Fc gamma receptor, MHC class 1 molecule, TNF receptor proteins, an Immunoglobulin protein, cytokine receptor, integrins, Signaling Lymphocytic Activation Molecules (SLAM proteins), activating NK cell receptors, BTLA, a Toll ligand receptor, ICAM-1, B7-H3, CDS, ICAM-1, GITR, BAFFR, LIGHT, HVEM (LIGHTR), KIRDS2, SLAMF7, NKp80 (KLRF1), NKp44, NKp30, NKp46, CD19, CD4, CD8alpha, CD8beta, IL-2R beta, IL-2R gamma, IL-7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, NKG2D, TNFR2, TRANCE/RANKL, DNAM1 (CD226), SLAMF4 (CD244, 2B4), CD84, CD96 (Tactile), CEACAM1, CRT AM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, CD19a, a ligand that specifically binds with CD83, or any combination thereof. The extracellular domain may be derived either from a natural or from a synthetic source.

Hinge Domains. As described herein, extracellular domains often comprise a hinge portion. This is a portion of the extracellular domain proximal to the cell membrane. The extracellular domain may further comprise a spacer region. A variety of hinges can be employed in accordance with the invention, including costimulatory molecules as discussed above, as well as immunoglobulin (Ig) sequences a 3X strep II spacer or other suitable molecules to achieve the desired special distance from the target cell. In some embodiments, the hinge region comprises the extracellular domain of CD28, or CD8 or a portion thereof as described herein.

Transmembrane Domains. The CAR-B can be designed to comprise a transmembrane domain that is fused or otherwise linked to the extracellular domain of the CAR-B-B. It can similarly be fused to the intracellular domain of the CAR-B. In one embodiment, the transmembrane domain that naturally is associated with one of the domains in a CAR-B is used. In some instances, the transmembrane domain can be selected or modified by amino acid substitution to avoid binding of such domains to the transmembrane domains of the same or different surface membrane proteins to minimize interactions with other members of the receptor complex. The transmembrane domain may be derived either from a natural or from a synthetic source. Where the source is natural, the domain may be derived from any membrane-bound or transmembrane protein. Transmembrane regions of particular use in this invention may be derived from (i.e. comprise) CD28, CD28T, OX-40, 4-1BB/CD137, CD2, CD7, CD27, CD30, CD40, programmed death-1 (PD-1), inducible T cell costimulator (ICOS), lymphocyte function-associated antigen-1 (LFA-1, CD1-1a/CD18), CD3 gamma, CD3 delta, CD3 epsilon, CD247, CD276 (B7-H3), LIGHT, (TNFSF14), NKG2C, CD79a (Immunoglobulin α), CD79b (Immunoglobulin β), DAP-10, Fc gamma receptor, MHC class 1 molecule, TNF receptor proteins, an Immunoglobulin protein, cytokine receptor, integrins, Signaling Lymphocytic Activation Molecules (SLAM proteins), activating NK cell receptors, BTLA, a Toll ligand receptor, ICAM-1, B7-H3, CDS, ICAM-1, GITR, BAFFR, LIGHT, HVEM (LIGHTR), KIRDS2, SLAMF7, NKp80 (KLRF1), NKp44, NKp30, NKp46, CD19, CD4, CD8alpha, CD8beta, IL-2R beta, IL-2R gamma, IL-7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, NKG2D, TNFR2, TRANCE/RANKL, DNAM1 (CD226), SLAMF4 (CD244, 2B4), CD84, CD96 (Tactile), CEACAM1, CRT AM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, CD19a, a ligand that specifically binds with CD83, or any combination thereof.

Optionally, short linkers may form linkages between any or some of the extracellular, transmembrane, and intracellular domains of the CAR-B.

In certain embodiments, the transmembrane domain in the CAR-B of the invention is the CD28 transmembrane domain. In one embodiment, the CD28 transmembrane domain comprises the nucleic acid sequence of SEQ ID NO: 1. In one embodiment, the CD28 transmembrane domain comprises the nucleic acid sequence that encodes the amino acid sequence of SEQ ID NO: 2. In one embodiment, the CD28 transmembrane domain comprises the nucleic acid sequence of SEQ ID NO: 3. In another embodiment, the CD28 transmembrane domain comprises the amino acid sequence of SEQ ID NO: 4.

In one embodiment, the transmembrane domain in the CAR-B of the invention is a CD8 transmembrane domain.

Intracellular (Cytoplasmic) Domains. The intracellular (IC, or cytoplasmic) domain of the CAR-B receptors of the invention can provide activation of at least one of the normal effector functions of the immune cell.

It will be appreciated that suitable intracellular molecules, include, but are not limited to CD79a (Immunoglobulin α), CD79b (Immunoglobulin β), CD40, CD19, CD137, Fcγr2a CD3; and MyD88. Intracellular molecules may further include CD28, CD28T, OX-40, 4-1BB/CD137, CD2, CD7, CD27, CD30, CD40, programmed death-1 (PD-1), inducible T cell costimulator (ICOS), lymphocyte function-associated antigen-1 (LFA-1, CD1-1a/CD18), CD3 gamma, CD3 delta, CD3 epsilon, CD247, CD276 (B7-H3), LIGHT, (TNFSF14), NKG2C, Ig alpha (CD79a), DAP-10, Fc gamma receptor, MHC class 1 molecule, TNF receptor proteins, an Immunoglobulin protein, cytokine receptor, integrins, Signaling Lymphocytic Activation Molecules (SLAM proteins), activating NK cell receptors, BTLA, a Toll ligand receptor, ICAM-1, B7-H3, CDS, ICAM-1, GITR, BAFFR, LIGHT, HVEM (LIGHTR), KIRDS2, SLAMF7, NKp80 (KLRF1), NKp44, NKp30, NKp46, CD19, CD4, CD8alpha, CD8beta, IL-2R beta, IL-2R gamma, IL-7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, NKG2D, TNFR2, TRANCE/RANKL, DNAM1 (CD226), SLAMF4 (CD244, 2B4), CD84, CD96 (Tactile), CEACAM1, CRT AM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, CD19a, a ligand that specifically binds with CD83, or any combination thereof. The cytoplasmic signaling sequences within the cytoplasmic signaling portion of the CAR-B of the invention may be linked to each other in a random or specified order.

The term "co-stimulatory" domain or molecule as used herein refers to a heterogenous group of cell surface molecules that act to amplify or counteract initial activating signals of the cell.

In one preferred embodiment, the cytoplasmic domain is designed to comprise the signaling domain of hCD19, wherein the hCD19 domain comprises the nucleic acid sequence set forth in SEQ ID NO. 5. In another embodiment, the cytoplasmic domain is designed to comprise the signaling domain of hCD40, wherein the hCD40 domain comprises the nucleic acid sequence set forth in SEQ ID NO. 7. In another embodiment, the cytoplasmic domain is designed to comprise the signaling domain of hCD40 and hCD79b, wherein the hCD40 domain comprises the nucleic acid sequence set forth in SEQ ID NO. 7 and the hCD79b domain comprises the nucleic acid sequence set forth in SEQ ID NO. 25. In another embodiment, the cytoplasmic domain is designed to comprise the signaling domain of hCD40 and hCD137, wherein the hCD40 domain comprises the nucleic acid sequence set forth in SEQ ID NO. 7 and the hCD137 domain comprises the nucleic acid sequence set forth in SEQ ID NO. 13. In another embodiment, the cytoplasmic domain is designed to comprise the signaling domain of hCD40 and hFcγr2a, wherein the hCD40 domain comprises the nucleic acid sequence set forth in SEQ ID NO. 7 and the hFcγr2a domain comprises the nucleic acid sequence set forth in SEQ ID NO. 17. In another embodiment, the cytoplasmic domain is designed to comprise the signaling domain of hCD40 and hMyd88, wherein the hCD40 domain comprises the nucleic acid sequence set forth in SEQ ID NO. 7 and the hMyd88 domain comprises the nucleic acid sequence set forth in SEQ ID NO. 21. In another embodiment, the cytoplasmic domain is designed to comprise the signaling domain of hCD79a, wherein the hCD79a domain comprises the nucleic acid sequence set forth in SEQ ID NO.

23. In another embodiment, the cytoplasmic domain is designed to comprise the signaling domain of hCD79b, wherein the hCD79b domain comprises the nucleic acid sequence set forth in SEQ ID NO. 25. These embodiments are preferably of human origin but may be derived from other species. In various embodiments the signaling domain comprises both hCD79a in tandem with hCD79b or another hCD79a domain. In various embodiments the signaling domain comprises both hCD79b in tandem with hCD79a or another hCD79b domain.

2. Modified B Cells

Modified B Cells that Express Payloads. In various embodiments of the present invention a modified B cell is provided that is capable of expressing a payload. As used herein the term "payload" refers to an amino acid sequence, a nucleic acid sequence encoding a peptide or protein, or an RNA molecule, for use as a therapeutic agent. In certain embodiments the payload is for delivery to the tumor or tumor microenvironment or the draining lymph node. In certain embodiments, it is desirable that the B cell deliver to the tumor or tumor microenvironment or draining lymph node a payload capable of, for example, increasing the number of cross-presenting dendritic cells (DCs) in tumors. Cross-presenting DCs will allow for improved presentation of tumor antigens. In various embodiments, the payload may be capable of activating and attracting T cells into tumors. Activating more T cells in tumors will complement the cross-presenting DCs to remold the tumor environment to have more potent antitumor immune capabilities. Payloads may also foment the formation of tertiary lymphoid structures (TLS) in tumors. Clinical studies have demonstrated that there is a relationship between B cells, TLS and responses to immune checkpoint blockade.

Nonexclusive examples of payloads of the present invention include: IL-1, IL-7, IL-8, IL-10, IL-12, IL-13, IL-17, IL-18, IL-21, interferon α, interferon β, interferon γ, TSLP, CCL21, FLT3L, XCL1, LIGHT(TNFSF14), OX40L, CD137L, CD40L, ICOSL, anti-CD3 antibody, CD47, TIM4-FC, CXCL13, CCL21, CD80, CD40L, IFNα A2, LIGHT, 4-1BBL, MDGF (C19orf10), FGF10, PDGF, agrin, TNF-α, GM-CSF, an anti-FAP antibody, an anti-TGF-β antibody; a TGF-0 trap, decoy or other inhibitory molecule; an anti-BMP antibody; a BMP trap, decoy or other inhibitory molecule.

Signaling for Payload Expression. In various embodiments of the present invention, the payload is expressed in the modified B cell as a DNA construct under the control of an activated transcriptional pathway. In certain embodiments, the expression of the payload is controlled of the Nuclear Factor of Activated T cell ("NFAT") pathway. The NFAT pathway is a transcription factor pathway activated during an immune response and is activated by the NFκB. In various embodiments, the modified B cell expresses both a payload and a CAR-B. In various embodiments, where the modified B cell expresses both a payload and a CAR-B, the CAR-B may further encode signaling molecules that induce activation of the NFκB pathway. Such molecules include but are not limited to: CD79a (Immunoglobulin α), CD79b (Immunoglobulin β), CD40, CD19, CD137, Fcγr2a, CD3ζ and MyD88.

In various embodiments, the invention relates to isolated B cells that express at least one payload. In various embodiments, the invention relates to isolated B cells that express more than one payload. In various embodiments, the invention relates to isolated B cells that express 1, 2, 3, 4, 5, 6, 7, 8, 9, 10, 11 or 12 different payloads.

Figure 2:
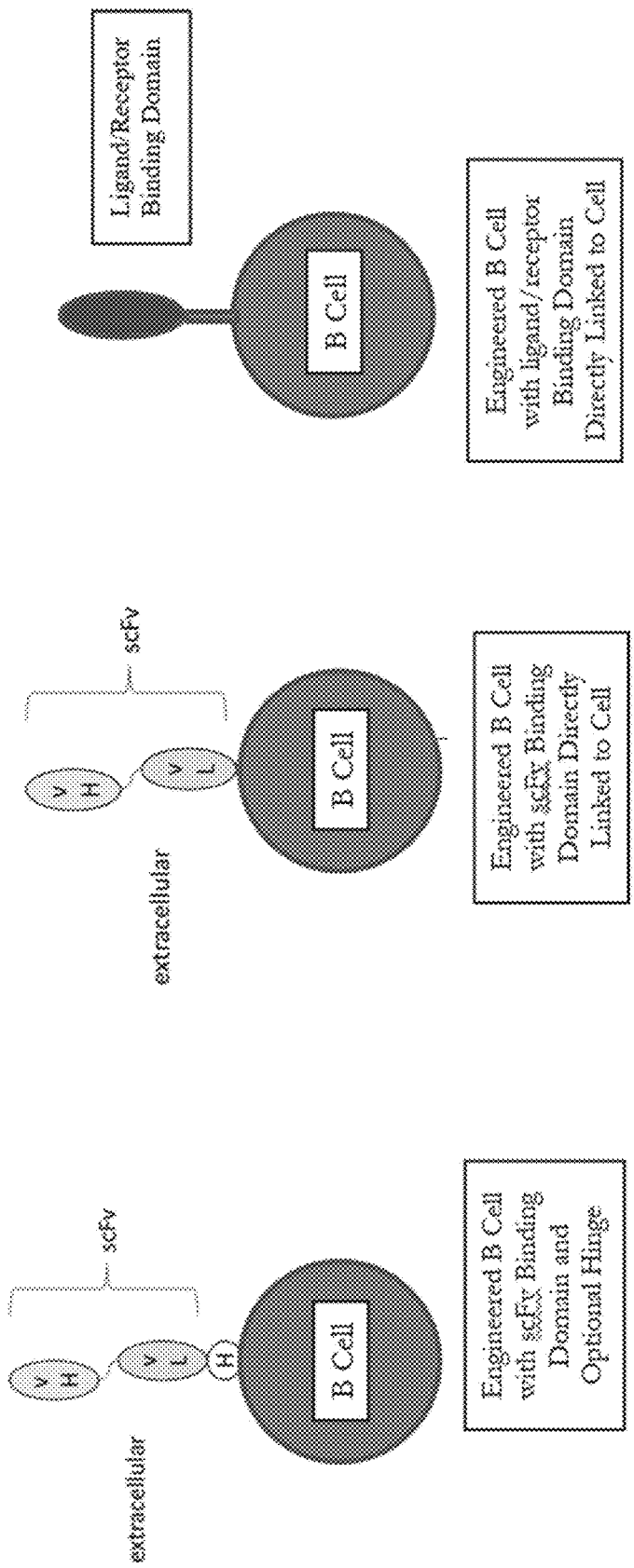
FIGS. 2A-2C show examples of engineered B cells with homing domains. In various embodiments, the engineered B cells may comprise (a) an scFv binding domain and optional hinge region; (b) an scFv binding domain directly linked to the cell through a transmembrane domain, or (c) a ligand/receptor binding domain directly linked to a cell through a transmembrane domain.
Figure 4:
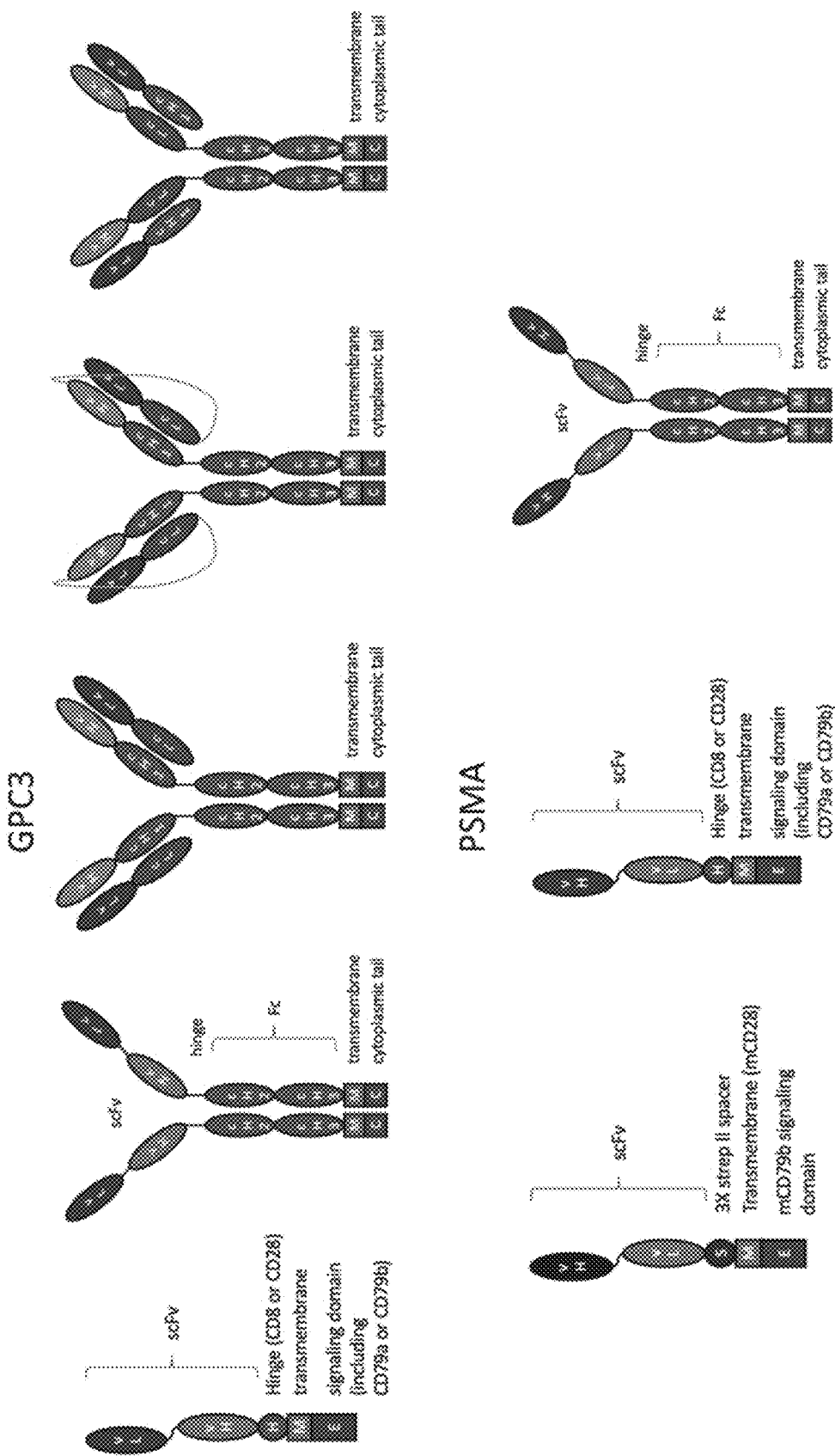
FIG. 4 shows examples of CAR-B receptors of the present invention capable of binding (A) GPC3 and (B) PSMA. The "C" domain corresponds to the native BCR C-terminus.

Modification of B Cells for homing. In various embodiments of the present invention, the engineered B cells can be modified with homing domains (e.g., as illustrated in FIG. 2) such that the B cells can home to a site/target of interest and activate upon interaction with the target. Additionally, B cell homing receptors expressed on B cell membranes that recognize addressins and ligands on target tissues, compound or derivatives thereof that alter the trafficking of B cells to a particular site, and inhibitory molecules inflammation and autoimmune activity of the B cells, can play a role in B cell homing and development of specialized immune responses.

Modified B cells that Express Integrin of Interest. The major homing receptors expressed by lymphocytes are the integrins, which are a large class of molecules characterized by a heterodimeric structure of α and β chains. In general, the pairing of specific α and β chains of the integrin determines the type of the homing receptor. For example, pairing of the α4 chain with β7 chain characterizes the major integrin molecule (α4β7) responsible for lymphocyte binding to Mucosal addressin cell adhesion molecule 1 (MAd-CAM-1) expressed on high endothelial venules (HEVs) in Peyer's patches (PP) and gastrointestinal (GI) tract lamina propria endothelial venules (LPVs). Similarly, pairing of the α4 chain with β1 chain characterizes the homing receptor (α4β1) for the skin.

In various embodiments of the present inventions, a B cell to be modified can be selected for in advance, with specific traits that mediate preferred localizations. For example, memory B cells expressing CXCR3 may be enriched for and then subjected to engineering. CXCR3 cells may be attracted to ligands expressed at sites of inflammation. As such, modified B cells can preferentially localize to such sites.

In various embodiments of the present invention, a modified B cell is provided that expresses the α4 and β7 chains of an integrin. It is desirable that expression of the α4β7 integrin will promote homing of the modified B cell to the colon. In various embodiments, a modified B cell is provided that expresses the α4 and β1 chains of an integrin. It is desirable that expression of the α4β1 integrin will promote homing of the modified B cell to the skin. In various embodiments, a modified B cell is provided that expresses a desired pairing of an α and a β chain of an integrin, such that the expressed integrin promotes homing of the modified B cell to a desired site/target of interest. Accordingly, in various embodiments, any desired combination of the α and β chains of an integrin is contemplated for expression in the B cells, such that the modified B cells expressing the specific integrin is targeted to a desired site/target of interest.

Modified B cells that Express Homing Receptors of Interest. B cells have an ability to home to inflammatory tissues and altering their homing receptor expression can complement their native homing tendencies. B cell localization is also driven by expression of attractant molecules (e.g., targets such as ligands and chemokines) at inflammatory sites in specific locations or tissues. Such molecules can also include antibodies, such as the MECA79 antibody that targets cells to peripheral node addressin (PNAd). Bahmani et al., J Clin Invest. 2018; 128(11):4770-4786; Azzi et al., Cell Rep. 2016; 15(6):1202-13. Accordingly, B cells can be engineered to express certain antibodies, proteins, and receptors that facilitate B cell homing to a site/target of interest and interactions of such B cells with the desired target. In certain instances, expression of such receptors redirects the B cells to the tissue of interest.

In various embodiments of the present invention, a modified B cell is provided that is capable of expressing a homing antibody, protein, or a receptor, expression of which is capable of directing the B cell to a specific site/target of interest. Exemplary homing of T cells to specific homing tissues (target tissues) using specific homing receptor/ligand pairs are set forth in Table 2. The same specific homing receptor/ligand pairs are also capable of facilitating homing of B cells to a specific homing tissue (target tissue). Accordingly, in various embodiments of the present invention, homing of the modified B cells to an exemplary homing tissue (target tissue) is facilitated using the corresponding homing receptor/ligand pairs as set forth in Table 2.

TABLE 2

$T_{eff}$ cell homing receptors and their cognate ligands mediating organotropic targeting

| Homing Tissue Type | $T_{eff}$ Cell Homing Receptor | Cognate Ligand |
|---|---|---|
| Skin | CLA (PSGL-1 glycoform) | E/P-selectin |
|  | CD43E | E-selectin |
|  | VLA-4 ($\alpha_4\beta_1$) | VCAM-1 |
|  | LFA-1 ($\alpha L\beta_2$) | ICAM-1 |
|  | CCR4 | CCL17 |
|  | CCR10 | CCL27 |
| Gut (intestine, colon, mLN, PP) | $\alpha_4\beta_7$ | MAdCAM-1 |
|  | CCR9[a] | CCL25[a] |
|  | CXCR4 | CXCL12 |
|  | Selectin ligands[b] | E/P-selectin[b] |
|  | VLA-4[b] | VCAM-1[b] |
|  | LFA-1[b] | ICAM-1[b] |
|  | CCR6[b] | CCL20 (MIP-3$\alpha$)[b] |
| Liver | CD44 | Hyaluronate |
|  | VLA-4 | VCAM-1 |
|  | CCR5 | CCL5 |
|  |  | VAP-1 |
|  | Selectin ligands[b] | E/P-selectin |
|  | $\alpha_4\beta_7$[b] | MAdCAM-1[b] |
| Lung | LFA-1 | ICAM-1 |
|  | CCR3 | CCL28 |
|  | CCR4 | CCL17 |
|  | CXCR4 | CXCL12 |
|  | Selectin ligands[b] | E/P-selectin[b] |
|  | VLA-4[b] | VCAM-1[b] |
|  | LFA-1[b] | ICAM-1[b] |
| Bone Marrow | CLA (PSGL-1 glycoform) | E/P-selectin |
|  | CD43E | E-selectin |
|  | VLA-4 | VCAM-1 |
|  | LFA-1 | ICAM-1[b] |
|  | CXCR4 | CXCL12 |
|  | $\alpha_4\beta_7$[b] | MAdCAM-1[b] |
| Heart | CCR5 | CCL4, CCL5 |
|  | CCR4 | ? |
|  | CXCR3 | CXCL10 |
|  | c-Met | HGF |
| Brain | VLA-4[b] | VCAM-1[b] |
|  | LFA-1[b] | ICAM-1[b] |
|  | CXCR3[b] | CXCL9/CXCL10[b] |
| Peripheral LN[c] | Selectin ligands[b] | E/P-selectin[b] |
|  | LFA-1[b] | ICAM-1[b] |
|  | CXCR3[b] | CXCL9/CXCL10[b] |

[a]Involved in $T_{eff}$ cell homing to the intestine but not colon.
[b]Inflammatory reactions, tissue injury.
[c]Under non-inflamed, steady-state conditions, $T_{eff}$ cells typically lose L-selectin and CCR7 expression and are largely restricted from LN access though may enter during inflammatory reactions (b) as shown. In contrast, both naïve T cells and $T_{cm}$ cells express L-selectin, CCR7, and CXCR4 and engage PNAd, CCL19/CCL21, and CXCL12, respectively, to undergo T-cell rolling and LFA-1/ICAM-1/2- mediated adhesion and transmigration into LNs.

Exemplary homing tissue (target tissue) type and ligand or chemokine that enables tissue-restricted B cell homing in accordance with the invention are set forth in Table 3.

TABLE 3

| Homing Tissue Type | Ligand/Chemokines |
|---|---|
| CNS | VCAM-1, CD62P, ligands for CCR1, 2, 5, CXCR3 |
| Liver | CD62P, VAP-1, CXCL16 |
| Small Intestine | MAdCAM, CD62P, CCL25 |
| Colon | MAdCAM, CD62P, CCL20, GPR15L |
| Skin | CD62E, CD62P, CCL17(22), ICAM-1 |
| Thymus | VCAM, CD62P, CCL25 |
| Peripheral Lymph Node | PNAd, CCL21, ICAM-1 |
| Peyer's Patch | MAdCAM, CCL21, CXCL13 |
| Bone Marrow | VCAM, CD62P, CXCL12, ICAM-1 |

In various embodiments of the present invention, a modified B cell is provided that expresses one or more of an antibody, a protein, or a receptor that facilitate homing of the modified B cell to the exemplary target/homing tissues using the specific homing receptor/ligand pairs as set forth in Table 2. In various embodiments of the present invention, a modified B cell is provided that expresses one or more of a homing receptor that facilitate homing of the modified B cell to the exemplary target/homing tissue using the ligand or chemokines are set forth in Tables 2 and/or 3. As used herein, the term "B cell homing" refers to localizing, targeting, trafficking, directing, or redirecting of the B cell of the present application to a site/target of interest, for example, a homing or target tissue, an inflammatory site in a specific location or tissue, or a tumor or tumor microenvironment, where delivery of therapeutic payloads is desirable. As used in the context of B cell homing, the term "antibody", "protein" or a "receptor" refers to an amino acid sequence, a nucleic acid sequence encoding a peptide or protein, or an RNA molecule, for use as a therapeutic agent, which when expressed in a modified B cell of the present invention will direct the B cell to a site/target of interest.

In certain embodiments, the homing antibody, protein, or receptor molecule is for homing/targeting the modified B cell expressing such a molecule to a site/target of interest. In certain embodiments, the homing antibody, protein, or receptor molecule is for homing/targeting the modified B cell expressing such a molecule to inflammatory sites in specific locations or tissues. In certain embodiments, the homing antibody, protein or receptor is for targeting the B cell to a tumor or tumor microenvironment and to the tumor draining lymph node In certain embodiments, targeting B cells to particular locations is desirable so that the engineered or modified B cells of the present invention can deliver therapeutic payloads to desired locations of interest, for example, a homing or target tissue, an inflammatory site in a specific location or tissue, or a tumor or tumor microenvironment. Accordingly, in certain embodiments, it is desirable that the B cells home to a site/target of interest, for example, a tumor or tumor microenvironment and tumor-draining lymph node and deliver to the site/target of interest a payload capable of, for example, increasing the number of cross-presenting dendritic cells (DCs) at the site/target of interest (e.g., in tumors).

In various embodiments, the homing antibody, protein, or receptor is expressed in the modified or engineered B cell as a DNA construct. In various embodiments, the homing antibody, protein, or receptor is expressed in the modified B cell as a DNA construct under the control of a constitutively activated transcriptional pathway. In various embodiments, the homing antibody, protein, or receptor involved in the B cell homing/targeting is either not naturally expressed in a B cell or is expressed at higher levels than is naturally expressed in a B cell. Exemplary homing of the modified B cells to specific homing/target tissues using specific homing receptor/ligand pairs in accordance with the present invention is set forth in Table 4. It should be understood that, notwithstanding the exemplary homing tissues, homing receptor, and ligand pairs set forth in Table 4, a modified B cell of the present invention may be engineered to express any homing antibody, protein, or a receptor (e.g., any homing receptor set for in Table 2), such that the modified B cell can be directed to a specific site/target of interest.

TABLE 4

| Homing Tissue Type | Homing Receptor | Ligand/Chemokine |
|---|---|---|
| Liver | CXCR6 | CXCL16 |
| Small Intestine | CCR9 | CCL25 |
| Large Intestine (Colon) | CCR6 | CCL20 |
| Lymph Node | CCR7 | CCL21 |
| Bone Marrow | CXCR4 | CXCL12 |
| Peyer's Patch | CCR7 and CXCR5 | CCL21 and CXCL13, respectively |
| Skin | CCR4 | CCL17(22) |

Nonexclusive examples of homing (target) tissue types for the specific homing receptor/ligand pairs of the present invention include: skin, gut (intestine, colon, mesenteric lymph nodes (mLN), Peyer's Patch (PP), small intestine), liver, lung, bone marrow, heart, peripheral lymph node (LN), CNS, thymus, and bone marrow.

Nonexclusive examples of homing receptors that can be paired with specific or corresponding attractants/ligands/chemokines of the present invention include: CLA (PSGL-1 glycoform), CLA (PSGL-1 glycoform), CCR10, CCR3, CCR4, CCR5, CCR6, CCR9, CD43E, CD44, c-Met, CXCR3, CXCR4, LFA-1, LFA-1 (αLβ2), Selectin ligands, VLA-4, VLA-4 (α4β1), and α4β7.

Nonexclusive examples of ligands/chemokines that can be paired with specific or corresponding homing receptors of the present invention include: CXCL16, CCL17, CCL17 (22), CCL20 (MIP-3α), CCL21, CCL25, CCL27, CCL28, CCL4, CCL5, CD62E, CD62P, CXCL10, CXCL12, CXCL13, CXCL16, CXCL9/CXCL10, CXCR3, E/P-selectin, E-selectin, GPR15L, HGF, Hyaluronate, ICAM-1, ligands for CCR1, 2, 5, MAdCAM, MAdCAM-1, PNAd, VAP-1, VCAM, and VCAM-1.

In certain embodiments of the present invention, a modified B cell is provided that express or have increased expression of the exemplary B cell homing receptors (e.g., as set forth in Table 2), such that the modified B cell is targeted to the corresponding homing tissue of interest that expresses the corresponding ligand/chemokines (e.g., as set forth in Tables 2 and/or 3). In certain embodiments of the present invention, a modified B cell is provided that co-expresses an integrin with a specific α and β chain pairing and a specific B cell homing receptor (e.g., as set forth in Tables 2 and/or 3), expression of which integrin and/or homing receptor promote or facilitate homing/targeting of the modified B cell to a site/target of interest. In some embodiments, a modified B cell is provided that co-expresses an α4β7 integrin and CCR9. It is desirable that co-expression of α4β7 and CCR9 will promote small intestine homing of the modified B cells of the present invention. In some embodiments, a modified B cell is provided that co-expresses an α4β1 integrin and CCR4. It is desirable that co-expression of α4β1 and CCR4 will promote small intestine homing of the modified B cells of the present invention.

Modified B cells that Express Immune Inhibitory Molecules. B cells are key contributors to many autoimmune diseases. However, B cells can be used therapeutically to antagonize autoimmunity. Specifically, B cells can be engineered to express at least one or more immune inhibitory molecules, which may decrease the autoimmune activity of the B cells, leading to decrease in an autoimmune disease. Immune inhibitory molecules are well known in the art. Such inhibitory molecules may include, but are not limited to, IL-10, TGF-β, PD-L1, PD-L2, LAG-3, and TIM-3. In certain embodiments of the present invention, a modified B cell is provided that is engineered to express at least one or more of an inhibitory molecule selected from IL-10, TGF-β, PD-L1, PD-L2, LAG-3, and TIM-3, or any combinations thereof, such that the inflammation at the site and autoimmune activity of the B cells localized to the site are decreased, thereby leading to a positive therapeutic response.

Compounds that alter B cell Trafficking. In certain embodiments of the present invention, a modified B cell is provided that is treated with at least one or more compound or derivatives thereof that alter the trafficking of B cells by inducing expression of a specific B cell integrin and/or a homing receptor. Compounds or derivatives thereof that alter the trafficking of B cells are well known in the art. In certain embodiments, a modified B cell is provided that is treated with all-trans-retinoic acid (ATRA) or derivatives thereof that promote homing of the B cells to gut (small intestine) due to the increased expression of α4β7 integrin and CCR9 homing receptor. As used herein, the term "compound" refers to a chemical, drug, a therapeutic agent, or derivatives thereof, that alter the trafficking of B cells in a desired manner.

In various embodiments of the present invention, a modified B cell engineered to co-express a specific integrin (e.g., with a specific α and β chain pairing) and a specific B cell homing receptor of interest is treated with at least one or more compounds or derivatives thereof that alter the trafficking of the modified B cells and promote homing of the cells to a specific site/target of interest due to the increased expression of the specific integrin and/or the homing receptor. In various embodiments, a B cell modified to co-express an integrin with a specific α and β chain pairings and a specific B cell homing receptor further expresses at least one or more immune inhibitory molecules, such that the autoimmune activity of the modified B cells targeted to a specific site of inflammation is decreased, leading to a decrease in the autoimmune disease. In some embodiments, a modified B cell engineered to express one or more immune inhibitory molecules, for example IL-10, TGF-β, PD-L1, PD-L2, LAG-3, and TIM-3, or combinations thereof, is treated with ATRA or derivatives thereof for a specified period of time, such that expression of the α4β7 integrin and CCR9 homing receptor is induced to promote B cell homing to a specific site/target of interest (e.g., the gut), but the inflammation at the site and autoimmune activity of B cells localized to the site are decreased, leading to a positive therapeutic response. In one embodiment, a modified B cell engineered to express one or more immune inhibitory molecules, for example IL-10, TGF-β, or combinations thereof, is treated with ATRA or derivatives thereof for a specified period of time, such that expression of the α4β7 integrin and CCR9 homing receptor is induced to promote B cell homing to a specific site/target of interest (e.g., the gut), but the inflammation at the site and autoimmune activity of B cells localized to the site are decreased, leading to a positive therapeutic response.

It is understood that, any B cell of the present invention modified to co-express a specific B cell integrin and homing receptor that targets the B cell to a particular homing/target tissue of interest, may be further engineered to express one or more immune inhibitory molecules for reducing inflammation and autoimmune activity of the B cells localized to the site, and/or treated with a compound that alter the homing/targeting of the modified B cells by inducing expression of the specific B cell integrin and/or the homing receptor.

Activation of B cells with TLR agonists and TLRs. B cells have a natural ability to uptake and present antigens recognized by their specific B cell receptors (BCRs). B cells activated by Toll-like receptors (TLRs) result in potent effector B cells in defending the body in an immune response. Expression of or increasing the expression of TLRs in B cells can provide a mechanism for potentiating B cells for innate signals regulating adaptive immune responses.

Activation of B cells with TLR agonists. In various embodiments of the present invention, a B cell is provided, where the B cell is treated in vitro with at least one TLR agonist. In various embodiments, the TLR can be a TLR1, TLR2, TLR3, TLR4, TLR5, TLR6, TLR7, TLR8, TLR9, TLR10, TLR11, TLR12, and/or a TLR13. In various embodiments, the TLR agonist preferentially binds to one or more TLR selected from the group consisting of TLR1, TLR2, TLR3, TLR4, TLR5, TLR6, TLR7, TLR8, TLR9, TLR10, TLR11, TLR12, and TLR13. TLR agonists are well known in the art and may include, but are not limited to, CpG-rich oligonucleotides and the double-stranded RNA mimic, polyinosinic acid:polycytidylic acid (poly-I:C). In various embodiments, the TLR agonist can be CpG oligonucleotides.

In various embodiments, each B cell may be treated with one TLR agonist. In various embodiments, each B cell may be treated with more than one TLR agonist. For example, each B cell may be treated 1, 2, 3, 4, 5, 6, 7, 8, 9, 10, 11, or 12 different TLR agonists. Alternatively, the patient may be administered a heterogeneous population of B cells, each B cell treated with a unique TLR agonist or a combination of TLR agonists. In some embodiments, the B cells for use a therapeutic agent is treated with one or more TLR agonists at the same time or in advance of the administration of the B cells to a subject or patient in need thereof. In certain embodiments, treatment with one or more TLR agonist is capable of producing more potent effector B cells for defending the body in an immune response. In certain embodiments, treatment with one or more TLR agonist is capable of potentiating B cells for immune responses. In some embodiments, treating a B cell of the present invention with at least one or more TLR agonists induces expression or activation of one or more TLRs.

Activation of B cells with TLR Expression. In various embodiments of the present invention, a modified B cell is provided that is capable of expressing a constitutively active TLR. In various embodiments, the TLR is expressed in the modified or engineered B cell as a DNA construct under the control of a constitutively activated transcriptional pathway. In various embodiments, the TLR is either not naturally expressed in a B cell or is expressed at higher levels than is naturally expressed in a B cell. In various embodiments, the TLR can be a TLR1, TLR2, TLR3, TLR4, TLR5, TLR6, TLR7, TLR8, TLR9, TLR10, TLR11, TLR12, and/or a TLR13.

In various embodiments, each B cell may express more than one constitutively active TLR. For example, each B cell may express 1, 2, 3, 4, 5, 6, 7, 8, 9, 10, 11, 12 or 13 different constitutively active TLRs. Alternatively, the patient may be administered a heterogeneous population of B cells, each B cell capable of expressing and/or secreting a unique TLR or combination of TLRs, which are constitutively active. In various embodiments, 1, 2, 3, 4, 5, 6, 7, 8, 9, 10, 11, 12 or 13 different constitutively active TLRs may be administered to the subject or patient through a heterogeneous population of B cells.

In certain embodiments of the present invention, the B cell is a modified B cell that expresses at least one constitutively active TLR. In certain embodiments, the modified B cell that expresses at least one constitutively active TLR is treated with one or more TLR agonist. In certain embodiments, the expression of the constitutively active TLR is capable of producing more potent effector B cells for defending the body in an immune response. In certain embodiments, the expression of the constitutively active TLR is capable of potentiating B cells for immune responses. In certain embodiments, the modified B cell expresses both a TLR that is constitutively active and any CAR-B of the present application. In various embodiments, the modified B cell expressing a TLR that is constitutively active and/or a CAR-B is further treated with one or more TLR agonist at the same time or in advance of the administration of the modified B cells to a subject or patient in need thereof. In certain embodiments, B cells may be engineered to express payloads and modifiers, such as TLRs, in the absence of CAR-B, for intratumoral administration.

Modified B Cells that Present Antigens Simultaneously in HLA Class I and Class II Molecules. B cells, in addition to their function in antibody production, also express high level of Human Leukocyte Antigen (HLA) class II molecules and can present antigens to CD4+ T cells (Hong et al., 2018, Immunity 49, 695-708). In various embodiments of the present invention, a modified B cell is provided that is capable of presenting specific antigens and/or antigen-derived epitopes of interest, such as tumor antigens or infectious disease antigens, simultaneously in both HLA class I and class II molecules. Tumor antigens and infectious disease antigens are well known in the art and are described in the foregoing sections. In certain embodiments, a specific antigen of interest, e.g., a tumor antigen or an infectious disease antigen, is fused to a targeting signal of a lysosomal protein that targets the antigen to the lysosomes and presents the antigen simultaneously and efficiently in both HLA class I and class II molecules. In some embodiments, the targeting signal is the targeting signal of lysosome-associated membrane protein-1 (LAMP1). In some embodiments, the targeting signal is capable of entering endosomal recycling compartments. The c-terminal sequence of Clec9A is such a targeting moiety. As used herein, a specific tumor antigen or an infectious disease antigen fused to a targeting signal refers to an amino acid sequence, a nucleic acid sequence encoding a peptide or protein, or an RNA molecule (e.g., an mRNA molecule), for use as a therapeutic agent. In one embodiment, a specific tumor antigen or an infectious disease antigen fused to a targeting signal refers to an mRNA molecule for use as a therapeutic agent. In certain embodiments, it is desirable that the specific tumor antigens and/or infectious disease antigens fused to a targeting signal, such as the targeting signal of LAMP1 or Clec9A, be targeted to the lysosomes or endosomes and presented simultaneously and efficiently in both HLA class I and class II molecules. In certain embodiments, it is desirable that electroporation of B cells (e.g., human B cells), before or after maturation, with an mRNA encoding specific tumor antigens and/or infectious disease antigens of interest fused to a targeting signal, such as the targeting signal of LAMP1 or Clec9A, be capable of simultaneously and efficiently presenting the specific antigens and/or antigen-derived epitopes in both HLA class I and class II molecules. In various embodiments, the specific tumor antigens and/or infectious disease antigens of interest is either not naturally presented by a B cell, is not presented by a B cell simultaneously in both HLA class I and class II molecules naturally, or is not presented by a B cell with high efficiencies in both HLA class I and class II molecules naturally. It is contemplated that, introduction of such electroporated B cells into a subject, e.g., a human host, will promote development of or potentiate antigen-specific immune responses by presenting specific antigens and/or antigen-derived epitopes of interest simultaneously and efficiently in both HLA class I and class II molecules.

In various embodiments, the invention relates to a nucleic acid sequence, e.g., an mRNA sequence, encoding at least one specific antigen of interest, e.g., a tumor antigen or an infectious disease antigen, fused to a targeting signal, such as the targeting signal of LAMP1, for use as a therapeutic agent in electroporation of B cells for simultaneously and efficiently presenting the specific antigen and/or antigen-derived epitopes in both HLA class I and class II molecules. In various embodiments, the invention relates to nucleic acid sequence, e.g., an mRNA sequence, encoding more than one (e.g., 1, 2, 3, 4, 5, or more) specific tumor antigen and/or an infectious disease antigen of interest fused to a targeting signal. In various embodiments, the invention relates to pools of different nucleic acid sequences, e.g., pools of different mRNA sequences, for use as a therapeutic agent in electroporation of B cells as described above, where each pool encodes at least one specific antigen of interest, e.g., a tumor antigen or an infectious disease antigen, fused to a targeting signal that is different from the other pools of the mRNA sequences. Accordingly, in some embodiments, the subject may be administered a homogeneous population of B cells, where each B cell is electroporated with an mRNA encoding at least one specific antigen of interest fused to a targeting signal. In some embodiments, the subject may be administered a homogeneous a population of B cells, where each B cell is electroporated with an mRNA encoding more than one specific antigen of interest fused to targeting signal. In some embodiments, the subject may be administered a heterogeneous population of B cells, where each B cell is electroporated with a combination of mRNAs each encoding at least one specific antigen of interest fused to a different targeting signal.

In some embodiments, the B cells for use in electroporation as described above may be any of the modified B cells of the present application. In some embodiments, the modified B cell comprises a chimeric antigen receptor for B cells (CAR-B). In various embodiments, the modified B cell can express a CAR-B and simultaneously and efficiently present specific antigen and/or antigen-derived epitopes of interest in both HLA class I and class II molecules.

In various embodiments, the invention relates to a method of administering an isolated B cell to a patient in need thereof. In various embodiments, a population of B cells may be administered to the patient. In various embodiments, each B cell may express more than one payload peptide or protein. For example, each B cell may express 1, 2, 3, 4, 5, 6, 7, 8, 9, 10, 11 or 12 different payloads. Alternatively, the patient may be administered a heterogeneous population of B cells, each B cell capable of expressing and/or secreting a unique payload or combination of payloads. In various embodiments, 1, 2, 3, 4, 5, 6, 7, 8, 9, 10, 11 or 12 different payloads may be administered to the patient through a heterogeneous population of B cells.

3. Methods of Treatment

In some aspects, the invention therefore comprises a method for treating or preventing a tumor or cancerous tissue, comprising administering to a patient in need thereof an effective amount of at least one CAR-B disclosed herein.

Methods are provided for treating diseases or disorders, including cancer. In some embodiments, the invention relates to creating a B cell-mediated immune response in a subject, comprising administering an effective amount of the engineered immune cells of the present application to the subject. In some embodiments, the B cell-mediated immune response is directed against a target cell or cells. In some embodiments, the engineered immune cell comprises a chimeric antigen receptor for B cells (CAR-B). In some embodiments, the target cell is a tumor cell. In some aspects, the invention comprises a method for treating or preventing a malignancy, said method comprising administering to a subject in need thereof an effective amount of at least one isolated antigen-binding molecule described herein. In some aspects, the invention comprises a method for treating or preventing a malignancy, said method comprising administering to a subject in need thereof an effective amount of at least one immune cell, wherein the immune cell comprises at least one chimeric antigen receptor.

In some aspects, the invention comprises a pharmaceutical composition comprising at least one antigen-binding molecule as described herein and a pharmaceutically acceptable excipient. In some embodiments, the pharmaceutical composition further comprises an additional active agent.

In some embodiments, the subject is diagnosed with a metastatic disease localized to the liver. In other embodiments, the metastatic disease is a cancer. In still other embodiments, the cancer metastasized from a primary tumor in the breast, colon, rectum, esophagus, lung, pancreas and/or stomach. In still other embodiments, the subject is diagnosed with unresectable metastatic liver tumors. In yet other embodiments, the subject is diagnosed with unresectable metastatic liver tumors from primary colorectal cancer. In some embodiments, the subject is diagnosed with hepatocellular carcinoma.

It will be appreciated that target doses for modified B cells can range from $1 \times 10^6$-$2 \times 10^{10}$ cells/kg, preferably $2 \times 10^6$ cells/kg, more preferably. It will be appreciated that doses above and below this range may be appropriate for certain subjects, and appropriate dose levels can be determined by the healthcare provider as needed. Additionally, multiple doses of cells can be provided in accordance with the invention.

Also provided are methods for reducing the size of a tumor in a subject, comprising administering to the subject a modified B cell of the present invention, wherein the cell comprises a CAR-B receptor comprising an antigen-binding domain that binds to an antigen on a tumor, a payload or both a CAR-B and a payload. In some embodiments, the subject has a solid tumor, or a blood malignancy such as lymphoma or leukemia. In some embodiments, the modified B cell is delivered to a tumor bed. In some embodiments, the cancer is present in the bone marrow of the subject.

Also provided are methods for homing B cells to a site/target of interest in a subject, comprising administering to the subject a modified B cell of the present invention, wherein the cell comprises an integrin, a homing antibody, protein, or a receptor that is attracted to a ligand, chemokine, or an attractant at the site/target of interest. In some embodiments, the site/target of interest is, for example, a homing or target tissue, an inflammatory site in a specific location or tissue, or a tumor or tumor microenvironment, where delivery of therapeutic payloads is desirable.

Also provided are methods for decreasing inflammation and autoimmune activity of B cells at a site/target of interest in a subject, comprising administering to the subject a modified B cell of the present invention, wherein the cell comprises an immune inhibitory molecule. In some embodiments, the site/target of interest is, for example, a homing or target tissue, an inflammatory site in a specific location or tissue, or a tumor or tumor microenvironment, where delivery of therapeutic payloads is desirable.

Also provided are methods for altering trafficking of B cells to a site/target of interest in a subject, comprising treating a B cell of the present invention with a compound or derivatives thereof suitable for altering B cell trafficking, and administering the treated B cell to the subject in need thereof. In some instances, the compound or derivatives thereof alters B cell trafficking by increasing the expression of an integrin, homing antibody, protein, receptor, or combinations thereof, expressed by the B cells.

Also provided are methods for potentiating B cells and/or producing potent effector B cells for increasing immune responses in a subject, comprising treating a B cell of the present invention with at least one or more TLR agonists, and administering the treated B cell to the subject in need thereof. In some embodiments, treating a B cell of the present invention with at least one or more TLR agonists induces expression or activation of one or more TLRs. In some embodiments, the method for potentiating B cells and/or producing potent effector B cells for increasing immune responses in a subject, further comprises administering to the subject a modified B cell of the present invention that expresses at least one or more constitutively active TLRs. Also provided are methods for potentiating B cells and/or producing potent effector B cells for increasing immune responses in a subject, comprising administering to the subject a modified B cell of the present invention, wherein the cell expresses a CAR-B receptor comprising an antigen-binding domain that binds to an antigen on a tumor, a constitutively active TLR or both a CAR-B and a constitutively active TLR, where the cell is treated with at least one or more TLR agonists at the same time or in advance of the administration of the cells to the subject.

Also provided are methods for increasing antigen-specific immune responses in a subject, comprising administering to the subject a modified B cell of the present invention, wherein the cell is electroporated with a nucleic acid sequence, e.g., an mRNA, encoding specific tumor antigens and/or infectious disease antigens fused to a targeting signal, such as the targeting signal of LAMP1 or Clec9A, for simultaneously and efficiently presenting the specific antigens and/or antigen-derived epitopes in both HLA class I and class II molecules. In some embodiments, the subject has a solid tumor, or a blood malignancy such as lymphoma or leukemia.

It is understood that the various embodiments of the methods of treatment using the engineered or modified B cells of the present application are not mutually exclusive and can be combined with each other in any way and without any restriction unless explicitly indicated, for achieving of facilitating any of the results and/or therapeutic responses contemplated herein.

In some embodiments, the modified B cells are autologous B cells. In some embodiments, the modified B cells are allogeneic B cells. In some embodiments, the modified B cells are heterologous B cells. In some embodiments, the modified B cells of the present application are transfected or transduced in vivo. In other embodiments, the engineered cells are transfected or transduced ex vivo.

As used herein, the term "subject" or "patient" means an individual. In some aspect, a subject is a mammal such as a human. In some aspect, a subject can be a non-human primate. Non-human primates include marmosets, monkeys, chimpanzees, gorillas, orangutans, and gibbons, to name a few. The term "subject" also includes domesticated animals, such as cats, dogs, etc., livestock (e.g., llama, horses, cows), wild animals (e.g., deer, elk, moose, etc.), laboratory animals (e.g., mouse, rabbit, rat, gerbil, guinea pig, etc.) and avian species (e.g., chickens, turkeys, ducks, etc.). Preferably, the subject is a human subject. More preferably, the subject is a human patient.

The methods can further comprise administering one or more chemotherapeutic agents. In certain embodiments, the chemotherapeutic agent is a lymphodepleting (preconditioning) chemotherapeutic. Beneficial preconditioning treatment regimens, along with correlative beneficial biomarkers are described in U.S. Provisional Patent Applications 62/262, 143 and 62/167,750, which are hereby incorporated by reference in their entirety herein. These describe, e.g., methods of conditioning a patient in need of a T cell therapy comprising administering to the patient specified beneficial doses of cyclophosphamide (between 200 mg/m$^2$/day and 2000 mg/m$^2$/day) and specified doses of fludarabine (between 20 mg/m$^2$/day and 900 mg/m$^2$/day). A preferred dose regimen involves treating a patient comprising administering daily to the patient about 500 mg/m$^2$/day of cyclophosphamide and about 60 mg/m$^2$/day of fludarabine for three days prior to administration of a therapeutically effective amount of engineered B cells to the patient.

In other embodiments, the antigen-binding molecule, transduced (or otherwise engineered) cells (such as CARs), and the chemotherapeutic agent are administered each in an amount effective to treat the disease or condition in the subject.

In certain embodiments, compositions comprising CAR-expressing immune effector cells disclosed herein may be administered in conjunction with any number of chemotherapeutic agents. Examples of chemotherapeutic agents include alkylating agents such as thiotepa and cyclophosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine resume; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofiran; spirogermanium; tenuazonic acid; triaziquone; 2, 2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxoids, e.g. paclitaxel (Taxol®, Bristol-Myers Squibb) and doxetaxel (Taxotere®, Rhone-Poulenc Rorer); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS2000; difluoromethylomithine (DMFO); retinoic acid derivatives such as Targretin™ (bexarotene), Panretin™, (alitretinoin); Ontak™ (denileukin diftitox); esperamicins; capecitabine; and pharmaceutically acceptable salts, acids or derivatives of any of the above. Also included in this definition are anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens such as flutamide, nilutamide, bicalutamide, leuprolide, and goserelin; and pharmaceutically acceptable salts, acids or derivatives of any of the above. Combinations of chemotherapeutic agents are also administered where appropriate, including, but not limited to CHOP, i.e., Cyclophosphamide (Cytoxan®) Doxorubicin (hydroxydoxorubicin), Fludarabine, Vincristine (Oncovin®), and Prednisone.

In some embodiments, the chemotherapeutic agent is administered at the same time or within one week after the administration of the engineered cell or nucleic acid. In other embodiments, the chemotherapeutic agent is administered from 1 to 4 weeks or from 1 week to 1 month, 1 week to 2 months, 1 week to 3 months, 1 week to 6 months, 1 week to 9 months, or 1 week to 12 months after the administration of the engineered cell or nucleic acid. In other embodiments, the chemotherapeutic agent is administered at least 1 month before administering the cell or nucleic acid. In some embodiments, the methods further comprise administering two or more chemotherapeutic agents.

A variety of additional therapeutic agents may be used in conjunction with the compositions described herein. For example, potentially useful additional therapeutic agents include PD-1 (or PD-L1) inhibitors such as nivolumab (Opdivo®), pembrolizumab (Keytruda®), pembrolizumab, pidilizumab, and atezolizumab (Tecentriq©). Other additional therapeutics include anti-CTLA-4 antibodies (e.g., Ipilimumab®), anti-LAG-3 antibodies (e.g., Relatlimab, BMS), alone or in combination with PD-1 and/or PD-L1 inhibitors.

Additional therapeutic agents suitable for use in combination with the invention include, but are not limited to, ibrutinib (Imbruvica®), ofatumumab (Arzerra®), rituximab (Rituxan®), bevacizumab (Avastin®), trastuzumab (Herceptin®), trastuzumab emtansine (KADCYLA®), imatinib (Gleevec®), cetuximab (Erbitux®), panitumumab (Vectibix®), catumaxomab, ibritumomab, ofatumumab, tositumomab, brentuximab, alemtuzumab, gemtuzumab, erlotinib, gefitinib, vandetanib, afatinib, lapatinib, neratinib, axitinib, masitinib, pazopanib, sunitinib, sorafenib, toceranib, lestaurtinib, axitinib, cediranib, lenvatinib, nintedanib, pazopanib, regorafenib, semaxanib, sorafenib, sunitinib, tivozanib, toceranib, vandetanib, entrectinib, cabozantinib, imatinib, dasatinib, nilotinib, ponatinib, radotinib, bosutinib, lestaurtinib, ruxolitinib, pacritinib, cobimetinib, selumetinib, trametinib, binimetinib, alectinib, ceritinib, crizotinib, aflibercept, adipotide, denileukin diftitox, mTOR inhibitors such as Everolimus and Temsirolimus, hedgehog inhibitors such as sonidegib and vismodegib, CDK inhibitors such as CDK inhibitor (palbociclib).

In additional embodiments, the composition comprising CAR-containing B cells can be administered with an anti-inflammatory agent. Anti-inflammatory agents or drugs include, but are not limited to, steroids and glucocorticoids (including betamethasone, budesonide, dexamethasone, hydrocortisone acetate, hydrocortisone, hydrocortisone, methylprednisolone, prednisolone, prednisone, triamcinolone), nonsteroidal anti-inflammatory drugs (NSAIDS) including aspirin, ibuprofen, naproxen, methotrexate, sulfasalazine, leflunomide, anti-TNF medications, cyclophosphamide and mycophenolate. Exemplary NSAIDs include ibuprofen, naproxen, naproxen sodium, Cox-2 inhibitors, and sialylates. Exemplary analgesics include acetaminophen, oxycodone, tramadol of proporxyphene hydrochloride. Exemplary glucocorticoids include cortisone, dexamethasone, hydrocortisone, methylprednisolone, prednisolone, or prednisone. Exemplary biological response modifiers include molecules directed against cell surface markers (e.g., CD4, CD5, etc.), cytokine inhibitors, such as the TNF antagonists, (e.g., etanercept (ENBREL®), adalimumab (HUMIRA®) and infliximab (REMICADE®)), chemokine inhibitors and adhesion molecule inhibitors. The biological response modifiers include monoclonal antibodies as well as recombinant forms of molecules. Exemplary DMARDs include azathioprine, cyclophosphamide, cyclosporine, methotrexate, penicillamine, leflunomide, sulfasalazine, hydroxychloroquine, Gold (oral (auranofin) and intramuscular) and minocycline.

In certain embodiments, the compositions described herein are administered in conjunction with a cytokine. "Cytokine" as used herein is meant to refer to proteins released by one cell population that act on another cell as intercellular mediators. Examples of cytokines are lymphokines, monokines, and traditional polypeptide hormones. Included among the cytokines are growth hormones such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor (HGF); fibroblast growth factor (FGF); prolactin; placental lactogen; mullerian-inhibiting substance; mouse gonadotropin-associated peptide; inhibin; activin; vascular endothelial growth factor; integrin; thrombopoietin (TPO); nerve growth factors (NGFs) such as NGF-beta; platelet-growth factor; transforming growth factors (TGFs) such as TGF-alpha and TGF-beta; insulin-like growth factor-I and -II; erythropoietin (EPO); osteoinductive factors; interferons such as interferon-alpha, beta, and -gamma; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1 alpha, IL-2, IL-3, IL-4, IL-5, IL-6, IL-7, IL-8, IL-9, IL-10, IL-11, IL-12; IL-15, a tumor necrosis factor such as TNF-alpha or TNF-beta; and other polypeptide factors including LIF and kit ligand (KL). As used herein, the term cytokine includes proteins from natural sources or from recombinant cell culture, and biologically active equivalents of the native sequence cytokines.

4. Methods of Making

A variety of known techniques can be utilized in making the polynucleotides, polypeptides, vectors, antigen-binding molecules, immune cells, compositions, and the like according to the invention.

Prior to the in vitro manipulation or genetic modification of the immune cells described herein, the cells may be obtained from a subject. In some embodiments, the immune cells comprise B cells. B cells can be obtained from a number of sources, including peripheral blood mononuclear cells (PBMCs), bone marrow, lymph nodes tissue, cord blood, thymus tissue, tissue from a site of infection, ascites, pleural effusion, spleen tissue, and tumors. In certain embodiments, B cells can be obtained from a unit of blood collected from the subject using any number of techniques known to the skilled person, such as FICOLL™ separation. Cells may preferably be obtained from the circulating blood of an individual by apheresis. The apheresis product typically contains lymphocytes, including T cells, monocytes, granulocytes, B cells, other nucleated white blood cells, red blood cells, and platelets. In certain embodiments, the cells collected by apheresis may be washed to remove the plasma fraction, and placed in an appropriate buffer or media for subsequent processing. The cells may be washed with PBS. As will be appreciated, a washing step may be used, such as by using a semiautomated flowthrough centrifuge for example, the Cobe™ 2991 cell processor, the Baxter CytoMate™, or the like. After washing, the cells may be resuspended in a variety of biocompatible buffers, or other saline solution with or without buffer. In certain embodiments, the undesired components of the apheresis sample may be removed.

The immune cells, such as B cells, can be genetically modified following isolation using known methods, or the immune cells can be activated and expanded (or differentiated in the case of progenitors) in vitro prior to being genetically modified. In another embodiment, the immune cells, such as B cells, are genetically modified with the chimeric B cell receptors described herein (e.g., transduced with a viral vector comprising one or more nucleotide sequences encoding a CAR-B) and then are activated and/or expanded in vitro. Methods for activating and expanding B cells are known in the art and are described, for example, in U.S. Pat. Nos. 6,905,874; 6,867,041; 6,797,514; and PCT WO 2012/079000, the contents of which are hereby incorporated by reference in their entirety. Generally, such methods include contacting PBMC or isolated B cells with a stimulatory agent and costimulatory agent generally attached to a bead or other surface, in a culture medium with appropriate cytokines, such as IL-2.

In other embodiments, the B cells may be activated and stimulated to proliferate with feeder cells and appropriate antibodies and cytokines using methods such as those described in U.S. Pat. Nos. 6,040,177; 5,827,642; and WO/2012129514, the contents of which are hereby incorporated by reference in their entirety.

Certain methods for making the constructs and engineered immune cells of the invention are described in PCT application PCT/US2015/14520, the contents of which are hereby incorporated by reference in their entirety. Additional methods of making the constructs and cells can be found in U.S. provisional patent application No. 62/244,036 the contents of which are hereby incorporated by reference in their entirety.

For cloning of polynucleotides, the vector may be introduced into a host cell (an isolated host cell) to allow replication of the vector itself and thereby amplify the copies of the polynucleotide contained therein. The cloning vectors may contain sequence components generally include, without limitation, an origin of replication, promoter sequences, transcription initiation sequences, enhancer sequences, and selectable markers. These elements may be selected as appropriate by a person of ordinary skill in the art. For example, the origin of replication may be selected to promote autonomous replication of the vector in the host cell.

In certain embodiments, the present disclosure provides isolated host cells containing the vector provided herein. The host cells containing the vector may be useful in expression or cloning of the polynucleotide contained in the vector. Suitable host cells can include, without limitation, prokaryotic cells, fungal cells, yeast cells, or higher eukaryotic cells such as mammalian cells. Suitable prokaryotic cells for this purpose include, without limitation, eubacteria, such as Gram-negative or Gram-positive organisms, for example, Enterobactehaceae such as *Escherichia*, e.g., *E. coli, Enterobacter, Erwinia, Klebsiella, Proteus, Salmonella*, e.g., *Salmonella typhimurium, Serratia*, e.g., *Serratia marc-escans*, and *Shigella*, as well as Bacilli such as *B. subtilis* and *B. licheniformis, Pseudomonas* such as *P. aeruginosa*, and *Streptomyces*.

The vector can be introduced to the host cell using any suitable methods known in the art, including, without limitation, DEAE-dextran mediated delivery, calcium phosphate precipitate method, cationic lipids mediated delivery, liposome mediated transfection, electroporation, microprojectile bombardment, receptor-mediated gene delivery, delivery mediated by polylysine, histone, chitosan, and peptides. Standard methods for transfection and transformation of cells for expression of a vector of interest are well known in the art. In a further embodiment, a mixture of different expression vectors can be used in genetically modifying a donor population of immune effector cells wherein each vector encodes a different CAR-Bs as disclosed herein. The resulting transduced immune effector cells form a mixed population of engineered cells, with a proportion of the engineered cells expressing more than one different CAR-Bs.

In one embodiment, the invention provides a method of storing genetically engineered cells expressing CAR-Bs that target a protein. This involves cryopreserving the immune cells such that the cells remain viable upon thawing. A fraction of the immune cells expressing the CAR-Bs can be cryopreserved by methods known in the art to provide a permanent source of such cells for the future treatment of patients afflicted with a malignancy. When needed, the cryopreserved transformed immune cells can be thawed, grown and expanded for more such cells.

As used herein, "cryopreserve" refers to the preservation of cells by cooling to sub-zero temperatures, such as (typically) 77 Kelvin or 196° C. (the boiling point of liquid nitrogen). Cryoprotective agents are often used at sub-zero temperatures to prevent the cells being preserved from damage due to freezing at low temperatures or warming to room temperature. Cryopreservative agents and optimal cooling rates can protect against cell injury. Cryoprotective agents which can be used in accordance with the invention include but are not limited to: dimethyl sulfoxide (DMSO) (Lovelock & Bishop, Nature, 1959, 183, 1394-1395; Ashwood-Smith, Nature, 1961, 190, 1204-1205), glycerol, polyvinylpyrrolidine (Rinfret, Ann. N.Y. Acad. Sci., 1960, 85, 576), and polyethylene glycol (Sloviter & Ravdin, Nature, 1962, 196, 48). The preferred cooling rate is 1°-3° C./minute.

The term, "substantially pure," is used to indicate that a given component is present at a high level. The component is desirably the predominant component present in a composition. Preferably it is present at a level of more than 30%, of more than 50%, of more than 75%, of more than 90%, or even of more than 95%, said level being determined on a dry weight/dry weight basis with respect to the total composition under consideration. At very high levels (e.g. at levels of more than 90%, of more than 95% or of more than 99%) the component can be regarded as being in "pure form." Biologically active substances of the present invention (including polypeptides, nucleic acid molecules, antigen-binding molecules, moieties) can be provided in a form that is substantially free of one or more contaminants with which the substance might otherwise be associated. When a composition is substantially free of a given contaminant, the contaminant will be at a low level (e.g., at a level of less than 10%, less than 5%, or less than 1% on the dry weight/dry weight basis set out above).

In some embodiments, the cells are formulated by first harvesting them from their culture medium, and then washing and concentrating the cells in a medium and container system suitable for administration (a "pharmaceutically acceptable" carrier) in a treatment-effective amount. Suitable infusion media can be any isotonic medium formulation, typically normal saline, Normosol™ R (Abbott) or Plasma-Lyte™ A (Baxter), but also 5% dextrose in water or Ringer's lactate can be utilized. The infusion medium can be supplemented with human serum albumin.

Desired treatment amounts of cells in the composition is generally at least 2 cells or is more typically greater than $10^2$ cells, and up to $10^6$, up to and including $10^8$ or $10^9$ cells and can be more than $10^{10}$ cells. The number of cells will depend upon the desired use for which the composition is intended, and the type of cells included therein. The density of the desired cells is typically greater than $10^6$ cells/ml and generally is greater than $10^7$ cells/ml, generally $10^8$ cells/ml or greater. The clinically relevant number of immune cells can be apportioned into multiple infusions that cumulatively equal or exceed $10^5$, $10^6$, $10^7$, $10^8$, $10^9$, $10^{10}$, $10^{11}$, or $10^{12}$ cells. In some aspects of the present invention, particularly since all the infused cells will be redirected to a particular target antigen, lower numbers of cells, in the range of $10^6$/kilogram ($10^6$-$10^{11}$ per patient) may be administered. CAR-B treatments may be administered multiple times at dosages within these ranges. The cells may be autologous, allogeneic, or heterologous to the patient undergoing therapy. In some aspects, different CAR-B cells are found in a single product. The composition can be as few as 2, 3, 4, 5, 6, 7, 8, 9 or up to 10 different CAR-B cells. These can consist of cells expressing a chimeric CAR protein and B cells expressing other CARs and/or payloads.

The B cells of the present invention may be administered either alone, or as a pharmaceutical composition in combination with diluents and/or with other components such as IL-2 or other cytokines or cell populations. Pharmaceutical compositions of the present invention may comprise a CAR-B expressing cell population, such as B cells, as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present invention are preferably formulated for intravenous administration. Treatment may also include one or more corticosteroid treatment, such as dexamethasone and/or methylprednisolone.

The compositions of the present application can comprise, consist essentially of, or consist of, the components disclosed.

The pharmaceutical compositions of the invention (solutions, suspensions or the like), may include one or more of the following: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfate; chelating agents such as ethylene-diaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. An injectable pharmaceutical composition is preferably sterile.

It will be appreciated that adverse events may be minimized by transducing the immune cells (containing one or more CAR-B) with a suicide gene. It may also be desired to incorporate an inducible "on" or "accelerator" switch into the immune cells. These techniques may employ the use of dimerization domains and optional activators of such domain dimerization. These techniques include, e.g., those described by Wu et al., Science 2014, 350(6258) utilizing FKBP/Rapalog dimerization systems in certain cells, the contents of which are incorporated by reference herein in their entirety. Additional dimerization technology is described in, e.g., Fegan et al. Chem. Rev. 2010, 110, 3315-3336 as well as U.S. Pat. Nos. 5,830,462; 5,834,266; 5,869,337; and 6,165,787, the contents of which are also incorporated by reference herein in their entirety. Additional dimerization pairs may include cyclosporine-A/cyclophilin, receptor, estrogen/estrogen receptor (optionally using tamoxifen), glucocorticoids/glucocorticoid receptor, tetracycline/tetracycline receptor, vitamin D/vitamin D receptor. Further examples of dimerization technology can be found in e.g., WO 2014/127261, WO 2015/090229, US 2014/0286987, US 2015/0266973, US 2016/0046700, U.S. Pat. No. 8,486,693, US 2014/0171649, and US 2012/0130076, the contents of which are further incorporated by reference herein in their entirety.

Suitable techniques include use of inducible caspase-9 (U.S. Appl. Pub. No. 2011/0286980) or a thymidine kinase, before, after or at the same time, as the cells are transduced with the CAR-B construct of the present invention. Additional methods for introducing suicide genes and/or "on" switches include CRISPR, TALENS, MEGATALEN, zinc fingers, RNAi, siRNA, shRNA, antisense technology, and other techniques known in the art.

Anti-CD20 or anti-CD19 represent additional means to reduce or eliminate engineered B cells if such cells are responsible for adverse events or pathologies.

It will be understood that descriptions herein are exemplary and explanatory only and are not restrictive of the invention as claimed. In this application, the use of the singular includes the plural unless specifically stated otherwise.

The section headings used herein are for organizational purposes only and are not to be construed as limiting the subject matter described. All documents, or portions of documents, cited in this application, including but not limited to patents, patent applications, articles, books, and treatises, are hereby expressly incorporated by reference in their entirety for any purpose. As utilized in accordance with the present disclosure, the following terms, unless otherwise indicated, shall be understood to have the following meanings:

In this application, the use of "or" means "and/or" unless stated otherwise. Furthermore, the use of the term "including", as well as other forms, such as "includes" and "included", is not limiting. Also, terms such as "element" or "component" encompass both elements and components comprising one unit and elements and components that comprise more than one subunit unless specifically stated otherwise.

The term "polynucleotide", "nucleotide", or "nucleic acid" includes both single-stranded and double-stranded nucleotide polymers. The nucleotides comprising the polynucleotide can be ribonucleotides or deoxyribonucleotides or a modified form of either type of nucleotide. Said modifications include base modifications such as bromouridine and inosine derivatives, ribose modifications such as 2', 3'-dideoxyribose, and internucleotide linkage modifications such as phosphorothioate, phosphorodithioate, phosphoroselenoate, phosphoro-diselenoate, phosphoro-anilothioate, phoshoraniladate and phosphoroamidate.

The term "oligonucleotide" refers to a polynucleotide comprising 200 or fewer nucleotides. Oligonucleotides can be single stranded or double stranded, e.g., for use in the construction of a mutant gene. Oligonucleotides can be sense or antisense oligonucleotides. An oligonucleotide can include a label, including a radiolabel, a fluorescent label, a hapten or an antigenic label, for detection assays. Oligonucleotides can be used, for example, as PCR primers, cloning primers or hybridization probes.

The term "control sequence" refers to a polynucleotide sequence that can affect the expression and processing of coding sequences to which it is ligated. The nature of such control sequences can depend upon the host organism. In particular embodiments, control sequences for prokaryotes can include a promoter, a ribosomal binding site, and a transcription termination sequence. For example, control sequences for eukaryotes can include promoters comprising one or a plurality of recognition sites for transcription factors, transcription enhancer sequences, and transcription termination sequence. "Control sequences" can include leader sequences (signal peptides) and/or fusion partner sequences.

As used herein, "operably linked" means that the components to which the term is applied are in a relationship that allows them to carry out their inherent functions under suitable conditions.

The term "vector" means any molecule or entity (e.g., nucleic acid, plasmid, bacteriophage or virus) used to transfer protein coding information into a host cell. The term "expression vector" or "expression construct" refers to a vector that is suitable for transformation of a host cell and contains nucleic acid sequences that direct and/or control (in conjunction with the host cell) expression of one or more heterologous coding regions operatively linked thereto. An expression construct can include, but is not limited to, sequences that affect or control transcription, translation, and, if introns are present, affect RNA splicing of a coding region operably linked thereto.

The term "host cell" refers to a cell that has been transformed, or is capable of being transformed, with a nucleic acid sequence and thereby expresses a gene of interest. The term includes the progeny of the parent cell, whether or not the progeny is identical in morphology or in genetic make-up to the original parent cell, so long as the gene of interest is present.

The term "transformation" refers to a change in a cell's genetic characteristics, and a cell has been transformed when it has been modified to contain new DNA or RNA. For example, a cell is transformed where it is genetically modified from its native state by introducing new genetic material via transfection, transduction, or other techniques. Following transfection or transduction, the transforming DNA can recombine with that of the cell by physically integrating into a chromosome of the cell, or can be maintained transiently as an episomal element without being replicated, or can replicate independently as a plasmid. A cell is considered to have been "stably transformed" when the transforming DNA is replicated with the division of the cell.

The term "transfection" refers to the uptake of foreign or exogenous DNA by a cell. A number of transfection techniques are well known in the art and are disclosed herein. See, e.g., Graham et al., VIROLOGY, 1973, 52:456; Sambrook et al., Molecular Cloning: A Laboratory Manual, 2001, supra; Davis et al., Basic Methods in Molecular Biology, 1986, Elsevier; Chu et al., Gene, 1981, 13:197.

The term "transduction" refers to the process whereby foreign DNA is introduced into a cell via viral vector. See, e.g., Jones et al., Genetics: principles and analysis, 1998, Boston: Jones & Bartlett Publ.

The terms "polypeptide" or "protein" refer to a macromolecule having the amino acid sequence of a protein, including deletions from, additions to, and/or substitutions of one or more amino acids of the native sequence. The terms "polypeptide" and "protein" specifically encompass antigen-binding molecules, antibodies, or sequences that have deletions from, additions to, and/or substitutions of one or more amino acid of antigen-binding protein. The term "polypeptide fragment" refers to a polypeptide that has an amino-terminal deletion, a carboxyl-terminal deletion, and/or an internal deletion as compared with the full-length native protein. Such fragments can also contain modified amino acids as compared with the native protein. Useful polypeptide fragments include immunologically functional fragments of antigen-binding molecules.

The term "isolated" means (i) free of at least some other proteins with which it would normally be found, (ii) is essentially free of other proteins from the same source, e.g., from the same species, (iii) separated from at least about 50 percent of polynucleotides, lipids, carbohydrates, or other materials with which it is associated in nature, (iv) operably associated (by covalent or noncovalent interaction) with a polypeptide with which it is not associated in nature, or (v) does not occur in nature.

A "variant" of a polypeptide (e.g., an antigen-binding molecule) comprises an amino acid sequence wherein one or more amino acid residues are inserted into, deleted from and/or substituted into the amino acid sequence relative to another polypeptide sequence. Variants include fusion proteins.

The term "identity" refers to a relationship between the sequences of two or more polypeptide molecules or two or more nucleic acid molecules, as determined by aligning and comparing the sequences. "Percent identity" means the percent of identical residues between the amino acids or nucleotides in the compared molecules and is calculated based on the size of the smallest of the molecules being compared. For these calculations, gaps in alignments (if any) are preferably addressed by a particular mathematical model or computer program (i.e., an "algorithm").

To calculate percent identity, the sequences being compared are typically aligned in a way that gives the largest match between the sequences. One example of a computer program that can be used to determine percent identity is the GCG program package, which includes GAP (Devereux et al., Nucl. Acid Res., 1984, 12, 387; Genetics Computer Group, University of Wisconsin, Madison, Wis.). The computer algorithm GAP is used to align the two polypeptides or polynucleotides for which the percent sequence identity is to be determined. The sequences are aligned for optimal matching of their respective amino acid or nucleotide (the "matched span", as determined by the algorithm). In certain embodiments, a standard comparison matrix (see, e.g., Dayhoff et al., 1978, Atlas of Protein Sequence and Structure, 1978, 5:345-352 for the PAM 250 comparison matrix; Henikoff et al., Proc. Natl. Acad. Sci. U.S.A. 1992, 89, 10915-10919 for the BLO-SUM 62 comparison matrix) is also used by the algorithm.

As used herein, the twenty conventional (e.g., naturally occurring) amino acids and their abbreviations follow conventional usage. See, e.g., Immunology A Synthesis (2nd Edition, Golub and Green, Eds., Sinauer Assoc., Sunderland, Mass. (1991)), which is incorporated herein by reference for any purpose. Stereoisomers (e.g., D-amino acids) of the twenty conventional amino acids, unnatural amino acids such as alpha-, alpha-disubstituted amino acids, N-alkyl amino acids, lactic acid, and other unconventional amino acids can also be suitable components for polypeptides of the present invention. Examples of unconventional amino acids include: 4-hydroxyproline, .gamma.-carboxy-glutamate, epsilon-N,N,N-trimethyllysine, e-N-acetyllysine, 0-phosphoserine, N-acetylserine, N-formylmethionine, 3-methylhistidine, 5-hydroxylysine, .sigma.-N-methylarginine, and other similar amino acids and imino acids (e.g., 4-hydroxyproline). In the polypeptide notation used herein, the left-hand direction is the amino terminal direction and the right-hand direction is the carboxy-terminal direction, in accordance with standard usage and convention.

Conservative amino acid substitutions can encompass non-naturally occurring amino acid residues, which are typically incorporated by chemical peptide synthesis rather than by synthesis in biological systems. These include peptidomimetics and other reversed or inverted forms of amino acid moieties. Naturally occurring residues can be divided into classes based on common side chain properties:
  a) hydrophobic: norleucine, Met, Ala, Val, Leu, Ile;
  b) neutral hydrophilic: Cys, Ser, Thr, Asn, Gln;
  c) acidic: Asp, Glu;
  d) basic: His, Lys, Arg;
  e) residues that influence chain orientation: Gly, Pro; and
  f) aromatic: Trp, Tyr, Phe.

For example, non-conservative substitutions can involve the exchange of a member of one of these classes for a member from another class.

In making changes to the antigen-binding molecule, the costimulatory or activating domains of the engineered T cell, according to certain embodiments, the hydropathic index of amino acids can be considered. Each amino acid has been assigned a hydropathic index on the basis of its hydrophobicity and charge characteristics. They are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5). See, e.g., Kyte et al., J. Mol. Biol., 1982, 157, 105-131. It is known that certain amino acids can be substituted for other amino acids having a similar hydropathic index or score and still retain a similar biological activity. It is also understood in the art that the substitution of like amino acids can be made effectively on the basis of hydrophilicity, particularly where the biologically functional protein or peptide thereby created is intended for use in immunological embodiments, as in the present case. Exemplary amino acid substitutions are set forth in Table 5.

TABLE 5

| Original Residues | Exemplary Substitutions | Preferred Substitutions |
|---|---|---|
| Ala | Val, Leu, Ile | Val |
| Arg | Lys, Gin, Asn | Lys |
| Asn | Gln | Gln |
| Asp | Glu | Glu |
| Cys | Ser, Ala | Ser |
| Gln | Asn | Asn |
| Glu | Asp | Asp |
| Gly | Pro, Ala | Ala |
| His | Asn, Gln, Lys, Arg | Arg |
| Ile | Leu, Val, Met, Ala, Phe, Norleucine | Leu |
| Leu | Norleucine, Ile, Va, Met, Ala, Phe | Ile |
| Lys | Arg, 1, 4 Diamino-butyric Acid, Gin, Asn | Arg |
| Met | Leu, Phe, Ile | Leu |
| Phe | Leu, Val, Ile, Ala, Tyr | Leu |
| Pro | Ala | Gly |
| Ser | Thr, Ala, Cys | Thr |
| Thr | Ser | Ser |
| Trp | Tyr, Phe | Tyr |
| Tyr | Trp, Phe, Thr, Ser | Phe |
| Val | Ile, Met, Leu, Phe, Ala, Norleucine | Leu |

The term "derivative" refers to a molecule that includes a chemical modification other than an insertion, deletion, or substitution of amino acids (or nucleic acids). In certain embodiments, derivatives comprise covalent modifications, including, but not limited to, chemical bonding with polymers, lipids, or other organic or inorganic moieties. In certain embodiments, a chemically modified antigen-binding molecule can have a greater circulating half-life than an antigen-binding molecule that is not chemically modified. In some embodiments, a derivative antigen-binding molecule is covalently modified to include one or more water soluble polymer attachments, including, but not limited to, polyethylene glycol, polyoxyethylene glycol, or polypropylene glycol.

Peptide analogs are commonly used in the pharmaceutical industry as non-peptide drugs with properties analogous to those of the template peptide. These types of non-peptide compound are termed "peptide mimetics" or "peptidomimetics." Fauchere, J. L., Adv. Drug Res., 1986, 15, 29; Veber, D. F. & Freidinger, R. M., Trends in Neuroscience, 1985, 8, 392-396; and Evans, B. E., et al., J. Med. Chem., 1987, 30, 1229-1239, which are incorporated herein by reference for any purpose.

The term "therapeutically effective amount" refers to the amount of CAR-B cells determined to produce a therapeutic response in a mammal. Such therapeutically effective amounts are readily ascertained by one of ordinary skill in the art.

The terms "patient" and "subject" are used interchangeably and include human and non-human animal subjects as well as those with formally diagnosed disorders, those without formally recognized disorders, those receiving medical attention, those at risk of developing the disorders, etc.

The term "treat" and "treatment" includes therapeutic treatments, prophylactic treatments, and applications in which one reduces the risk that a subject will develop a disorder or other risk factor. Treatment does not require the complete curing of a disorder and encompasses embodiments in which one reduces symptoms or underlying risk factors. The term "prevent" does not require the 100% elimination of the possibility of an event. Rather, it denotes that the likelihood of the occurrence of the event has been reduced in the presence of the compound or method.

Standard techniques can be used for recombinant DNA, oligonucleotide synthesis, and tissue culture and transformation (e.g., electroporation, lipofection). Enzymatic reactions and purification techniques can be performed according to manufacturer's specifications or as commonly accomplished in the art or as described herein. The foregoing techniques and procedures can be generally performed according to conventional methods well known in the art and as described in various general and more specific references that are cited and discussed throughout the present specification. See, e.g., Sambrook et al., Molecular Cloning: A Laboratory Manual (2d ed., Cold Spring Harbor Laboratory Press, Cold Spring Harbor, N.Y. (1989)), which is incorporated herein by reference for any purpose.

5. Sequences

The following sequences will further exemplify the invention:

CD28 Transmembrane Domain—Mouse

```
                                            (SEQ ID NO: 1)
TTCTGGGCCCTTGTGGTGGTTGCCGGAGTGCTGTTTTGCTATGGGCTCCT

GGTTACCGTTGCCCTTTGTGTGATTTGGACC
```

CD28 Transmembrane Domain—Mouse

```
                                            (SEQ ID NO: 2)
             FWALVVVAGVLFCYGLLVTVALCVIWT
```

CD28 Transmembrane Domain—Human

```
                                            (SEQ ID NO: 3)
TTTTGGGTATTGGTAGTGGTGGGCGGAGTTTTAGCCTGCTACAGCCTCCT

GGTAACAGTGGCTTTTATCATCTTTTGGGTG
```

CD28 Transmembrane Domain—Human

```
                                            (SEQ ID NO: 4)
             FWVLVVVGGVLACYSLLVTVAFIIFWV
```

CD19 Cytoplasmic Domain—Human

```
                                            (SEQ ID NO: 5)
CAGCGGGCTTTAGTCTTGCGGCGTAAACGTAAAGAATGACAGATCCAAC

TCGCAGGTTCTTCAAAGTGACCCCCCCACCTGGGTCCGGACCGCAGAACC

AATATGGGAATGTCCTGTCTCTGCCTACGCCTACAAGTGGACTGGGTAGG

GCTCAGAGGTGGGCTGCCGGTCTCGGCGGAACTGCGCCATCTTACGGAAA

TCCCTCCTCCGACGTTCAGGCAGACGGGGCCCTGGGGTCTCGATCCCCGC

CTGGTGTTGGACCAGAAGAGGAAGAGGGCGAGGGCTACGAAGAGCCCGAC

TCCGAAGAGGACAGTGAGTTTTACGAGAACGACAGCAACCTGGGGCAGGA

TCAGCTGTCACAGGATGGCTCAGGATATGAAAACCCTGAGGACGAGCCTT

TGGGGCCTGAAGATGAGGACTCCTTTTCTAATGCAGAGTCATATGAGAAT

GAGGACGAAGAATTGACTCAACCCGTGGCAAGAACAATGGATTTCCTCAG

TCCACACGGGAGTGCATGGGACCCCTCCAGAGAGGCTACTAGCCTCGGTT

CTCAAAGCTATGAGGACATGAGGGGTATTCTGTACGCAGCGCCTCAGTTG

AGGTCCATCCGCGGCCAGCCAGGCCCAAACCATGAGGAAGATGCCGATTC

TTACGAAAACATGGACAACCCCGATGGTCCTGACCCCGCATGGGGGGCG

GCGGGAGGATGGGCACCTGGTCTACTCGC
```

CD19 Cytoplasmic Domain—Human

```
                                            (SEQ ID NO: 6)
QRALVLRRKRKRMTDPTRRFFKVTPPPGSGPQNQYGNVLSLPTPTSGLGR

AQRWAAGLGGTAPSYGNPSSDVQADGALGSRSPPGVGPEEEEGEGYEEPD

SEEDSEFYENDSNLGQDQLSQDGSGYENPEDEPLGPEDEDSFSNAESYEN

EDEELTQPVARTMDFLSPHGSAWDPSREATSLGSQSYEDMRGILYAAPQL

RSIRGQPGPNHEEDADSYENMDNPDGPDPAWGGGRMGTWSTR
```

CD40 Cytoplasmic Domain—Human

```
                                            (SEQ ID NO: 7)
AAGAAGGTTGCAAAAAAACCTACTAATAAGGCTCCCCATCCTAAGCAAGA

GCCCCAAGAAATTAACTTTCCCGATGATCTTCCGGGTTCTAACACGGC

AGCCCCGGTGCAGGAGACCCTGCATGGTTGTCAACCCGTCACTCAGGA

GGACGGGAAAGAGTCTCGTATCTCCGTCCAGGAGAGACAG
```

CD40 Cytoplasmic Domain—Human

```
                                            (SEQ ID NO: 8)
KKVAKKPTNKAPHPKQEPQEINFPDDLPGSNTAAPVQETLHGCQPVTQED

GKESRISVQERQ
```

CD40+CD79b Cytoplasmic Domain—Human

```
                                            (SEQ ID NO: 9)
AAGAAGGTTGCAAAAAAACCTACTAATAAGGCTCCCCATCCTAAGCAAGA

GCCCCAAGAAATTAACTTTCCCGATGATCTTCCGGGTTCTAACACGGCAG

CCCCGGTGCAGGAGACCCTGCATGGTTGTCAACCCGTCACTCAGGAGGAC

GGGAAAGAGTCTCGTATCTCCGTCCAGGAGAGACAGGACAAGGACGATAG

TAAAGCAGGGATGGAGGAGGACCATACATACGAGGGACTGGATATCGATC

AGACAGCCACGTACGAAGACATTGTGACACTGAGAACTGGCGAGGTGAAG

TGGTCAGTGGGAGAACATCCGGGGCAGGAA
```

CD40+CD79b Cytoplasmic Domain—Human (SEQ ID NO: 10)
KKVAKKPTNK APHPKQEPQE INFPDDLPGS NTAAPVQETL
HGCQPVTQED GKESRISVQE RQDKDDSKAG MEEDHTYEGL
DIDQTATYED IVTLRTGEVK WSVGEHPGQE CD40+CD137 Cytoplasmic Domain—Human (SEQ ID NO: 11)
AAGAAGGTTGCAAAAAAACCTACTAATAAGGCTCCCCATCCTAAGCAAGA
GCCCCAAGAAATTAACTTTCCCGATGATCTTCCGGGTTCTAACACGGCAG
CCCCGGTGCAGGAGACCCTGCATGGTTGTCAACCCGTCACTCAGGAGGAC
GGGAAAGAGTCTCGTATCTCCGTCCAGGAGAGACAGAAAAGAGGCCGAAA
AAAGCTGCTGTACATCTTCAAACAACCCTTCATGCGACCTGTTCAGACGA
CACAGGAGGAGGACGGCTGCAGCTGTAGGTTTCCCGAAGAAGAGGAGGGA
GGATGCGAACTT CD40+CD137 Cytoplasmic Domain—Human (SEQ ID NO: 12)
KKVAKKPTNKAPHPKQEPQEINFPDDLPGSNTAAPVQETLHGCQPVTQED
GKESRISVQERQKRGRKKLLYIFKQPFMRPVQTTQEEDGCSCRFPEEEEG
GCEL CD137 Cytoplasmic Domain—Human (SEQ ID NO: 13)
AAAAGAGGCCGAAAAAAGCTGCTGTACATCTTCAAACAACCCTTCATGCG
ACCTGTTCAGACGACACAGGAGGAGGACGGCTGCAGCTGTAGGTTTCCCG
AAGAAGAGGAGGGAGGATGCGAACTT CD137 Cytoplasmic Domain—Human (SEQ ID NO: 14)
KRGRKKLLYIFKQPFMRPVQTTQEEDGCSCRFPEEEEGGCEL CD40 and Fc Gamma Receptor 2a Cytoplasmic Domain—Human (SEQ ID NO: 15)
AAGAAGGTTGCAAAAAAACCTACTAATAAGGCTCCCCATCCTAAGCAAGA
GCCCCAAGAAATTAACTTTCCCGATGATCTTCCGGGTTCTAACACGGCAG
CCCCGGTGCAGGAGACCCTGCATGGTTGTCAACCCGTCACTCAGGAGGAC
GGGAAAGAGTCTCGTATCTCCGTCCAGGAGAGACAGCGCAAAAAACGTAT
AAGCGCAAACTCTACAGATCCAGTAAAAGCCGCGCAATTCGAGCCTCCCG
GCCGCCAGATGATTGCAATACGGAAACGTCAACTGGAGGAAACTAATAAT
GACTATGAGACGGCCGACGGTGGATACATGACCCTTAATCCCCGCGCGCC
AACCGACGATGATAAGAACATATATCTGACGCTCCCCCCTAACGATCACG
TTAACAGTAATAAT CD40 and Fc Gamma Receptor 2a Cytoplasmic Domain—Human (SEQ ID NO: 16)
KKVAKKPTNKAPHPKQEPQEINFPDDLPGSNTAAPVQETLHGCQPVTQED
GKESRISVQERQRKKRISANSTDPVKAAQFEPPGRQMIAIRKRQLEETNN
DYETADGGYMTLNPRAPTDDDKNIYLTLPPNDHVNSNN Fc Gamma Receptor 2a Cytoplasmic Domain—Human (SEQ ID NO: 17)
CGCAAAAAACGTATAAGCGCAAACTCTACAGATCCAGTAAAAGCCGCGCA
ATTCGAGCCTCCCGGCCGCCAGATGATTGCAATACGGAAACGTCAACTGG
AGGAAACTAATAATGACTATGAGACGGCCGACGGTGGATACATGACCCTT
AATCCCCGCGCGCCAACCGACGATGATAAGAACATATATCTGACGCTCCC
CCCTAACGATCACGTTAACAGTAATAAT Fc Gamma Receptor 2a Cytoplasmic Domain—Human (SEQ ID NO: 18)
RKKRISANSTDPVKAAQFEPPGRQMIAIRKRQLEETNNDYETADGGYMTL
NPRAPTDDDKNIYLTLPPNDHVNSNN Myd88+CD40 Cytoplasmic Domain—Human (SEQ ID NO: 19)
ATGGCGGCGGGCGGGCCCGGCGCCGGAAGCGCCGCGCCAGTCTCATCTAC
GTCCAGTCTGCCACTGGCTGCCCTGAACATGAGAGTGAGACGCCGTTTAT
CCCTCTTCCTGAATGTGCGGACCCAGGTCGCCGCTGATTGGACCGCCCTG
GCCGAAGAGATGGACTTTGAATACTTGGAAATCAGACAGCTGGAAACACA
GGCAGACCCAACCGGGAGACTGCTTGACGCCTGGCAGGGACGCCCAGGGG
CAAGTGTTGGTCGGTTACTGGAGCTTTTAACTAAGTTGGGCCGCGATGAC
GTGCTGTTGGAGTTAGGACCCAGTATCGAGGAGGATTGTCAGAAATACAT
CTTGAAACAGCAGCAGGAGGAGGCGGAAAAGCCCCTGCAGGTGGCGGCCG
TTGACAGCAGTGTACCCAGAACAGCTGAGCTGGCCGGCATCACAACCCTG
GATGATCCCCTGGGCCACATGCCTGAGAGGTTCGACGCTTTCATAAAGAA
GGTTGCAAAAAAACCTACTAATAAGGCTCCCCATCCTAAGCAAGAGCCCC
AAGAAATTAACTTTCCCGATGATCTTCCGGGTTCTAACACGGCAGCCCCG
GTGCAGGAGACCCTGCATGGTTGTCAACCCGTCACTCAGGAGGACGGGAA
AGAGTCTCGTATCTCCGTCCAGGAGAGACAG Myd88+CD40 Cytoplasmic Domain—Human (SEQ ID NO: 20)
MAAGGPGAGSAAPVSSTSSLPLAALNMRVRRRLSLFLNVRTQVAADWTAL
AEEMDFEYLEIRQLETQADPTGRLLDAWQGRPGASVGRLLELLTKLGRDD
VLLELGPSIEEDCQKYILKQQQEEAEKPLQVAAVDSSVPRTAELAGITTL
DDPLGHMPERFDAFIKKVAKKPTNKAPHPKQEPQEINFPDDLPGSNTAAP
VQETLHGCQPVTQEDGKESRISVQERQ Myd88 Cytoplasmic Domain—Human (SEQ ID NO: 21)
ATGGCGGCGGGCGGGCCCGGCGCCGGAAGCGCCGCGCCAGTCTCATCTAC
GTCCAGTCTGCCACTGGCTGCCCTGAACATGAGAGTGAGACGCCGTTTAT
CCCTCTTCCTGAATGTGCGGACCCAGGTCGCCGCTGATTGGACCGCCCTG
GCCGAAGAGATGGACTTTGAATACTTGGAAATCAGACAGCTGGAAACACA
GGCAGACCCAACCGGGAGACTGCTTGACGCCTGGCAGGGACGCCCAGGGG
CAAGTGTTGGTCGGTTACTGGAGCTTTTAACTAAGTTGGGCCGCGATGAC
GTGCTGTTGGAGTTAGGACCCAGTATCGAGGAGGATTGTCAGAAATACAT
CTTGAAACAGCAGCAGGAGGAGGCGGAAAAGCCCCTGCAGGTGGCGGCCG
TTGACAGCAGTGTACCCAGAACAGCTGAGCTGGCCGGCATCACAACCCTG
GATGATCCCCTGGGCCACATGCCTGAGAGGTTCGACGCTTTCATA Myd88 Cytoplasmic Domain—Human (SEQ ID NO: 22)
MAAGGPGAGSAAPVSSTSSLPLAALNMRVRRRLSLFLNVRTQVAADWTAL
AEEMDFEYLEIRQLETQADPTGRLLDAWQGRPGASVGRLLELLTKLGRDD
VLLELGPSIEEDCQKYILKQQQEEAEKPLQVAAVDSSVPRTAELAGITTL
DDPLGHMPERFDAFI CD79a Cytoplasmic Domain—Human (SEQ ID NO: 23)
AGGAAACGATGGCAGAACGAGAAGCTCGGGTTGGATGCCGGGGATGAATA
TGAAGATGAAAACCTTTATGAAGGCCTGAACCTGGACGACTGCTCCATGT
ATGAGGACATCTCCCGGGGCCTCCAGGGCACCTACCAGGATGTGGGCAGC
CTCAACATAGGAGATGTCCAGCTGGAGAAGCCG CD79a Cytoplasmic Domain—Human (SEQ ID NO: 24)
RKRWQNEKLGLDAGDEYEDENLYEGLNLDDCSMYEDISRGLQGTYQDVGS
LNIGDVQLEKP CD79b Cytoplasmic Domain—Human (SEQ ID NO: 25)
CTGGACAAGGATGACAGCAAGGCTGGCATGGAGGAAGATCACACCTACGA
GGGCCTGGACATTGACCAGACAGCCACCTATGAGGACATAGTGACGCTGC
GGACAGGGGAAGTGAAGTGGTCTGTAGGTGAGCACCCAGGCCAGGAG CD79b Cytoplasmic Domain—Human (SEQ ID NO: 26)
LDKDDSKAGMEEDHTYEGLDIDQTATYEDIVTLRTGEVKWSVGEHPQE CD8 Hinge Domain—Human (SEQ ID NO: 27)
TTCGTGCCTGTGTTCCTCCCAGCTAAGCCCACTACCACCCCCGCTCCAAG
GCCGCCCACGCCCGCTCCTACTATTGCTAGTCAGCCTTTAAGTTTACGAC
CCGAAGCTTGCAGGCCCGCCGCCGGCGGCGCTGTGCACACCAGGGGGCTT
GATTTTGCCTGCGAC CD8 Hinge Domain—Human (SEQ ID NO: 28)
FVPVFLPAKPTTTPAPRPPTPAPTIASQPLSLRPEACRPAAGGAVHTRGL
DFACD Spacer with 3X Strep II Tag (SEQ ID NO: 29)
GGCGCTGGTAGTGGCGGTAACTGGAGCCACCCTCAATTTGAGAAGGCGG
GTCAGGCGGATCAGGTGGTAGTGGTGGGTCCAACTGGAGCCATCCGCAAT
TTGAAAAGGGCGGAAGCGGCGGTTCCGGCGGTTCAGGCGGTAGCAACTGG
TCACATCCGCAATTTGAGAAAGGCGGGTCAGGCGGCGGG Spacer with 3X Strep II Tag (SEQ ID NO: 30)
GAGSGGNWSHPQFEKGGSGGSGGSGGSNWSHPQFEKGGSGGSGGSGGSNW
SHPQFEKGGSGGG Human IgG1 Fc (Transmembrane Form)

(SEQ ID NO: 31)
CCCAAGAGCTGCGACAAGACCCACACCTGCCCCCCCTGCCCAGCCCCAGA
GCTGCTGGGCGGACCCTCCGTGTTCCTGTTCCCCCCCAAGCCCAAGGACA
CCCTGATGATCAGCAGGACCCCCGAGGTGACCTGCGTGGTGGTGGACGTG
AGCCACGAGGACCCAGAGGTGAAGTTCAACTGGTACGTGGACGGCGTGGA
GGTGCACAACGCCAAGACCAAGCCCAGAGAGGAGCAGTACAACAGCACCT
ACAGGGTGGTGTCCGTGCTGACCGTGCTGCACCAGGACTGGCTGAACGGC
AAGGAATACAAGTGCAAGGTCTCCAACAAGGCCCTGCCAGCCCCCATCGA
AAAGACCATCAGCAAGGCCAAGGGCCAGCCACGGGAGCCCCAGGTGTACA
CCCTGCCCCCTCCCGGGAGGAGATGACCAAGAACCAGGTGTCCCTGACC
TGTCTGGTGAAGGGCTTCTACCCCAGCGACATCGCCGTGGAGTGGGAGAG
CAACGGCCAGCCCGAGAACAACTACAAGACCACCCCCCCAGTGCTGGACA
GCGACGGCAGCTTCTTCCTGTACAGCAAGCTGACCGTGGACAAGTCCAGG
TGGCAGCAGGGCAACGTGTTCAGCTGCAGCGTGATGCACGAGGCCCTGCA
CAACCACTACACCCAGAAGAGCCTGAGCCTGTCCCCCGAGCTGCAACTGG
AGGAGAGCTGTGCGGAGGCGCAGGACGGGAGCTGGACGGGCTGTGGACG
ACCATCACCATCTTCATCACACTCTTCCTGTTAAGCGTGTGCTACAGTGC
CACCGTCACCTTCTTCAAGGTGAAGTGGATCTTCTCCTCGGTGGTGGACC
TGAAGCAGACCATCATCCCCGACTACAGGAACATGATCGGACAGGGGGCC
TGA

Human IgG1 Fc (Transmembrane Form)

(SEQ ID NO: 32)
PKSCDKTHTCPPCPAPELLGGPSVFLFPPKPKDTLMISRTPEVTCVVVDV
SHEDPEVKFNWYVDGVEVHNAKTKPREEQYNSTYRVVSVLTVLHQDWLNG
KEYKCKVSNKALPAPIEKTISKAKGQPREPQVYTLPPSREEMTKNQVSLT
CLVKGFYPSDIAVEWESNGQPENNYKTTPPVLDSDGSFFLYSKLTVDKSR
WQQGNVFSCSVMHEALHNHYTQKSLSLSPELQLEESCAEAQDGELDGLWT
TITIFITLFLLSVCYSATVTFFKVKWIFSSVVDLKQTIIPDYRNMIGQGA

Anti-huPSMA scFv (SEQ ID NO: 33)
GAGGTTCAACTTGTTCAATCTGGGGCAGAAGTGAAGAAGCCCGGGGCATC
TGTGAAAGTATCATGCAAAACATCCGGCTATACGTTTACCGAATACACCA
TTCACTGGGTCAGACAGGCTCCCGGTCAAAGCCTCGAATGGATGGGAAAT
ATTAACCCTAACAATGGCGGAACCACATATAATCAGAAATTCCAAGGCCG
AGTGACGATAACTGTCGATAAGAGTACGTCCACAGCTTACATGGAACTCA
GCTCTTTGAGATCCGAAGACACTGCAGTTTATTATTGTGCAGCTGGATGG
AACTTCGACTATTGGGGACAAGGGACTCTTGTTACGGTGTCCAGTGGCAA
ACCAGGTAGTGGTAAACCCGGAAGCGGCAAGCCCGGGAGCGGTAAACCTG
GTAGCGACATCGTCATGACTCAAAGCCCTGACTCACTCGCCGTGAGCCTG
GGAGAGCGTGCAACGCTATCTTGTCGGGCCTCTCAGGATGTCGGAACTGC
TGTAGACTGGTATCAACAGAAACCTGACCAATCACCAAAACTCCTGATTT
ATTGGGCCTCAACACGTCACACAGGAGTGCCAGATAGGTTCACAGGTAGT
GGCAGTGGAACTGATTTTACTTTGACAATTAGCAGCCTGCAAGCCGAAGA
TGTAGCCGTTTACTTCTGTCAACAATATAACTCATACCCACTAACGTTCG
GTGCCGGGACGAAGGTAGAGATTAAA Anti-huPSMA scFv (SEQ ID NO: 34)
EVQLVQSGAE VKKPGASVKV SCKTSGYTFT EYTIHWVRQA
PGQSLEWMGN INPNNGGTTY NQKFQGRVTI TVDKSTSTAY
MELSSLRSED TAVYYCAAGW NFDYWGQGTL VTVSSGKPGS
GKPGSGKPGS GKPGSDIVMT QSPDSLAVSL GERATLSCRA
SQDVGTAVDW YQQKPDQSPK LLIYWASTRH TGVPDRFTGS
GSGTDFTLTI SSLQAEDVAV YFCQQYNSYP LTFGAGTKVE
IK Anti-Sarcoglycan scFv (SEQ ID NO: 35)
GAAGTCCAATTGGTTGAAAGCGGTGGTGGACTCGTCAAACCTGGCGGTAG
CCTTAAACTTTCATGTGCCGCAAGCGGCTTCACGTTTAGTAACTATGCTA
TGAGTTGGGTCCGCCAAAGTCCAGAAAAGCGCCTCGAATGGGTGGCGGAG
ATCTCTGGAGGAGGAACATATACATATTATCCAGACACCATGACCGGTAG
GTTTACAATCTCAAGAGACAACGCTAAGAACACCCTGTACCTGGAAATGT
CAAGCCTGAGATCAGAAGATACGGCCATGTATTATTGTACGCGCCTACTC
GACTATTGGGGTCAAGGAACTTCCGTGACGGTGTCAAGCGGAGGAGGTGG
GAGCGGAGGAGGCGGAAGTGGCGGTGGTGGCTCTGGTGGCGGTGGAAGTG
ATATAGTGATGACGCAAGCTGCCTTTTCAAACCCTGTTACTTTGGGGACT
AGCGCATCAATCTCCTGTAGGTCCAGCAAATCTTTGCTGCACAGTAATGG
AATCACCTATCTTTTCTGGTATTTGCAAAAGCCTGGGCAGAGCCCGCAAC
TGCTGATCTATCAAATGTCAAATCTTGCTTCCGGAGTTCCAGACCGCTTC
TCAAGTTCCGGGTCCGGCACTGATTTTACCTTGAGAATTTCTAGGGTCGA
AGCTGAAGACGTCGGTGTCTATTATTGCGCGCAAAACCTTGAGCTTCCAT
ACACCTTCGGGGGGGGCACAAAACTTGAGATCAAG Anti-Sarcoglycan scFv (SEQ ID NO: 36)
EVQLVESGGGLVKPGGSLKLSCAASGFTFSNYAMSWVRQSPEKRLEWVAE
ISGGGTYTYYPDTMTGRFTISRDNAKNTLYLEMSSLRSEDTAMYYCTRLL
DYWGQGTSVTVSSGGGGSGGGGSGGGGSGGGGSDIVMTQAAFSNPVTLGT
SASISCRSSKSLLHSNGITYLFWYLQKPGQSPQLLIYQMSNLASGVPDRF
SSSGSGTDFTLRISRVEAEDVGVYYCAQNLELPYTFGGGTKLEIK Anti-Hu GPC3 scFv (SEQ ID NO: 37)
CAGTCTGTGTTGACGCAGCCGCCCTCAGTGTCTGCGGCCCCAGGACAGAG
GGTCACCATCTCCTGCTCTGGAACCAGGTCCAACATTGGGAGTGATTATG
TTTCCTGGTACCAACACCTCCCAGGAACAGCCCCCAAACTCCTCGTTTAT
GGCGATAATCTGCGACCCTCAGGGATTCCTGACCGATTCTCTGCCTCCAA
GTCTGGCACGTCAGCCACCCTGGGCATCACCGGACTCCAGACTGGGGACG
AGGCCGATTATTACTGCGGCACATGGGATTACACCCTGAATGGTGTGGTG
TTCGGCGGAGGGACCAAGCTGACCGTCCTAGGTTCTAGAGGTGGTGGTGG
TAGCGGCGGCGGCGGCTCTGGTGGTGGTGGATCCCTCGAGATGGCCCAGG
TGCAGCTGGTGGAGTCTGGGGGAGGCTTGGTACAGCCTGGGGGGTCCCTG
AGACTCTCCTGTGCAGCCTCTGGATTCACCTTTAGCAGCTATGCCATGAG
CTGGGTCCGCCAGGCTCCAGGGAAGGGGCTGGAGTGGGTCTCAGTTATTT
ATAGCGGTGGTAGTAGCACATACTATGCAGACTCCGTGAAGGGCCGGTTC
ACCATCTCCAGAGATAATTCCAAGAACACGCTGTATCTGCAAATGAACAG
CCTGAGAGCCGAGGACACGGCCGTATATTACTGTGCGCGCACTTCTTACC
TGAACCATGGTGATTACTGGGGTCAAGGTACTCTGGTGACCGTGTCTAGC
GCCGCTGCA Anti-Hu GPC3 scFv (SEQ ID NO: 38)
QSVLTQPPSVSAAPGQRVTISCSGTRSNIGSDYVSWYQHLPGTAPKLLVY
GDNLRPSGIPDRFSASKSGTSATLGITGLQTGDEADYYCGTWDYTLNGVV

FGGGTKLTVLGSRGGGGSGGGGSGGGGSLEMAQVQLVESGGGLVQPGGSL

RLSCAASGFTFSSYAMSWVRQAPGKGLEWVSVIYSGGSSTYYADSVKGRF

TISRDNSKNTLYLQMNSLRAEDTAVYYCARTSYLNHGDYWGQGTLVTVSS

AAA pWF-82

(SEQ ID NO: 39)
GAGGTTCAACTTGTTCAATCTGGGGCAGAAGTGAAGAAGCCCGGGGCATC

TGTGAAAGTATCATGCAAAACATCCGGCTATACGTTTACCGAATACACCA

TTCACTGGGTCAGACAGGCTCCCGGTCAAAGCCTCGAATGGATGGGAAAT

ATTAACCCTAACAATGGCGGAACCACATATAATCAGAAATTCCAAGGCCG

AGTGACGATAACTGTCGATAAGAGTACGTCCACAGCTTACATGGAACTCA

GCTCTTTGAGATCCGAAGACACTGCAGTTTATTATTGTGCAGCTGGATGG

AACTTCGACTATTGGGGACAAGGGACTCTTGTTACGGTGTCCAGTGGCAA

ACCAGGTAGTGGTAAACCCGGAAGCGGCAAGCCCGGGAGCGGTAAACCTG

GTAGCGACATCGTCATGACTCAAAGCCCTGACTCACTCGCCGTGAGCCTG

GGAGAGCGTGCAACGCTATCTTGTCGGGCCTCTCAGGATGTCGGAACTGC

TGTAGACTGGTATCAACAGAAACCTGACCAATCACCAAAACTCCTGATTT

ATTGGGCCTCAACACGTCACACAGGAGTGCCAGATAGGTTCACAGGTAGT

GGCAGTGGAACTGATTTTACTTTGACAATTAGCAGCCTGCAAGCCGAAGA

TGTAGCCGTTTACTTCTGTCAACAATATAACTCATACCCACTAACGTTCG

GTGCCGGGACGAAGGTAGAGATTAAATTCGTGCCTGTGTTCCTCCCAGCT

AAGCCCACTACCACCCCGCTCCAAGGCCGCCCACGCCCGCTCCTACTAT

TGCTAGTCAGCCTTTAAGTTTACGACCCGAAGCTTGCAGGCCCGCCGCCG

GCGGCGCTGTGCACACCAGGGGGCTTGATTTTGCCTGCGACTTTTGGGTA

TTGGTAGTGGTGGGCGGAGTTTTAGCCTGCTACAGCCTCCTGGTAACAGT

GGCTTTTATCATCTTTTGGGTGCAGCGGGCTTTAGTCTTGCGGCGTAAAC

GTAAAAGAATGACAGATCCAACTCGCAGGTTCTTCAAAGTGACCCCCCCA

CCTGGGTCCGGACCGCAGAACCAATATGGGAATGTCCTGTCTCTGCCTAC

GCCTACAAGTGGACTGGGTAGGGCTCAGAGGTGGGCTGCCGGTCTCGGCG

GAACTGCGCCATCTTACGGAAATCCCTCCTCCGACGTTCAGGCAGACGGG

GCCCTGGGGTCTCGATCCCCGCCTGGTGTTGGACCAGAAGAGGAAGAGGG

CGAGGGCTACGAAGAGCCCGACTCCGAAGAGGACAGTGAGTTTTACGAGA

ACGACAGCAACCTGGGGCAGGATCAGCTGTCACAGGATGGCTCAGGATAT

GAAAACCCTGAGGACGAGCCTTTGGGGCCTGAAGATGAGGACTCCTTTTC

TAATGCAGAGTCATATGAGAATGAGGACGAAGAATTGACTCAACCCGTGG

CAAGAACAATGGATTTCCTCAGTCCACACGGGAGTGCATGGGACCCCTCC

AGAGAGGCTACTAGCCTCGGTTCTCAAAGCTATGAGGACATGAGGGGTAT

TCTGTACGCAGCGCCTCAGTTGAGGTCCATCCGCGGCCAGCCAGGCCCAA

ACCATGAGGAAGATGCCGATTCTTACGAAAACATGGACAACCCCGATGGT

CCTGACCCCGCATGGGGGGGGGGGAGGATGGGCACCTGGTCTACTCGCT

AG pWF-82

(SEQ ID NO: 40)
EVQLVQSGAE VKKPGASVKV SCKTSGYTFT EYTIHWVRQA

PGQSLEWMGN INPNNGGTTY NQKFQGRVTI TVDKSTSTAY

MELSSLRSED TAVYYCAAGW NFDYWGQGTL VTVSSGKPGS

GKPGSGKPGS GKPGSDIVMT QSPDSLAVSL GERATLSCRA

SQDVGTAVDW YQQKPDQSPK LLIYWASTRH TGVPDRFTGS

GSGTDFTLTI SSLQAEDVAV YFCQQYNSYP LTFGAGTKVE

IKFVPVFLPA KPTTTPAPRP PTPAPTIASQ PLSLRPEACR

PAAGGAVHTR GLDFACDFWV LVVVGGVLAC YSLLVTVAFI

IFWVQRALVL RRKRKRMTDP TRRFFKVTPP PGSGPQNQYG

NVLSLPTPTS GLGRAQRWAA GLGGTAPSYG NPSSDVQADG

ALGSRSPPGV GPEEEEGEGY EEPDSEEDSE FYENDSNLGQ

DQLSQDGSGY ENPEDEPLGP EDEDSFSNAE SYENEDEELT

QPVARTMDFL SPHGSAWDPS REATSLGSQS YEDMRGILYA

APQLRSIRGQ PGPNHEEDAD SYENMDNPDG PDPAWGGGGR

MGTWSTRpWF-83

(SEQ ID NO: 41)
GAGGTTCAACTTGTTCAATCTGGGGCAGAAGTGAAGAAGCCCGGGGCATC

TGTGAAAGTATCATGCAAAACATCCGGCTATACGTTTACCGAATACACCA

TTCACTGGGTCAGACAGGCTCCCGGTCAAAGCCTCGAATGGATGGGAAAT

ATTAACCCTAACAATGGCGGAACCACATATAATCAGAAATTCCAAGGCCG

AGTGACGATAACTGTCGATAAGAGTACGTCCACAGCTTACATGGAACTCA

GCTCTTTGAGATCCGAAGACACTGCAGTTTATTATTGTGCAGCTGGATGG

AACTTCGACTATTGGGGACAAGGGACTCTTGTTACGGTGTCCAGTGGCAA

ACCAGGTAGTGGTAAACCCGGAAGCGGCAAGCCCGGGAGCGGTAAACCTG

GTAGCGACATCGTCATGACTCAAAGCCCTGACTCACTCGCCGTGAGCCTG

GGAGAGCGTGCAACGCTATCTTGTCGGGCCTCTCAGGATGTCGGAACTGC

TGTAGACTGGTATCAACAGAAACCTGACCAATCACCAAAACTCCTGATTT

ATTGGGCCTCAACACGTCACACAGGAGTGCCAGATAGGTTCACAGGTAGT

GGCAGTGGAACTGATTTTACTTTGACAATTAGCAGCCTGCAAGCCGAAGA

TGTAGCCGTTTACTTCTGTCAACAATATAACTCATACCCACTAACGTTCG

GTGCCGGGACGAAGGTAGAGATTAAATTCGTGCCTGTGTTCCTCCCAGCT

AAGCCCACTACCACCCCGCTCCAAGGCCGCCCACGCCCGCTCCTACTAT

TGCTAGTCAGCCTTTAAGTTTACGACCCGAAGCTTGCAGGCCCGCCGCCG

GCGGCGCTGTGCACACCAGGGGGCTTGATTTTGCCTGCGACTTTTGGGTA

```
TTGGTAGTGGTGGGCGGAGTTTTAGCCTGCTACAGCCTCCTGGTAACAGT
GGCTTTTATCATCTTTTGGGTGCTGGACAAGGATGACAGCAAGGCTGGCA
TGGAGGAAGATCACACCTACGAGGGCCTGGACATTGACCAGACAGCCACC
TATGAGGACATAGTGACGCTGCGGACAGGGGAAGTGAAGTGGTCTGTAGG
TGAGCACCCAGGCCAGGAGTGA
``` pWF-83

(SEQ ID NO: 42)
```
EVQLVQSGAE VKKPGASVKV SCKTSGYTFT EYTIHWVRQA
PGQSLEWMGN INPNNGGTTY NQKFQGRVTI TVDKSTSTAY
MELSSLRSED TAVYYCAAGW NFDYWGQGTL VTVSSGKPGS
GKPGSGKPGS GKPGSDIVMT QSPDSLAVSL GERATLSCRA
SQDVGTAVDW YQQKPDQSPK LLIYWASTRH TGVPDRFTGS
GSGTDFTLTI SSLQAEDVAV YFCQQYNSYP LTFGAGTKVE
IKFVPVFLPA KPTTTPAPRP PTPAPTIASQ PLSLRPEACR
PAAGGAVHTR GLDFACDFWV LVVVGGVLAC YSLLVTVAFI
IFWVLDKDDS KAGMEEDHTY EGLDIDQTAT YEDIVTLRTG
EVKWSVGEHP GQE-
``` pWF-84:

(SEQ ID NO: 43)
```
GAGGTTCAACTTGTTCAATCTGGGGCAGAAGTGAAGAAGCCCGGGGCATC
TGTGAAAGTATCATGCAAAACATCCGGCTATACGTTTACCGAATACACCA
TTCACTGGGTCAGACAGGCTCCCGGTCAAAGCCTCGAATGGATGGGAAAT
ATTAACCCTAACAATGGCGGAACCACATATAATCAGAAATTCCAAGGCCG
AGTGACGATAACTGTCGATAAGAGTACGTCCACAGCTTACATGGAACTCA
GCTCTTTGAGATCCGAAGACACTGCAGTTTATTATTGTGCAGCTGGATGG
AACTTCGACTATTGGGACAAGGGACTCTTGTTACGGTGTCCAGTGGCAA
ACCAGGTAGTGGTAAACCCGGAAGCGGCAAGCCCGGGAGCGGTAAACCTG
GTAGCGACATCGTCATGACTCAAAGCCCTGACTCACTCGCCGTGAGCCTG
GGAGAGCGTGCAACGCTATCTTGTCGGGCCTCTCAGGATGTCGGAACTGC
TGTAGACTGGTATCAACAGAAACCTGACCAATCACCAAAACTCCTGATTT
ATTGGGCCTCAACACGTCACACAGGAGTGCCAGATAGGTTCACAGGTAGT
GGCAGTGGAACTGATTTTACTTTGACAATTAGCAGCCTGCAAGCCGAAGA
TGTAGCCGTTTACTTCTGTCAACAATATAACTCATACCCACTAACGTTCG
GTGCCGGGACGAAGGTAGAGATTAAATTCGTGCCTGTGTTCCTCCCAGCT
AAGCCCACTACCACCCCGCTCCAAGGCCGCCCACGCCCGCTCCTACTAT
TGCTAGTCAGCCTTTAAGTTTACGACCCGAAGCTTGCAGGCCCGCCGCCG
GCGGCGCTGTGCACACCAGGGGGCTTGATTTTGCCTGCGACTTTTGGGTA
TTGGTAGTGGTGGGCGGAGTTTTAGCCTGCTACAGCCTCCTGGTAACAGT
GGCTTTTATCATCTTTTGGGTGAAGAAGGTTGCAAAAAAACCTACTAATA
AGGCTCCCCATCCTAAGCAAGAGCCCCAAGAAATTAACTTTCCCGATGAT
```

```
CTTCCGGGTTCTAACACGGCAGCCCCGGTGCAGGAGACCCTGCATGGTTG
TCAACCCGTCACTCAGGAGGACGGGAAAGAGTCTCGTATCTCCGTCCAGG
AGAGACAGGACAAGGACGATAGTAAAGCAGGGATGGAGGAGGACCATACA
TACGAGGGACTGGATATCGATCAGACAGCCACGTACGAAGACATTGTGAC
ACTGAGAACTGGCGAGGTGAAGTGGTCAGTGGGAGAACATCCGGGGCAGG
AATAA
``` pWF-84:

(SEQ ID NO: 44)
```
EVQLVQSGAE VKKPGASVKV SCKTSGYTFT EYTIHWVRQA
PGQSLEWMGN INPNNGGTTY NQKFQGRVTI TVDKSTSTAY
MELSSLRSED TAVYYCAAGW NFDYWGQGTL VTVSSGKPGS
GKPGSGKPGS GKPGSDIVMT QSPDSLAVSL GERATLSCRA
SQDVGTAVDW YQQKPDQSPK LLIYWASTRH TGVPDRFTGS
GSGTDFTLTI SSLQAEDVAV YFCQQYNSYP LTFGAGTKVE
IKFVPVFLPA KPTTTPAPRP PTPAPTIASQ PLSLRPEACR
PAAGGAVHTR GLDFACDFWV LVVVGGVLAC YSLLVTVAFI
IFWVKKVAKK PTNKAPHPKQ EPQEINFPDD LPGSNTAAPV
QETLHGCQPV TQEDGKESRI SVQERQDKDD SKAGMEEDHT
YEGLDIDQTA TYEDIVTLRT GEVKWSVGEH PGQE-
``` pWF-85:

(SEQ ID NO: 45)
```
GAGGTTCAACTTGTTCAATCTGGGGCAGAAGTGAAGAAGCCCGGGGCATC
TGTGAAAGTATCATGCAAAACATCCGGCTATACGTTTACCGAATACACCA
TTCACTGGGTCAGACAGGCTCCCGGTCAAAGCCTCGAATGGATGGGAAAT
ATTAACCCTAACAATGGCGGAACCACATATAATCAGAAATTCCAAGGCCG
AGTGACGATAACTGTCGATAAGAGTACGTCCACAGCTTACATGGAACTCA
GCTCTTTGAGATCCGAAGACACTGCAGTTTATTATTGTGCAGCTGGATGG
AACTTCGACTATTGGGACAAGGGACTCTTGTTACGGTGTCCAGTGGCAA
ACCAGGTAGTGGTAAACCCGGAAGCGGCAAGCCCGGGAGCGGTAAACCTG
GTAGCGACATCGTCATGACTCAAAGCCCTGACTCACTCGCCGTGAGCCTG
GGAGAGCGTGCAACGCTATCTTGTCGGGCCTCTCAGGATGTCGGAACTGC
TGTAGACTGGTATCAACAGAAACCTGACCAATCACCAAAACTCCTGATTT
ATTGGGCCTCAACACGTCACACAGGAGTGCCAGATAGGTTCACAGGTAGT
GGCAGTGGAACTGATTTTACTTTGACAATTAGCAGCCTGCAAGCCGAAGA
TGTAGCCGTTTACTTCTGTCAACAATATAACTCATACCCACTAACGTTCG
GTGCCGGGACGAAGGTAGAGATTAAATTCGTGCCTGTGTTCCTCCCAGCT
AAGCCCACTACCACCCCGCTCCAAGGCCGCCCACGCCCGCTCCTACTAT
TGCTAGTCAGCCTTTAAGTTTACGACCCGAAGCTTGCAGGCCCGCCGCCG
GCGGCGCTGTGCACACCAGGGGGCTTGATTTTGCCTGCGACTTTTGGGTA
TTGGTAGTGGTGGGCGGAGTTTTAGCCTGCTACAGCCTCCTGGTAACAGT
```

```
GGCTTTTATCATCTTTTGGGTGAAGAAGGTTGCAAAAAAACCTACTAATA
AGGCTCCCCATCCTAAGCAAGAGCCCCAAGAAATTAACTTTCCCGATGAT
CTTCCGGGTTCTAACACGGCAGCCCCGGTGCAGGAGACCCTGCATGGTTG
TCAACCCGTCACTCAGGAGGACGGGAAGAGTCTCGTATCTCCGTCCAGG
AGAGACAGAAAAGAGGCCGAAAAAAGCTGCTGTACATCTTCAAACAACCC
TTCATGCGACCTGTTCAGACGACACAGGAGGAGGACGGCTGCAGCTGTAG
GTTTCCCGAAGAAGAGGAGGGAGGATGCGAACTTTAA
``` pWF-85:

```
                                    (SEQ ID NO: 46)
    EVQLVQSGAE VKKPGASVKV SCKTSGYTFT EYTIHWVRQA
    PGQSLEWMGN INPNNGGTTY NQKFQGRVTI TVDKSTSTAY
    MELSSLRSED TAVYYCAAGW NFDYWGQGTL VTVSSGKPGS
    GKPGSGKPGS GKPGSDIVMT QSPDSLAVSL GERATLSCRA
    SQDVGTAVDW YQQKPDQSPK LLIYWASTRH TGVPDRFTGS
    GSGTDFTLTI SSLQAEDVAV YFCQQYNSYP LTFGAGTKVE
    IKFVPVFLPA KPTTTPAPRP PTPAPTIASQ PLSLRPEACR
    PAAGGAVHTR GLDFACDFWV LVVVGGVLAC YSLLVTVAFI
    IFWVKKVAKK PTNKAPHPKQ EPQEINFPDD LPGSNTAAPV
    QETLHGCQPV TQEDGKESRI SVQERQKRGR KKLLYIFKQP
    FMRPVQTTQE EDGCSCRFPE EEEGGCEL-
``` pWF-86

```
                                    (SEQ ID NO: 150)
GAGGTTCAACTTGTTCAATCTGGGGCAGAAGTGAAGAAGCCCGGGGCATC
TGTGAAAGTATCATGCAAAACATCCGGCTATACGTTTACCGAATACACCA
TTCACTGGGTCAGACAGGCTCCCGGTCAAAGCCTCGAATGGATGGGAAAT
ATTAACCCTAACAATGGCGGAACCACATATAATCAGAAATTCCAAGGCCG
AGTGACGATAACTGTCGATAAGAGTACGTCCACAGCTTACATGGAACTCA
GCTCTTTGAGATCCGAAGACACTGCAGTTTATTATTGTGCAGCTGGATGG
AACTTCGACTATTGGGGACAAGGGACTCTTGTTACGGTGTCCAGTGGCAA
ACCAGGTAGTGGTAAACCCGGAAGCGGCAAGCCCGGGAGCGGTAAACCTG
GTAGCGACATCGTCATGACTCAAAGCCCTGACTCACTCGCCGTGAGCCTG
GGAGAGCGTGCAACGCTATCTTGTCGGGCCTCTCAGGATGTCGGAACTGC
TGTAGACTGGTATCAACAGAAACCTGACCAATCACCAAAACTCCTGATTT
ATTGGGCCTCAACACGTCACACAGGAGTGCCAGATAGGTTCACAGGTAGT
GGCAGTGGAACTGATTTTACTTTGACAATTAGCAGCCTGCAAGCCGAAGA
TGTAGCCGTTTACTTCTGTCAACAATATAACTCATACCCACTAACGTTCG
GTGCCGGGACGAAGGTAGAGATTAAATTCGTGCCTGTGTTCCTCCCAGCT
AAGCCCACTACCACCCCCGCTCCAAGGCCGCCCACGCCCGCTCCTACTAT
TGCTAGTCAGCCTTTAAGTTTACGACCCGAAGCTTGCAGGCCCGCCGCCG
GCGGCGCTGTGCACACCAGGGGGCTTGATTTTGCCTGCGACTTTTGGGTA
```

```
TTGGTAGTGGTGGGCGGAGTTTTAGCCTGCTACAGCCTCCTGGTAACAGT
GGCTTTTATCATCTTTTGGGTGAAGAAGGTTGCAAAAAAACCTACTAATA
AGGCTCCCCATCCTAAGCAAGAGCCCCAAGAAATTAACTTTCCCGATGAT
CTTCCGGGTTCTAACACGGCAGCCCCGGTGCAGGAGACCCTGCATGGTTG
TCAACCCGTCACTCAGGAGGACGGGAAGAGTCTCGTATCTCCGTCCAGG
AGAGACAGCGCAAAAAACGTATAAGCGCAAACTCTACAGATCCAGTAAAA
GCCGCGCAATTCGAGCCTCCCGGCCGCCAGATGATTGCAATACGGAAACG
TCAACTGGAGGAAACTAATAATGACTATGAGACGGCCGACGGTGGATACA
TGACCCTTAATCCCCGCGCGCCAACCGACGATGATAAGAACATATATCTG
ACGCTCCCCCCTAACGATCACGTTAACAGTAATAATTAA
``` pWF-86:

```
                                    (SEQ ID NO: 47)
    EVQLVQSGAE VKKPGASVKV SCKTSGYTFT EYTIHWVRQA
    PGQSLEWMGN INPNNGGTTY NQKFQGRVTI TVDKSTSTAY
    MELSSLRSED TAVYYCAAGW NFDYWGQGTL VTVSSGKPGS
    GKPGSGKPGS GKPGSDIVMT QSPDSLAVSL GERATLSCRA
    SQDVGTAVDW YQQKPDQSPK LLIYWASTRH TGVPDRFTGS
    GSGTDFTLTI SSLQAEDVAV YFCQQYNSYP LTFGAGTKVE
    IKFVPVFLPA KPTTTPAPRP PTPAPTIASQ PLSLRPEACR
    PAAGGAVHTR GLDFACDFWV LVVVGGVLAC YSLLVTVAFI
    IFWVKKVAKK PTNKAPHPKQ EPQEINFPDD LPGSNTAAPV
    QETLHGCQPV TQEDGKESRI SVQERQRKKR ISANSTDPVK
    AAQFEPPGRQ MIAIRKRQLE ETNNDYETAD GGYMTLNPRA
    PTDDDKNIYL TLPPNDHVNS NN-
``` pWF-87:

```
                                    (SEQ ID NO: 48)
GAGGTTCAACTTGTTCAATCTGGGGCAGAAGTGAAGAAGCCCGGGGCAT
CTGTGAAAGTATCATGCAAAACATCCGGCTATACGTTTACCGAATACAC
CATTCACTGGGTCAGACAGGCTCCCGGTCAAAGCCTCGAATGGATGGGA
AATATTAACCCTAACAATGGCGGAACCACATATAATCAGAAATTCCAAG
GCCGAGTGACGATAACTGTCGATAAGAGTACGTCCACAGCTTACATGGA
ACTCAGCTCTTTGAGATCCGAAGACACTGCAGTTTATTATTGTGCAGCT
GGATGGAACTTCGACTATTGGGGACAAGGGACTCTTGTTACGGTGTCCA
GTGGCAAACCAGGTAGTGGTAAACCCGGAAGCGGCAAGCCCGGGAGCGG
TAAACCTGGTAGCGACATCGTCATGACTCAAAGCCCTGACTCACTCGCC
GTGAGCCTGGGAGAGCGTGCAACGCTATCTTGTCGGGCCTCTCAGGATG
TCGGAACTGCTGTAGACTGGTATCAACAGAAACCTGACCAATCACCAAA
ACTCCTGATTTATTGGGCCTCAACACGTCACACAGGAGTGCCAGATAGG
TTCACAGGTAGTGGCAGTGGAACTGATTTTACTTTGACAATTAGCAGCC
TGCAAGCCGAAGATGTAGCCGTTTACTTCTGTCAACAATATAACTCATA
```

CCCACTAACGTTCGGTGCCGGGACGAAGGTAGAGATTAAATTCGTGCCT
GTGTTCCTCCCAGCTAAGCCCACTACCACCCCCGCTCCAAGGCCGCCCA
CGCCCGCTCCTACTATTGCTAGTCAGCCTTTAAGTTTACGACCCGAAGC
TTGCAGGCCCGCCGCCGGCGGCGCTGTGCACACCAGGGGGCTTGATTTT
GCCTGCGACTTTTGGGTATTGGTAGTGGTGGGCGGAGTTTTAGCCTGCT
ACAGCCTCCTGGTAACAGTGGCTTTTATCATCTTTTGGGTGATGGCGGC
GGGCGGGCCCGGCGCCGGAAGCGCCGCGCCAGTCTCATCTACGTCCAGT
CTGCCACTGGCTGCCCTGAACATGAGAGTGAGACGCCGTTTATCCCTCT
TCCTGAATGTGCGGACCCAGGTCGCCGCTGATTGGACCGCCCTGGCCGA
AGAGATGGACTTTGAATACTTGGAAATCAGACAGCTGGAAACACAGGCA
GACCCAACCGGGAGACTGCTTGACGCCTGGCAGGACGCCCAGGGGCAA
GTGTTGGTCGGTTACTGGAGCTTTTAACTAAGTTGGGCCGCGATGACGT
GCTGTTGGAGTTAGGACCCAGTATCGAGGAGGATTGTCAGAAATACATC
TTGAAACAGCAGCAGGAGGAGGCGGAAAAGCCCCTGCAGGTGGCGGCCG
TTGACAGCAGTGTACCCAGAACAGCTGAGCTGGCCGGCATCACAACCCT
GGATGATCCCCTGGGCCACATGCCTGAGAGGTTCGACGCTTTCATAAAG
AAGGTTGCAAAAAAACCTACTAATAAGGCTCCCCATCCTAAGCAAGAGC
CCCAAGAAATTAACTTTCCCGATGATCTTCCGGGTTCTAACACGGCAGC
CCCGGTGCAGGAGACCCTGCATGGTTGTCAACCCGTCACTCAGGAGGAC
GGGAAAGAGTCTCGTATCTCCGTCCAGGAGAGACAGTGA
``` pWF-87:

```
                                       (SEQ ID NO: 49)
EVQLVQSGAEVKKPGASVKVSCKTSGYTFTEYTIHWVRQAPGQSLEWMG
NINPNNGGTTYNQKFQGRVTITVDKSTSTAYMELSSLRSEDTAVYYCAA
GWNFDYWGQGTLVTVSSGKPGSGKPGSGKPGSGKPGSDIVMTQSPDSLA
VSLGERATLSCRASQDVGTAVDWYQQKPDQSPKLLIYWASTRHTGVPDR
FTGSGSGTDFTLTISSLQAEDVAVYFCQQYNSYPLTFGAGTKVEIKFVP
VFLPAKPTTTPAPRPPTPAPTIASQPLSLRPEACRPAAGGAVHTRGLDF
ACDFWVLVVVGGVLACYSLLVTVAFIIFWVMAAGGPGAGSAAPVSSTSS
LPLAALNMRVRRRLSLFLNVRTQVAADWTALAEEMDFEYLEIRQLETQA
DPTGRLLDAWQGRPGASVGRLLELLTKLGRDDVLLELGPSIEEDCQKYI
LKQQQEEAEKPLQVAAVDSSVPRTAELAGITTLDDPLGHMPERFDAFIK
KVAKKPTNKAPHPKQEPQEINFPDDLPGSNTAAPVQETLHGCQPVTQED
GKESRISVQERQ-
``` pWF-88:

```
                                       (SEQ ID NO: 50)
GAGGTTCAACTTGTTCAATCTGGGGCAGAAGTGAAGAAGCCCGGGGCAT
CTGTGAAAGTATCATGCAAAACATCCGGCTATACGTTTACCGAATACAC
CATTCACTGGGTCAGACAGGCTCCCGGTCAAAGCCTCGAATGGATGGGA
AATATTAACCCTAACAATGGCGGAACCACATATAATCAGAAATTCCAAG
GCCGAGTGACGATAACTGTCGATAAGAGTACGTCCACAGCTTACATGGA
ACTCAGCTCTTTGAGATCCGAAGACACTGCAGTTTATTATTGTGCAGCT
GGATGGAACTTCGACTATTGGGGACAAGGGACTCTTGTTACGGTGTCCA
GTGGCAAACCAGGTAGTGGTAAACCCGGAAGCGGCAAGCCCGGGAGCGG
TAAACCTGGTAGCGACATCGTCATGACTCAAAGCCCTGACTCACTCGCC
GTGAGCCTGGGAGAGCGTGCAACGCTATCTTGTCGGCCTCTCAGGATG
TCGGAACTGCTGTAGACTGGTATCAACAGAAACCTGACCAATCACCAAA
ACTCCTGATTTATTGGGCCTCAACACGTCACACAGGAGTGCCAGATAGG
TTCACAGGTAGTGGCAGTGGAACTGATTTTACTTTGACAATTAGCAGCC
TGCAAGCCGAAGATGTAGCCGTTTACTTCTGTCAACAATATAACTCATA
CCCACTAACGTTCGGTGCCGGGACGAAGGTAGAGATTAAATTCGTGCCT
GTGTTCCTCCCAGCTAAGCCCACTACCACCCCCGCTCCAAGGCCGCCCA
CGCCCGCTCCTACTATTGCTAGTCAGCCTTTAAGTTTACGACCCGAAGC
TTGCAGGCCCGCCGCCGGCGGCGCTGTGCACACCAGGGGGCTTGATTTT
GCCTGCGACTTTTGGGTATTGGTAGTGGTGGGCGGAGTTTTAGCCTGCT
ACAGCCTCCTGGTAACAGTGGCTTTTATCATCTTTTGGGTGAGGAAACG
ATGGCAGAACGAGAAGCTCGGGTTGGATGCCGGGGATGAATATGAAGAT
GAAAACCTTTATGAAGGCCTGAACCTGGACGACTGCTCCATGTATGAGG
ACATCTCCCGGGGCCTCCAGGGCACCTACCAGGATGTGGGCAGCCTCAA
CATAGGAGATGTCCAGCTGGAGAAGCCGTGA
``` pWF-88:

```
                                       (SEQ ID NO: 51)
EVQLVQSGAEVKKPGASVKVSCKTSGYTFTEYTIHWVRQAPGQSLEWMG
NINPNNGGTTYNQKFQGRVTITVDKSTSTAYMELSSLRSEDTAVYYCAA
GWNFDYWGQGTLVTVSSGKPGSGKPGSGKPGSGKPGSDIVMTQSPDSLA
VSLGERATLSCRASQDVGTAVDWYQQKPDQSPKLLIYWASTRHTGVPDR
FTGSGSGTDFTLTISSLQAEDVAVYFCQQYNSYPLTFGAGTKVEIKFVP
VFLPAKPTTTPAPRPPTPAPTIASQPLSLRPEACRPAAGGAVHTRGLDF
ACDFWVLVVVGGVLACYSLLVTVAFIIFWVRKRWQNEKLGLDAGDEYED
ENLYEGLNLDDCSMYEDISRGLQGTYQDVGSLNIGDVQLEKP-
``` pWF-89:

```
                                       (SEQ ID NO: 52)
GAGGTTCAACTTGTTCAATCTGGGGCAGAAGTGAAGAAGCCCGGGGCAT
CTGTGAAAGTATCATGCAAAACATCCGGCTATACGTTTACCGAATACAC
CATTCACTGGGTCAGACAGGCTCCCGGTCAAAGCCTCGAATGGATGGGA
AATATTAACCCTAACAATGGCGGAACCACATATAATCAGAAATTCCAAG
GCCGAGTGACGATAACTGTCGATAAGAGTACGTCCACAGCTTACATGGA
ACTCAGCTCTTTGAGATCCGAAGACACTGCAGTTTATTATTGTGCAGCT
GGATGGAACTTCGACTATTGGGGACAAGGGACTCTTGTTACGGTGTCCA
GTGGCAAACCAGGTAGTGGTAAACCCGGAAGCGGCAAGCCCGGGAGCGG
```

-continued

TAAACCTGGTAGCGACATCGTCATGACTCAAAGCCCTGACTCACTCGCC
GTGAGCCTGGGAGAGCGTGCAACGCTATCTTGTCGGGCCTCTCAGGATG
TCGGAACTGCTGTAGACTGGTATCAACAGAAACCTGACCAATCACCAAA
ACTCCTGATTTATTGGGCCTCAACACGTCACACAGGAGTGCCAGATAGG
TTCACAGGTAGTGGCAGTGGAACTGATTTTACTTTGACAATTAGCAGCC
TGCAAGCCGAAGATGTAGCCGTTTACTTCTGTCAACAATATAACTCATA
CCCACTAACGTTCGGTGCCGGGACGAAGGTAGAGATTAAATTCGTGCCT
GTGTTCCTCCCAGCTAAGCCCACTACCACCCCCGCTCCAAGGCCGCCCA
CGCCCGCTCCTACTATTGCTAGTCAGCCTTTAAGTTTACGACCCGAAGC
TTGCAGGCCCGCCGCCGGCGGCGCTGTGCACACCAGGGGGCTTGATTTT
GCCTGCGACTTTTGGGTATTGGTAGTGGTGGGCGGAGTTTTAGCCTGCT
ACAGCCTCCTGGTAACAGTGGCTTTTATCATCTTTTGGGTGCTGGACAA
GGATGACAGCAAGGCTGGCATGGAGGAAGATCACACCTACGAGGGCCTG
GACATTGACCAGACAGCCACCTATGAGGACATAGTGACGCTGCGGACAG
GGGAAGTGAAGTGGTCTGTAGGTGAGCACCCAGGCCAGGAGTGA pWF-89:

(SEQ ID NO: 53)
EVQLVQSGAEVKKPGASVKVSCKTSGYTFTEYTIHWVRQAPGQSLEWMG
NINPNNGGTTYNQKFQGRVTITVDKSTSTAYMELSSLRSEDTAVYYCAA
GWNFDYWGQGTLVTVSSGKPGSGKPGSGKPGSGKPGSDIVMTQSPDSLA
VSLGERATLSCRASQDVGTAVDWYQQKPDQSPKLLIYWASTRHTGVPDR
FTGSGSGTDFTLTISSLQAEDVAVYFCQQYNSYPLTFGAGTKVEIKFVP
VFLPAKPTTTPAPRPPTPAPTIASQPLSLRPEACRPAAGGAVHTRGLDF
ACDFWVLVVVGGVLACYSLLVTVAFIIFWVLDKDDSKAGMEEDHTYEGL
DIDQTATYEDIVTLRTGEVKWSVGEHPGQE pWF-391:

(SEQ ID NO: 54)
GAGGTTCAACTTGTTCAATCTGGGGCAGAAGTGAAGAAGCCCGGGGCAT
CTGTGAAAGTATCATGCAAAACATCCGGCTATACGTTTACCGAATACAC
CATTCACTGGGTCAGACAGGCTCCCGGTCAAAGCCTCGAATGGATGGGA
AATATTAACCCTAACAATGGCGGAACCACATATAATCAGAAATTCCAAG
GCCGAGTGACGATAACTGTCGATAAGAGTACGTCCACAGCTTACATGGA
ACTCAGCTCTTTGAGATCCGAAGACACTGCAGTTTATTATTGTGCAGCT
GGATGGAACTTCGACTATTGGGGACAAGGGACTCTTGTTACGGTGTCCA
GTGGCAAACCAGGTAGTGGTAAACCCGGAAGCGGCAAGCCCGGGAGCGG
TAAACCTGGTAGCGACATCGTCATGACTCAAAGCCCTGACTCACTCGCC
GTGAGCCTGGGAGAGCGTGCAACGCTATCTTGTCGGGCCTCTCAGGATG
TCGGAACTGCTGTAGACTGGTATCAACAGAAACCTGACCAATCACCAAA
ACTCCTGATTTATTGGGCCTCAACACGTCACACAGGAGTGCCAGATAGG
TTCACAGGTAGTGGCAGTGGAACTGATTTTACTTTGACAATTAGCAGCC
TGCAAGCCGAAGATGTAGCCGTTTACTTCTGTCAACAATATAACTCATA
CCCACTAACGTTCGGTGCCGGGACGAAGGTAGAGATTAAAGGCGCTGGT
AGTGGCGGTAACTGGAGCCACCCTCAATTTGAGAAGGGCGGGTCAGGCG
GATCAGGTGGTAGTGGTGGGTCCAACTGGAGCCATCCGCAATTTGAAAA
GGGCGGAAGCGGCGGTTCCGGCGGTTCAGGCGGTAGCAACTGGTCACAT
CCGCAATTTGAGAAAGGCGGGTCAGGCGGCGGGTTTTGGGCTCTCGTGG
TGGTGGCTGGAGTGCTTTTCTGCTATGGCCTGCTGGTAACCGTGGCCCT
TTGTGTAATCTGGACCGATAAAGACGATGGAAAAGCCGGGATGGAAGAA
GACCATACCTACGAGGGGCTCAATATTGATCAAACCGCCACGTATGAAG
ACATTGTAACACTGCGCACAGGTGAGGTCAAGTGGTCCGTCGGTGAACA
CCCAGGACAAGAATAA pWF-391:

(SEQ ID NO: 55)
EVQLVQSGAEVKKPGASVKVSCKTSGYTFTEYTIHWVRQAPGQSLEWMG
NINPNNGGTTYNQKFQGRVTITVDKSTSTAYMELSSLRSEDTAVYYCAA
GWNFDYWGQGTLVTVSSGKPGSGKPGSGKPGSGKPGSDIVMTQSPDSLA
VSLGERATLSCRASQDVGTAVDWYQQKPDQSPKLLIYWASTRHTGVPDR
FTGSGSGTDFTLTISSLQAEDVAVYFCQQYNSYPLTFGAGTKVEIKGAG
SGGNWSHPQFEKGGSGGSGGSGGSNWSHPQFEKGGSGGSGGSGGSNWSH
PQFEKGGSGGGFWALVVVAGVLFCYGLLVTVALCVIWTDKDDGKAGMEE
DHTYEGLNIDQTATYEDIVTLRTGEVKWSVGEHPGQE pWF-394:

(SEQ ID NO: 56)
GAAGTCCAATTGGTTGAAAGCGGTGGTGGACTCGTCAAACCTGGCGGTA
GCCTTAAACTTTCATGTGCCGCAAGCGGCTTCACGTTTAGTAACTATGC
TATGAGTTGGGTCCGCCAAAGTCCAGAAAAGCGCCTCGAATGGGTGGCG
GAGATCTCTGGAGGAGGAACATATACATATTATCCAGACACCATGACCG
GTAGGTTTACAATCTCAAGAGACAACGCTAAGAACACCCTGTACCTGGA
AATGTCAAGCCTGAGATCAGAAGATACGGCCATGTATTATTGTACGCGC
CTACTCGACTATTGGGGTCAAGGAACTTCCGTGACGGTGTCAAGCGGAG
GAGGTGGGAGCGGAGGAGGCGGAAGTGGCGGTGGTGGCTCTGGTGGCGG
TGGAAGTGATATAGTGATGACGCAAGCTGCCTTTTCAAACCCTGTTACT
TTGGGGACTAGCGCATCAATCTCCTGTAGGTCCAGCAAATCTTTGCTGC
ACAGTAATGGAATCACCTATCTTTTCTGGTATTTGCAAAAGCCTGGGCA
GAGCCCGCAACTGCTGATCTATCAAATGTCAAATCTTGCTTCCGGAGTT
CCAGACCGCTTCTCAAGTTCCGGGTCCGGCACTGATTTTACCTTGAGAA
TTTCTAGGGTCGAAGCTGAAGACGTCGGTGTCTATTATTGCGCGCAAAA
CCTTGAGCTTCCATACACCTTCGGGGGGGCACAAAACTTGAGATCAAG
GGCGCTGGGAGCGGCGGGAATTGGAGTCATCCACAATTCGAAAAGGGTG
GTCCGGCGGCAGTGGTGGAAGCGGCGGGAGTAACTGGTCACATCCCCA

-continued

GTTTGAGAAAGGCGGTAGTGGTGGCAGCGGCGGTAGTGGTGGCAGTAAT

TGGAGCCATCCCCAATTCGAAAAGGGCGGTTCCGGCGGCGGATTTTGGG

CTCTTGTTGTGGTGGCCGGAGTATTGTTTTGCTATGGCCTGCTCGTTAC

AGTGGCATTGTGCGTAATTTGGACTGATAAAGACGACGGCAAAGCCGGG

ATGGAAGAAGATCACACCTATGAGGGGCTTAATATAGATCAAACAGCCA

CATATGAAGATATTGTGACTCTAAGGACTGGAGAGGTTAAATGGAGTGT

GGGTGAGCATCCAGGACAAGAATAA pWF-394:

(SEQ ID NO: 57)
EVQLVESGGGLVKPGGSLKLSCAASGFTFSNYAMSWVRQSPEKRLEWVA

EISGGGTYTYYPDTMTGRFTISRDNAKNTLYLEMSSLRSEDTAMYYCTR

LLDYWGQGTSVTVSSGGGGSGGGGSGGGGSGGGGSDIVMTQAAFSNPVT

LGTSASISCRSSKSLLHSNGITYLFWYLQKPGQSPQLLIYQMSNLASGV

PDRESSSGSGTDFTLRISRVEAEDVGVYYCAQNLELPYTFGGGTKLEIK

GAGSGGNWSHPQFEKGSGGSGGSGGSNWSHPQFEKGGSGGSGGSGGSN

WSHPQFEKGSGGGFWALVVVAGVLFCYGLLVTVALCVIWTDKDDGKAG

MEEDHTYEGLNIDQTATYEDIVTLRTGEVKWSVGEHPGQE pWF-396:

(SEQ ID NO: 58)
CAGTCTGTGTTGACGCAGCCGCCCTCAGTGTCTGCGGCCCCAGGACAGA

GGGTCACCATCTCCTGCTCTGGAACCAGGTCCAACATTGGGAGTGATTA

TGTTTCCTGGTACCAACACCTCCCAGGAACAGCCCCCAAACTCCTCGTT

TATGGCGATAATCTGCGACCCTCAGGGATTCCTGACCGATTCTCTGCCT

CCAAGTCTGGCACGTCAGCCACCCTGGGCATCACCGGACTCCAGACTGG

GGACGAGGCCGATTATTACTGCGGCACATGGGATTACACCCTGAATGGT

GTGGTGTTCGGCGGAGGGACCAAGCTGACCGTCCTAGGTTCTAGAGGTG

GTGGTGGTAGCGGCGGCGGCGGCTCTGGTGGTGGTGGATCCCTCGAGAT

GGCCCAGGTGCAGCTGGTGGAGTCTGGGGGAGGCTTGGTACAGCCTGGG

GGGTCCCTGAGACTCTCCTGTGCAGCCTCTGGATTCACCTTTAGCAGCT

ATGCCATGAGCTGGGTCCGCCAGGCTCCAGGGAAGGGGCTGGAGTGGGT

CTCAGTTATTTATAGCGGTGGTAGTAGCACATACTATGCAGACTCCGTG

AAGGGCCGGTTCACCATCTCCAGAGATAATTCCAAGAACACGCTGTATC

TGCAAATGAACAGCCTGAGAGCCGAGGACACGGCCGTATATTACTGTGC

GCGCACTTCTTACCTGAACCATGGTGATTACTGGGGTCAAGGTACTCTG

GTGACCGTGTCTAGCGCCGCTGCATTCGTGCCTGTGTTCCTCCCAGCTA

AGCCCACTACCACCCCGCTCCAAGGCCGCCCACGCCCGCTCCTACTAT

TGCTAGTCAGCCTTTAAGTTTACGACCCGAAGCTTGCAGGCCCGCCGCC

GGCGGCGCTGTGCACACCAGGGGGCTTGATTTTGCCTGCGACTTTTGGG

TATTGGTAGTGGTGGGCGGAGTTTTAGCCTGCTACAGCCTCCTGGTAAC

AGTGGCTTTTATCATCTTTTGGGTGAGGAAACGATGGCAGAACGAGAAG

CTCGGGTTGGATGCCGGGGATGAATATGAAGATGAAAACCTTTATGAAG

GCCTGAACCTGGACGACTGCTCCATGTATGAGGACATCTCCCGGGGCCT

CCAGGGCACCTACCAGGATGTGGGCAGCCTCAACATAGGAGATGTCCAG

CTGGAGAAGCCGTGA pWF-396:

(SEQ ID NO: 59)
QSVLTQPPSVSAAPGQRVTISCSGTRSNIGSDYVSWYQHLPGTAPKLLV

YGDNLRPSGIPDRFSASKSGTSATLGITGLQTGDEADYYCGTWDYTLNG

VVFGGGTKLTVLGSRGGGGSGGGGSGGGGSLEMAQVQLVESGGGLVQPG

GSLRLSCAASGFTFSSYAMSWVRQAPGKGLEWVSVIYSGGSSTYYADSV

KGRFTISRDNSKNTLYLQMNSLRAEDTAVYYCARTSYLNHGDYWGQGTL

VTVSSAAAFVPVFLPAKPTTTPAPRPPTPAPTIASQPLSLRPEACRPAA

GGAVHTRGLDFACDFWVLVVVGGVLACYSLLVTVAFIIFWVRKRWQNEK

LGLDAGDEYEDENLYEGLNLDDCSMYEDISRGLQGTYQDVGSLNIGDVQ

LEKP pWF-397:

(SEQ ID NO: 60)
CAGTCTGTGTTGACGCAGCCGCCCTCAGTGTCTGCGGCCCCAGGACAGAG

GGTCACCATCTCCTGCTCTGGAACCAGGTCCAACATTGGGAGTGATTATG

TTTCCTGGTACCAACACCTCCCAGGAACAGCCCCCAAACTCCTCGTTTAT

GGCGATAATCTGCGACCCTCAGGGATTCCTGACCGATTCTCTGCCTCCAA

GTCTGGCACGTCAGCCACCCTGGGCATCACCGGACTCCAGACTGGGGACG

AGGCCGATTATTACTGCGGCACATGGGATTACACCCTGAATGGTGTGGTG

TTCGGCGGAGGGACCAAGCTGACCGTCCTAGGTTCTAGAGGTGGTGGTGG

TAGCGGCGGCGGCGGCTCTGGTGGTGGTGGATCCCTCGAGATGGCCCAGG

TGCAGCTGGTGGAGTCTGGGGGAGGCTTGGTACAGCCTGGGGGGTCCCTG

AGACTCTCCTGTGCAGCCTCTGGATTCACCTTTAGCAGCTATGCCATGAG

CTGGGTCCGCCAGGCTCCAGGGAAGGGGCTGGAGTGGGTCTCAGTTATTT

ATAGCGGTGGTAGTAGCACATACTATGCAGACTCCGTGAAGGGCCGGTTC

ACCATCTCCAGAGATAATTCCAAGAACACGCTGTATCTGCAAATGAACAG

CCTGAGAGCCGAGGACACGGCCGTATATTACTGTGCGCGCACTTCTTACC

TGAACCATGGTGATTACTGGGGTCAAGGTACTCTGGTGACCGTGTCTAGC

GCCGCTGCATTCGTGCCTGTGTTCCTCCCAGCTAAGCCCACTACCACCCC

CGCTCCAAGGCCGCCCACGCCCGCTCCTACTATTGCTAGTCAGCCTTTAA

GTTTACGACCCGAAGCTTGCAGGCCCGCCGCCGGCGGCGCTGTGCACACC

AGGGGGCTTGATTTTGCCTGCGACTTTTGGGTATTGGTAGTGGTGGGCGG

AGTTTTAGCCTGCTACAGCCTCCTGGTAACAGTGGCTTTTATCATCTTTT

GGGTGCTGGACAAGGATGACAGCAAGGCTGGCATGGAGGAAGATCACACC

-continued

TACGAGGGCCTGGACATTGACCAGACAGCCACCTATGAGGACATAGTGAC
GCTGCGGACAGGGGAAGTGAAGTGGTCTGTAGGTGAGCACCCAGGCCAGG
AGTGA pWF-397:

(SEQ ID NO: 61)
QSVLTQPPSVSAAPGQRVTISCSGTRSNIGSDYVSWYQHLPGTAPKLLVY
GDNLRPSGIPDRFSASKSGTSATLGITGLQTGDEADYYCGTWDYTLNGVV
FGGGTKLTVLGSRGGGGSGGGGSGGGGSLEMAQVQLVESGGGLVQPGGSL
RLSCAASGFTFSSYAMSWVRQAPGKGLEWVSVIYSGGSSTYYADSVKGRF
TISRDNSKNTLYLQMNSLRAEDTAVYYCARTSYLNHGDYWGQGTLVTVSS
AAAFVPVFLPAKPTTTPAPRPPTPAPTIASQPLSLRPEACRPAAGGAVHT
RGLDFACDFWVLVVVGGVLACYSLLVTVAFIIFWVLDKDDSKAGMEEDHT
YEGLDIDQTATYEDIVTLRTGEVKWSVGEHPGQE pWF-460:

(SEQ ID NO: 62)
CAGTCTGTGTTGACGCAGCCGCCCTCAGTGTCTGCGGCCCCAGGACAGAG
GGTCACCATCTCCTGCTCTGGAACCAGGTCCAACATTGGGAGTGATTATG
TTTCCTGGTACCAACACCTCCCAGGAACAGCCCCCAAACTCCTCGTTTAT
GGCGATAATCTGCGACCCTCAGGGATTCCTGACCGATTCTCTGCCTCCAA
GTCTGGCACGTCAGCCACCCTGGGCATCACCGGACTCCAGACTGGGGACG
AGGCCGATTATTACTGCGGCACATGGGATTACACCCTGAATGGTGTGGTG
TTCGGCGGAGGGACCAAGCTGACCGTCCTAGGTTCTAGAGGTGGTGGTGG
TAGCGGCGGCGGCGGCTCTGGTGGTGGTGGATCCCTCGAGATGGCCCAGG
TGCAGCTGGTGGAGTCTGGGGGAGGCTTGGTACAGCCTGGGGGGTCCCTG
AGACTCTCCTGTGCAGCCTCTGGATTCACCTTTAGCAGCTATGCCATGAG
CTGGGTCCGCCAGGCTCCAGGGAAGGGGCTGGAGTGGGTCTCAGTTATTT
ATAGCGGTGGTAGTAGCACATACTATGCAGACTCCGTGAAGGGCCGGTTC
ACCATCTCCAGAGATAATTCCAAGAACACGCTGTATCTGCAAATGAACAG
CCTGAGAGCCGAGGACACGGCCGTATATTACTGTGCGCGCACTTCTTACC
TGAACCATGGTGATTACTGGGGTCAAGGTACTCTGGTGACCGTGTCTAGC
CCCAAGAGCTGCGACAAGACCCACACCTGCCCCCCCTGCCCAGCCCCAGA
GCTGCTGGGCGGACCCTCCGTGTTCCTGTTCCCCCCCAAGCCCAAGGACA
CCCTGATGATCAGCAGGACCCCCGAGGTGACCTGCGTGGTGGTGGACGTG
AGCCACGAGGACCCAGAGGTGAAGTTCAACTGGTACGTGGACGGCGTGGA
GGTGCACAACGCCAAGACCAAGCCCAGAGAGGAGCAGTACAACAGCACCT
ACAGGGTGGTGTCCGTGCTGACCGTGCTGCACCAGGACTGGCTGAACGGC
AAGGAATACAAGTGCAAGGTCTCCAACAAGGCCCTGCCAGCCCCCATCGA
AAAGACCATCAGCAAGGCCAAGGGCCAGCCACGGGAGCCCCAGGTGTACA
CCCTGCCCCCCTCCCGGGAGGAGATGACCAAGAACCAGGTGTCCCTGACC
TGTCTGGTGAAGGGCTTCTACCCCAGCGACATCGCCGTGGAGTGGGAGAG

CAACGGCCAGCCCGAGAACAACTACAAGACCACCCCCCCAGTGCTGGACA
GCGACGGCAGCTTCTTCCTGTACAGCAAGCTGACCGTGGACAAGTCCAGG
TGGCAGCAGGGCAACGTGTTCAGCTGCAGCGTGATGCACGAGGCCCTGCA
CAACCACTACACCCAGAAGAGCCTGAGCCTGTCCCCCGAGCTGCAACTGG
AGGAGAGCTGTGCGGAGGCGCAGGACGGGGAGCTGGACGGGCTGTGGACG
ACCATCACCATCTTCATCACACTCTTCCTGTTAAGCGTGTGCTACAGTGC
CACCGTCACCTTCTTCAAGGTGAAGTGGATCTTCTCCTCGGTGGTGGACC
TGAAGCAGACCATCATCCCCGACTACAGGAACATGATCGGACAGGGGGCC
TGA pWF-460:

(SEQ ID NO: 63)
QSVLTQPPSVSAAPGQRVTISCSGTRSNIGSDYVSWYQHLPGTAPKLLVY
GDNLRPSGIPDRFSASKSGTSATLGITGLQTGDEADYYCGTWDYTLNGVV
FGGGTKLTVLGSRGGGGSGGGGSGGGGSLEMAQVQLVESGGGLVQPGGSL
RLSCAASGFTFSSYAMSWVRQAPGKGLEWVSVIYSGGSSTYYADSVKGRF
TISRDNSKNTLYLQMNSLRAEDTAVYYCARTSYLNHGDYWGQGTLVTVSS
PKSCDKTHTCPPCPAPELLGGPSVFLFPPKPKDTLMISRTPEVTCVVVDV
SHEDPEVKFNWYVDGVEVHNAKTKPREEQYNSTYRVVSVLTVLHQDWLNG
KEYKCKVSNKALPAPIEKTISKAKGQPREPQVYTLPPSREEMTKNQVSLT
CLVKGFYPSDIAVEWESNGQPENNYKTTPPVLDSDGSFFLYSKLTVDKSR
WQQGNVFSCSVMHEALHNHYTQKSLSLSPELQLEESCAEAQDGELDGLWT
TITIFITLFLLSVCYSATVTFFKVKWIFSSVVDLKQTIIPDYRNMIGQGA pWF-428:

(SEQ ID NO: 64)
CAGTCTGTGTTGACGCAGCCGCCCTCAGTGTCTGCGGCCCCAGGACAGAG
GGTCACCATCTCCTGCTCTGGAACCAGGTCCAACATTGGGAGTGATTATG
TTTCCTGGTACCAACACCTCCCAGGAACAGCCCCCAAACTCCTCGTTTAT
GGCGATAATCTGCGACCCTCAGGGATTCCTGACCGATTCTCTGCCTCCAA
GTCTGGCACGTCAGCCACCCTGGGCATCACCGGACTCCAGACTGGGGACG
AGGCCGATTATTACTGCGGCACATGGGATTACACCCTGAATGGTGTGGTG
TTCGGCGGAGGGACCAAGCTGACCGTCCTAGGTCAGCCCAAGGCCAACCC
CACTGTCACTCTGTTCCCGCCCTCCTCTGAGGAGCTCCAAGCCAACAAGG
CCACACTAGTGTGTCTGATCAGTGACTTCTACCCGGGAGCTGTGACAGTG
GCCTGGAAGGCAGATGGCAGCCCCGTCAAGGCGGGAGTGGAGACCACCAA
ACCCTCCAAACAGAGCAACAACAAGTACGCGGCCAGCAGCTACCTGAGCC
TGACGCCCGAGCAGTGGAAGTCCCACAGAAGCTACAGCTGCCAGGTCACG
CATGAAGGGAGCACCGTGGAGAAGACAGTGGCCCCTACAGAATGTTCA pWF-428:

(SEQ ID NO: 65)
QSVLTQPPSVSAAPGQRVTISCSGTRSNIGSDYVSWYQHLPGTAPKLLVY
GDNLRPSGIPDRFSASKSGTSATLGITGLQTGDEADYYCGTWDYTLNGVV
FGGGTKLTVLGQPKANPTVTLFPPSSEELQANKATLVCLISDFYPGAVTV
AWKADGSPVKAGVETTKPSKQSNNKYAASSYLSLTPEQWKSHRSYSCQVT
HEGSTVEKTVAPTECS pWF-429:

(SEQ ID NO: 66)
CAGGTGCAGCTGGTGGAGTCTGGGGGAGGCTTGGTACAGCCTGGGGGGTC
CCTGAGACTCTCCTGTGCAGCCTCTGGATTCACCTTTAGCAGCTATGCCA
TGAGCTGGGTCCGCCAGGCTCCAGGGAAGGGGCTGGAGTGGGTCTCAGTT
ATTTATAGCGGTGGTAGTAGCACATACTATGCAGACTCCGTGAAGGGCCG
GTTCACCATCTCCAGAGATAATTCCAAGAACACGCTGTATCTGCAAATGA
ACAGCCTGAGAGCCGAGGACACGGCCGTATATTACTGTGCGCGCACTTCT
TACCTGAACCATGGTGATTACTGGGGTCAAGGTACTCTGGTGACCGTGTC
TAGCGCCTCCACCAAGGGCCCATCGGTCTTCCCCCTGGCACCCTCCTCCA
AGAGCACCTCTGGGGGCACAGCGGCCCTGGGCTGCCTGGTCAAGGACTAC
TTCCCCGAACCGGTGACGGTGTCGTGGAACTCAGGCGCCCTGACCAGCGG
CGTGCACACCTTCCCGGCTGTCCTACAGTCCTCAGGACTCTACTCCCTCA
GCAGCGTGGTGACCGTGCCCTCCAGCAGCTTGGGCACCCAGACCTACATC
TGCAACGTGAACCACAAGCCCAGCAACACCAAGGTGGACAAGAGAGTGGA
GCCCAAGAGCTGCGACAAGACCCACACCTGCCCCCCCTGCCCAGCCCCAG
AGCTGCTGGGCGGACCCTCCGTGTTCCTGTTCCCCCCCAAGCCCAAGGAC
ACCCTGATGATCAGCAGGACCCCCGAGGTGACCTGCGTGGTGGTGGACGT
GAGCCACGAGGACCCAGAGGTGAAGTTCAACTGGTACGTGGACGGCGTGG
AGGTGCACAACGCCAAGACCAAGCCCAGAGAGGAGCAGTACAACAGCACC
TACAGGGTGGTGTCCGTGCTGACCGTGCTGCACCAGGACTGGCTGAACGG
CAAGGAATACAAGTGCAAGGTCTCCAACAAGGCCCTGCCAGCCCCCATCG
AAAAGACCATCAGCAAGGCCAAGGGCCAGCCACGGGAGCCCCAGGTGTAC
ACCCTGCCCCCCTCCCGGGAGGAGATGACCAAGAACCAGGTGTCCCTGAC
CTGTCTGGTGAAGGGCTTCTACCCCAGCGACATCGCCGTGGAGTGGGAGA
GCAACGGCCAGCCCGAGAACAACTACAAGACCACCCCCCCAGTGCTGGAC
AGCGACGGCAGCTTCTTCCTGTACAGCAAGCTGACCGTGGACAAGTCCAG
GTGGCAGCAGGGCAACGTGTTCAGCTGCAGCGTGATGCACGAGGCCCTGC
ACAACCACTACACCCAGAAGAGCCTGAGCCTGTCCCCCGAGCTGCAACTG
GAGGAGAGCTGTGCGGAGGCGCAGGACGGGGAGCTGGACGGGCTGTGGAC
GACCATCACCATCTTCATCACACTCTTCCTGTTAAGCGTGTGCTACAGTG
CCACCGTCACCTTCTTCAAGGTGAAGTGGATCTTCTCCTCGGTGGTGGAC
CTGAAGCAGACCATCATCCCCGACTACAGGAACATGATCGGACAGGGGGC
CTGA pWF-429:

(SEQ ID NO: 67)
QVQLVESGGGLVQPGGSLRLSCAASGFTFSSYAMSWVRQAPGKGLEWVSV
IYSGGSSTYYADSVKGRFTISRDNSKNTLYLQMNSLRAEDTAVYYCARTS
YLNHGDYWGQGTLVTVSSASTKGPSVFPLAPSSKSTSGGTAALGCLVKDY
FPEPVTVSWNSGALTSGVHTFPAVLQSSGLYSLSSVVTVPSSSLGTQTYI
CNVNHKPSNTKVDKRVEPKSCDKTHTCPPCPAPELLGGPSVFLFPPKPKD
TLMISRTPEVTCVVVDVSHEDPEVKFNWYVDGVEVHNAKTKPREEQYNST
YRVVSVLTVLHQDWLNGKEYKCKVSNKALPAPIEKTISKAKGQPREPQVY
TLPPSREEMTKNQVSLTCLVKGFYPSDIAVEWESNGQPENNYKTTPPVLD
SDGSFFLYSKLTVDKSRWQQGNVFSCSVMHEALHNHYTQKSLSLSPELQL
EESCAEAQDGELDGLWTTITIFITLFLLSVCYSATVTFFKVKWIFSSVVD
LKQTIIPDYRNMIGQGA-

Mu CXCL13

(SEQ ID NO: 68)
ATGAGACTTTCAACAGCAACACTCCTCCTGTTGCTGGCTTCATGTCTGAG
CCCTGGTCATGGTATTTTGGAGGCCCACTATACAAATCTCAAATGTCGGT
GTTCAGGCGTAATATCCACCGTAGTCGGCCTGAACATTATCGATAGGATT
CAGGTTACACCCCCCGGGAACGGATGTCCTAAGACCGAGGTGGTGATTTG
GACCAAGATGAAGAAGGTCATTTGTGTGAACCCACGGGCTAAATGGCTGC
AGCGTCTTTTGCGACACGTGCAGTCCAAGAGCTTGTCCAGCACACCTCAG
GCCCCAGTTAGCAAGCGACGTGCAGCC

Mu CXCL13

(SEQ ID NO: 69)
MRLSTATLLLLLASCLSPGHGILEAHYTNLKCRCSGVISTVVGLNIIDR
IQVTPPGNGCPKTEVVIWTKMKKVICVNPRAKWLQRLLRHVQSKSLSST
PQ APVSKRRAA

Mu FLT3LG (SEQ ID NO: 70)
ATGACAGTGCTGGCCCCCGCGTGGTCTCCCAATAGCTCACTCCTCCTCTT
GCTGCTACTGCTCAGCCCATGCCTCAGGGGCACCCCCGATTGTTACTTCA
GCCACAGCCCAATCTCCTCCAACTTCAAAGTGAAATTTAGGGAACTGACC
GACCACCTGCTGAAAGATTATCCTGTGACTGTGGCAGTGAACCTGCAAGA
CGAAAAGCATTGTAAGGCGCTATGGAGCCTCTTTCTTGCCCAACGATGGA
TTGAGCAACTCAAAACTGTAGCCGGAAGCAAATGCAGACGCTACTGGAG
GACGTGAATACTGAGATTCACTTCGTTACCAGTTGTACTTTCCAGCCACT
GCCAGAGTGTCTCAGGTTTGTGCAGACTAATATCAGCCACCTGCTGAAGG
ATACTTGCACCCAGCTCCTGGCTCTCAAGCCTTGTATAGGCAAGGCTTGT
CAAAATTTTAGCAGGTGTCTCGAAGTCCAGTGCCAGCCAGATTCATCCAC
ACTGCTGCCGCCCCGAAGCCCTATCGCACTCGAAGCGACAGAGTTGCCAG

Mu FLT3LG

AGCCTCGTCCCAGACAGCTTCTGCTGCTGCTACTTCTGCTGCTGCCGCTA
ACTCTGGTGCTACTTGCTGCCGCCTGGGGCCTCAGATGGCAACGCGCCAG
ACGCCGAGGCGAACTCCACCCTGGGGTGCCACTGCCATCCCACCCA (SEQ ID NO: 71)
MTVLAPAWSPNSSLLLLLLLLSPCLRGTPDCYFSHSPISSNFKVKFRELT
DHLLKDYPVTVAVNLQDEKHCKALWSLFLAQRWIEQLKTVAGSKMQTLLE
DVNTEIHFVTSCTFQPLPECLRFVQTNISHLLKDTCTQLLALKPCIGKAC
QNFSRCLEVQCQPDSSTLLPPRSPIALEATELPEPRPRQLLLLLLLLLPL
TLVLLAAAWGLRWQRARRRGELHPGVPLPS HP

Mu XCL1

(SEQ ID NO: 72)
ATGCGACTCTTGTTGTTGACTTTTCTCGGAGTGTGCTGCCTGACACCCTG
GGTCGTAGAGGGAGTTGGCACTGAAGTACTAGAAGAGTCCTCCTGCGTTA
ACCTGCAGACACAGCGGCTCCCAGTCCAGAAAATTAAGACCTACATTATA
TGGGAAGGAGCAATGCGAGCGGTGATTTTTGTGACCAAGAGGGGTCTCAA
GATTTGCGCGGACCCTGAGGCCAAGTGGGTCAAAGCAGCTATTAAGACAG
TAGACGGAAGAGCCTCCACCAGGAAGAATATGGCAGAAACTGTACCGACC
GGTGCGCAGCGGTCAACATCTACCGCAATCACACTCACCGGC

Mu XCL1

(SEQ ID NO: 73)
MRLLLLTFLGVCCLTPWVVEGVGTEVLEESSCVNLQTQRLPVQKIKTYII
WEGAMRAVIFVTKRGLKICADPEAKWVKAAIKTVDGRASTRKNMAETVPT
GAQRSTSTAI TLTG

Mu Tim4(ECD)-muIgG2a Fc (SEQ ID NO: 74)
ATGAGCAAGGGCCTTCTCCTGCTGTGGCTAGTAACTGAATTGTGGTGGTT
GTACCTGACACCTGCCGCTAGTGAGGACACCATCATTGGTTTCCTTGGGC
AGCCCGTCACCCTCCCTTGCCATTACCTAAGCTGGAGCCAGTCACGGAAC
TCTATGTGCTGGGGAAAGGGGTCATGCCCTAATTCCAAGTGCAACGCCGA
GCTGTTGCGCACGGACGGCACCAGAATAATCTCAAGAAAGTCCACCAAGT
ATACGCTGCTCGGCAAGGTGCAATTCGGTGAAGTGAGCTTGACCATAAGT
AACACCAACCGCGGTGACTCCGGAGTTTATTGTTGCAGGATCGAAGTGCC
AGGCTGGTTTAACGACGTGAAGAAAACGTGCGGCTGGAACTGAGGAGGG
CAACTACGACCAAGAAACCAACAACCACGACGAGACCTACCACCACTCCT
TACGTGACAACCACGACACCGGAGCTGTTGCCAACTACCGTCATGACAAC
ATCTGTGTTGCCAACTACCACCCCCCCCAAACGCTCGCGACAACTGCCT
TTTCCACAGCCGTTACCACATGTCCTTCCACCACCCCAGGCTCTTTTTCT
CAAGAAACTACCAAGGGATCAGCTTTTACCACCGAGTCTGAAACTCTCCC
AGCAAGTAATCACTCACAGCGGTCAATGATGACCATCAGCACAGACATCG
CTGTCTTGAGACCTACTGGCAGCAATCCAGGCATTCTGCCCTCCACTTCA
CAGCTGACTACCCAAAAGACTACACTAACCACCAGCGAAAGTCTGCAGAA
AACTACAAAGAGCCATCAAATAAACTCCCGGCAGACTCCCAGAGGGCCCA
CAATCAAGCCCTGTCCTCCATGCAAATGCCCAGCACCTAACCTCTTGGGT
GGACCATCCGTCTTCATCTTCCCTCCAAAGATCAAGGATGTACTCATGAT
CTCCCTGAGCCCCATAGTCACATGTGTGGTGGTGGATGTGAGCGAGGATG
ACCCAGATGTCCAGATCAGCTGGTTTGTGAACAACGTGGAAGTACACACA
GCTCAGACACAAACCCATAGAGAGGATTACAACAGTACTCTCCGGGTGGT
CAGTGCCCTCCCCATCCAGCACCAGGACTGGATGAGTGGCAAGGAGTTCA
AATGCAAGGTCAACAACAAAGACCTCCCAGCGCCCATCGAGAGAACCATC
TCAAAACCCAAAGGGTCAGTAAGAGCTCCACAGGTATATGTCTTGCCTCC
ACCAGAAGAAGAGATGACTAAGAAACAGGTCACTCTGACCTGCATGGTCA
CAGACTTCATGCCTGAAGACATTTACGTGGAGTGGACCAACAACGGGAAA
ACAGAGCTAAACTACAAGAACACTGAACCAGTCCTGGACTCTGATGGTTC
TTACTTCATGTACAGCAAGCTGAGAGTGGAAAAGAAGAACTGGGTGGAAA
GAAATAGCTACTCCTGTTCAGTGGTCCACGAGGGTCTGCACAATCACCAC
ACGACTAAGAGCTTCTCCCGGACTCCGGGTAAA

Mu Tim4(ECD)-muIgG2a Fc (SEQ ID NO: 75)
MSKGLLLLWLVTELWWLYLTPAASEDTIIGFLGQPVTLPCHYLSWSQSRN
SMCWGKGSCPNSKCNAELLRTDGTRIISRKSTKYTLLGKVQFGEVSLTIS
NTNRGDSGVYCCRIEVPGWFNDVKKNVRLELRRATTTKKPTTTTRPTTTP
YVTTTTPELLPTTVMTTSVLPTTTPPQTLATTAFSTAVTTCPSTTPGSFS
QETTKGSAFTTESETLPASNHSQRSMMTISTDIAVLRPTGSNPGILPSTS
QLTTQKTTLTTSESLQKTTKSHQINSRQTPRGPTIKPCPPCKCPAPNLLG
GPSVFIFPPKIKDVLMISLSPIVTCVVVDVSEDDPDVQISWFVNNVEVHT
AQTQTHREDYNSTLRVVSALPIQHQDWMSGKEFKCKVNNKDLPAPIERTI
SKPKGSVRAPQVYVLPPPEEEMTKKQVTLTCMVTDFMPEDIYVEWTNNGK
TELNYKNTEPVLDSDGSYFMYSKLRVEKKNWVERNSYSCSVVHEGLHNHH
TTKSFSRTPGK

Mu 4-1BB-L (SEQ ID NO: 76)
ATGGATCAGCATACACTGGACGTGGAAGATACAGCCGATGCCAGACACCC
TGCTGGAACGTCCTGTCCCAGCGACGCTGCCCTGCTCAGAGACACCGGGC
TGCTCGCAGATGCTGCTCTGCTGAGTGATACCGTTCGGCCAACTAACGCG
GCCCTACCCACAGATGCCGCATATCCCGCGGTAAATGTCAGGGACCGGGA
AGCTGCCTGGCACCGGCCCTCAATTTCTGCTCTAGACATCCGAAACTGT
ACGGTCTGGTCGCACTGGTACTGCTGCTACTTATAGCAGCTTGTGTTCCC
ATATTTACCCGCACTGAACCCAGACCCGCTCTCACTATTACAACTTCACC
AAACTTGGGCACACGTGAAAACAATGCAGATCAGGTTACCCCTGTAAGTC

-continued

```
ATATTGGATGCCCCAACACCACACAACAGGGAAGTCCGGTGTTTGCAAAA
CTCCTTGCTAAGAATCAGGCTTCACTGTGTAACACTACTCTTAATTGGCA
CTCACAAGACGGGGCCGGGAGTAGCTATCTCAGCCAAGGTCTCCGCTATG
AAGAAGATAAGAAAGAGTTGGTGGTGGACAGCCCAGGACTCTACTACGTC
TTCCTGGAGCTAAAACTAAGCCCCACTTTTACTAACACTGGACATAAGGT
CCAAGGTTGGGTGTCCCTCGTACTTCAAGCTAAACCCCAGGTGGACGACT
TCGATAACCTGGCGTTGACAGTTGAGCTCTTTCCTTGCTCTATGGAAAAT
AAGCTCGTGGATCGGAGCTGGTCTCAACTGTTGCTGCTTAAAGCCGGTCA
TCGTCTGTCTGTTGGACTACGCGCATACTTGCATGGAGCCCAGGACGCAT
ATCGTGATTGGGAACTGAGCTACCCGAATACCACTAGCTTTGGACTATTT
CTTGTTAAACCAGATAATCCTTGGGAG
```

Mu 4-1BB-L (SEQ ID NO: 77)
MDQHTLDVEDTADARHPAGTSCPSDAALLRDTGLLADAALLSDTVRPTNA
ALPTDAAYPAVNVRDREAAWPPALNFCSRHPKLYGLVALVLLLLIAACVP
IFTRTEPRPALTITTSPNLGTRENNADQVTPVSHIGCPNTTQQGSPVFAK
LLAKNQASLCNTTLNWHSQDGAGSSYLSQGLRYEEDKKELVVDSPGLYYV
FLELKLSPTFTNTGHKVQGWVSLVLQAKPQVDDFDNLALTVELFPCSMEN
KLVDRSWSQLLLLKAGHRLSVGLRAYLHGAQDAYRDWELSYPNTTSFGLF
LVKPDNPWE

Mu LIGHT (Cleavage-Deficient Mutant)

(SEQ ID NO: 78)
```
ATGGAGAGCGTAGTGCAACCCAGCGTATTTGTGGTGGATGGACAGACCGA
CATCCCATTCAGACGCTTGGAACAGAACCACCGAAGAAGGCGGTGCGGCA
CCGTCCAGGTGTCCCTCGCTCTCGTGCTGCTGCTTGGTGCTGGCCTCGCA
ACACAAGGGTGGTTTCTTTTGAGACTCCATCAACGCTTGGGAGACATAGT
GGCCCACCTGCCTGATGGTGGGAAGGGCTCTTGGCAGGACCAGCGATCAC
ACCAGGCTAACCCCGCCGCTCACCTGACAGGGGCGAATGCCAGCTTGATC
GGAATAGGTGGGCCGCTGCTGTGGGAAACTAGGCTTGGACTTGCCTTTCT
GAGAGGGCTTACATACCATGACGGAGCCCTCGTAACAATGGAGCCTGGTT
ATTACTACGTGTACAGTAAGGTGCAGCTTTCTGGAGTCGGGTGTCCCCAG
GGGCTGGCTAACGGACTGCCCATCACTCATGGACTATACAAACGCACATC
CAGATATCCTAAAGAGCTGGAACTGTTGGTGTCCCGTAGGAGCCCGTGTG
GCAGGGCCAACTCTTCCCGTGTGTGGTGGACTCCTCTTTTCTGGGCGGC
GTGGTCCATCTGGAAGCTGGTGAGGAAGTCGTCGTAAGAGTACCTGGAAA
CCGTCTGGTTCGCCCCCGCGATGGCACCAGGTCCTACTTCGGAGCTTTCA
TGGTA
```

Mu LIGHT (Cleavage-Deficient Mutant)

(SEQ ID NO: 79)
MESVVQPSVFVVDGQTDIPFRRLEQNHRRRRCGTVQVSLALVLLLGAGLA
TQGWFLLRLHQRLGDIVAHLPDGGKGSWQDQRSHQANPAAHLTGANASLI
GIGGPLLWETRLGLAFLRGLTYHDGALVTMEPGYYYVYSKVQLSGVGCPQ
GLANGLPITHGLYKRTSRYPKELELLVSRRSPCGRANSSRVWWDSSFLGG
VVHLEAGEEVVVRVPGNRLVRPRDGTRSYFGAFMV

Mu IL12 (Transmembrane Form)

(SEQ ID NO: 80)
```
ATGTGCCCACAGAAACTCACAATTTCTTGGTTCGCAATCGTCCTGCTGGT
GTCACCCCTGATGGCAATGTGGGAGTTGGAAAAGGATGTATACGTCGTCG
AGGTCGACTGGACACCTGACGCTCCGGGTGAAACTGTCAACCTCACTTGC
GATACTCCTGAAGAGGACGACATCACGTGGACGAGCGACCAGCGACATGG
AGTGATAGGGTCTGGCAAGACGCTTACTATCACGGTTAAGGAATTTCTCG
ACGCAGGGCAGTACACATGTCACAAGGGCGGCGAGACTCTGAGCCACTCC
CATTTGCTGCTGCACAAGAAGGAGAATGGTATCTGGTCTACCGAAATCCT
GAAGAATTTTAAGAACAAGACTTTTCTGAAATGCGAGGCCCCAAATTATT
CCGGACGTTTCACTTGCAGTTGGCTCGTTCAAAGAAATATGGACTTGAAA
TTTAACATTAAATCCAGCTCTTCATCTCCTGACAGCAGGGCCGTAACTTG
TGGAATGGCTTCATTGTCAGCTGAGAAAGTTACGCTTGACCAAAGGGATT
ATGAGAAATACAGCGTGAGTTGCCAGGAAGATGTGACATGTCCAACGGCA
GAGGAAACGTTGCCAATTGAGCTCGCTTTGGAAGCTCGTCAACAAAACAA
GTATGAAAACTATAGTACTAGCTTCTTCATACGGGACATCATCAAACCAG
ATCCACCTAAGAATTTGCAGATGAAGCCTCTGAAGAATTCACAAGTCGAG
GTATCCTGGGAATACCCAGATTCATGGTCCACTCCTCATAGTTACTTTAG
CCTGAAATTCTTTGTACGCATACAGCGGAAGAAGGAGAAAATGAAGGAGA
CGGAAGAAGGCTGCAATCAGAAAGGCGCTTTTCTTGTTGAAAAGACGAGC
ACTGAGGTTCAATGCAAAGGCGGGAATGTATGTGTTCAAGCCCAAGATAG
GTATTATAATAGCTCCTGCTCTAAGTGGGCTTGCGTACCATGCAGAGTTA
GAAGTGGCTCAACCTCAGGCTCCGGAAAACCTGGTTCCGGTGAAGGTTCC
ACAAAAGGGCGTGTGATTCCTGTGTCCGGCCCAGCTAGGTGTCTCTCCCA
GTCACGGAATCTCCTGAAAACCACGGATGACATGGTAAAGACAGCTAGGG
AGAAACTCAAGCACTACTCCTGCACAGCTGAGGATATCGATCATGAGGAC
ATCACCAGGGACCAGACATCCACTCTGAAAACTTGCCTGCCTTTGGAACT
CCACAAGAACGAATCTTGTCTGGCAACGCGTGAAACGAGTTCTACTACAA
GAGGGTCCTGTCTTCCCCCTCAAAAGACAAGCCTTATGATGACCTTGTGT
CTCGGTAGCATTTATGAGGACCTAAAGATGTATCAAACCGAGTTTCAGGC
TATCAATGCAGCGCTCCAGAATCATAACCATCAGCAGATCATTCTTGACA
AAGGAATGCTCGTGGCCATTGATGAACTAATGCAGAGCCTAAACCACAAT
GGCGAGACTCTTCGACAGAAACCGCCTGTGGGCAGGCCGATCCATATAG
AGTCAAAATGAAACTGTGTATTCTCCTGCATGCATTTAGTACTCGTGTAG
```

-continued

TGACTATTAACAGAGTGATGGGTTACCTTTCCTCAGCTAATACACTTGTC

CTCTTTGGCGCTGGGTTCGGCGCCGTCATAACGGTTGTTGTCATCGTGGT

AATAATCAAGTGCTTTTGCAAGCACAGGTCTTGTTTTCGCAGGAATGAAG

CCTCTAGAGAAACAAATAATTCACTGACCTTTGGCCCCGAAGAAGCTCTT

GCAGAGCAAACGGTGTTTCTC

Mu IL12 (Transmembrane Form)

(SEQ ID NO: 81)
MCPQKLTISWFAIVLLVSPLMAMWELEKDVYVVEVDWTPDAPGETVNLTC

DTPEEDDITWTSDQRHGVIGSGKTLTITVKEFLDAGQYTCHKGGETLSHS

HLLLLHKKENGIWSTEILKNFKNKTFLKCEAPNYSGRFTCSWLVQRNMDLK

FNIKSSSSSPDSRAVTCGMASLSAEKVTLDQRDYEKYSVSCQEDVTCPTA

EETLPIELALEARQQNKYENYSTSFFIRDIIKPDPPKNLQMKPLKNSQVE

VSWEYPDSWSTPHSYFSLKFFVRIQRKKEKMKETEEGCNQKGAFLVEKTS

TEVQCKGGNVCVQAQDRYYNSSCSKWACVPCRVRSGSTSGSGKPGSGEGS

TKGRVIPVSGPARCLSQSRNLLKTTDDMVKTAREKLKHYSCTAEDIDHED

ITRDQTSTLKTCLPLELHKNESCLATRETSSTTRGSCLPPQKTSLMMTLC

LGSIYEDLKMYQTEFQAINAALQNHNHQQIILDKGMLVAIDELMQSLNHN

GETLRQKPPVGEADPYRVKMKLCILLHAFSTRVVTINRVMGYLSSANTLV

LFGAGFGAVITVVVIVVIIKCFCKHRSCFRRNEASRETNNSLTFGPEEAL

AEQTVFL

Mu IL12 (Secreted Form)

(SEQ ID NO: 82)
ATGTGTCAGTCACGCTATCTTCTCTTCCTTGCTACTCTGGCCTTGCTCAA

TCACTTGTCCCTTGCTCGTGTGATTCCTGTGTCCGGCCCAGCTAGGTGTC

TCTCCCAGTCACGGAATCTCCTGAAAACCACGGATGACATGGTAAAGACA

GCTAGGGAGAAACTCAAGCACTACTCCTGCACAGCTGAGGATATCGATCA

TGAGGACATCACCAGGGACCAGACATCCACTCTGAAAACTTGCCTGCCTT

TGGAACTCCACAAGAACGAATCTTGTCTGGCAACGCGTGAAACGAGTTCT

ACTACAAGAGGGTCCTGTCTTCCCCCTCAAAAGACAAGCCTTATGATGAC

CTTGTGTCTCGGTAGCATTTATGAGGACCTAAAGATGTATCAAACCGAGT

TTCAGGCTATCAATGCAGCGCTCCAGAATCATAACCATCAGCAGATCATT

CTTGACAAAGGAATGCTCGTGGCCATTGATGAACTAATGCAGAGCCTAAA

CCACAATGGCGAGACTCTTCGACAGAAACCGCCTGTGGGCGAGGCCGATC

CATATAGAGTCAAAATGAAACTGTGTATTCTCCTGCATGCATTTAGTACT

CGTGTAGTGACTATTAACAGAGTGATGGGTTACCTTTCCTCAGCTGGAAG

CGGCGCCACCAACTTCTCCCTGCTGAAGCAGGCCGGCGACGTGGAGGAGA

ACCCCGGCCCCATGTGCCCACAGAAACTCACAATTTCTTGGTTCGCAATC

GTCCTGCTGGTGTCACCCCTGATGGCAATGTGGGAGTTGGAAAAGGATGT

ATACGTCGTCGAGGTCGACTGGACACCTGACGCTCCGGGTGAAACTGTCA

ACCTCACTTGCGATACTCCTGAAGAGGACGACATCACGTGGACGAGCGAC

CAGCGACATGGAGTGATAGGGTCTGGCAAGACGCTTACTATCACGGTTAA

GGAATTTCTCGACGCAGGGCAGTACACATGTCACAAGGGCGGCGAGACTC

TGAGCCACTCCCATTTGCTGCTGCACAAGAAGGAGAATGGTATCTGGTCT

ACCGAAATCCTGAAGAATTTTAAGAACAAGACTTTTCTGAAATGCGAGGC

CCCAAATTATTCCGGACGTTTCACTTGCAGTTGGCTCGTTCAAAGAAATA

TGGACTTGAAATTTAACATTAAATCCAGCTCTTCATCTCCTGACAGCAGG

GCCGTAACTTGTGGAATGGCTTCATTGTCAGCTGAGAAAGTTACGCTTGA

CCAAAGGGATTATGAGAAATACAGCGTGAGTTGCCAGGAAGATGTGACAT

GTCCAACGGCAGAGGAAACGTTGCCAATTGAGCTCGCTTTGGAAGCTCGT

CAACAAAACAAGTATGAAAACTATAGTACTAGCTTCTTCATACGGGACAT

CATCAAACCAGATCCACCTAAGAATTTGCAGATGAAGCCTCTGAAGAATT

CACAAGTCGAGGTATCCTGGGAATACCCAGATTCATGGTCCACTCCTCAT

AGTTACTTTAGCCTGAAATTCTTTGTACGCATACAGCGGAAGAAGGAGAA

AATGAAGGAGACGGAAGAAGGCTGCAATCAGAAAGGCGCTTTTCTTGTTG

AAAAGACGAGCACTGAGGTTCAATGCAAAGGCGGGAATGTATGTGTTCAA

GCCCAAGATAGGTATTATAATAGCTCCTGCTCTAAGTGGGCTTGCGTACC

ATGCAGAGTTAGAAGT

Mu IL12 (Secreted Form)

(SEQ ID NO: 83)
MCQSRYLLFLATLALLNHLSLARVIPVSGPARCLSQSRNLLKTTDDMVKT

AREKLKHYSCTAEDIDHEDITRDQTSTLKTCLPLELHKNESCLATRETSS

TTRGSCLPPQKTSLMMTLCLGSIYEDLKMYQTEFQAINAALQNHNHQQII

LDKGMLVAIDELMQSLNHNGETLRQKPPVGEADPYRVKMKLCILLHAFST

RVVTINRVMGYLSSAGSGATNFSLLKQAGDVEENPGPMCPQKLTISWFAI

VLLVSPLMAMWELEKDVYVVEVDWTPDAPGETVNLTCDTPEEDDITWTSD

QRHGVIGSGKTLTITVKEFLDAGQYTCHKGGETLSHSHLLLHKKENGIWS

TEILKNFKNKTFLKCEAPNYSGRFTCSWLVQRNMDLKFNIKSSSSSPDSR

AVTCGMASLSAEKVTLDQRDYEKYSVSCQEDVTCPTAEETLPIELALEAR

QQNKYENYSTSFFIRDIIKPDPPKNLQMKPLKNSQVEVSWEYPDSWSTPH

SYFSLKFFVRIQRKKEKMKETEEGCNQKGAFLVEKTSTEVQCKGGNVCVQ

AQDRYYNSSCSKWACVPCRV RS

Mu IFN Alpha A2

(SEQ ID NO: 84)
ATGGCCAGGCTTTGCGCTTTTCTCGTCATGCTGATCGTCATGAGTTACTG

GTCCATTTGCAGCCTCGGATGTGATCTGCCCCACACCTACAACCTGCGCA

ACAAACGAGCTCTCAAAGTGTTGGCCCAAATGAGGCGGTTGCCCTTCCTT

TCCTGTCTCAAAGACAGGCAAGATTTTGGATTTCCACTAGAGAAAGTAGA

CAATCAACAGATACAGAAAGCTCAAGCTATCCCCGTGTTGAGGGACTTGA

CTCAACAGACGTTGAATCTATTTACTAGCAAGGCCAGCTCTGCTGCTTGG

AATGCCACCCTTCTTGACTCATTTTGCAATGACCTACATCAACAACTGAA

-continued

```
TGATCTCCAAACATGTTTGATGCAGCAGGTAGGTGTCCAAGAACCCCGC

TTACTCAGGAAGACGCCCTTCTGGCTGTCCGCAAGTACTTTCACAGAATC

ACAGTGTACCTGCGCGAAAAGAAACACTCCCCCTGCGCTTGGGAAGTGGT

CAGGGCCGAGGTTTGGCGAGCCCTGAGTAGCTCCGTCAATCTCCTTCCTC

GGTTGTCCGAGGAGAAAGAG
```

Mu IFN Alpha A2

(SEQ ID NO: 85)
MARLCAFLVMLIVMSYWSICSLGCDLPHTYNLRNKRALKVLAQMRRLPFL
SCLKDRQDFGFPLEKVDNQQIQKAQAIPVLRDLTQQTLNLFTSKASSAAW
NATLLDSFCNDLHQQLNDLQTCLMQQVGVQEPPLTQEDALLAVRKYFHRI
TVYLREKKHSPCAWEVVRAEVWRALSSSVNLLPRLSEEKE

Mu CD80

(SEQ ID NO: 86)
```
ATGGCTTGCAACTGTCAGCTCATGCAAGATACTCCCCTGCTTAAGTTTCC

CTGCCCTAGACTCATTCTCCTCTTCGTCCTTCTCATTCGCCTAAGCCAGG

TGAGTTCCGATGTGGATGAACAACTGAGTAAATCTGTCAAGGATAAAGTT

CTGCTCCCATGCCGCTACAATAGCCCCCATGAGGACGAGTCCGAAGATAG

GATTTACTGGCAGAAACATGATAAGGTGGTGCTATCCGTCATTGCCGGTA

AATTGAAGGTGTGGCCCGAATATAAGAATAGAACCCTGTATGACAACACA

ACTTATAGCCTAATCATCCTCGGTCTCGTACTGAGCGACCGAGGTACTTA

CTCATGCGTTGTGCAGAAGAAGGAGCGCGGAACATACGAAGTCAAGCACC

TTGCATTGGTGAAATTGTCAATAAAAGCTGACTTTTCAACTCCTAATATT

ACTGAATCAGGTAACCCTTCCGCAGACACTAAAAGAATTACATGCTTCGC

CTCTGGCGGGTTTCCCAAACCACGGTTCTCTTGGCTAGAGAATGGGAGAG

AACTTCCAGGTATCAATACAACCATCTCTCAAGACCCAGAATCAGAACTG

TACACCATCTCCAGCCAACTCGATTTCAATACCACAAGAAATCATACAAT

AAAATGTCTGATAAAGTACGGAGATGCACATGTCTCTGAAGATTTCACAT

GGGAGAAACCACCAGAGGACCCGCCAGACAGCAAGAATACACTTGTCCTC

TTTGGCGCTGGGTTCGGCGCCGTCATAACGGTTGTTGTCATCGTGGTAAT

AATCAAGTGCTTTTGCAAGCACAGGTCTTGTTTTCGCAGGAATGAAGCCT

CTAGAGAAACAAATAATTCACTGACCTTTGGCCCCGAAGAAGCTCTTGCA

GAGCAAACGGTGTTTCTC
```

Mu CD80

(SEQ ID NO: 87)
MACNCQLMQDTPLLKFPCPRLILLFVLLIRLSQVSSDVDEQLSKSVKDKV
LLPCRYNSPHEDESEDRIYWQKHDKVVLSVIAGKLKVWPEYKNRTLYDNT
TYSLIILGLVLSDRGTYSCVVQKKERGTYEVKHLALVKLSIKADFSTPNI
TESGNPSADTKRITCFASGGFPKPRFSWLENGRELPGINTTISQDPESEL
YTISSQLDFNTTRNHTIKCLIKYGDAHVSEDFTWEKPPEDPPDSKNTLVL
FGAGFGAVITVVVIVVIIKCFCKHRSCFRR NEASRETNNS LTFGPEEA
LAEQTVFL

Mu CD40-L (SEQ ID NO: 88)
```
ATGATCGAAACTTATTCCCAACCCTCACCGCGCTCAGTAGCAACTGGCCT

ACCAGCCAGCATGAAGATATTCATGTACCTCTTGACTGTATTCTTGATCA

CGCAAATGATTGGTAGTGTTTTGTTCGCCGTTTATCTCCACAGGCGCCTG

GATAAAGTTGAAGAAGAGGTTAATCTCCATGAAGACTTCGTGTTCATTAA

GAAACTCAAAAGATGTAACAAAGGTGAGGGATCTCTGTCTCTTCTGAACT

GTGAGGAGATGCGACGGCAATTCGAGGACCTCGTAAAAGACATAACTCTC

AACAAAGAAGAGAAGAAAGAAAACTCTTTCGAGATGCAACGGGGCGACGA

GGACCCTCAAATTGCCGCACATGTCGTTTCTGAAGCGAATTCCAATGCCG

CGTCCGTGCTCCAGTGGGCGAAGAAGGGATACTACACGATGAAGAGCAAC

CTTGTGATGCTTGAAAATGGCAAGCAGCTCACAGTTAAACGCGAGGGACT

CTACTATGTATACACCCAAGTGACCTTTTGTTCCAACCGGGAGCCAAGTA

GCCAACGCCCGTTCATCGTTGGGCTGTGGCTCAAGCCTTCTTCAGGGAGT

GAACGAATCCTTCTCAAGGCAGCCAACACGCATTCCAGCAGCCAACTGTG

TGAGCAACAATCCGTGCATCTTGGCGGGTCTTTGAGCTGCAAGCGGGCG

CCTCTGTGTTCGTGAATGTTACCGAAGCCAGCCAGGTTATCCACCGCGTG

GGTTTCAGTAGTTTTGGCCTGCTCAAGCTG
```

Mu CD40-L (SEQ ID NO: 89)
MIETYSQPSPRSVATGLPASMKIFMYLLTVFLITQMIGSVLFAVYLHRRL
DKVEEEVNLHEDFVFIKKLKRCNKGEGSLSLLNCEEMRRQFEDLVKDITL
NKEEKKENSFEMQRGDEDPQIAAHVVSEANSNAASVLQWAKKGYYTMKSN
LVMLENGKQLTVKREGLYYVYTQVTFCSNREPSSQRPFIVGLWLKPSSGS
ERILLKAANTHSSSQLCEQQSVHLGGVFELQAGASVFVNVTEASQVIHRV
GFSSFGLLKL

Mu IL21

(SEQ ID NO: 90)
```
ATGGAGCGTACTCTGGTCTGCCTTGTTGTGATATTCTTGGGACAGTTGC

ACACAAATCATCACCCCAAGGACCGGATAGACTCCTCATACGCCTGCGCC

ATCTGATTGACATTGTCGAGCAGTTGAAGATTTATGAGAACGACCTGGAC

CCTGAACTATTGAGCGCGCCTCAAGACGTCAAAGGGCATTGCGAGCATGC

TGCATTTGCATGTTTTCAGAAAGCTAAGCTCAAACCAAGTAATCCCGGTA

ACAATAAAACATTCATCATCGACCTGGTGGCCCAACTAAGACGCCGGTTG

CCGGCGCGCCGGGTGGTAAGAAACAGAAACATATTGCTAAATGCCCCTC

TTGCGACTCTTACGAGAAAAGGACACCTAAGGAATTCCTCGAACGATTGA

AATGGTTGTTGCAGAAGATGATCCATCAACATCTGAGC
```

Mu IL21

(SEQ ID NO: 91)
MERTLVCLVVIFLGTVAHKSSPQGPDRLLIRLRHLIDIVEQLKIYENDLD
PELLSAPQDVKGHCEHAAFACFQKAKLKPSNPGNNKTFIIDLVAQLRRRL
PARRGGKKQKHIAKCPSCDSYEKRTPKEFLERLKWLLQKMIHQHLS

Mu CCL21

(SEQ ID NO: 92)
ATGGCACAAATGATGACACTGTCCCTACTTAGTCTAGTTCTAGCTTTGTG
TATTCCCTGGACTCAAGGCAGTGACGGAGGAGGACAAGACTGCTGCCTCA
AATATTCTCAAAAGAAAATCCCTTATTCTATAGTCCGAGGTTACCGTAAG
CAAGAACCGAGTCTAGGTTGTCCTATCCCCGCAATCCTCTTTCTACCACG
GAAACATAGCAAACCAGAATTGTGCGCCAACCCAGAAGAGGGTTGGGTCC
AAAAATTTGATGAGGCGCCTTGACCAACCACCGGCCCCGGGTAAACAATCA
CCGGGGTGTCGGAAGAATAGGGGTACATCCAAATCCGGGAAGAAAGGGAA
GGGGAGTAAGGGCTGTAAGAGAACGGAACAAACTCAACCTAGCAGAGGT

Mu CCL21

(SEQ ID NO: 93)
MAQMMTLSLLSLVLALCIPWTQGSDGGGQDCCLKYSQKKIPYSIVRGYRK
QEPSLGCPIPAILFLPRKHSKPELCANPEEGWVQNLMRRLDQPPAPGKQS
PGCRKNRGTSKSGKKGKGSKGCKRTEQTQPSRG

Anti-Mu CD3 scFv-Transmembrane (SEQ ID NO: 94)
ATGGAAACCGACACATTGCTCCTCTGGGTTCTCCTTCTATGGGTCCCCGG
TTCCACCGGAGATATCCAAATGACACAATCACCCAGCAGCCTGCCTGCCT
CTCTGGGCGACCGCGTTACCATCAATTGTCAAGCTTCCCAAGATATAAGT
AATTATCTCAACTGGTACCAGCAAAAGCCCGGTAAAGCGCCTAAATTGCT
GATTTATTATACTAATAAAACTCGCAGATGGAGTTCCTAGTAGATTTTCTG
GTTCAGGGAGTGGACGGGACTCCAGTTTTACCATATCAAGTCTGGAATCC
GAGGATATCGGCAGCTACTATTGCCAGCAATATTATAATTACCCTTGGAC
TTTTGGACCCGGGACTAAACTTGAGATCAAAAGAGGCGGAGGAGGCAGTG
GTGGTGGTGGATCAGGCGGCGGTGGTAGTGAGGTACAACTCGTGGAATCA
GGCGGCGGACTGGTCCAACCCGGCAAGAGCCTTAAACTCTCTTGTGAGGC
CAGTGGATTTACATTCAGCGGTTATGGAATGCACTGGGTGAGACAAGCTC
CCGGCAGGGGCCTAGAATCAGTGGCGTACATCACCAGCTCATCAATAAAC
ATTAAATACGCTGATGCAGTCAAGGGCCGGTTTACTGTATCCCGCGACAA
CGCTAAGAATCTTCTCTTTCTGCAAATGAACATACTTAAGAGCGAGGATA
CTGCCATGTATTATTGTGCCCGCTTCGATTGGGATAAGAATTATTGGGGA
CAAGGCACCATGGTTACCGTTAGTAGTCCAAACATCACATCAAATAATAG
CAACCCCGTGGAAGGGGACGACTCTGTTTCACTCACCTGTGATTCCTATA
CCGATCCTGATAATATCAACTATCTATGGTCTCGTAACGGTGAAAGTCTC AGCGAAGGCGACCGGTTGAAACTCTCCGAAGGTAACAGAACCCTTACGCT
TCTGAACGTCACCCGGAACGATACCGGGCCCTATGTTTGCGAAACTAGGA
ACCCTGTTAGCGTGAATCGTAGCGACCCTTTCTCCCTAAATAATACTCTA
GTGCTATTCGGAGCGGGATTCGGTGCCGTCATCACAGTAGTCGTTATTGT
AGTCATTATTAAATGCTTTTGTAAACATAGGTCTTGCTTCAGAAGAAATG
AGGCCAGCCGTGAAACTAATAATTCCCTGACCTTTGGGCCCGAAGAAGCT
TTGGCTGAACAGACTGTGTTTCTC Anti-Mu CD3 scFv-Transmembrane (SEQ ID NO: 95)
METDTLLLWVLLLWVPGSTGDIQMTQSPSSLPASLGDRVTINCQASQDIS
NYLNWYQQKPGKAPKLLIYYTNKLADGVPSRFSGSGSGRDSSFTISSLES
EDIGSYYCQQYYNYPWTFGPGTKLEIKRGGGGSGGGGSGGGGSEVQLVES
GGGLVQPGKSLKLSCEASGFTFSGYGMHWVRQAPGRGLESVAYITSSSIN
IKYADAVKGRFTVSRDNAKNLLFLQMNILKSEDTAMYYCARFDWDKNYWG
QGTMVTVSSPNITSNNSNPVEGDDSVSLTCDSYTDPDNINYLWSRNGESL
SEGDRLKLSEGNRTLTLLNVTRNDTGPYVCETRNPVSVNRSDPFSLNNTL
VLFGAGFGAVITVVVIVVIIKCFCKHRSCFRRNEASRETNNSLTFGPEEA
LAEQTVFL Mu TSLP (SEQ ID NO: 96)
ATGGTTCTTCTCAGGAGCCTCTTCATCCTGCAAGTACTAGTACGGATGGG
GCTAACTTACAACTTTTCTAACTGCAACTTCACGTCAATTACGAAAATAT
ATTGTAACATAATTTTTCATGACCTGACTGGAGATTTGAAAGGGCTAAG
TTCGAGCAAATCGAGGACTGTGAGAGCAAGCCAGCTTGTCTCCTGAAAAT
CGAGTACTATACTCTCAATCCTATCCCTGGCTGCCCTTCACTCCCCGACA
AAACATTTGCCCGGAGAACAAGAGAAGCCCTCAATGACCACTGCCCAGGC
TACCCTGAAACTGAGAGAAATGACGGTACTCAGGAAATGGCACAAGAAG
TCCAAAACATCTGCCTGAATCAAACCTCACAAATTCTAAGATTGTGGTAT
TCCTTCATGCAATCTCCAGAA Mu TSLP (SEQ ID NO: 97)
MVLLRSLFILQVLVRMGLTYNFSNCNFTSITKIYCNIIFHDLTGDLKGAK
FEQIEDCESKPACLLKIEYYTLNPIPGCPSLPDKTFARRTREALNDHCPG
YPETERNDGTQEMAQEVQNICLNQTSQILRLWYSFMQSPE Mu GM-CSF (SEQ ID NO: 98)
ATGTGGCTGCAGAATTTACTTTTCCTGGGCATTGTGGTCTACAGCCTCTC
AGCACCCACCCGCTCACCCATCACTGTCACCCGGCCTTGGAAGCATGTAG
AGGCCATCAAAGAAGCCCTGAACCTCCTGGATGACATGCCTGTCACGTTG
AATGAAGAGGTAGAAGTCGTCTCTAACGAGTTCTCCTTCAAGAAGCTAAC -continued

ATGTGTGCAGACCCGCCTGAAGATATTCGAGCAGGGTCTACGGGGCAATT

TCACCAAACTCAAGGGCGCCTTGAACATGACAGCCAGCTACTACCAGACA

TACTGCCCCCCAACTCCGGAAACGGACTGTGAAACACAAGTTACCACCTA

TGCGGATTTCATAGACAGCCTTAAAACCTTTCTGACTGATATCCCCTTTG

AATGCAAAAAACCAGGCCAAAAA

Mu GM-CSF (SEQ ID NO: 99)
MWLQNLLFLGIVVYSLSAPTRSPITVTRPWKHVEAIKEALNLLDDMPVTL

NEEVEVVSNEFSFKKLTCVQTRLKIFEQGLRGNFTKLKGALNMTASYYQT

YCPPTPETDCETQVTTYADFIDSLKTFLTDIPFECKKPGQK

Mu IFN Gamma (SEQ ID NO: 100)
ATGAACGCTACACACTGCATCTTGGCTTTGCAGCTCTTCCTCATGGCTGT

TTCTGGCTGTTACTGCCACGGCACAGTCATTGAAAGCCTAGAAAGTCTGA

ATAACTATTTTAACTCAAGTGGCATAGATGTGGAAGAAAAGAGTCTCTTC

TTGGATATCTGGAGGAACTGGCAAAAGGATGGTGACATGAAAATCCTGCA

GAGCCAGATTATCTCTTTCTACCTCAGACTCTTTGAAGTCTTGAAAGACA

ATCAGGCCATCAGCAACAACATAAGCGTCATTGAATCACACCTGATTACT

ACCTTCTTCAGCAACAGCAAGGCGAAAAAGGATGCATTCATGAGTATTGC

CAAGTTTGAGGTCAACAACCCACAGGTCCAGCGCCAAGCATTCAATGAGC

TCATCCGAGTGGTCCACCAGCTGTTGCCGGAATCCAGCCTCAGGAAGCGG

AAAAGGAGTCGCTGC

Mu IFN Gamma (SEQ ID NO: 101)
MNATHCILALQLFLMAVSGCYCHGTVIESLESLNNYFNSSGIDVEEKSLF

LDIWRNWQKDGDMKILQSQIISFYLRLFEVLKDNQAISNNISVIESHLIT

TFFSNSKAKKDAFMSIAKFEVNNPQVQRQAFNELIRVVHQLLPESSLRKR

KRSRC

Mu IL7

(SEQ ID NO: 102)
ATGTTCCATGTTTCTTTTAGATATATCTTTGGAATTCCTCCACTGATCCT

TGTTCTGCTGCCTGTCACATCATCTGAGTGCCACATTAAAGACAAAGAAG

GTAAAGCATATGAGAGTGTACTGATGATCAGCATCGATGAATTGGACAAA

ATGACAGGAACTGATAGTAATTGCCCGAATAATGAACCAAACTTTTTTAG

AAAACATGTATGTGATGATACAAAGGAAGCTGCTTTTCTAAATCGTGCTGC

CTCGCAAGTTGAAGCAATTTCTTAAAATGAATATCAGTGAAGAATTCAAT

GTCCACTTACTAACAGTATCACAAGGCACACAAACACTGGTGAACTGCAC

AAGTAAGGAAGAAAAAAACGTAAAGGAACAGAAAAAGAATGATGCATGTT

TCCTAAAGAGACTACTGAGAGAAATAAAAACTTGTTGGAATAAAATTTTG

AAGGGCAGTATA

Mu IL7

(SEQ ID NO: 103)
MFHVSFRYIFGIPPLILVLLPVTSSECHIKDKEGKAYESVLMISIDELDK

MTGTDSNCPNNEPNFFRKHVCDDTKEAAFLNRAARKLKQFLKMNISEEFN

VHLLTVSQGTQTLVNCTSKEEKNVKEQKKNDACFLKRLLREIKTCWNKIL

KGSI

Mu ICOS-L (SEQ ID NO: 104)
ATGCAGCTAAAGTGTCCCTGTTTTGTGTCCTTGGGAACCAGGCAGCCTGT

TTGGAAGAAGCTCCATGTTTCTAGCGGGTTCTTTTCTGGTCTTGGTCTGT

TCTTGCTGCTGTTGAGCAGCCTCTGTGCTGCCTCTGCAGAGACTGAAGTC

GGTGCAATGGTGGGCAGCAATGTGGTGCTCAGCTGCATTGACCCCCACAG

ACGCCATTTCAACTTGAGTGGTCTGTATGTCTATTGGCAAATCGAAAACC

CAGAAGTTTCGGTGACTTACTACCTGCCTTACAAGTCTCCAGGGATCAAT

GTGGACAGTTCCTACAAGAACAGGGGCCATCTGTCCCTGGACTCCATGAA

GCAGGGTAACTTCTCTCTGTACCTGAAGAATGTCACCCCTCAGGATACCC

AGGAGTTCACATGCCGGGTATTTATGAATACAGCCACAGAGTTAGTCAAG

ATCTTGGAAGAGGTGGTCAGGCTGCGTGTGGCAGCAAACTTCAGTACACC

TGTCATCAGCACCTCTGATAGCTCCAACCCGGGCCAGGAACGTACCTACA

CCTGCATGTCCAAGAATGGCTACCCAGAGCCCAACCTGTATTGGATCAAC

ACAACGGACAATAGCCTAATAGACACGGCTCTGCAGAATAACACTGTCTA

CTTGAACAAGTTGGGCCTGTATGATGTAATCAGCACATTAAGGCTCCCTT

GGACATCTCGTGGGGATGTTCTGTGCTGCGTAGAGAATGTGGCTCTCCAC

CAGAACATCACTAGCATTAGCCAGGCAGAAAGTTTCACTGGAAATAACAC

AAAGAACCCACAGGAAACCCACAATAATGAGTTAAAAGTCCTTGTCCCCG

TCCTTGCTGTACTGGCGGCAGCGGCATTCGTTTCCTTCATCATATACAGA

CGCACGCGTCCCCACCGAAGCTATACAGGACCCAAGACTGTACAGCTTGA

ACTTACAGACCACGCC

Mu ICOS-L (SEQ ID NO: 105)
MQLKCPCFVSLGTRQPVWKKLHVSSGFFSGLGLFLLLLSSLCAASAETEV

GAMVGSNVVLSCIDPHRRHFNLSGLYVYWQIENPEVSVTYYLPYKSPGIN

VDSSYKNRGHLSLDSMKQGNFSLYLKNVTPQDTQEFTCRVFMNTATELVK

ILEEVVRLRVAANFSTPVISTSDSSNPGQERTYTCMSKNGYPEPNLYWIN

TTDNSLIDTALQNNTVYLNKLGLYDVISTLRLPWTSRGDVLCCVENVALH

QNITSISQAESFTGNNTKNPQETHNNELKVLVPVLAVLAAAAFVSFIIYR

RTRPHRSYTGPKTVQLELTD HA

Mu CD47

(SEQ ID NO: 106)
ATGTGGCCCTTGGCGGCGGCGCTGTTGCTGGGCTCCTGCTGCTGCGGTTC

AGCTCAACTACTGTTTAGTAACGTCAACTCCATAGAGTTCACTTCATGCA

ATGAAACTGTGGTCATCCCTTGCATCGTCCGTAATGTGGAGGCGCAAAGC

ACCGAAGAAATGTTTGTGAAGTGGAAGTTGAACAAATCGTATATTTTCAT

CTATGATGGAAATAAAAATAGCACTACTACAGATCAAAACTTTACCAGTG

CAAAAATCTCAGTCTCAGACTTAATCAATGGCATTGCCTCTTTGAAAATG

GATAAGCGCGATGCCATGGTGGGAAACTACACTTGCGAAGTGACAGAGTT

ATCCAGAGAAGGCAAAACAGTTATAGAGCTGAAAAACCGCACGGTTTCGT

GGTTTTCTCCAAATGAAAAGATCCTCATTGTTATTTTCCCAATTTTGGCT

ATACTCCTGTTCTGGGGAAAGTTTGGTATTTTAACACTCAAATATAAATC

CAGCCATACGAATAAGAGAATCATTCTGCTGCTCGTTGCCGGGCTGGTGC

TCACAGTCATCGTGGTTGTTGGAGCCATCCTTCTCATCCCAGGAGAAAAG

CCCGTGAAGAATGCTTCTGGACTTGGCCTCATTGTAATCTCTACGGGGAT

ATTAATACTACTTCAGTACAATGTGTTTATGACAGCTTTTGGAATGACCT

CTTTCACCATTGCCATATTGATCACTCAAGTGCTGGGCTACGTCCTTGCT

TTGGTCGGGCTGTGTCTCTGCATCATGGCATGTGAGCCAGTGCACGGCCC

CCTTTTGATTTCAGGTTTGGGGATCATAGCTCTAGCAGAACTACTTGGAT

TAGTTTATATGAAGTTTGTCGCTTCCAACCAGAGGACTATCCAACCTCCT

AGGAATAGG

Mu CD47

(SEQ ID NO: 107)
MWPLAAALLLGSCCCGSAQLLFSNVNSIEFTSCNETVVIPCIVRNVEAQS

TEEMFVKWKLNKSYIFIYDGNKNSTTTDQNFTSAKISVSDLINGIASLKM

DKRDAMVGNYTCEVTELSREGKTVIELKNRTVSWFSPNEKILIVIFPILA

ILLFWGKFGILTLKYKSSHTNKRIILLLVAGLVLTVIVVVGAILLIPGEK

PVKNASGLGLIVISTGILILLQYNVFMTAFGMTSFTIAILITQVLGYVLA

LVGLCLCIMACEPVHGPLLISGLGIIALAELLGLVYMKFVASNQRTIQPP

RNR

Mu Sarcoglycan Alpha:

(SEQ ID NO: 108)
ATGGCAGCAGCAGTAACTTGGATACCTCTCCTGGCAGGTCTCCTGGCAGG

ACTGAGGGACACCAAGGCCCAGCAGACAACTTTACACCTACTTGTGGGTC

GTGTGTTTGTGCATCCTTTGGAACATGCCACCTTCCTGCGCCTTCCAGAA

CACGTTGCGGTGCCACCCACTGTCCGACTCACCTACCACGCTCACCTCCA

GGGACATCCAGACCTGCCCAGGTGGCTGCACTACACACAGCGCAGTCCCT

ATAACCCTGGCTTCCTCTACGGCTCCCCCACTCCAGAAGATCGTGGGTAC

CAAGTCATCGAGGTCACAGCCTACAATCGAGACAGTTTTGACACCACTAG

ACAGAGGCTGCTGCTGCTGATTGGGGACCCCGAAGGTCCCCGGTTGCCAT

ACCAAGCTGAGTTCCTGGTGCGCAGCCATGATGTGGAGGAGGTGCTGCCC

ACCACACCTGCCAACCGCTTCCTCACCGCCTTGGGGGGACTGTGGGAGCC

AGGAGAGCTTCAGCTGCTCAACATCACTTCCGCCTTGGACCGGGGAGGCC

GAGTCCCTCTTCCTATTGAGGGACGGAAGGAAGGGGTATACATTAAGGTA

GGCTCTGCCACACCCTTCTCCACCTGCCTGAAGATGGTGGCGTCGCCCGA

CAGCTATGCCCGTTGTGCCCAGGGACAGCCTCCACTACTGTCCTGCTACG

ACACTTTGGCACCCCACTTCCGCGTTGACTGGTGCAATGTGTCTCTGGTA

GACAAGTCAGTACCCGAGCCCCTGGATGAGGTACCTACTCCAGGCGATGG

GATCTTGGAGCACGACCCGTTCTTCTGCCCACCCACTGAAGCCACAGACC

GAGACTTCCTGACAGATGCCTTGGTGACCCTCTTGGTGCCTTTGTTGGTG

GCTCTGCTGCTTACTCTGTTGCTGGCTTACATCATGTGCTTTCGGCGTGA

AGGACGGCTGAAGAGAGACATGGCCACCTCTGACATCCAGATGTTTCACC

ACTGTTCCATCCATGGAATACAGAAGAGCTTCGGCAGATGGCAGCCAGC

CGAGAGGTGCCCCGGCCTCTTTCCACCTTGCCCATGTTTAATGTTCGTAC

AGGAGAGCGGTTACCTCCCCGAGTAGACAGCGCACAGATGCCTCTTATCC

TGGACCAGCAC

Mu Sarcoglycan Alpha:

(SEQ ID NO: 109)
MAAAVTWIPLLAGLLAGLRDTKAQQTTLHLLVGRVFVHPLEHATFLRLPE

HVAVPPTVRLTYHAHLQGHPDLPRWLHYTQRSPYNPGFLYGSPTPEDRGY

QVIEVTAYNRDSFDTTRQRLLLLIGDPEGPRLPYQAEFLVRSHDVEEVLP

TTPANRFLTALGGLWEPGELQLLNITSALDRGGRVPLPIEGRKEGVYIKV

GSATPFSTCLKMVASPDSYARCAQGQPPLLSCYDTLAPHFRVDWCNVSLV

DKSVPEPLDEVPTPGDGILEHDPFFCPPTEATDRDFLTDALVTLLVPLLV

ALLLTLLLAYIMCFRREGRLKRDMATSDIQMFHHCSIHGNTEELRQMAAS

REVPRPLSTLPMFNVRTGERLPPRVDSAQM PLILDQH

Mu FGF10

(SEQ ID NO: 110)
ATGTGGAAATGGATACTGACACATTGTGCCTCAGCCTTTCCCCACCTGCC

GGGCTGCTGTTGCTGCTTCTTGTTGCTCTTTTTGGTGTCTTCGTTCCCTG

TCACCTGCCAAGCTCTTGGTCAGGACATGGTGTCACAGGAGGCCACCAAC

TGCTCTTCTTCCTCCTCGTCCTTCTCCTCTCCTTCCAGTGCGGGAAGGCA

TGTGCGGAGCTACAATCACCTCCAAGGAGATGTCCGCTGGAGAAGGCTGT

TCTCCTTCACCAAGTACTTTCTCACGATTGAGAAGAACGGCAAGGTCAGC

GGGACCAAGAATGAAGACTGTCCGTACAGTGTCCTGGAGATAACATCAGT

GGAAATCGGAGTTGTTGCCGTCAAAGCCATCAACAGCAACTATTACTTAG

CCATGAACAAGAAGGGGAAACTCTATGGCTCAAAAGAGTTTAACAACGAC

TGTAAGCTGAAAGAGAGAATAGAGGAAAATGGATACAACACCTATGCATC

TTTTAACTGGCAGCACAATGGCAGGCAAATGTATGTGGCATTGAATGAA

Mu FGF10

(SEQ ID NO: 111)
MWKWILTHCASAFPHLPGCCCCFLLLFLVSSFPVTCQALGQDMVSQEATN
CSSSSSSFSSPSSAGRHVRSYNHLQGDVRWRRLFSFTKYFLTIEKNGKVS
GTKNEDCPYSVLEITSVEIGVVAVKAINSNYYLAMNKKGKLYGSKEFNND
CKLKERIEENGYNTYASFNWQHNGRQMYVALNGKGAPRRGQKTRRKNTSA
HFLPMTIQT

Mu Agrin (SEQ ID NO: 112)
ATGCCTCCTCTGCCACTGGAACACAGACCCAGGCAGCAGCCTGGTGCCTC
CGTGCTGGTTCGGTACTTCATGATCCCCTGCAACATCTGCTTGATCCTCT
TGGCTACTTCTACGTTGGGCTTTGCGGTGCTGCTTTTCCTCAGCAACTAC
AAACCTGGGATCCACTTCACAGCAGCGCCTTCTATGCCTCCTGATGTGTG
CAGGGGAATGTTATGTGGCTTTGGTGCTGTGTGTGAACCTAGTGTTGAGG
ATCCAGGCCGGGCCTCCTGTGTGTGCAAGAAGAATGTCTGCCCTGCTATG
GTAGCTCCTGTGTGTGGCTCAGATGCTTCCACCTATAGCAACGAGTGTGA
GCTACAGCGTGCACAGTGCAACCAGCAACGGCGCATCCGCCTACTCCGCC
AAGGGCCATGTGGGTCCCGGGACCCCTGTGCCAATGTGACCTGCAGTTTC
GGTAGTACCTGTGTACCTTCAGCCGATGGACAGACCGCCTCGTGTCTGTG
TCCTACAACCTGCTTTGGGGCCCCTGATGGCACAGTGTGTGGCAGTGATG
GTGTTGACTACCCTAGTGAGTGCCAGCTGCTCCGTCATGCCTGTGCCAAC
CAGGAGCACATCTTTAAGAAGTTCGATGGTCCTTGTGACCCCTGCCAGGG
CAGCATGTCAGACCTGAATCATATTTGCCGGGTGAACCCACGTACACGGC
ACCCAGAAATGCTTCTGCGGCCTGAGAACTGCCCCGCCCAACACACACCT
ATCTGTGGAGATGATGGGGTCACCTATGAAAACGACTGTGTCATGAGCCG
TATAGGTGCAGCCCGTGGCCTGCTTCTCCAGAAAGTGCGCTCTGGTCAAT
GCCAGACTCGAGACCAGTGCCCGGAGACCTGCCAGTTTAACTCTGTATGC
CTGTCCCGCCGCGCCGTCCCCACTGTTCCTGCGATCGCGTCACCTGTGA
TGGGGCTTACAGGCCAGTGTGTGCCCAGGATGGGCACACGTATGACAATG
ACTGTTGGCGCCAACAGGCCGAGTGTCGACAACAGCAGACCATTCCCCCC
AAGCACCAGGGCCCGTGTGACCAGACCCCATCCCCGTGCCGTGGAGCGCA
GTGTGCATTTGGGGCAACATGCACAGTGAAGAATGGGAAAGCTGTGTGCG
AGTGCCAGCGGGTGTGCTCGGCGGCTACGATCCTGTGTGCGGCAGTGAT
GGTGTCACTTACGGCAGTGTGTGCGAGCTGGAATCCATGGCCTGTACCCT
TGGGCGGGAAATCCGAGTGGCCCGCAGAGGACCGTGTGACCGATGTGGGC
AGTGCCGGTTTGGATCCTTGTGCGAGGTGGAGACTGGACGCTGTGTGTGC
CCCTCTGAGTGTGTGGAGTCAGCCCAGCCCGTATGTGGCTCTGACGGACA
CACATATGCTAGTGAATGTGAGCTGCATGTCCACGCCTGTACACACCAGA
TCAGCCTATACGTGGCCTCAGCCGGACACTGCCAGACCTGTGGAGAAACA
GTTTGTACCTTTGGGGCTGTGTGCTCAGCTGGACAGTGTGTATGTCCCCG
TTGTGAGCACCCCCCACCTGGCCCTGTGTGCGGCAGTGATGGCGTCACCT
ACCTCAGTGCCTGTGAGCTCCGAGAGGCTGCCTGTCAGCAGCAGGTACAA
ATTGAGGAGGCCCGTGCAGGGCCGTGTGAGCCGGCTGAGTGTGGCTCAGG
GGGCTCTGGGTCTGGGGAAGACAATGCGTGTGAGCAGGAGCTGTGTCGGC
AGCATGGTGGTGTCTGGGATGAGGACTCAGAAGACGGGCCGTGTGTCTGT
GACTTTAGTTGCCAGAGTGTCCTTAAAAGCCCAGTGTGTGGCTCAGATGG
AGTCACCTATAGCACGGAGTGCCATCTGAAGAAGGCCAGATGTGAAGCGC
GGCAAGAGCTGTACGTCGCTGCTCAGGGAGCCTGCCGGGCCCTACCTTG
GCTCCACTGCTACCTATGGCCTCCCCACACTGTGCCCAAACCCCCTATGG
CTGCTGCCAGGACAATGTCACTGCTGCCCAGGGTGTGGGCTTGGCTGGCT
GTCCCAGCACCTGCCATTGCAACCCACACGGCTCCTATAGCGGCACTTGT
GACCCAGTCACAGGGCAGTGCTCCTGCCGACCAGGTGTAGGAGGCCTCAG
GTGTGATCGCTGTGAGCCTGGCTTCTGGAACTTCCGTGGCATTGTCACCG
ATGGACATAGTGGTTGCACTCCCTGCAGCTGTGACCCTCGGGGTGCTGTA
AGAGATGACTGTGAGCAGATGACTGGATTGTGTTCCTGTAGACCTGGTGT
GGCTGGTCCCAAGTGTGGGCAGTGTCCAGATGGTCAAGCCCTGGGCCATC
TTGGCTGTGAAGCAGATCCCACAACACCAGTGACTTGTGTGGAAATGCAC
TGTGAGTTTGGCGCCTCCTGCGTAGAGGAGGCTGGTTTTGCCCAGTGTGT
CTGCCCAACTCTCACATGTCCAGAGGCTAACTCTACCAAGGTCTGTGGAT
CAGATGGTGTCACATACGGCAATGAATGCCAGCTGAAGACCATTGCCTGC
CGCCAGCGTCTGGACATCTCCATTCAGAGTCTTGGTCCATGCCGGGAGAG
TGTTGCTCCTGGGGTTTCCCCTACATCTGCATCTATGACCACCCCAAGGC
ATATCCTGAGCAGGACACTGGCGTCTCCCCACAGCAGCCTTCCTCTGTCT
CCCAGCACTACTGCCCATGATTGGCCCACCCCATTACCCACATCACCTCA
GACCGTAGTCGGCACCCCCAGGAGCACTGCAGCCACACCCTCTGATGTGG
CCAGTCTTGCTACAGCGATCTTCAGGGAATCTGGCAGCACCAACGGCAGT
GGCGATGAGGAGCTCAGTGGCGATGAGGAGGCCAGTGGGGGGGTCTGGG
GGACTTGAGCCCCGGTGGGCAGCGTTGTGGTGACCCACGGGCCACCCAT
CGAGAGGGCTTCCTGTTACAACTCACCTTTGGGCTGCTGCTCAGATGGCA
AGACACCCTCACTGGACTCAGAAGGCTCCAACTGTCCAGCTACCAAGGCA
TTCCAGGGCGTGCTGGAGCTTGAGGGGGTCGAGGGACAGGAACTGTTCTA
CACACCAGAGATGGCTGACCCCAAGTCAGAGTTGTTTGGGGAGACTGCAA
GGAGCATTGAGAGCACGCTGGACGACCTGTTCCGGAATTCGGATGTTAAG
AAGGACTTCTGGAGCATCCGCCTACGGGAACTGGGGCCTGGCAAATTAGT
CCGTGCCATTGTGGATGTTCACTTTGACCCCACCACAGCCTTCCAGGCAC
CAGATGTGGGTCAGGCCTTGCTCCAACAGATCCAGGTATCCAGGCCGTGG
GCCCTGGCAGTGAGGAGGCCTCTGCGGGAGCATGTGCGATTCTTGGACTT
TGACTGGTTTCCCACTTTTTTTACGGGAGCTGCAACAGGAACCACAGCTG -continued

```
CTGTGGCCACAGCCAGAGCCACCACTGTGAGCCGACTGTCTGCCTCTTCT
GTCACCCCACGAGTCTACCCCAGTTACACCAGCCGGCCTGTTGGCAGAAC
TACGGCACCGCTAACCACTCGCCGGCCACCAACCACTACCGCCAGTATTG
ACCGACCTCGGACTCCAGGCCCGCAACGGCCCCCAAAGTCCTGTGATTCC
CAGCCTTGCCTCCACGGAGGTACCTGCCAGGACCTGGATTCTGGCAAGGG
TTTCAGCTGCAGCTGTACTGCAGGCAGGGCTGGCACTGTCTGTGAGAAAG
TGCAGCTCCCTCTGTGCCAGCTTTTAAGGGCCACTCCTTCTTGGCCTTC
CCCACCCTCCGAGCCTACCACACGCTGCGTCTGGCACTAGAATTCCGGGC
GCTGGAGACAGAGGGACTGCTGCTCTACAATGGCAATGCACGTGGCAAAG
ATTTCCTGGCTCTGGCTCTGTTGGATGGTCATGTACAGTTCAGGTTCGAC
ACGGGCTCAGGGCCGGCGGTGCTAACAAGCTTAGTGCCAGTGGAACCGGG
ACGGTGGCACCGCCTCGAGTTGTCACGGCATTGGCGGCAGGGCACACTTT
CTGTGGATGGCGAGGCTCCTGTTGTAGGTGAAAGTCCGAGTGGCACTGAT
GGCCTCAACTTGGACACGAAGCTCTATGTGGGTGGTCTCCCAGAAGAACA
AGTTGCCACGGTGCTTGATCGGACCTCTGTGGGCATCGGCCTGAAAGGAT
GCATTCGTATGTTGGACATCAACAACCAGCAGCTGGAGCTGAGCGATTGG
CAGAGGGCTGTGGTTCAAAGCTCTGGTGTGGGGAATGCGGAGACCATCC
CTGCTCACCTAACCCCTGCCATGGCGGGGCCCTCTGCCAGGCCCTGGAGG
CTGGCGTGTTCCTCTGTCAGTGCCCACCTGGCCGCTTTGGCCCAACTTGT
GCAGATGAAAAGAACCCCTGCCAACCGAACCCCTGCCACGGGTCAGCCCC
CTGCCATGTGCTTTCCAGGGGTGGGGCCAAGTGTGCGTGCCCCCTGGGAC
GCAGTGGTTCCTTCTGTGAGACAGTCCTGGAGAATGCTGGCTCCCGGCCC
TTCCTGGCTGACTTTAATGGCTTCTCCTACCTGGAACTGAAAGGCTTGCA
CACCTTCGAGAGAGACCTAGGGGAGAAGATGGCGCTGGAGATGGTGTTCT
TGGCTCGTGGGCCCAGTGGCTTACTCCTCTACAATGGGCAGAAGACGGAT
GGCAAGGGGGACTTTGTATCCCTGGCCCTGCATAACCGGCACCTAGAGTT
CCGCTATGACCTTGGCAAGGGGGCTGCAATCATCAGGAGCAAAGAGCCCA
TAGCCCTGGGCACCTGGGTTAGGGTATTCCTGGAACGAAATGGCCGCAAG
GGTGCCCTTCAAGTGGGTGATGGGCCCCGTGTGCTAGGGGAATCTCCGAA
ATCCCGCAAGGTCCCGCACACCATGCTCAACCTCAAGGAGCCCCTCTATG
TGGGGGGAGCTCCTGACTTCAGCAAGCTGGCTCGGGGCGCTGCAGTGGCC
TCCGGCTTTGATGGTGCCATCCAGCTGGTGTCTCTAAGAGGCCATCAGCT
GCTGACTCAGGAGCATGTGTTGCGGGCAGTAGATGTAGCGCCTTTTGCAG
GCCACCCTTGTACCCAGGCCGTGGACAACCCCTGCCTTAATGGGGGCTCC
TGTATCCCGAGGGAAGCCACTTATGAGTGCCTGTGTCCTGGGGGCTTCTC
TGGGCTGCACTGCGAGAAGGGGATAGTTGAGAAGTCAGTGGGGGACCTAG
AAACACTGGCCTTTGATGGGCGGACCTACATCGAGTACCTCAATGCTGTG
ACTGAGAGCGAGCTGACCAATGAGATCCCAGCCCCCGAAACTCTGGATTC
CCGGGCCCTTTTCAGTGAGAAAGCGCTGCAGAGCAACCACTTTGAGCTGA
GCTTACGCACTGAGGCCACGCAGGGGCTGGTGCTGTGGATTGGAAAGGTT
GGAGAACGTGCAGACTACATGGCTCTGGCCATTGTGGATGGGCACCTACA
```

-continued

```
ACTGAGCTATGACCTAGGCTCCCAGCCAGTTGTGCTGCGCTCCACTGTGA
AGGTCAACACCAACCGCTGGCTTCGAGTCAGGGCTCACAGGGAGCACAGG
GAAGGTTCCCTTCAGGTGGGCAATGAAGCCCCTGTGACTGGCTCTTCCCC
GCTGGGTGCCACACAATTGGACACAGATGGAGCCCTGTGGCTTGGAGGCC
TACAGAAGCTTCCTGTGGGCAGGCTCTCCCCAAGGCCTATGGCACGGGT
TTTGTGGGCTGTCTGCGGGACGTGGTAGTGGGCCATCGCCAGCTGCATCT
GCTGGAGGACGCTGTCACCAAACCAGAGCTAAGACCCTGCCCCACTCTCT
GA
```

Mu Agrin (SEQ ID NO: 113)
MPPLPLEHRPRQQPGASVLVRYFMIPCNICLILLATSTLGFAVLLFLSNY
KPGIHFTAAPSMPPDVCRGMLCGFGAVCEPSVEDPGRASCVCKKNVCPAM
VAPVCGSDASTYSNECELQRAQCNQQRRIRLLRQGPCGSRDPCANVTCSF
GSTCVPSADGQTASCLCPTTCFGAPDGTVCGSDGVDYPSECQLLRHACAN
QEHIFKKFDGPCDPCQGSMSDLNHICRVNPRTRHPEMLLRPENCPAQHTP
ICGDDGVTYENDCVMSRIGAARGLLLQKVRSGQCQTRDQCPETCQFNSVC
LSRRGRPHCSCDRVTCDGAYRPVCAQDGHTYDNDCWRQQAECRQQQTIPP
KHQGPCDQTPSPCRGAQCAFGATCTVKNGKAVCECQRVCSGGYDPVCGSD
GVTYGSVCELESMACTLGREIRVARRGPCDRCGQCRFGSLCEVETGRCVC
PSECVESAQPVCGSDGHTYASECELHVHACTHQISLYVASAGHCQTCGET
VCTFGAVCSAGQCVCPRCEHPPPGPVCGSDGVTYLSACELREAACQQQVQ
IEEARAGPCEPAECGSGGSGSGEDNACEQELCRQHGGVWDEDSEDGPCVC
DFSCQSVLKSPVCGSDGVTYSTECHLKKARCEARQELYVAAQGACRGPTL
APLLPMASPHCAQTPYGCCQDNVTAAQGVGLAGCPSTCHCNPHGSYSGTC
DPVTGQCSCRPGVGGLRCDRCEPGFWNFRGIVTDGHSGCTPCSCDPRGAV
RDDCEQMTGLCSCRPGVAGPKCGQCPDGQALGHLGCEADPTTPVTCVEMH
CEFGASCVEEAGFAQCVCPTLTCPEANSTKVCGSDGVTYGNECQLKTIAC
RQRLDISIQSLGPCRESVAPGVSPTSASMTTPRHILSRTLASPHSSLPLS
PSTTAHDWPTPLPTSPQTVVGTPRSTAATPSDVASLATAIFRESGSTNGS
GDEELSGDEEASGGGSGGLEPPVGSVVVTHGPPIERASCYNSPLGCCSDG
KTPSLDSEGSNCPATKAFQGVLELEGVEGQELFYTPEMADPKSELFGETA
RSIESTLDDLFRNSDVKKDFWSIRLRELGPGKLVRAIVDVHFDPTTAFQA
VPDGQALLQQIQVSRPWALAVRRPLREHVRFLDFDWFPTFFTGAATGTTA
AVATARATTVSRLSASSVTPRVYPSYTSRPVGRTTAPLTTRRPPTTTASI
DRPRTPGPQRPPKSCDSQPCLHGGTCQDLDSGKGFSCSCTAGRAGTVCEK
VQLPSVPAFKGHSFLAFPTLRAYHTLRLALEFRALETEGLLLYNGNARGK
DFLALALLDGHVQFRFDTGSGPAVLTSLVPVEPGRWHRLELSRHWRQGTL
SVDGEAPVVGESPSGTDGLNLDTKLYVGGLPEEQVATVLDRTSVGIGLKG
CIRMLDINNQQLELSDWQRAVVQSSGVGECGDHPCSPNPCHGGALCQALE
AGVFLCQCPPGRFGPTCADEKNPCQPNPCHGSAPCHVLSRGGAKCACPLG
```

-continued

RSGSFCETVLENAGSRPFADFNGFSYLELKGLHTFERDLGEKMALEMVFL
ARGPSGLLLYNGQKTDGKGDFVSLALHNRHLEFRYDLGKGAAIIRSKEPI
ALGTWVRVFLERNGRKGALQVGDGPRVLGESPKSRKVPHTMLNLKEPLYV
GGAPDFSKLARGAAVASGFDGAIQLVSLRGHQLLTQEHVLRAVDVAPFAG
HPCTQAVDNPCLNGGSCIPREATYECLCPGGFSGLHCEKGIVEKSVGDLE
TLAFDGRTYIEYLNAVTESELTNEIPAPETLDSRALFSEKALQSNHFELS
LRTEATQGLVLWIGKVGERADYMALAIVDGHLQLSYDLGSQPVVLRSTVK
VNTNRWLRVRAHREHREGSLQVGNEAPVTGSSPLGATQLDTDGALWLGGL
QKLPVGQALPKAYGTGFVGCLRDVVVGHRQLHLLEDAVTKPELRPCPTL

Mu IL10

(SEQ ID NO: 114)
ATGCCTGGCTCAGCACTGCTATGCTGCCTGCTCTTACTGACTGGCATGAG
GATCAGCAGGGGCCAGTACAGCCGGGAAGACAATAACTGCACCCACTTCC
CAGTCGGCCAGAGCCACATGCTCCTAGAGCTGCGGACTGCCTTCAGCCAG
GTGAAGACTTTCTTTCAAACAAAGGACCAGCTGGACAACATACTGCTAAC
CGACTCCTTAATGCAGGACTTTAAGGGTTACTTGGGTTGCCAAGCCTTAT
CGGAAATGATCCAGTTTTACCTGGTAGAAGTGATGCCCCAGGCAGAGAAG
CATGGCCCAGAAATCAAGGAGCATTTGAATTCCCTGGGTGAGAAGCTGAA
GACCCTCAGGATGCGGCTGAGGCGCTGTCATCGATTTCTCCCCTGTGAAA
ATAAGAGCAAGGCAGTGGAGCAGGTGAAGAGTGATTTTAATAAGCTCCAA
GACCAAGGTGTCTACAAGGCCATGAATGAATTTGACATCTTCATCAACTG
CATAGAAGCATACATGATGATCAAAATGAAAAGCTAA

Mu IL10

(SEQ ID NO: 115)
MPGSALLCCLLLLTGMRISRGQYSREDNNCTHFPVGQSHMLLELRTAFSQ
VKTFFQTKDQLDNILLTDSLMQDFKGYLGCQALSEMIQFYLVEVMPQAEK
HGPEIKEHLNSLGEKLKTLRMRLRRCHRFLPCENKSKAVEQVKSDFNKLQ
DQGVYKAMNEFDIFINCIEAYMMIKMKS

Mu MYDGF (C19orf10)

(SEQ ID NO: 116)
ATGGCAGCCCCCAGCGGAGGCTTCTGGACTGCGGTGGTCCTGGCGGCCG
CAGCGCTGAAATTGGCCGCCGCTGTGTCCGAGCCCACCACCGTGCCATT
TGACGTGAGGCCCGGAGGGGTCGTGCATTCGTTCTCCCAGGACGTAGGA
CCCGGGAACAAGTTTACATGTACATTCACCTACGCTTCCCAAGGAGGGA
CCAACGAGCAATGGCAGATGAGCCTGGGGACAAGTGAAGACAGCCAGCA
CTTTACCTGTACCATCTGGAGGCCCCAGGGGAAATCCTACCTCTACTTC
ACACAGTTCAAGGCTGAGTTGCGAGGTGCTGAGATCGAGTATGCCATGG
CCTACTCCAAAGCCGCATTTGAGAGAGAGAGTGATGTCCCCCTGAAAAG
TGAGGAGTTTGAAGTGACCAAGACAGCAGTGTCTCACAGGCCTGGGGCC

-continued
TTCAAAGCTGAGCTCTCCAAGCTGGTGATCGTAGCCAAGGCGGCACGCT
CGGAGCTGTGA

Mu MYDGF (C19orf10)

(SEQ ID NO: 117)
MAAPSGGFWTAVVLAAAALKLAAAVSEPTTVPFDVRPGGVVHSFSQDVGP
GNKFTCTFTYASQGGTNEQWQMSLGTSEDSQHFTCTIWRPQGKSYLYFTQ
FKAELRGAEIEYAMAYSKAAFERESDVPLKSEEFEVTKTAVSHRPGAFKA
ELSKLVIVAKAARSEL pWF-521

(SEQ ID NO: 118)
CAGTCTGTGTTGACGCAGCCGCCCTCAGTGTCTGCGGCCCCAGGACAGAG
GGTCACCATCTCCTGCTCTGGAACCAGGTCCAACATTGGGAGTGATTATG
TTTCCTGGTACCAACACCTCCCAGGAACAGCCCCCAAACTCCTCGTTTAT
GGCGATAATCTGCGACCCTCAGGGATTCCTGACCGATTCTCTGCCTCCAA
GTCTGGCACGTCAGCCACCCTGGGCATCACCGGACTCCAGACTGGGGACG
AGGCCGATTATTACTGCGGCACATGGGATTACACCCTGAATGGTGTGGTG
TTCGGCGGAGGGACCAAGCTGACCGTCCTAGGTCAGCCCAAGGCCAACCC
CACTGTCACTCTGTTCCCGCCCTCCTCTGAGGAGCTCCAAGCCAACAAGG
CCACACTAGTGTGTCTGATCAGTGACTTCTACCCGGGAGCTGTGACAGTG
GCCTGGAAGGCAGATGGCAGCCCCGTCAAGGCGGGAGTGGAGACCACCAA
ACCCTCCAAACAGAGCAACAACAAGTACGCGGCCAGCAGCTACCTGAGCC
TGACGCCCGAGCAGTGGAAGTCCCACAGAAGCTACAGCTGCCAGGTCACG
CATGAAGGGAGCACCGTGGAGAAGACAGTGGCCCCTACAGAATGTTCAGG
CGCCGGATCTGGTGGAAACTGGAGTCATCCCCAATTCGAGAAGGGCGGAA
GCGGTGGGAGTGGCGGGTCCGGTGGAAGCAACTGGTCACACCCACAATTC
GAGAAAGGCGGTTCTGGCGGATCTGGTGGATCTGGCGGAAGTAACTGGTC
TCATCCTCAATTCGAAAAGGGCGGAAGCGGTGGCGGCAGGCTAGGTGGAG
GCTCAGTGCAGGTGCAGCTGGTGGAGTCTGGGGGAGGCTTGGTACAGCCT
GGGGGGTCCCTGAGACTCTCCTGTGCAGCCTCTGGATTCACCTTTAGCAG
CTATGCCATGAGCTGGGTCCGCCAGGCTCCAGGGAAGGGGCTGGAGTGGG
TCTCAGTTATTTATAGCGGTGGTAGTAGCACATACTATGCAGACTCCGTG
AAGGGCCGGTTCACCATCTCCAGAGATAATTCCAAGAACACGCTGTATCT
GCAAATGAACAGCCTGAGAGCCGAGGACACGGCCGTATATTACTGTGCGC
GCACTTCTTACCTGAACCATGGTGATTACTGGGGTCAAGGTACTCTGGTG
ACCGTGTCTAGCGCCTCCACCAAGGGCCCATCGGTCTTCCCCCTGGCACC
CTCCTCCAAGAGCACCTCTGGGGGCACAGCGGCCCTGGGCTGCCTGGTCA
AGGACTACTTCCCCGAACCGGTGACGGTGTCGTGGAACTCAGGCGCCCTG
ACCAGCGGCGTGCACACCTTCCCGGCTGTCCTACAGTCCTCAGGACTCTA
CTCCCTCAGCAGCGTGGTGACCGTGCCCTCCAGCAGCTTGGGCACCCAGA
CCTACATCTGCAACGTGAACCACAAGCCCAGCAACACCAAGGTGGACAAG

-continued

AGAGTGGAGCCCAAGAGCTGCGACAAGACCCACACCTGCCCCCCCTGCCC
AGCCCCAGAGCTGCTGGGCGGACCCTCCGTGTTCCTGTTCCCCCCCAAGC
CCAAGGACACCCTGATGATCAGCAGGACCCCCGAGGTGACCTGCGTGGTG
GTGGACGTGAGCCACGAGGACCCAGAGGTGAAGTTCAACTGGTACGTGGA
CGGCGTGGAGGTGCACAACGCCAAGACCAAGCCCAGAGAGGAGCAGTACA
ACAGCACCTACAGGGTGGTGTCCGTGCTGACCGTGCTGCACCAGGACTGG
CTGAACGGCAAGGAATACAAGTGCAAGGTCTCCAACAAGGCCCTGCCAGC
CCCCATCGAAAAGACCATCAGCAAGGCCAAGGGCCAGCCACGGGAGCCCC
AGGTGTACACCCTGCCCCCCTCCCGGGAGGAGATGACCAAGAACCAGGTG
TCCCTGACCTGTCTGGTGAAGGGCTTCTACCCCAGCGACATCGCCGTGGA
GTGGGAGAGCAACGGCCAGCCCGAGAACAACTACAAGACCACCCCCCCAG
TGCTGGACAGCGACGGCAGCTTCTTCCTGTACAGCAAGCTGACCGTGGAC
AAGTCCAGGTGGCAGCAGGGCAACGTGTTCAGCTGCAGCGTGATGCACGA
GGCCCTGCACAACCACTACACCCAGAAGAGCCTGAGCCTGTCCCCCGAGC
TGCAACTGGAGGAGAGCTGTGCGGAGGCGCAGGACGGGGAGCTGGACGGG
CTGTGGACGACCATCACCATCTTCATCACACTCTTCCTGTTAAGCGTGTG
CTACAGTGCCACCGTCACCTTCTTCAAGGTGAAGTGGATCTTCTCCTCGG
TGGTGGACCTGAAGCAGACCATCATCCCCGACTACAGGAACATGATCGGA
CAGGGGGCCTGA pWF-521

(SEQ ID NO: 119)
QSVLTQPPSVSAAPGQRVTISCSGTRSNIGSDYVSWYQHLPGTAPKLLVY
GDNLRPSGIPDRFSASKSGTSATLGITGLQTGDEADYYCGTWDYTLNGVV
FGGGTKLTVLGQPKANPTVTLFPPSSEELQANKATLVCLISDFYPGAVTV
AWKADGSPVKAGVETTKPSKQSNNKYAASSYLSLTPEQWKSHRSYSCQVT
HEGSTVEKTVAPTECSGAGSGGNWSHPQFEKGGSGGSGGSGGSNWSHPQF
EKGGSGGSGGSGGSNWSHPQFEKGGSGGGRLGGGSVQVQLVESGGGLVQP
GGSLRLSCAASGFTFSSYAMSWVRQAPGKGLEWVSVIYSGGSSTYYADSV
KGRFTISRDNSKNTLYLQMNSLRAEDTAVYYCARTSYLNHGDYWGQGTLV
TVSSASTKGPSVFPLAPSSKSTSGGTAALGCLVKDYFPEPVTVSWNSGAL
TSGVHTFPAVLQSSGLYSLSSVVTVPSSSLGTQTYICNVNHKPSNTKVDK
RVEPKSCDKTHTCPPCPAPELLGGPSVFLFPPKPKDTLMISRTPEVTCVV
VDVSHEDPEVKFNWYVDGVEVHNAKTKPREEQYNSTYRVVSVLTVLHQDW
LNGKEYKCKVSNKALPAPIEKTISKAKGQPREPQVYTLPPSREEMTKNQV
SLTCLVKGFYPSDIAVEWESNGQPENNYKTTPPVLDSDGSFFLYSKLTVD
KSRWQQGNVFSCSVMHEALHNHYTQKSLSLSPELQLEESCAEAQDGELDG
LWTTITIFITLFLLSVCYSATVTFFKVKWIFSSVVDLKQTIIPDYRNMIG
QGA pWF-533

(SEQ ID NO: 120)
CAGTCTGTGTTGACGCAGCCGCCCTCAGTGTCTGCGGCCCCAGGACAGAG
GGTCACCATCTCCTGCTCTGGAACCAGGTCCAACATTGGGAGTGATTATG
TTTCCTGGTACCAACACCTCCCAGGAACAGCCCCCAAACTCCTCGTTTAT
GGCGATAATCTGCGACCCTCAGGGATTCCTGACCGATTCTCTGCCTCCAA
GTCTGGCACGTCAGCCACCCTGGGCATCACCGGACTCCAGACTGGGGACG
AGGCCGATTATTACTGCGGCACATGGGATTACACCCTGAATGGTGTGGTG
TTCGGCGGAGGGACCAAGCTGACCGTCCTAtcttcaGCCTCCACCAAGGG
CCCATCGGTCTTCCCCCTGGCACCCTCCTCCAAGAGCACCTCTGGGGGCA
CAGCGGCCCTGGGCTGCCTGGTCAAGGACTACTTCCCCGAACCGGTGACG
GTGTCGTGGAACTCAGGCGCCCTGACCAGCGGCGTGCACACCTTCCCGGC
TGTCCTACAGTCCTCAGGACTCTACTCCCTCAGCAGCGTGGTGACCGTGC
CCTCCAGCAGCTTGGGCACCCAGACCTACATCTGCAACGTGAACCACAAG
CCCAGCAACACCAAGGTGGACAAGAGAGTGGAGCCCAAGAGCTGC pWF-533

(SEQ ID NO: 121)
QSVLTQPPSVSAAPGQRVTISCSGTRSNIGSDYVSWYQHLPGTAPKLLVY
GDNLRPSGIPDRFSASKSGTSATLGITGLQTGDEADYYCGTWDYTLNGVV
FGGGTKLTVLSSASTKGPSVFPLAPSSKSTSGGTAALGCLVKDYFPEPVT
VSWNSGALTSGVHTFPAVLQSSGLYSLSSVVTVPSSSLGTQTYICNVNHK
PSNTKVDKRVEPKSC pWF-534

(SEQ ID NO: 122)
CAGGTGCAGCTGGTGGAGTCTGGGGGAGGCTTGGTACAGCCTGGGGGGTC
CCTGAGACTCTCCTGTGCAGCCTCTGGATTCACCTTTAGCAGCTATGCCA
TGAGCTGGGTCCGCCAGGCTCCAGGGAAGGGGCTGGAGTGGGTCTCAGTT
ATTTATAGCGGTGGTAGTAGCACATACTATGCAGACTCCGTGAAGGGCCG
GTTCACCATCTCCAGAGATAATTCCAAGAACACGCTGTATCTGCAAATGA
ACAGCCTGAGAGCCGAGGACACGGCCGTATATTACTGTGCGCGCACTTCT
TACCTGAACCATGGTGATTACTGGGGTCAAGGTACTCTGGTGACCGTGTC
TAGCGCCTCCGTGGCTGCACCATCTGTCTTCATCTTCCCGCCATCTGATG
AGCAGTTGAAATCTGGAACTGCCTCTGTTGTGTGCCTGCTGAATAACTTC
TATCCCAGAGAGGCCAAAGTACAGTGGAAGGTGGATAACGCCCTCCAATC
GGGTAACTCCCAGGAGAGTGTCACAGAGCAGGACAGCAAGGACAGCACCT
ACAGCCTCAGCAGCACCCTGACGCTGAGCAAAGCAGACTACGAGAAACAC
AAAGTCTACGCCTGCGAAGTCACCCATCAGGGCCTGAGCTCGCCCGTCAC
AAAGAGCTTCAACAGGGGAGAGTGTGACAAGACCCACACCTGCCCCCCCT
GCCCAGCCCCAGAGCTGCTGGGCGGACCCTCCGTGTTCCTGTTCCCCCCC
AAGCCCAAGGACACCCTGATGATCAGCAGGACCCCCGAGGTGACCTGCGT

```
GGTGGTGGACGTGAGCCACGAGGACCCAGAGGTGAAGTTCAACTGGTACG

TGGACGGCGTGGAGGTGCACAACGCCAAGACCAAGCCCAGAGAGGAGCAG

TACAACAGCACCTACAGGGTGGTGTCCGTGCTGACCGTGCTGCACCAGGA

CTGGCTGAACGGCAAGGAATACAAGTGCAAGGTCTCCAACAAGGCCCTGC

CAGCCCCCATCGAAAAGACCATCAGCAAGGCCAAGGGCCAGCCACGGGAG

CCCCAGGTGTACACCCTGCCCCCCTCCCGGGAGGAGATGACCAAGAACCA

GGTGTCCCTGACCTGTCTGGTGAAGGGCTTCTACCCCAGCGACATCGCCG

TGGAGTGGGAGAGCAACGGCCAGCCCGAGAACAACTACAAGACCACCCCC

CCAGTGCTGGACAGCGACGGCAGCTTCTTCCTGTACAGCAAGCTGACCGT

GGACAAGTCCAGGTGGCAGCAGGGCAACGTGTTCAGCTGCAGCGTGATGC

ACGAGGCCCTGCACAACCACTACACCCAGAAGAGCCTGAGCCTGTCCCCC

GAGCTGCAACTGGAGGAGAGCTGTGCGGAGGCGCAGGACGGGGAGCTGGA

CGGGCTGTGGACGACCATCACCATCTTCATCACACTCTTCCTGTTAAGCG

TGTGCTACAGTGCCACCGTCACCTTCTTCAAGGTGAAGTGGATCTTCTCC

TCGGTGGTGGACCTGAAGCAGACCATCATCCCCGACTACAGGAACATGAT

CGGACAGGGGCCTGA
``` pWF-534

(SEQ ID NO: 123)
QVQLVESGGGLVQPGGSLRLSCAASGFTFSSYAMSWVRQAPGKGLEWVSV
IYSGGSSTYYADSVKGRFTISRDNSKNTLYLQMNSLRAEDTAVYYCARTS
YLNHGDYWGQGTLVTVSSASVAAPSVFIFPPSDEQLKSGTASVVCLLNNF
YPREAKVQWKVDNALQSGNSQESVTEQDSKDSTYSLSSTLTLSKADYEKH
KVYACEVTHQGLSSPVTKSFNRGECDKTHTCPPCPAPELLGGPSVFLFPP
KPKDTLMISRTPEVTCVVVDVSHEDPEVKFNWYVDGVEVHNAKTKPREEQ
YNSTYRVVSVLTVLHQDWLNGKEYKCKVSNKALPAPIEKTISKAKGQPRE
PQVYTLPPSREEMTKNQVSLTCLVKGFYPSDIAVEWESNGQPENNYKTTP
PVLDSDGSFFLYSKLTVDKSRWQQGNVFSCSVMHEALHNHYTQKSLSLSP
ELQLEESCAEAQDGELDGLWTTITIFITLFLLSVCYSATVTFFKVKWIFS
SVVDLKQTIIPDYRNMIGQGA

Mu IL15

(SEQ ID NO: 124)
```
ATGAAAATTTTGAAACCATATATGAGGAATACATCCATCTCGTGCTACTT

GTGTTTCCTTCTAAACAGTCACTTTTTAACTGAGGCTGGCATTCATGTCT

TCATTTTGGGCTGTGTCAGTGTAGGTCTCCCTAAAACAGAGGCCAACTGG

ATAGATGTAAGATATGACCTGGAGAAAATTGAAAGCCTTATTCAATCTAT

TCATATTGACACCACTTTATACACTGACAGTGACTTTCATCCCAGTTGCA

AAGTTACTGCAATGAACTGCTTTCTCCTGGAATTGCAGGTTATTTTACAT

GAGTACAGTAACATGACTCTTAATGAAACAGTAAGAAACGTGCTCTACCT

TGCAAACAGCACTCTGTCTTCTAACAAGAATGTAGCAGAATCTGGCTGCA

AGGAATGTGAGGAGCTGGAGGAGAAAACCTTCACAGAGTTTTTGCAAAGC

TTTATACGCATTGTCCAAATGTTCATCAACACGTCC
```

Mu IL15

(SEQ ID NO: 125)
MKILKPYMRNTSISCYLCFLLNSHFLTEAGIHVFILGCVSVGLPKTEANW
IDVRYDLEKIESLIQSIHIDTTLYTDSDFHPSCKVTAMNCFLLELQVILH
EYSNMTLNETVRNVLYLANSTLSSNKNVAESGCKECEELEEKTFTEFLQS
FIRIVQMFINTS

Anti-Human GPC3 CAR (79a)

(SEQ ID NO: 126)
```
CAGTCTGTGTTGACGCAGCCGCCCTCAGTGTCTGCGGCCCCAGGACAGAG

GGTCACCATCTCCTGCTCTGGAACCAGGTCCAACATTGGGAGTGATTATG

TTTCCTGGTACCAACACCTCCCAGGAACAGCCCCCAAACTCCTCGTTTAT

GGCGATAATCTGCGACCCTCAGGGATTCCTGACCGATTCTCTGCCTCCAA

GTCTGGCACGTCAGCCACCCTGGGCATCACCGGACTCCAGACTGGGGACG

AGGCCGATTATTACTGCGGCACATGGGATTACACCCTGAATGGTGTGGTG

TTCGGCGGAGGGACCAAGCTGACCGTCCTAGGTTCTAGAGGTGGTGGTGG

TAGCGGCGGCGGCGGCTCTGGTGGTGGTGGATCCCTCGAGATGGCCCAGG

TGCAGCTGGTGGAGTCTGGGGGAGGCTTGGTACAGCCTGGGGGGTCCCTG

AGACTCTCCTGTGCAGCCTCTGGATTCACCTTTAGCAGCTATGCCATGAG

CTGGGTCCGCCAGGCTCCAGGGAAGGGGCTGGAGTGGGTCTCAGTTATTT

ATAGCGGTGGTAGTAGCACATACTATGCAGACTCCGTGAAGGGCCGGTTC

ACCATCTCCAGAGATAATTCCAAGAACACGCTGTATCTGCAAATGAACAG

CCTGAGAGCCGAGGACACGGCCGTATATTACTGTGCGCGCACTTCTTACC

TGAACCATGGTGATTACTGGGGTCAAGGTACTCTGGTGACCGTGTCTAGC

GCCGCTGCAGTGGTCCCCGTGCTGCAGAAAGTTAATAGCACCACCACTAA

ACCTGTCCTGAGGACTCCTAGTCCAGTGCACCCAACAGGGACCAGTCAGC

CACAGAGACCGGAAGACTGCAGACCAAGAGGTTCAGTGAAGGGAACCGGC

CTGGATTTCGCCTGCGATTTTTGGGCCCTGGTCGTCGTCGCAGGAGTTTT

GTTTTGCTATGGACTGCTCGTCACAGTTGCTTTGTGTGTTATCTGGACAA

GGAAACGGTGGCAAAATGAGAAGTTTGGGGTGGACATGCCAGATGACTAT

GAAGATGAAAATCTCTATGAGGGCCTGAACCTTGATGACTGTTCTATGTA

TGAGGACATCTCCAGGGGACTCCAGGGCACCTACCAGGATGTGGGCAACC

TCCACATTGGAGATGCCCAGCTGGAAAAGCCATGA
```

Anti-Human GPC3 CAR (79a)

(SEQ ID NO: 127)
QSVLTQPPSVSAAPGQRVTISCSGTRSNIGSDYVSWYQHLPGTAPKLLVY
GDNLRPSGIPDRFSASKSGTSATLGITGLQTGDEADYYCGTWDYTLNGVV
FGGGTKLTVLGSRGGGGSGGGGSGGGGSLEMAQVQLVESGGGLVQPGGSL

-continued
RLSCAASGFTFSSYAMSWVRQAPGKGLEWVSVIYSGGSSTYYADSVKGRF

TISRDNSKNTLYLQMNSLRAEDTAVYYCARTSYLNHGDYWGQGTLVTVSS

AAA*VVPVLQKVNSTTTKPVLRTPSPVHPTGTSQPQRPEDCRPRGSVKGTG*

*LDFACDFWALVVVAGVLFCYGLLVTVALCVIWT*R*KRWQNEKFGVDMPDDY*

*EDENLYEGLNLDDCSMYEDISRGLQGTYQDVGNLHIGDAQLEKP*

Anti-Human PSMA(XENP14484) CAR 79a (SEQ ID NO: 128)
GAGGTTCAACTTGTTCAATCTGGGGCAGAAGTGAAGAAGCCCGGGGCATC

TGTGAAAGTATCATGCAAAACATCCGGCTATACGTTTACCGAATACACCA

TTCACTGGGTCAGACAGGCTCCCGGTCAAAGCCTCGAATGGATGGGAAAT

ATTAACCCTAACAATGGCGGAACCACATATAATCAGAAATTCCAAGGCCG

AGTGACGATAACTGTCGATAAGAGTACGTCCACAGCTTACATGGAACTCA

GCTCTTTGAGATCCGAAGACACTCAGTTTATTATTGTGCAGCTGGATGG

AACTTCGACTATTGGGGACAAGGGACTCTTGTTACGGTGTCCAGTGGCAA

ACCAGGTAGTGGTAAACCCGGAAGCGGCAAGCCCGGGAGCGGTAAACCTG

GTAGCGACATCGTCATGACTCAAAGCCCTGACTCACTCGCCGTGAGCCTG

GGAGAGCGTGCAACGCTATCTTGTCGGGCCTCTCAGGATGTCGGAACTGC

TGTAGACTGGTATCAACAGAAACCTGACCAATCACCAAAACTCCTGATTT

ATTGGGCCTCAACACGTCACACAGGAGTGCCAGATAGGTTCACAGGTAGT

GGCAGTGGAACTGATTTTACTTTGACAATTAGCAGCCTGCAAGCCGAAGA

TGTAGCCGTTTACTTCTGTCAACAATATAACTCATACCCACTAACGTTCG

GTGCCGGGACGAAGGTAGAGATTAAAGTGGTCCCCGTGCTGCAGAAAGTT

AATAGCACCACCACTAAACCTGTCCTGAGGACTCCTAGTCCAGTGCACCC

AACAGGGACCAGTCAGCCACAGAGACCGGAAGACTGCAGACCAAGAGGTT

CAGTGAAGGGAACCGGCCTGGATTTCGCCTGCGATTTTTGGGCCCTGGTC

GTCGTCGCAGGAGTTTTGTTTTGCTATGGACTGCTCGTCACAGTTGCTTT

GTGTGTTATCTGGACAAGGAAACGGTGGCAAAATGAGAAGTTTGGGGTGG

ACATGCCAGATGACTATGAAGATGAAAATCTCTATGAGGGCCTGAACCTT

GATGACTGTTCTATGTATGAGGACATCTCCAGGGGACTCCAGGGCACCTA

CCAGGATGTGGGCAACCTCCACATTGGAGATGCCCAGCTGGAAAAGCCAT

GA

Anti-Human PSMA(XENP14484) CAR 79a (SEQ ID NO: 129)
EVQLVQSGAEVKKPGASVKVSCKTSGYTFTEYTIHWVRQAPGQSLEWMGN

INPNNGGTTYNQKFQGRVTITVDKSTSTAYMELSSLRSEDTAVYYCAAGW

NFDYWGQGTLVTVSSGKPGSGKPGSGKPGSGKPGSDIVMTQSPDSLAVSL

GERATLSCRASQDVGTAVDWYQQKPDQSPKLLIYWASTRHTGVPDRFTGS

GSGTDFTLTISSLQAEDVAVYFCQQYNSYPLTFGAGTKVEIK*VVPVLQKV*

*NSTTTKPVLRTPSPVHPTGTSQPQRPEDCRPRGSVKGTGLDFACDFWALV*

-continued
*VVAGVLFCYGLLVTVALCVIWT*R*KRWQNEKFGVDMPDDYEDENLYEGLNL*

*DDCSMYEDISRGLQGTYQDVGNLHIGDAQLEKP*

Mouse IL 12a-Mouse IgG2a Fc (SEQ ID NO: 130)
ATGTGTCAGTCACGCTATCTTCTCTTCCTTGCTACTCTGGCCTTGCTCAA

TCACTTGTCCCTTGCTCGTGTGATTCCTGTGTCCGGCCCAGCTAGGTGTC

TCTCCCAGTCACGGAATCTCCTGAAAACCACGGATGACATGGTAAAGACA

GCTAGGGAGAAACTCAAGCACTACTCCTGCACAGCTGAGGATATCGATCA

TGAGGACATCACCAGGGACCAGACATCCACTCTGAAAACTTGCCTGCCTT

TGGAACTCCACAAGAACGAATCTTGTCTGGCAACGCGTGAAACGAGTTCT

ACTACAAGAGGGTCCTGTCTTCCCCCTCAAAAGACAAGCCTTATGATGAC

CTTGTGTCTCGGTAGCATTTATGAGGACCTAAAGATGTATCAAACCGAGT

TTCAGGCTATCAATGCAGCGCTCCAGAATCATAACCATCAGCAGATCATT

CTTGACAAAGGAATGCTCGTGGCCATTGATGAACTAATGCAGAGCCTAAA

CCACAATGGCGAGACTCTTCGACAGAAACCGCCTGTGGGCGAGGCCGATC

CATATAGAGTCAAAATGAAACTGTGTATTCTCCTGCATGCATTTAGTACT

CGTGTAGTGACTATTAACAGAGTGATGGGTTACCTTTCCTCAGCTCCCAG

AGGGCCCACAATCAAGCCCTGTCCTCCATGCAAATGCCCAGCACCTAACC

TCTTGGGTGGACCATCCGTCTTCATCTTCCCTCCAAAGATCAAGGATGTA

CTCATGATCTCCCTGAGCCCCATAGTCACATGTGTGGTGGTGGATGTGAG

CGAGGATGACCCAGATGTCCAGATCAGCTGGTTTGTGAACAACGTGGAAG

TACACACAGCTCAGACACAAACCCATAGAGAGGATTACAACAGTACTCTC

CGGGTGGTCAGTGCCCTCCCCATCCAGCACCAGGACTGGATGAGTGGCAA

GGAGTTCAAATGCAAGGTCAACAACAAAGACCTCCCAGCGCCCATCGAGA

GAACCATCTCAAAACCCAAAGGGTCAGTAAGAGCTCCACAGGTATATGTC

TTGCCTCCACCAGAAGAAGAGATGACTAAGAAACAGGTCACTCTGACCTG

CATGGTCACAGACTTCATGCCTGAAGACATTTACGTGGAGTGGACCAACA

ACGGGAAAACAGAGCTAAACTACAAGAACACTGAACCAGTCCTGGACTCT

GATGGTTCTTACTTCATGTACAGCAAGCTGAGAGTGGAAAAGAAGAACTG

GGTGGAAAGAAATAGCTACTCCTGTTCAGTGGTCCACGAGGGTCTGCACA

ATCACCACGACTAAGAGCTTCTCCCGGACTCCGGGTAAATAG

Mouse IL 12a-Mouse IgG2a Fc (SEQ ID NO: 131)
MCQSRYLLFLATLALLNHLSLARVIPVSGPARCLSQSRNLLKTTDDMVKT

AREKLKHYSCTAEDIDHEDITRDQTSTLKTCLPLELHKNESCLATRETSS

TTRGSCLPPQKTSLMMTLCLGSIYEDLKMYQTEFQAINAALQNHNHQQII

LDKGMLVAIDELMQSLNHNGETLRQKPPVGEADPYRVKMKLCILLHAFST

RVVTINRVMGYLSSAPRGPTIKPCPPCKCPAPNLLGGPSVFIFPPKIKDV

LMISLSPIVTCVVVDVSEDDPDVQISWFVNNVEVHTAQTQTHREDYNSTL

RVVSALPIQHQDWMSGKEFKCKVNNKDLPAPIERTISKPKGSVRAPQVYV

LPPPEEEMTKKQVTLTCMVTDFMPEDIYVEWTNNGKTELNYKNTEPVLDS

DGSYFMYSKLRVEKKNWVERNSYSCSVVHEGLHNHHTTKSFSRTPGK*

Mouse IL 12b-Mouse IgG2a Fc (SEQ ID NO: 132)
ATGTGCCCACAGAAACTCACAATTTCTTGGTTCGCAATCGTCCTGCTGGT

GTCACCCCTGATGGCAATGTGGGAGTTGGAAAAGGATGTATACGTCGTCG

AGGTCGACTGGACACCTGACGCTCCGGGTGAAACTGTCAACCTCACTTGC

GATACTCCTGAAGAGGACGACATCACGTGGACGAGCGACCAGCGACATGG

AGTGATAGGGTCTGGCAAGACGCTTACTATCACGGTTAAGGAATTTCTCG

ACGCAGGGCAGTACACATGTCACAAGGGCGGCGAGACTCTGAGCCACTCC

CATTTGCTGCTGCACAAGAAGGAGAATGGTATCTGGTCTACCGAAATCCT

GAAGAATTTTAAGAACAAGACTTTTCTGAAATGCGAGGCCCCAAATTATT

CCGGACGTTTCACTTGCAGTTGGCTCGTTCAAAGAAATATGGACTTGAAA

TTTAACATTAAATCCAGCTCTTCATCTCCTGACAGCAGGGCCGTAACTTG

TGGAATGGCTTCATTGTCAGCTGAGAAAGTTACGCTTGACCAAAGGGATT

ATGAGAAATACAGCGTGAGTTGCCAGGAAGATGTGACATGTCCAACGGCA

GAGGAAACGTTGCCAATTGAGCTCGCTTTGGAAGCTCGTCAACAAAACAA

GTATGAAAACTATAGTACTAGCTTCTTCATACGGGACATCATCAAACCAG

ATCCACCTAAGAATTTGCAGATGAAGCCTCTGAAGAATTCACAAGTCGAG

GTATCCTGGGAATACCCAGATTCATGGTCCACTCCTCATAGTTACTTTAG

CCTGAAATTCTTTGTACGCATACAGCGGAAGAAGGAGAAAATGAAGGAGA

CGGAAGAAGGCTGCAATCAGAAAGGCGCTTTTCTTGTTGAAAAGACGAGC

ACTGAGGTTCAATGCAAAGGCGGGAATGTATGTGTTCAAGCCCAAGATAG

GTATTATAATAGCTCCTGCTCTAAGTGGGCTTGCGTACCATGCAGAGTTA

GAAGTCCCAGAGGGCCCACAATCAAGCCCTGTCCTCCATGCAAATGCCCA

GCACCTAACCTCTTGGGTGGACCATCCGTCTTCATCTTCCCTCCAAAGAT

CAAGGATGTACTCATGATCTCCCTGAGCCCCATAGTCACATGTGTGGTGG

TGGATGTGAGCGAGGATGACCCAGATGTCCAGATCAGCTGGTTTGTGAAC

AACGTGGAAGTACACACAGCTCAGACACAAACCCATAGAGAGGATTACAA

CAGTACTCTCCGGGTGGTCAGTGCCCTCCCCATCCAGCACCAGGACTGGA

TGAGTGGCAAGGAGTTCAAATGCAAGGTCAACAACAAAGACCTCCCAGCG

CCCATCGAGAGAACCATCTCAAAACCCAAAGGGTCAGTAAGAGCTCCACA

GGTATATGTCTTGCCTCCACCAGAAGAAGAGATGACTAAGAAACAGGTCA

CTCTGACCTGCATGGTCACAGACTTCATGCCTGAAGACATTTACGTGGAG

TGGACCAACAACGGGAAAACAGAGCTAAACTACAAGAACACTGAACCAGT

CCTGGACTCTGATGGTTCTTACTTCATGTACAGCAAGCTGAGAGTGGAAA

AGAAGAACTGGGTGGAAAGAAATAGCTACTCCTGTTCAGTGGTCCACGAG

GGTCTGCACAATCACCACACGACTAAGAGCTTCTCCCGGACTCCGGGTAA

ATAG

Mouse IL 12b-Mouse IgG2a Fc (SEQ ID NO: 133)
MCPQKLTISWFAIVLLVSPLMAMWELEKDVYVVEVDWTPDAPGETVNLTC

DTPEEDDITWTSDQRHGVIGSGKTLTITVKEFLDAGQYTCHKGGETLSHS

HLLLHKKENGIWSTEILKNFKNKTFLKCEAPNYSGRFTCSWLVQRNMDLK

FNIKSSSSSPDSRAVTCGMASLSAEKVTLDQRDYEKYSVSCQEDVTCPTA

EETLPIELALEARQQNKYENYSTSFFIRDIIKPDPPKNLQMKPLKNSQVE

VSWEYPDSWSTPHSYFSLKFFVRIQRKKEKMKETEEGCNQKGAFLVEKTS

TEVQCKGGNVCVQAQDRYYNSSCSKWACVPCRVRSPRGPTIKPCPPCKCP

APNLLGGPSVFIFPPKIKDVLMISLSPIVTCVVVDVSEDDPDVQISWFVN

NVEVHTAQTQTHREDYNSTLRVVSALPIQHQDWMSGKEFKCKVNNKDLPA

PIERTISKPKGSVRAPQVYVLPPPEEEMTKKQVTLTCMVTDFMPEDIYVE

WTNNGKTELNYKNTEPVLDSDGSYFMYSKLRVEKKNWVERNSYSCSVVHE

GLHNHHTTKSFSRTPGK

Mouse IL 12a-Mouse IgG2a Fc (Silent)

(SEQ ID NO: 134)
ATGTGTCAGTCACGCTATCTTCTCTTCCTTGCTACTCTGGCCTTGCTCAA

TCACTTGTCCCTTGCTCGTGTGATTCCTGTGTCCGGCCCAGCTAGGTGTC

TCTCCCAGTCACGGAATCTCCTGAAAACCACGGATGACATGGTAAAGACA

GCTAGGGAGAAACTCAAGCACTACTCCTGCACAGCTGAGGATATCGATCA

TGAGGACATCACCAGGGACCAGACATCCACTCTGAAAACTTGCCTGCCTT

TGGAACTCCACAAGAACGAATCTTGTCTGGCAACGCGTGAAACGAGTTCT

ACTACAAGAGGGTCCTGTCTTCCCCCTCAAAAGACAAGCCTTATGATGAC

CTTGTGTCTCGGTAGCATTTATGAGGACCTAAAGATGTATCAAACCGAGT

TTCAGGCTATCAATGCAGCGCTCCAGAATCATAACCATCAGCAGATCATT

CTTGACAAAGGAATGCTCGTGGCCATTGATGAACTAATGCAGAGCCTAAA

CCACAATGGCGAGACTCTTCGACAGAAACCGCCTGTGGGCGAGGCCGATC

CATATAGAGTCAAAATGAAACTGTGTATTCTCCTGCATGCATTTAGTACT

CGTGTAGTGACTATTAACAGAGTGATGGGTTACCTTTCCTCAGCTCCCAG

AGGGCCCACAATCAAGCCCTGTCCTCCATGCAAATGCCCAGCACCTAACG

CTGCCGGTGGACCATCCGTCTTCATCTTCCCTCCAAAGATCAAGGATGTA

CTCATGATCTCCCTGAGCCCCATAGTCACATGTGTGGTGGTGGATGTGAG

CGAGGATGACCCAGATGTCCAGATCAGCTGGTTTGTGAACAACGTGGAAG

TACACACAGCTCAGACACAAACCCATAGAGAGGATTACAACAGTACTCTC

CGGGTGGTCAGTGCCCTCCCCATCCAGCACCAGGACTGGATGAGTGGCAA

GGAGTTCAAATGCAAGGTCAACAACAAAGACCTCGGAGCGCCCATCGAGA

GAACCATCTCAAAACCCAAAGGGTCAGTAAGAGCTCCACAGGTATATGTC

TTGCCTCCACCAGAAGAAGAGATGACTAAGAAACAGGTCACTCTGACCTG

CATGGTCACAGACTTCATGCCTGAAGACATTTACGTGGAGTGGACCAACA

ACGGGAAAACAGAGCTAAACTACAAGAACACTGAACCAGTCCTGGACTCT

GATGGTTCTTACTTCATGTACAGCAAGCTGAGAGTGGAAAAGAAGAACTG

GGTGGAAAGAAATAGCTACTCCTGTTCAGTGGTCCACGAGGGTCTGCACA

ATCACCACACGACTAAGAGCTTCTCCCGGACTCCGGGTAAATGA

Mouse IL 12a-Mouse IgG2a Fc (Silent)

(SEQ ID NO: 135)
MCQSRYLLFLATLALLNHLSLARVIPVSGPARCLSQSRNLLKTTDDMVKT

AREKLKHYSCTAEDIDHEDITRDQTSTLKTCLPLELHKNESCLATRETSS

TTRGSCLPPQKTSLMMTLCLGSIYEDLKMYQTEFQAINAALQNHNHQQII

LDKGMLVAIDELMQSLNHNGETLRQKPPVGEADPYRVKMKLCILLHAFST

RVVTINRVMGYLSSAPRGPTIKPCPPCKCPAPNAAGGPSVFIFPPKIKDV

LMISLSPIVTCVVVDVSEDDPDVQISWFVNNVEVHTAQTQTHREDYNSTL

RVVSALPIQHQDWMSGKEFKCKVNNKDLGAPIERTISKPKGSVRAPQVYV

LPPPEEEMTKKQVTLTCMVTDFMPEDIYVEWTNNGKTELNYKNTEPVLDS

DGSYFMYSKLRVEKKNWVERNSYSCSVVHEGLHNHHTTKSFSRTPGK*

Mouse IL 12b-Mouse IgG2a Fc (Silent)

(SEQ ID NO: 136)
ATGTGCCCACAGAAACTCACAATTTCTTGGTTCGCAATCGTCCTGCTGGT

GTCACCCCTGATGGCAATGTGGGAGTTGGAAAAGGATGTATACGTCGTCG

AGGTCGACTGGACACCTGACGCTCCGGGTGAAACTGTCAACCTCACTTGC

GATACTCCTGAAGAGGACGACATCACGTGGACGAGCGACCAGCGACATGG

AGTGATAGGGTCTGGCAAGACGCTTACTATCACGGTTAAGGAATTTCTCG

ACGCAGGGCAGTACACATGTCACAAGGGCGGCGAGACTCTGAGCCACTCC

CATTTGCTGCTGCACAAGAAGGAGAATGGTATCTGGTCTACCGAAATCCT

GAAGAATTTTAAGAACAAGACTTTTCTGAAATGCGAGGCCCCAAATTATT

CCGGACGTTTCACTTGCAGTTGGCTCGTTCAAAGAAATATGGACTTGAAA

TTTAACATTAAATCCAGCTCTTCATCTCCTGACAGCAGGGCCGTAACTTG

TGGAATGGCTTCATTGTCAGCTGAGAAAGTTACGCTTGACCAAAGGGATT

ATGAGAAATACAGCGTGAGTTGCCAGGAAGATGTGACATGTCCAACGGCA

GAGGAAACGTTGCCAATTGAGCTCGCTTTGGAAGCTCGTCAACAAAACAA

GTATGAAAACTATAGTACTAGCTTCTTCATACGGGACATCATCAAACCAG

ATCCACCTAAGAATTTGCAGATGAAGCCTCTGAAGAATTCACAAGTCGAG

GTATCCTGGGAATACCCAGATTCATGGTCCACTCCTCATAGTTACTTTAG

CCTGAAATTCTTTGTACGCATACAGCGGAAGAAGGAGAAAATGAAGGAGA

CGGAAGAAGGCTGCAATCAGAAAGGCGCTTTTCTTGTTGAAAAGACGAGC

ACTGAGGTTCAATGCAAAGGCGGGAATGTATGTGTTCAAGCCCAAGATAG

GTATTATAATAGCTCCTGCTCTAAGTGGGCTTGCGTACCATGCAGAGTTA

GAAGTCCCAGAGGGCCCACAATCAAGCCCTGTCCTCCATGCAAATGCCCA

GCACCTAACGCTGCCGGTGGACCATCCGTCTTCATCTTCCCTCCAAAGAT

CAAGGATGTACTCATGATCTCCCTGAGCCCCATAGTCACATGTGTGGTGG

TGGATGTGAGCGAGGATGACCCAGATGTCCAGATCAGCTGGTTTGTGAAC

AACGTGGAAGTACACACAGCTCAGACACAAACCCATAGAGAGGATTACAA

CAGTACTCTCCGGGTGGTCAGTGCCCTCCCCATCCAGCACCAGGACTGGA

TGAGTGGCAAGGAGTTCAAATGCAAGGTCAACAACAAAGACCTCGGAGCG

CCCATCGAGAGAACCATCTCAAAACCCAAAGGGTCAGTAAGAGCTCCACA

GGTATATGTCTTGCCTCCACCAGAAGAAGAGATGACTAAGAAACAGGTCA

CTCTGACCTGCATGGTCACAGACTTCATGCCTGAAGACATTTACGTGGAG

TGGACCAACAACGGGAAAACAGAGCTAAACTACAAGAACACTGAACCAGT

CCTGGACTCTGATGGTTCTTACTTCATGTACAGCAAGCTGAGAGTGGAAA

AGAAGAACTGGGTGGAAAGAAATAGCTACTCCTGTTCAGTGGTCCACGAG

GGTCTGCACAATCACCACACGACTAAGAGCTTCTCCCGGACTCCGGGTAA

ATGA

Mouse IL 12b-Mouse IgG2a Fc (Silent)

(SEQ ID NO: 137)
MCPQKLTISWFAIVLLVSPLMAMWELEKDVYVVEVDWTPDAPGETVNLTC

DTPEEDDITWTSDQRHGVIGSGKTLTITVKEFLDAGQYTCHKGGETLSHS

HLLLHKKENGIWSTEILKNFKNKTFLKCEAPNYSGRFTCSWLVQRNMDLK

FNIKSSSSSPDSRAVTCGMASLSAEKVTLDQRDYEKYSVSCQEDVTCPTA

EETLPIELALEARQQNKYENYSTSFFIRDIIKPDPPKNLQMKPLKNSQVE

VSWEYPDSWSTPHSYFSLKFFVRIQRKKEKMKETEEGCNQKGAFLVEKTS

TEVQCKGGNVCVQAQDRYYNSSCSKWACVPCRVRSPRGPTIKPCPPCKCP

APNAAGGPSVFIFPPKIKDVLMISLSPIVTCVVVDVSEDDPDVQISWFVN

NVEVHTAQTQTHREDYNSTLRVVSALPIQHQDWMSGKEFKCKVNNKDLGA

PIERTISKPKGSVRAPQVYVLPPPEEEMTKKQVTLTCMVTDFMPEDIYVE

WTNNGKTELNYKNTEPVLDSDGSYFMYSKLRVEKKNWVERNSYSCSVVHE

GLHNHHTTKSFSRTPGK

CD3 Zeta Cytoplasmic Domain—Human (SEQ ID NO: 138)
RVKFSRSADAPAYQQGQNQLYNELNLGRREEYDVLDKRRGRDPEMGGKPQ

RRKNPQEGLYNELQKDKMAEAYSEIGMKGERRRGKGHDGLYQGLSTATKD

TYDALHMQALPPR

CD3 Zeta Cytoplasmic Domain—Human (SEQ ID NO: 139)
AGAGTGAAGTTCAGCAGGAGCGCAGACGCCCCCGCGTACCAGCAGGGCCA

GAACCAGCTCTATAACGAGCTCAATCTAGGACGAAGAGAGGAGTACGATG

TTTTGGACAAGAGACGTGGCCGGGACCCTGAGATGGGGGGAAAGCCGCAG

AGAAGGAAGAACCCTCAGGAAGGCCTGTACAATGAACTGCAGAAAGATAA

GATGGCGGAGGCCTACAGTGAGATTGGGATGAAAGGCGAGCGCCGGAGGG

GCAAGGGGCACGATGGCCTTTACCAGGGTCTCAGTACAGCCACCAAGGAC

ACCTACGACGCCCTTCACATGCAGGCCCTGCCCCCTCGCTAA pWF-506

(SEQ ID NO: 140)
METDTLLLWVLLLWVPGSTGQSVLTQPPSVSAAPGQRVTISCSGTRSNIG
SDYVSWYQHLPGTAPKLLVYGDNLRPSGIPDRFSASKSGTSATLGITGLQ
TGDEADYYCGTWDYTLNGVVFGGGTKLTVLGSRGGGGSGGGGSGGGGSLE
MAQVQLVESGGGLVQPGGSLRLSCAASGFTFSSYAMSWVRQAPGKGLEWV
SVIYSGGSSTYYADSVKGRFTISRDNSKNTLYLQMNSLRAEDTAVYYCAR
TSYLNHGDYWGQGTLVTVSSPKSCDKTHTCPPCPAPELLGGPSVFLFPPK
PKDTLMISRTPEVTCVVVDVSHEDPEVKFNWYVDGVEVHNAKTKPREEQY
NSTYRVVSVLTVLHQDWLNGKEYKCKVSNKALPAPIEKTISKAKGQPREP
QVYTLPPSREEMTKNQVSLTCLVKGFYPSDIAVEWESNGQPENNYKTTPP
VLDSDGSFFLYSKLTVDKSRWQQGNVFSCSVMHEALHNHYTQKSLSLSPE
LQLEESCAEAQDGELDGLWTTITIFITLFLLSVCYSATVTFFKVKWIFSS
VVDLKQTIIPDYRNMIGQGA pWF-506

(SEQ ID NO: 141)
ATGGAAACCGATACACTGCTGCTGTGGGTGCTGCTGCTGTGGGTGCCAGG
ATCTACCGGTCAGTCTGTGTTGACGCAGCCGCCCTCAGTGTCTGCGGCCC
CAGGACAGAGGGTCACCATCTCCTGCTCTGGAACCAGGTCCAACATTGGG
AGTGATTATGTTTCCTGGTACCAACACCTCCCAGGAACAGCCCCCAAACT
CCTCGTTTATGGCGATAATCTGCGACCCTCAGGGATTCCTGACCGATTCT
CTGCCTCCAAGTCTGGCACGTCAGCCACCCTGGGCATCACCGGACTCCAG
ACTGGGGACGAGGCCGATTATTACTGCGGCACATGGGATTACACCCTGAA
TGGTGTGGTGTTCGGCGGAGGGACCAAGCTGACCGTCCTAGGTTCTAGAG
GTGGTGGTGGTAGCGGCGGCGGCGGCTCTGGTGGTGGTGGATCCCTCGAG
ATGGCCCAGGTGCAGCTGGTGGAGTCTGGGGGAGGCTTGGTACAGCCTGG
GGGGTCCCTGAGACTCTCCTGTGCAGCCTCTGGATTCACCTTTAGCAGCT
ATGCCATGAGCTGGGTCCGCCAGGCTCCAGGGAAGGGGCTGGAGTGGGTC
TCAGTTATTTATAGCGGTGGTAGTAGCACATACTATGCAGACTCCGTGAA
GGGCCGGTTCACCATCTCCAGAGATAATTCCAAGAACACGCTGTATCTGC
AAATGAACAGCCTGAGAGCCGAGGACACGGCCGTATATTACTGTGCGCGC
ACTTCTTACCTGAACCATGGTGATTACTGGGGTCAAGGTACTCTGGTGAC
CGTGTCTAGCCCCAAGAGCTGCGACAAGACCCACACCTGCCCCCCCTGCC
CAGCCCCAGAGCTGCTGGGCGGACCCTCCGTGTTCCTGTTCCCCCCCAAG
CCCAAGGACACCCTGATGATCAGCAGGACCCCCGAGGTGACCTGCGTGGT
GGTGGACGTGAGCCACGAGGACCCAGAGGTGAAGTTCAACTGGTACGTGG
ACGGCGTGGAGGTGCACAACGCCAAGACCAAGCCCAGAGAGGAGCAGTAC
AACAGCACCTACAGGGTGGTGTCCGTGCTGACCGTGCTGCACCAGGACTG
GCTGAACGGCAAGGAATACAAGTGCAAGGTCTCCAACAAGGCCCTGCCAG
CCCCCATCGAAAAGACCATCAGCAAGGCCAAGGGCCAGCCACGGGAGCCC
CAGGTGTACACCCTGCCCCCCTCCCGGGAGGAGATGACCAAGAACCAGGT

GTCCCTGACCTGTCTGGTGAAGGGCTTCTACCCCAGCGACATCGCCGTGG
AGTGGGAGAGCAACGGCCAGCCCGAGAACAACTACAAGACCACCCCCCCA
GTGCTGGACAGCGACGGCAGCTTCTTCCTGTACAGCAAGCTGACCGTGGA
CAAGTCCAGGTGGCAGCAGGGCAACGTGTTCAGCTGCAGCGTGATGCACG
AGGCCCTGCACAACCACTACACCCAGAAGAGCCTGAGCCTGTCCCCCGAG
CTGCAACTGGAGGAGAGCTGTGCGGAGGCGCAGGACGGGGAGCTGGACGG
GCTGTGGACGACCATCACCATCTTCATCACACTCTTCCTGTTAAGCGTGT
GCTACAGTGCCACCGTCACCTTCTTCAAGGTGAAGTGGATCTTCTCCTCG
GTGGTGGACCTGAAGCAGACCATCATCCCCGACTACAGGAACATGATCGG
ACAGGGGGCCTGA pWF-507:

(SEQ ID NO: 142)
METDTLLLWVLLLWVPGSTGQSVLTQPPSVSAAPGQRVTISCSGTRSNIG
SDYVSWYQHLPGTAPKLLVYGDNLRPSGIPDRFSASKSGTSATLGITGLQ
TGDEADYYCGTWDYTLNGVVFGGGTKLTVLGQPKANPTVTLFPPSSEELQ
ANKATLVCLISDFYPGAVTVAWKADGSPVKAGVETTKPSKQSNNKYAASS
YLSLTPEQWKSHRSYSCQVTHEGSTVEKTVAPTECS pWF-507:

(SEQ ID NO: 143)
ATGGAAACCGATACACTGCTGCTGTGGGTGCTGCTGCTGTGGGTGCCAGG
ATCTACCGGTCAGTCTGTGTTGACGCAGCCGCCCTCAGTGTCTGCGGCCC
CAGGACAGAGGGTCACCATCTCCTGCTCTGGAACCAGGTCCAACATTGGG
AGTGATTATGTTTCCTGGTACCAACACCTCCCAGGAACAGCCCCCAAACT
CCTCGTTTATGGCGATAATCTGCGACCCTCAGGGATTCCTGACCGATTCT
CTGCCTCCAAGTCTGGCACGTCAGCCACCCTGGGCATCACCGGACTCCAG
ACTGGGGACGAGGCCGATTATTACTGCGGCACATGGGATTACACCCTGAA
TGGTGTGGTGTTCGGCGGAGGGACCAAGCTGACCGTCCTAGGTCAGCCCA
AGGCCAACCCCACTGTCACTCTGTTCCCGCCCTCCTCTGAGGAGCTCCAA
GCCAACAAGGCCACACTAGTGTGTCTGATCAGTGACTTCTACCCGGGAGC
TGTGACAGTGGCCTGGAAGGCAGATGGCAGCCCCGTCAAGGCGGGAGTGG
AGACCACCAAACCCTCCAAACAGAGCAACAACAAGTACGCGGCCAGCAGC
TACCTGAGCCTGACGCCCGAGCAGTGGAAGTCCCACAGAAGCTACAGCTG
CCAGGTCACGCATGAAGGGAGCACCGTGGAGAAGACAGTGGCCCCTACAG
AATGTTCATAG pWF-508:

(SEQ ID NO: 144)
MVFTPQILGLMLFWISASRGQVQLVESGGGLVQPGGSLRLSCAASGFTFS
SYAMSWVRQAPGKGLEWVSVIYSGGSSTYYADSVKGRFTISRDNSKNTLY
LQMNSLRAEDTAVYYCARTSYLNHGDYWGQGTLVTVSSASTKGPSVFPLA

PSSKSTSGGTAALGCLVKDYFPEPVTVSWNSGALTSGVHTFPAVLQSSGL

YSLSSVVTVPSSSLGTQTYICNVNHKPSNTKVDKRVEPKSCDKTHTCPPC

PAPELLGGPSVFLFPPKPKDTLMISRTPEVTCVVVDVSHEDPEVKFNWYV

DGVEVHNAKTKPREEQYNSTYRVVSVLTVLHQDWLNGKEYKCKVSNKALP

APIEKTISKAKGQPREPQVYTLPPSREEMTKNQVSLTCLVKGFYPSDIAV

EWESNGQPENNYKTTPPVLDSDGSFFLYSKLTVDKSRWQQGNVFSCSVMH

EALHNHYTQKSLSLSPELQLEESCAEAQDGELDGLWTTITIFITLFLLSV

CYSATVTFFKVKWIFSSVVDLKQTIIPDYRNMIGQGA pWF-508:

(SEQ ID NO: 145)
ATGGTGTTTACACCGCAAATATTGGGGCTCATGCTTTTCTGGATCAGTGC

AAGCAGGGGACAGGTGCAGCTGGTGGAGTCTGGGGGAGGCTTGGTACAGC

CTGGGGGGTCCCTGAGACTCTCCTGTGCAGCCTCTGGATTCACCTTTAGC

AGCTATGCCATGAGCTGGGTCCGCCAGGCTCCAGGGAAGGGGCTGGAGTG

GGTCTCAGTTATTTATAGCGGTGGTAGTAGCACATACTATGCAGACTCCG

TGAAGGGCCGGTTCACCATCTCCAGAGATAATTCCAAGAACACGCTGTAT

CTGCAAATGAACAGCCTGAGAGCCGAGGACACGGCCGTATATTACTGTGC

GCGCACTTCTTACCTGAACCATGGTGATTACTGGGGTCAAGGTACTCTGG

TGACCGTGTCTAGCGCCTCCACCAAGGGCCCATCGGTCTTCCCCCTGGCA

CCCTCCTCCAAGAGCACCTCTGGGGGCACAGCGGCCCTGGGCTGCCTGGT

CAAGGACTACTTCCCCGAACCGGTGACGGTGTCGTGGAACTCAGGCGCCC

TGACCAGCGGCGTGCACACCTTCCCGGCTGTCCTACAGTCCTCAGGACTC

TACTCCCTCAGCAGCGTGGTGACCGTGCCCTCCAGCAGCTTGGGCACCCA

GACCTACATCTGCAACGTGAACCACAAGCCCAGCAACACCAAGGTGGACA

AGAGAGTGGAGCCCAAGAGCTGCGACAAGACCCACACCTGCCCCCCCTGC

CCAGCCCCAGAGCTGCTGGGCGGACCCTCCGTGTTCCTGTTCCCCCCCAA

GCCCAAGGACACCCTGATGATCAGCAGGACCCCCGAGGTGACCTGCGTGG

TGGTGGACGTGAGCCACGAGGACCCAGAGGTGAAGTTCAACTGGTACGTG

GACGGCGTGGAGGTGCACAACGCCAAGACCAAGCCCAGAGAGGAGCAGTA

CAACAGCACCTACAGGGTGGTGTCCGTGCTGACCGTGCTGCACCAGGACT

GGCTGAACGGCAAGGAATACAAGTGCAAGGTCTCCAACAAGGCCCTGCCA

GCCCCCATCGAAAAGACCATCAGCAAGGCCAAGGGCCAGCCACGGGAGCC

CCAGGTGTACACCCTGCCCCCCTCCCGGGAGGAGATGACCAAGAACCAGG

TGTCCCTGACCTGTCTGGTGAAGGGCTTCTACCCCAGCGACATCGCCGTG

GAGTGGGAGAGCAACGGCCAGCCCGAGAACAACTACAAGACCACCCCCCC

AGTGCTGGACAGCGACGGCAGCTTCTTCCTGTACAGCAAGCTGACCGTGG

ACAAGTCCAGGTGGCAGCAGGGCAACGTGTTCAGCTGCAGCGTGATGCAC

GAGGCCCTGCACAACCACTACACCCAGAAGAGCCTGAGCCTGTCCCCCGA

GCTGCAACTGGAGGAGAGCTGTGCGGAGGCGCAGGACGGGGAGCTGGACG

GGCTGTGGACGACCATCACCATCTTCATCACACTCTTCCTGTTAAGCGTG

TGCTACAGTGCCACCGTCACCTTCTTCAAGGTGAAGTGGATCTTCTCCTC

GGTGGTGGACCTGAAGCAGACCATCATCCCCGACTACAGGAACATGATCG

GACAGGGGGCCTGA pWF-509:

(SEQ ID NO: 146)
METDTLLLWVLLLWVPGSTGQSVLTQPPSVSAAPGQRVTISCSGTRSNIG

SDYVSWYQHLPGTAPKLLVYGDNLRPSGIPDRFSASKSGTSATLGITGLQ

TGDEADYYCGTWDYTLNGVVFGGGTKLTVLGSRGGGSGGGGSGGGGSLE

MAQVQLVESGGGLVQPGGSLRLSCAASGFTFSSYAMSWVRQAPGKGLEWV

SVIYSGGSSTYYADSVKGRFTISRDNSKNTLYLQMNSLRAEDTAVYYCAR

TSYLNHGDYWGQGTLVTVSSAAAFVPVFLPAKPTTTPAPRPPTPAPTIAS

QPLSLRPEACRPAAGGAVHTRGLDFACDFWVLVVVGGVLACYSLLVTVAF

IIFWVLDKDDSKAGMEEDHTYEGLDIDQTATYEDIVTLRTGEVKWSVGEH

PGQE pWF-509:

(SEQ ID NO: 147)
ATGGAAACCGATACACTGCTGCTGTGGGTGCTGCTGCTGTGGGTGCCAGG

ATCTACCGGTCAGTCTGTGTTGACGCAGCCGCCCTCAGTGTCTGCGGCCC

CAGGACAGAGGGTCACCATCTCCTGCTCTGGAACCAGGTCCAACATTGGG

AGTGATTATGTTTCCTGGTACCAACACCTCCCAGGAACAGCCCCCAAACT

CCTCGTTTATGGCGATAATCTGCGACCCTCAGGGATTCCTGACCGATTCT

CTGCCTCCAAGTCTGGCACGTCAGCCACCCTGGGCATCACCGGACTCCAG

ACTGGGGACGAGGCCGATTATTACTGCGGCACATGGGATTACACCCTGAA

TGGTGTGGTGTTCGGCGGAGGGACCAAGCTGACCGTCCTAGGTTCTAGAG

GTGGTGGTGGTAGCGGCGGCGGCGGCTCTGGTGGTGGTGGATCCCTCGAG

ATGGCCCAGGTGCAGCTGGTGGAGTCTGGGGGAGGCTTGGTACAGCCTGG

GGGGTCCCTGAGACTCTCCTGTGCAGCCTCTGGATTCACCTTTAGCAGCT

ATGCCATGAGCTGGGTCCGCCAGGCTCCAGGGAAGGGGCTGGAGTGGGTC

TCAGTTATTTATAGCGGTGGTAGTAGCACATACTATGCAGACTCCGTGAA

GGGCCGGTTCACCATCTCCAGAGATAATTCCAAGAACACGCTGTATCTGC

AAATGAACAGCCTGAGAGCCGAGGACACGGCCGTATATTACTGTGCGCGC

ACTTCTTACCTGAACCATGGTGATTACTGGGGTCAAGGTACTCTGGTGAC

CGTGTCTAGCGCCGCTGCATTCGTGCCTGTGTTCCTCCCAGCTAAGCCCA

CTACCACCCCGCTCCAAGGCCGCCCACGCCCGCTCCTACTATTGCTAGT

CAGCCTTTAAGTTTACGACCCGAAGCTTGCAGGCCCGCCGCCGGCGGCGC

TGTGCACACCAGGGGCTTGATTTTGCCTGCGACTTTTGGGTATTGGTAG

TGGTGGGCGGAGTTTTAGCCTGCTACAGCCTCCTGGTAACAGTGGCTTTT

ATCATCTTTTGGGTGCTGGACAAGGATGACAGCAAGGCTGGCATGGAGGA

-continued

AGATCACACCTACGAGGGCCTGGACATTGACCAGACAGCCACCTATGAGG

ACATAGTGACGCTGCGGACAGGGGAAGTGAAGTGGTCTGTAGGTGAGCAC

CCAGGCCAGGAGTGA pWF-510:

(SEQ ID NO: 148)
METDTLLLWVLLLWVPGSTGQSVLTQPPSVSAAPGQRVTISCSGTRSNIG

SDYVSWYQHLPGTAPKLLVYGDNLRPSGIPDRFSASKSGTSATLGITGLQ

TGDEADYYCGTWDYTLNGVVFGGGTKLTVLGSRGGGGSGGGGSGGGGSLE

MAQVQLVESGGGLVQPGGSLRLSCAASGFTFSSYAMSWVRQAPGKGLEWV

SVIYSGGSSTYYADSVKGRFTISRDNSKNTLYLQMNSLRAEDTAVYYCAR

TSYLNHGDYWGQGTLVTVSSAAAFVPVFLPAKPTTTPAPRPPTPAPTIAS

QPLSLRPEACRPAAGGAVHTRGLDFACDFWVLVVVGGVLACYSLLVTVAF

IIFWVRKRWQNEKLGLDAGDEYEDENLYEGLNLDDCSMYEDISRGLQGTY

QDVGSLNIGDVQLEKP pWF-510:

(SEQ ID NO: 149)
ATGGAAACCGATACACTGCTGCTGTGGGTGCTGCTGCTGTGGGTGCCAGG

ATCTACCGGTCAGTCTGTGTTGACGCAGCCGCCCTCAGTGTCTGCGGCCC

CAGGACAGAGGGTCACCATCTCCTGCTCTGGAACCAGGTCCAACATTGGG

AGTGATTATGTTTCCTGGTACCAACACCTCCCAGGAACAGCCCCCAAACT

CCTCGTTTATGGCGATAATCTGCGACCCTCAGGGATTCCTGACCGATTCT

CTGCCTCCAAGTCTGGCACGTCAGCCACCCTGGGCATCACCGGACTCCAG

ACTGGGGACGAGGCCGATTATTACTGCGGCACATGGGATTACACCCTGAA

TGGTGTGGTGTTCGGCGGAGGGACCAAGCTGACCGTCCTAGGTTCTAGAG

GTGGTGGTGGTAGCGGCGGCGGCGGCTCTGGTGGTGGTGGATCCCTCGAG

ATGGCCCAGGTGCAGCTGGTGGAGTCTGGGGGAGGCTTGGTACAGCCTGG

GGGGTCCCTGAGACTCTCCTGTGCAGCCTCTGGATTCACCTTTAGCAGCT

ATGCCATGAGCTGGGTCCGCCAGGCTCCAGGGAAGGGGCTGGAGTGGGTC

TCAGTTATTTATAGCGGTGGTAGTAGCACATACTATGCAGACTCCGTGAA

GGGCCGGTTCACCATCTCCAGAGATAATTCCAAGAACACGCTGTATCTGC

AAATGAACAGCCTGAGAGCCGAGGACACGGCCGTATATTACTGTGCGCGC

ACTTCTTACCTGAACCATGGTGATTACTGGGGTCAAGGTACTCTGGTGAC

CGTGTCTAGCGCCGCTGCATTCGTGCCTGTGTTCCTCCCAGCTAAGCCCA

CTACCACCCCCGCTCCAAGGCCGCCCACGCCCGCTCCTACTATTGCTAGT

CAGCCTTTAAGTTTACGACCCGAAGCTTGCAGGCCCGCCGCCGGCGGCGC

TGTGCACACCAGGGGGCTTGATTTTGCCTGCGACTTTTGGGTATTGGTAG

TGGTGGGCGGAGTTTTAGCCTGCTACAGCCTCCTGGTAACAGTGGCTTTT

ATCATCTTTTGGGTGAGGAAACGATGGCAGAACGAGAAGCTCGGGTTGGA

TGCCGGGGATGAATATGAAGATGAAAACCTTTATGAAGGCCTGAACCTGG

ACGACTGCTCCATGTATGAGGACATCTCCCGGGGCCTCCAGGGCACCTAC

CAGGATGTGGGCAGCCTCAACATAGGAGATGTCCAGCTGGAGAAGCCGTG
A

INCORPORATION BY REFERENCE

All publications, patents, and patent applications mentioned in this specification are herein incorporated by reference to the same extent as if each individual publication, patent, or patent application was specifically and individually indicated to be incorporated by reference. However, the citation of a reference herein should not be construed as an acknowledgement that such reference is prior art to the present invention. To the extent that any of the definitions or terms provided in the references incorporated by reference differ from the terms and discussion provided herein, the present terms and definitions control.

EQUIVALENTS

The foregoing written specification is considered to be sufficient to enable one skilled in the art to practice the invention. The foregoing description and examples detail certain preferred embodiments of the invention and describe the best mode contemplated by the inventors. It will be appreciated, however, that no matter how detailed the foregoing may appear in text, the invention may be practiced in many ways and the invention should be construed in accordance with the appended claims and any equivalents thereof.

The following examples, including the experiments conducted and results achieved, are provided for illustrative purposes only and are not to be construed as limiting the present invention.

EXAMPLES

Example 1—Chimeric Antigen Receptor for B Cells (CAR-B) Constructs to Bind PSMA DNA Constructs. Exemplary CAR-B constructs were designed to recognize Prostate Specific Membrane Antigen ("PSMA"). PSMA is an antigen that is expressed more highly on prostate cancer cells than on other non-cancerous cells. Various construct were made comprising an extracellular domain that comprised an scFv specific for PSMA, an extracellular hinge region from CD8, a CD28 transmembrane domain, and various intracellular signaling domains. A list of the constructs is provided in Table 6:

TABLE 6

| Construct | Description |
| --- | --- |
| pWF-82 | pTLPW-SFFV-XENP14484 scFv-hCD8H-hCD28M-hCD19E (SEQ ID NOS. 39 and 40) |
| pWF-83 | pTLPW-SFFV-XENP14484 scFv-hCD8H-hCD28M-hCD40E (SEQ ID NOS. 41 and 42) |
| pWF-84 | pTLPW-SFFV-XENP14484 scFv-hCD8H-hCD28M-h(CD40 + CD79b)E (SEQ ID NOS. 43 and 44) |
| pWF-85 | pTLPW-SFFV-XENP14484 scFv-hCD8H-hCD28M-h(CD40 + CD137)E (SEQ ID NOS. 45 and 46) |
| pWF-86 | pTLPW-SFFV-XENP14484 scFv-hCD8H-hCD28M-h(CD40 + Fcγr2a)E (SEQ ID NOS. 47) |
| pWF-87 | pTLPW-SFFV-XENP14484 scFv-hCD8H-hCD28M-h(hMyd88 + CD40)E (SEQ ID NOS. 48 and 49) |
| pWF-88 | pTLPW-SFFV-XENP14484 scFv-hCD8H-hCD28M-hCD79aE (SEQ ID NOS. 50 and 51) |

TABLE 6-continued

| Construct | Description |
| --- | --- |
| pWF-89 | pTLPW-SFFV-XENP14484 scFv-hCD8H-hCD28M-hCD79bE (SEQ ID NOS. 52 and 53) |

Figure 5:
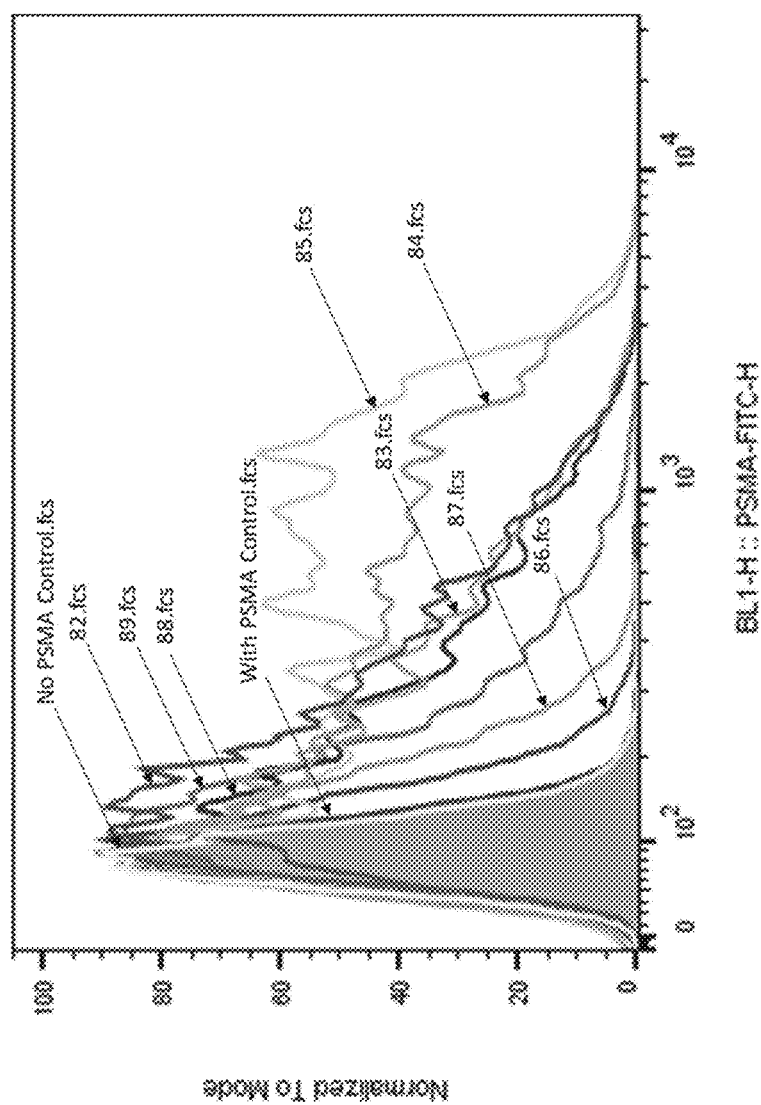
FIG. 5 sets forth expression of various anti-PSMA CARs on the surface of HEK-293 cells.

Expression of anti-PSMA CAR-B on HEK-293 Cells. The constructs encoding pWF82 to pWF89 were used to prepare lentivirus in Lentix cells using the Takara lentivirus preparation kit. Expression of the various CAR-B constructs was measured using flow cytometry using antibodies specific for PSMA (biotin-PSMA, Sinobiological and is depicted in FIG. 5.

Expression of anti-PSMA CAR-B in Human B Cells. To measure expression and binding of anti-PSMA CAR-B's in B cells, two additional constructs were made:

TABLE 7

| Construct | Description |
| --- | --- |
| pWF-391 | pMMLV(LTR)-hEF1a promoter-anti hPSMA (XENP14484)-CBCR (SEQ ID NOS. 54 and 55) |
| pWF-394 | pMMLV(LTR)-hEF1a promoter-anti sarcoglycan CBCR1 (SEQ ID NOS. 56 and 57) |

A MMLV based vector was used for the preparation of the retrovirus. The retrovirus was used to infect mouse B cells isolated from the spleen. After transduction, B cells were further expanded on feeder cells expressing CD40L and soluble IL-4. The expression of anti-PSMA CAR-B was detected by using recombinant biotin-PSMA. PE-labeled streptavidin was used to detect PSMA binding in HEK-293 cells.

Figures 6A, 6B, 6C:
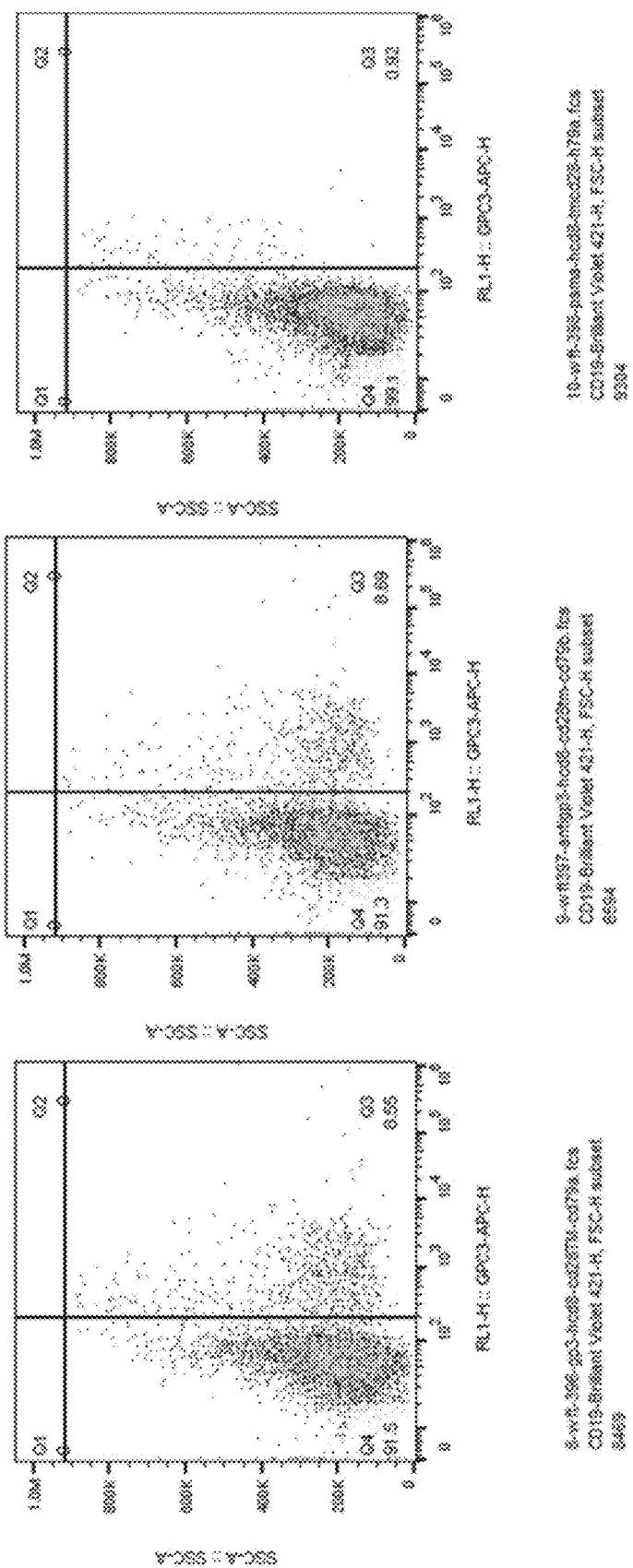
FIGS. 6A-6C set forth a FACS Plot illustrating interrogation of binding of anti-PSMA CAR and of anti-sarcoglycan CAR to PSMA. B cells expressing anti-PSMA CAR-B constructs pWF396 and pWF397 bound PSMA whereas the B cells expressing pWF398 (anti-sarcoglycan CAR-B) did not bind PSMA.
Figure 7:
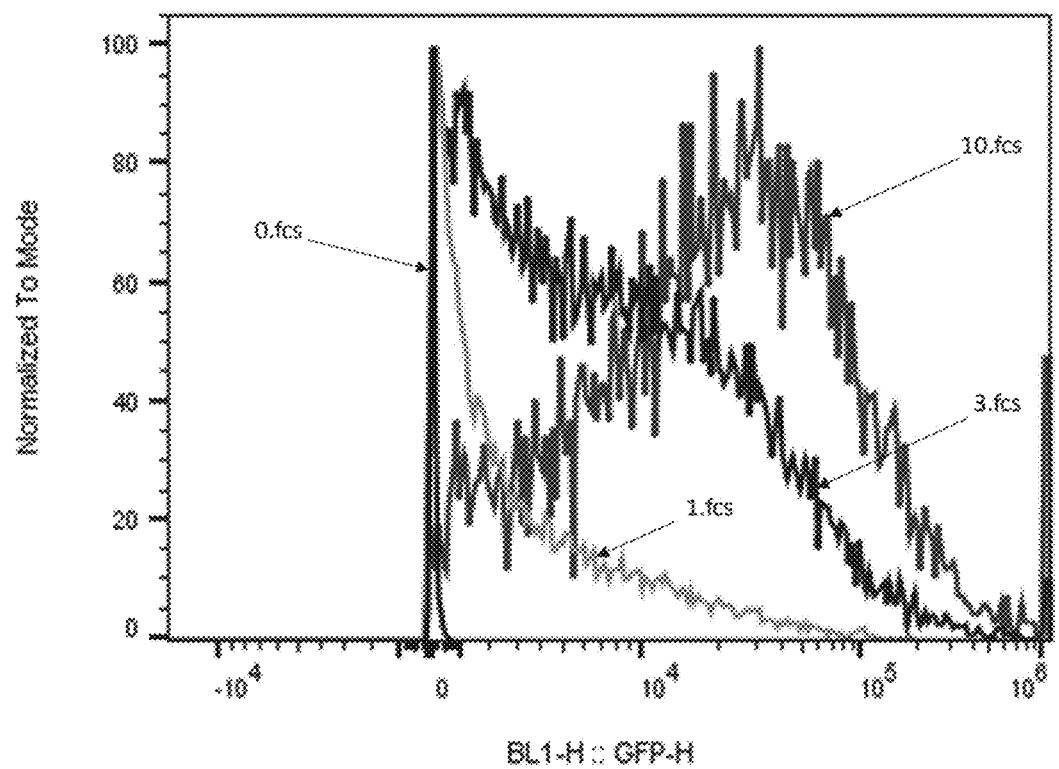
FIG. 7 illustrates the ability of adenovirus F35 encoding GFP to transduce human B cells. Human B cells were isolated from peripheral blood. The B cells were infected with adenovirus encoding GFP. 0, 1, 3, 10 ul, representing the microliter volume of the adenovirus preparation used to infect human B cells. The titer of the adenovirus preparations were approximately $1 \times e^{12}$ particles/ml.

Results. The results of this experiment are depicted in FIG. 6 and demonstrate that it is possible to create mouse B cell that expresses a CAR-B that can bind with specificity to an antigen. For example, B cells expressing pWF396 or pWF397 bound to PSMA whereas the B cells expressing pWF394 did not bind PSMA pWF398 was designed to bind sarcoglycan not PSMA).

Example 2—Chimeric Antigen Receptor on B Cells (CAR-B) Constructs to Bind GPC3

DNA Construct. Exemplary CAR constructs were designed to recognize glypican-3 (GPC-3). Glypican-3 is expressed on hepatocellular carcinoma cells among other tumor types, but not on most non-cancer cells. GPC3 can be used to target an anti-GPC3 CAR to hepatocellular carcinoma, as well as other cancers in which GPC3 is expressed (e.g. ovarian clear cell carcinoma, pediatric cancers, lung cancers (i.e. lung adenocarcinoma and lung squamous cell carcinoma), urothelial carcinoma, thyroid cancer, gastric cancer, and others). Various construct were made comprising an extracellular domain that comprised an scFv specific for GPC-3, an extracellular hinge region from CD8, a CD28 transmembrane domain, and various intracellular signaling domains. An additional anti-PSMA CAR-B was constructed as a control for these experiments. A list of the constructs is provided in Table 8.

TABLE 8

| Construct | Description |
| --- | --- |
| pWF-396 | pMMLV(LTR)-hEF1a promoter-anti-GPC3 scFv-hCD8H-hCD28M-hCD79aE (SEQ ID NOS. 58 and 59) |

TABLE 8-continued

| Construct | Description |
| --- | --- |
| pWF-397 | pMMLV(LTR)-hEF1a promoter-anti-GPC3 scFv-hCD8H-hCD28M-hCD79bE (SEQ ID NOS. 60 and 61) |
| pWF-398 | pMMLV(LTR)-hEF1a promoter-anti-hPSMA (XENP14484) scFv-hCD8H-hCD28M-hCD79aE (SEQ ID NOS. 62 and 63) |

Expression of anti-GPC-3 on HEK-293 Cell. Lentiviral transductions were used to express GPC3 CAR-B proteins on the surface of HEK293 cells. Expression was determined by flow cytometry with an anti-idiotype antibody specific for GPC-3 (Eureka Therapeutics).

Expression of anti-GPC-3 CAR-B in Human B Cells. pWF 396, 397 and 398 encoding CAR constructs were used to prepare MMLV retrovirus. This retrovirus was used to transduce mouse B cells isolated by negative selection (Stem Cell Technologies) and activated for 24 hours by co-culture with HeLa cells expressing CD40L and the addition of soluble IL-4. 48 hours post-transduction, expression was confirmed using flow cytometry. The expression of the CAR-B was detected using an anti-idiotype antibody against human GPC3. The anti-idiotype antibody was obtained from Eureka Therapeutics.

Results. Mouse B cells expressing anti-GPC-3 CAR-Bs, pWF-396 and 397, were expressed and specifically bound by anti-GPC3 idiotype antibody.

Example 3—Adenovirus Variant F35 Expressing GFP

Adenovirus variant F35 expressing GFP was demonstrated to efficiently infect human B cells. Human B cells were isolated from the peripheral blood. The B cells were infected with adenovirus encoding GFP at volumes of 0, 1, 3, 10 μL. The titer of the adenovirus preparations were approximately $1 \times e^{12}$ particles/ml.

Example 4—Delivering Payloads to Tumor Cells

Figure 8:
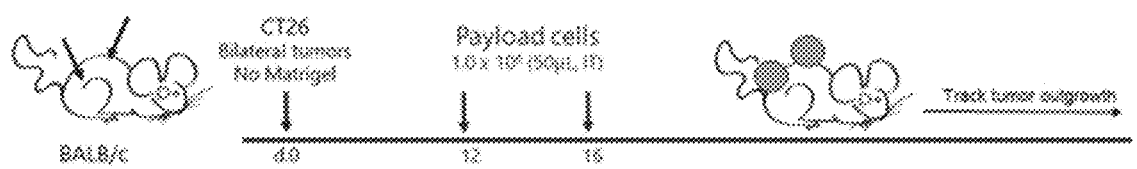
FIG. 8 describes an experiment where BALB/c mice were injected with CT26 bilateral tumors at day zero. At day 12 and day 16, tumor-bearing mice were injected intra-tumorally with payload-expressing cells at a volume of $10^6$ in 50 µL.

A large screening study was conducted to examine the effect of payloads on NIH3T3 fibroblasts in a CT26 Model. Payloads included various immunomodulators, including cytokines and chemokines. First, BALB/c mice were injected with CT26 tumors into their left and right flank. See FIG. 8. Twelve and sixteen days later, mice were injected into the right flank tumor, with various combinations of 4-5 payloads. Tumor volume was measured for up to 35 days.

Generation of the BALB/C CT26 tumor model. A total of 139 mice were injected with CT26 tumors into their left and right flanks.

Selection of Payload. Twelve peptides were identified for their potential to (i) recruit and activate dendritic cells; (ii) initiate homing and guidance of dendritic cells and T cells into the tumor site; and (iii) activate effector T cells. The payloads screened are listed in Table 9.

TABLE 9

| Payload | SEQ ID NO. |
| --- | --- |
| FLT3L | 70, 71 |
| XCL1 | 72, 73 |
| TIM4-Fc | 74, 75 |

TABLE 9-continued

| Payload | SEQ ID NO. |
| --- | --- |
| CXCL13 | 68, 69 |
| mCCL21 | 92, 93 |
| mCD80 - membrane bound | 86, 87 |
| mCD40L - membrane bound | 88, 89 |
| mIFNa A2 | 84, 85 |
| mIL-12 | 80, 81 |
| mIL-21 | 90, 91 |
| mLIGHT mutant | 78, 79 |
| M4-1BBL-membrane bound | 76, 77 |
| mIL-15 | 124, 125 |

Each was either given a combination of 4-5 payloads, all 12 payloads, or 3T3 cells (without payload) or saline as a control. In total, there were twenty-seven groups (n=5 mice/group). The experimental groups are identified in Table 10.

TABLE 10

| Group # | Treatment |
| --- | --- |
| 1 | FLT3L, XCL1, CXCL13, TIM4-Fc, TLR |
| 2 | FLT3L, XCL1, CXCL13, CD80-MB |
| 3 | FLT3L, XCL1, CXCL13, CD40L-MB, TLR |
| 4 | FLT3L, XCL1, CXCL13, IL-12 and TM |
| 5 | FLT3L, XCL1, CXCL13, 4-1BBL-MB |
| 6 | FLT3L, XCLI, CXCL13, IFNa A2 |
| 7 | FLT3L, XCL1, LIGHT, TIM4-Fc |
| 8 | FLT3L, XCL1, LIGHT, CD80-MB |
| 9 | FLT3L, XCL1, LIGHT, CD40L-MB, TLR |
| 10 | FLT3L, XCL1, LIGHT, IL-12 and TM |
| 11 | FLT3L, XCL1, LIGHT, 4-1BBL-MB |
| 12 | FLT3L, XCL1, LIGHT, IFNa A2 |
| 13 | FLT3L, XCL1, IL-21, TIM4-Fc |
| 14 | FLT3L, XCL1, IL-21, CD80-MB |
| 15 | FLT3L, XCL1, IL-21, CD40L-MB |
| 16 | FLT3L, XCL1, IL-21, IL-12 and TM |
| 17 | FLT3L, XCL1, IL-21, 4-1BBL-MB |
| 18 | FLT3L, XCL1, IL-21, IFNa A2 |
| 19 | FLT3L, XCL1, CCL21, TIM4-Fc |
| 20 | FLT3L, XCL1, CCL21, CD80-MB |
| 21 | FLT3L, XCL1, CCL21, CD40L-MB |
| 22 | FLT3L, XCL1, CCL21, IL-12 and TM |
| 23 | FLT3L, XCL1, CCL21, 4-1BBL-MB |
| 24 | FLT3L, XCL1, CCL21, IFNa A2 |
| 25 | All Payloads |
| 26 | Saline |
| 27 | 3t3 cells (no payload) |

Dosing. Tumor volume was between 100 mm$^3$ and 150 mm$^3$ at the time of the first injection. For the groups receiving 4 payloads, each payload was delivered at 2.5×10$^5$ cells per injection for a total of 10$^6$ cells. For the groups receiving 5 payloads, each pay load was delivered at [x] cells per injection for a total of 3×10$^6$ cells. The fifth payload was co-administered with Poly(I:C), which is a ds-RNA analog. Payloads were administered by intra-tumor injection. The volume of administration was 50 μL for all groups except the poly (I:C) group and the large 12-way group, where the volume was 150 μL.

Payload Administration Procedures. Cells were harvested with versene (not in the presences of trypsin). Once collected, the cells were counted, spun and resuspended in a volume that could be adjusted to 20×10$^6$/ml after the cells are recounted. TLR agonist (Invivogen Cat #ODN:1826) by resuspending lyophilized powder in water provided. TLR agonist was resuspended at 10 mg/ml and heated to 70 deg C. and then let to sit at RT for 1 hour prior to using. The dose of TLR agonist is 50 μg in 50 μl.

Figure 9:
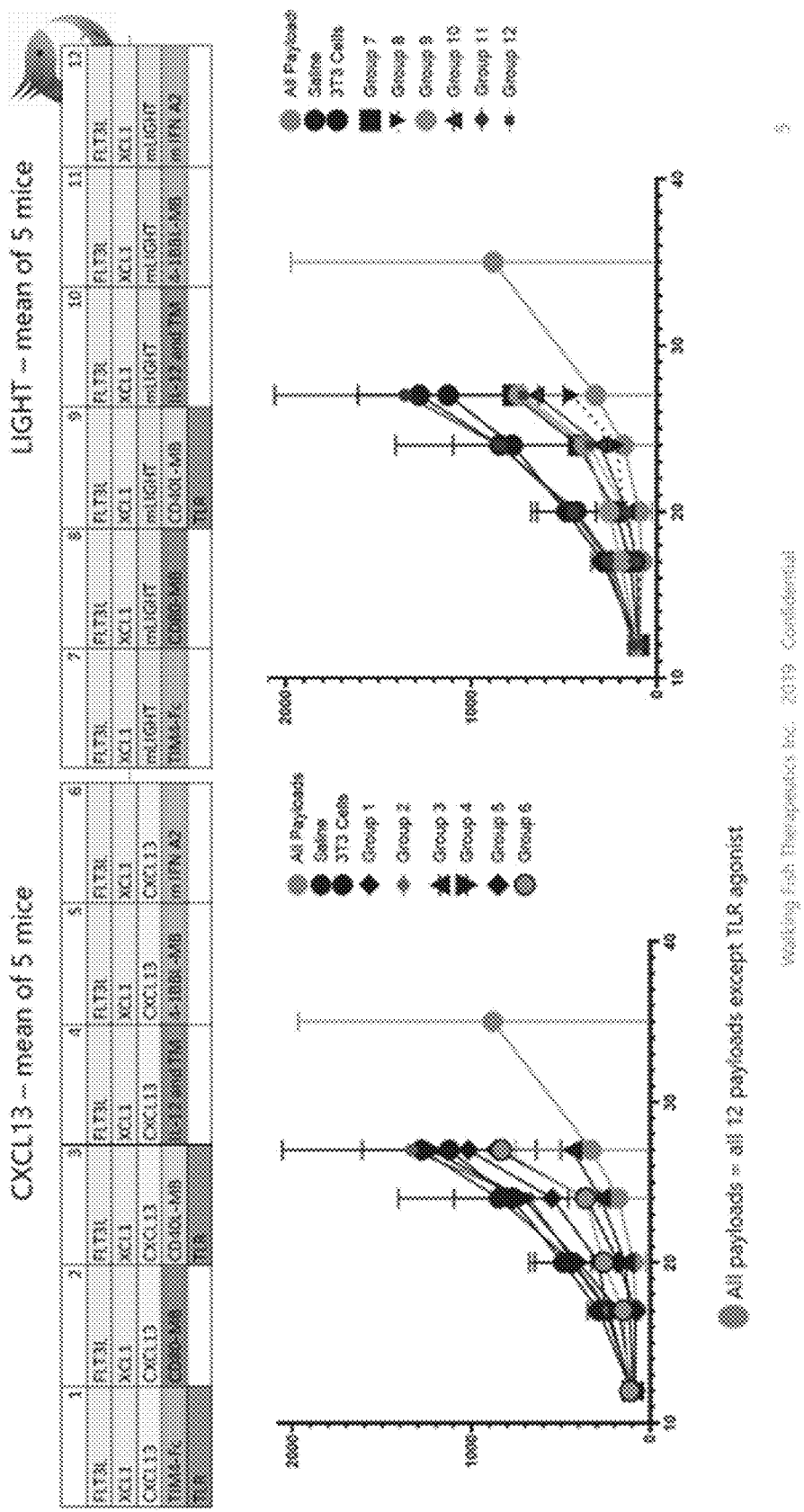
FIG. 9 illustrates the effect of 12 different combinations of payloads injected intra-tumorally on tumor volume over 30-35 days as compared to saline and 3T3 cells (without a payload).
Figure 10:
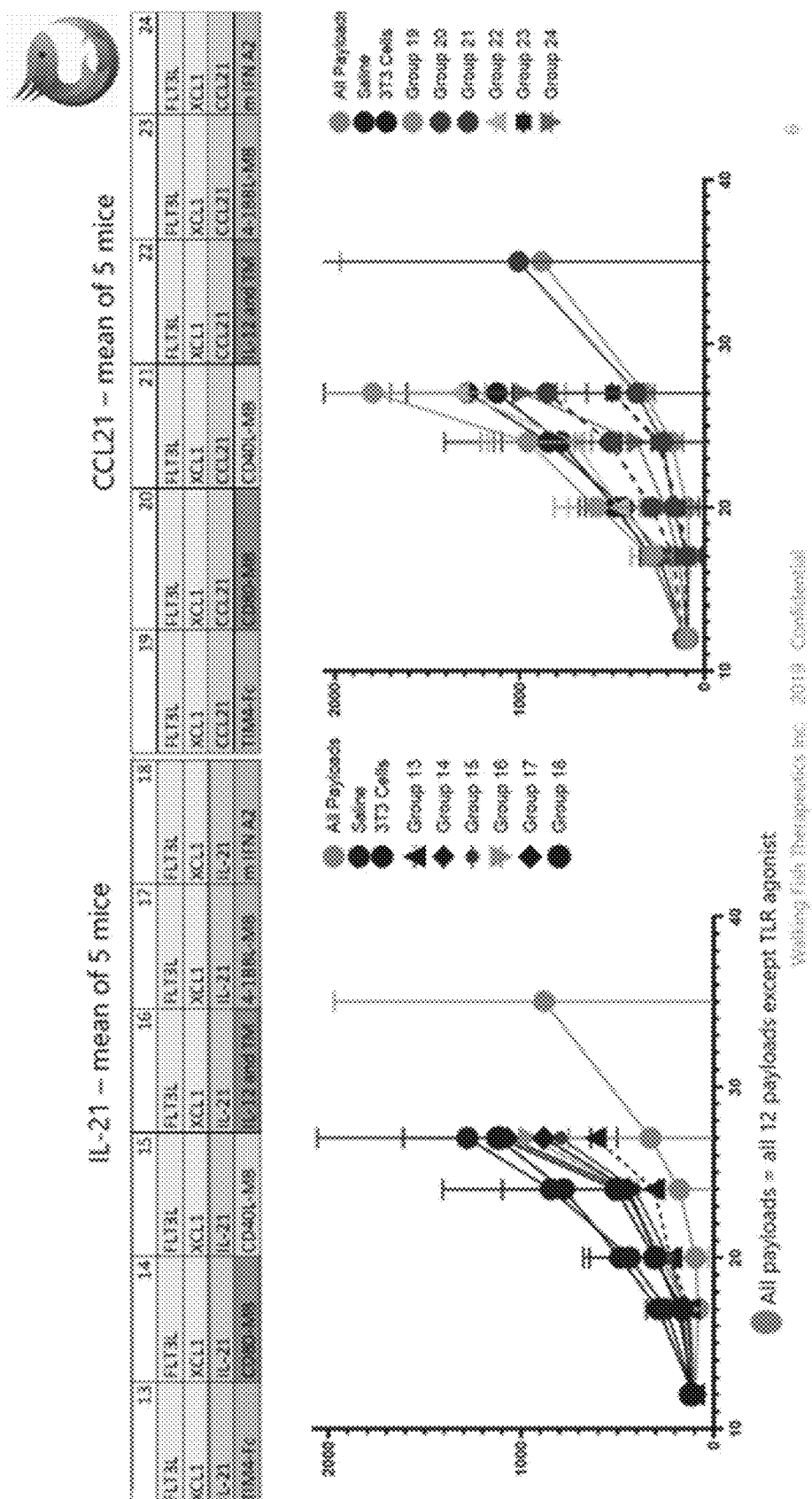
FIG. 10 illustrates the effect of 12 different combinations of payloads injected intra-tumorally on tumor volume over 30-35 days as compared to saline and 3T3 cells (without a payload).
Figure 11C:
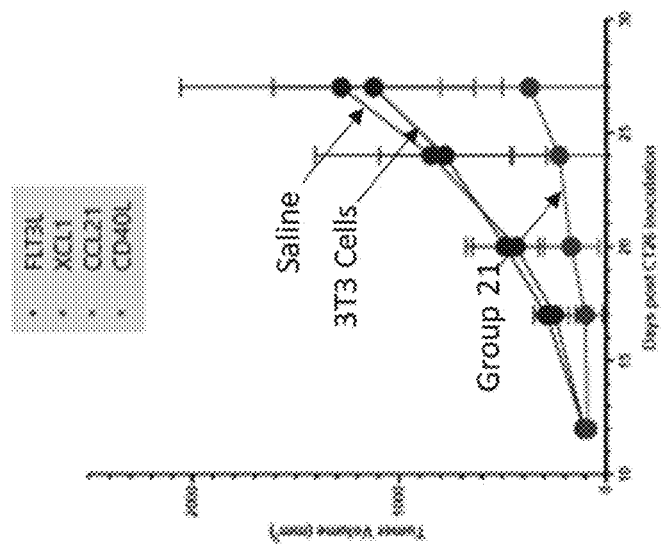
FIGS. 11A-11C illustrate the effect of the top three combinations of payloads injected intra-tumorally on tumor volume over 30 days as compared to saline and 3T3 cells (without a payload).
Figure 11B:
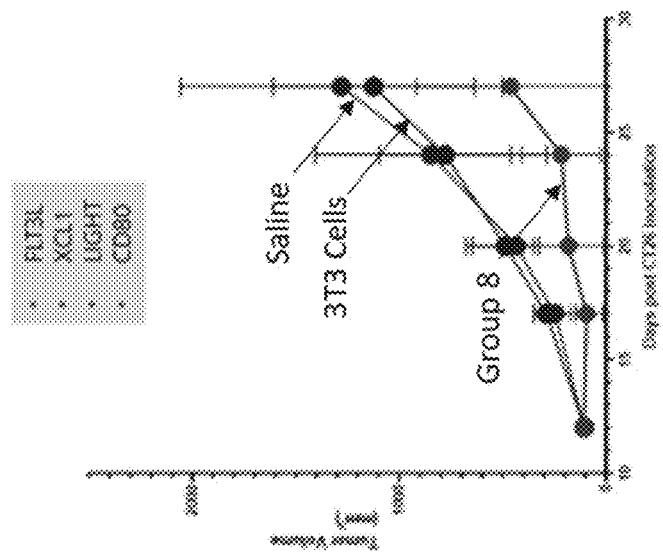
Figure 11A:
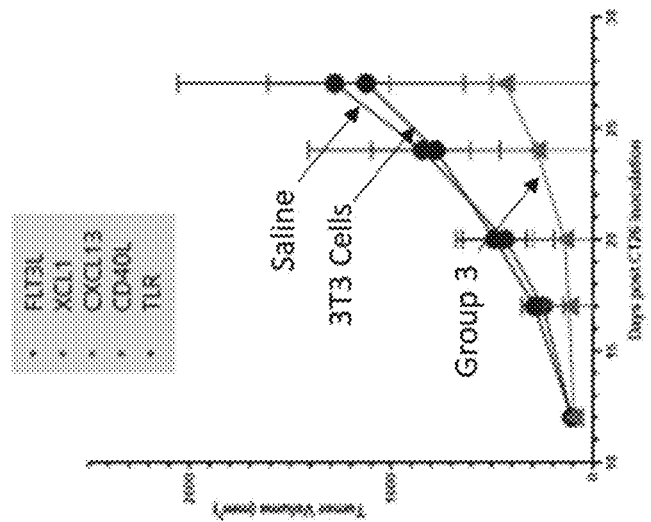

Results. The results are depicted in FIGS. 9-11. Several combinations of payloads injected ipsilaterally demonstrated antitumor activity in the contralateral tumors manifested as delayed tumor growth in this model. Groups 3, 8 and 21 showed the most significant impairment of tumor growth over 30 days.

Example 5—Modified B Cells that Express and Secrete Payloads

Experimental Design. A BALB/c mouse CT26 tumor model was used to evaluate the efficacy of modified B cells expressing various payload on tumor volume and survival. Mice were injected with tumor cells at a volume of 100 μL. On day 6 once tumors had reached a volume of 175 mm$^3$, mice were injected with modified B cells expressing various payloads as described below. Tumor volume and survival were measured for 17 days.

Isolation of Mouse PBMCs. Mouse PBMCs or splenocytes are isolated from blood or spleen, respectively. PBMCs are isolated using Lympholyte-M (CedarLane, Cat #CL5030). Splenocytes are isolated by manual cell separation through a 70 micron nylon cell strainer. B cells are then isolated from PBMCs or splenocytes via immunomagnetic negative selection using EasySep® Mouse B cell Isolation Kit (Stem Cell Technologies, Cat #19854).

Selection of Payloads. Nucleic acid sequences expressing payload peptides or proteins are transfected or transduced into isolated B cells. The following twelve peptides were identified for their potential to (i) recruit and activate dendritic cells; (ii) initiate homing and guidance of dendritic cells and T cells into the tumor site; and (iii) activate effector T cells. The payloads screened are listed in Table 9.

Each mouse was either given a combination of 4-5 payloads, or isolated B cells (without payload) or saline as a control. In total, there were twenty-seven groups (n=5 mice/group). The experimental groups are identified in Table 11.

TABLE 11

| Group # | Treatment |
| --- | --- |
| 3 | FLT3L, XCL1, CXCL13, CD40L-MB, TLR |
| 8 | FLT3L, XCL1, mLIGHT, CD80-MB |
| 21 | FLT3L, XCL1, CCL21, CD40L-MB |
| 26 | Saline |
| 27 | B cells (no payload) |

Generation of Payload Expressing B Cells. For transfection, purified or cultured B cells are washed and suspended in Cytoporation Medium T (BTX, Cat #47-0002) at 5×10$^6$ to 25×10$^6$ cells per ml and mixed with 7.5 pg to 50 pg RNA (RNA constructs are designed and prepped in house or purchased from TriLink using CleanCap® and fully substituted with Pseudo-U). 200 μL cell/RNA suspension electroporated using BTX Agilpulse® Electroporation System.

Dosing. Tumor volume was between 100 mm$^3$ and 150 mm$^3$ at the time of the first injection. For the groups receiving 4 payloads, each payload was delivered at 2.5×10$^5$ cells per injection for a total of 10$^6$ cells delivered. For the groups receiving 5 payloads, each pay load was delivered at 2.5×10$^5$ cells per injection for a total of 1.25×10$^6$ cells delivered. Payloads were injected intra-tumor. The volume of administration was 50 μL for groups receiving 4 payloads, the volume of administration was 100 μl. for groups receiving 5 payloads.

Payload Administration Procedures. Cells were harvested with versene (not in the presence of trypsin). Once collected, the cells were counted, spun and resuspended in a volume that could be adjusted to 20×10⁶/ml. TLR agonist (Invivo-Gen Cat #ODN:1826) by resuspending lyophilized powder in water provided. TLR agonist was resuspended at 10 mg/ml and heated to 70° C. and then let to sit at RT for 1 hour prior to using. The dose of TLR agonist is 50 pg in 50 µl.

Example 6—Anti-Tumor Activity of Intratumorally Injected B Cells

Mouse splenocytes were obtained and isolated via manual cell separation utilizing a 70 micron nylon cell strainer. Autologous (BALB/c) or allogeneic (C57Bl/6) donor mice were used (data shown utilized allogeneic B cells). B cells were isolated from the splenocytes above using immuno-magnetic negative selection via the EasySep® Mouse B Cell Isolation Kit (Stem Cell Technologies®, Cat #19854).

Figure 12:
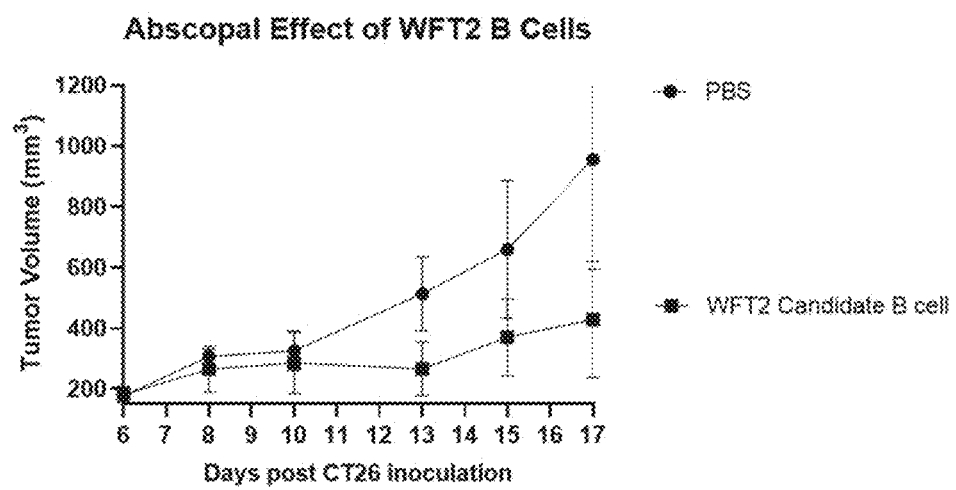
FIG. 12 illustrates the abscopal effect of intratumorally injected B cells. B cells were then injected either (i) fresh or (ii) first stimulated for 16-24 hours in growth media (RPMI, 10% FBS, 1% Pen/Strep, 5 ng/ml recombinant mouse IL-4, 100 uM beta-mercaptoethanol) with 5 µg/ml Lipopolysaccharide. $5 \times 10^6$ B cells were then intratumorally injected into the CT26 mouse model, and anti-tumor responses in the distal (abscopal) tumor where measured. Tumors were implanted at day 0, and at day 6 palpable tumor mass was observed. Treatment was initiated on day 6 intratumorally.

B cells were then injected either (i) fresh or (ii) first stimulated for 16-24 hours in growth media (RPMI, 10% FBS, 1% Pen/Strep, 5 ng/ml recombinant mouse IL-4, 100 uM beta-mercaptoethanol) with 5 µg/ml Lipopolysaccha-ride. 5×10⁶ B cells were then intratumorally injected into the CT26 mouse model, and anti-tumor responses in the distal (abscopal) tumor where measured. Tumors were implanted at day 0, and at day 6 palpable tumor mass was observed. Treatment was initiated on day 6 intratumorally. The results are set forth in FIG. 12.

Example 7—Expression of Chimeric Antigen Receptor (CAR) in B Cells Using RNA Electroporation to Make CAR B Cells Mouse PBMCs or splenocytes were isolated from blood or spleen as follows. Mouse PBMCs were isolated using Lympholyte-M (CedarLane, Cat #CL5030), and splenocytes were isolated by manual cell separation via passage through a 70 micron nylon cell strainer. B cells were then isolated from PBMCs or splenocytes, respectively, via immunomag-netic negative selection using the EasySep® Mouse B Cell Isolation Kit (Stem Cell Technologies, Cat #19854).

B cells were then stimulated for 16-24 hours in growth media (RPMI, 10% FBS, 1% Pen/Strep, 5 ng/ml recombi-nant mouse IL-4, and 100 uM beta-mercaptoethanol) with 5-15 ug/ml lipopolysaccharide. B cells were then transduced or transfected using known techniques (viral transfection or electroporation) to achieve either stable or transient expres-sion of CAR-B. A strep II tag was incorporated for post-translational detection. Representative CAR-Bs depicted are as follows:
1. XENP PSMA CBCR (3X strep II tag)
2. HyHEL10 CBCR (3X strep II tag)
3. D1.3-M3 HEL CBCR (3X strep II tag)

Figures 13A, 13B, 13C:
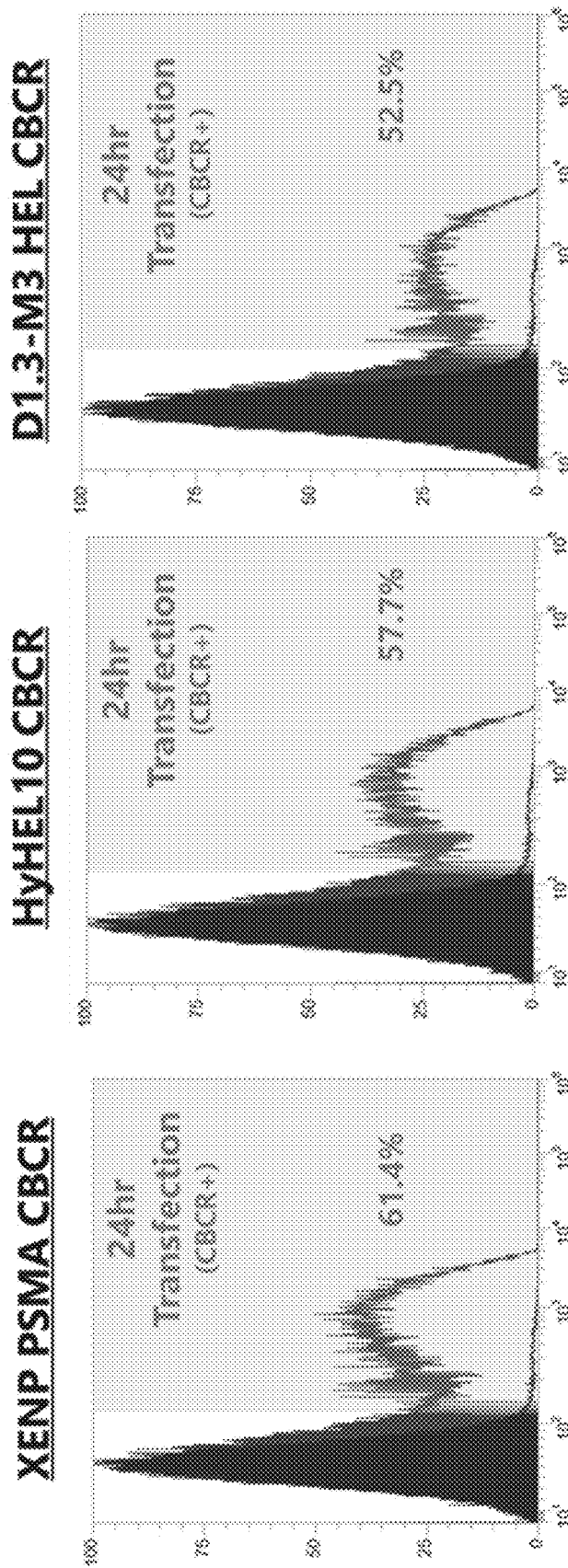
FIGS. 13A-13C illustrates expression of three CAR-B receptors (also referred to as CAR-B receptors) in mouse B cells 24 hours post transfection.

For transfection, purified or cultured B cells were washed and suspended in Cytoporation Medium T (BTX, Cat #47-0002) at 5×10⁶ to 25×10⁶ cells per ml and mixed with 7.5 ug to 50 ug RNA (RNA constructs were designed and prepped either in-house or purchased from TriLink using CleanCap® and fully substituted with Pseudo-U). A 200 ul cell/RNA suspension was obtained and electroporated using the BTX AgilePulse® Electroporation System. Cells were then washed in PBS and prepped for IV injection into immune-incompetent mice with established HepG2 tumor cells that express respective antigen (e.g. GPC3, HEL, PSMA). Trans-lation and expression of protein of interest was then mea-sured using an anti-Strep II tag antibody. The results are set forth in FIG. 13. In FIG. 13, the X axis shows strength of expression signal as measured by flow cytometry, and the Y axis sets forth percent of cells expressing the desired protein of interest (PSMA, HEL).

This experiment demonstrates that the desired RNA sequence/s are successfully transfected or transduced (ac-cordingly), the RNA is successfully translated, and the desired protein of interest is expressed on the cell surface.

Example 8—Modified B Cells Expressing Integrins and Homing Receptors

Nucleic acid constructs expressing an integrin, a homing receptor, or both are constructed using known techniques. Mouse and Human B cells are transfected or transduced (accordingly) with the nucleic acid constructs to express the integrin, the homing receptor, or both. These modified cells are administered intravenously into mice or a human host. Time-lapse imaging will measure accumulation of the modi-fied B cells at the site/target of interest, such as a homing or target tissue, an inflammatory site in a specific location or tissue, or a tumor or tumor microenvironment, to establish that expression of an integrin and/or a homing receptor of defined homing specificity endows the B cells with the ability to home to and accumulate at the site/target of interest where delivery of therapeutic payloads is desirable. A screening study is conducted according to the techniques of Example 5 to examine delivery and effect of payloads at the site/target of interest.

Example 9—Altering B Cell Trafficking

Isolated B cells are cultured with a specific concentration of all-trans-retinoic acid (ATRA) or derivatives thereof that induce expression of α4β7 integrin and the homing receptor CCR9. Thereafter, the B cells are harvested and adminis-tered intravenously into mice. There are two experimental groups of the recipient mice. The first group of mice are pre-treated with DSS or TNBS to induce gut inflammation. The second group of mice are not treated with DSS or TNBS. Inflammation similar to that observed in human intestinal bowl diseases is induced by pretreatment with DSS or TNBS. Administered B cells treated with ATRA or derivative thereof will home to areas of inflammation con-sistent with their homing potential due to increased expres-sion of α4β7 integrin and the homing receptor CCR9.

Example 10—Modified B Cells Expressing Immune Inhibitory Molecules

Nucleic acid constructs expressing an immune inhibitory molecule selected from IL-10, TGF-β, PD-L1, PD-L2, LAG-3, and TIM-3, or any combinations thereof, are con-structed using known techniques. Mouse and Human B cells are transfected or transduced (accordingly) with the nucleic acid constructs to express one or more of the immune inhibitory molecules listed above. These modified cells are administered intravenously into mice or a human host or elsewhere near or at sites of inflammation. Time-lapse imaging will measure accumulation of the modified B cells at a site/target of interest, such as a homing or target tissue, an inflammatory site in a specific location or tissue, or a tumor or tumor microenvironment, to establish that inflam-mation at the site and autoimmune activity of the B cells localized to the site are decreased, thereby leading to a positive therapeutic response.

Example 11—Activation of B Cells with TLRs

B cells are treated with TLR agonists and/or modified to express a constitutively active TLR for use in potentiating B cells for immune responses and producing potent effector B cells to increase antigen-specific immune responses in a subject. Isolated mouse or human B cells are treated in vitro with a TLR agonist at the same time or in advance of the administration of the B cells. In some instances, the mouse or human B cells are treated with more than one TLR agonists.

A modified B cell, transfected or transduced with or without a CAR-B construct of the foregoing examples, is engineered to express one or more constitutively active TLRs. Each TLR is introduced into the modified B cell (transduced or transfected using known techniques) as a DNA construct under the control of a constitutively activated transcriptional pathway. A modified B cell, expressing one or more constitutively active TLRs (with or without a CAR-B construct), is also treated with one or more TLR agonists at the same time or in advance of the administration of the modified B cells to a subject or patient in need thereof. Time-lapse imaging and other known techniques will measure accumulation of the modified B cells in the desired location and confirm expression of the TLR(s) and any expressed CAR-B of a defined specificity.

This experiment will demonstrate that the desired DNA sequence/s encoding specific TLR(s) of interest are successfully transfected or transduced (accordingly) into B cells with or without a CAR-B construct and treated with or without TLR agonist(s), the RNA is successfully translated, the desired TLR(s) are expressed in the B cells for producing potent effector B cells potentiating B cells for immune responses.

Example 12—Antigen Presentation Both in HLA Class I and Class H Molecules Using RNA Electroporated B Cells mRNA Constructs. Exemplary mRNA constructs are designed by fusing a specific antigen, e.g., a tumor antigen or an infectious disease antigen, to the targeting signal of a the lysosomal protein LAMP1, to target the specific antigen to the lysosomes and present the antigen simultaneously and efficiently in both HLA class I and class II molecules. Tumor antigens and infectious disease antigens are well known in the art and can include any antigen of interest against which an immune response is desired. Various mRNA constructs are made encoding at least one specific antigen of interest fused to the targeting signal of LAMP1 that is capable of presenting the specific antigen simultaneously and efficiently by both HLA class I and class II molecules when transfected into a suitable immune cell.

Experimental Design. Isolated mouse or human B cells are electroporated in vitro with an mRNA construct described above (i.e., encoding a specific antigen of interest fused to the targeting signal of LAMP1) using known mRNA electroporation techniques. In some instances, the mouse or human B cells are also transduced or transfected using known techniques with a CAR-B construct according to any of the foregoing examples. The mRNA electroporated B cells, transduced with or without a CAR-B construct of interest, are introduced intravenously into mice or a human host. Time-lapse imaging will measure accumulation of the modified B cells in the desired location and also confirm expression of CAR-B of a defined specificity. Translation and expression of the specific tumor antigens or infectious disease antigens of interest are measured using known techniques to establish that the antigens of interest are targeted to the lysosomes and presented simultaneously and efficiently by both HLA class I and class II molecules.

This experiment will demonstrate that the desired mRNA sequence/s encoding specific antigens of interest fused to a targeting signal are successfully transfected into B cells (which, if desired, are also transduced with a CAR-B construct), the mRNA is successfully translated, and the electroporated and modified B cells simultaneously and efficiently present the specific antigen of interest by both HLA class I and class II molecules for increasing antigen-specific immune responses in a subject.

Figure 14:
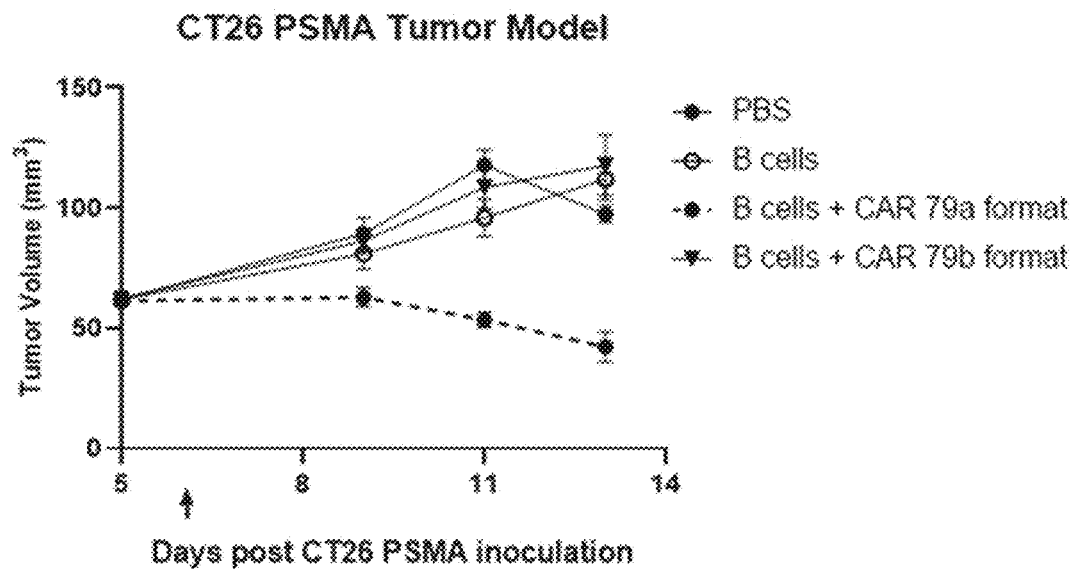
FIG. 14 illustrates the efficacy of PSMA-specific CAR engineered murine B cells on tumor volume and survival in BALB/c mice with CT26-PSMA tumors.

Example 13—B Cells Expressing a PSMA-Specific CAR Reduce Tumor Growth in CT26-PSMA Tumors Mouse Tumor Model. A BALB/c CT26-PSMA tumor model engineered to express human PSMA was used to evaluate the efficacy of PSMA-specific CAR engineered murine B cells on tumor volume and survival. Eight-week-old BALB/c mice were injected on one hind flank with $1.0 \times 10^6$ CT26-PSMA tumor cells in a volume of 50 µl. On day 5 when the tumor volume reached approximately 60 mm$^3$ the mice were distributed equally into 3 groups of 10 mice. Treatment of mice was started on day 6 using murine B cells engineered with mRNA encoding two different PSMA-specific CAR formats or un-engineered B cells administered intravenously at a dose of $1.5 \times 10^6$ cells in 100 µl, or saline on day 6. Tumor volume was measured using calipers on day 5, 9, 11, and 13. There was a statistically significant tumor reduction of 57% in the PSMA-CAR group (format 79a) relative to saline on day 13. There was not a significant reduction of tumor volume on day 13 in the PSMA-CAR treatment group (format 79b) relative to saline (FIG. 14).

Engineering of Murine B Cells. Mouse splenocytes were isolated from BALB/c donor spleens by manual cell separation through a 70 micron nylon cell strainer. B cells were then isolated from splenocytes via immunomagnetic negative selection using EasySep Mouse B cell Isolation Kit (Stem Cell Technologies, Cat #19854). B cells were stimulated for 24 hours in growth media (RPMI, 10% FBS, 25 mM HEPES, 1% Pen/Strep, 5 ng/ml recombinant mouse IL-4, 100 µM beta-mercaptoethanol) with anti-CD40 (250 ng/ml). Cells were then electroporated with 20 µg CAR mRNA construct per $3.6 \times 10^6$ B cells using BTX AgilePulse electroporation system set at 280V for 1 ms. Cells were washed and resuspended in PBS at a concentration of $15 \times 10^6$ B cells/ml. 100 µl of cell suspension were used per dose.

PSMA construct CD79a: pmRNA_d7_13_anti hPSMA (XENP14484) scFv-mCD8H-mCD28M-mCD79aE #ab-1

PSMA construct CD79b: pmRNA_d7_13_anti hPSMA (XENP14484) scFv-mCD8H-mCD28M-mCD79bE #ac-1

Figure 15:
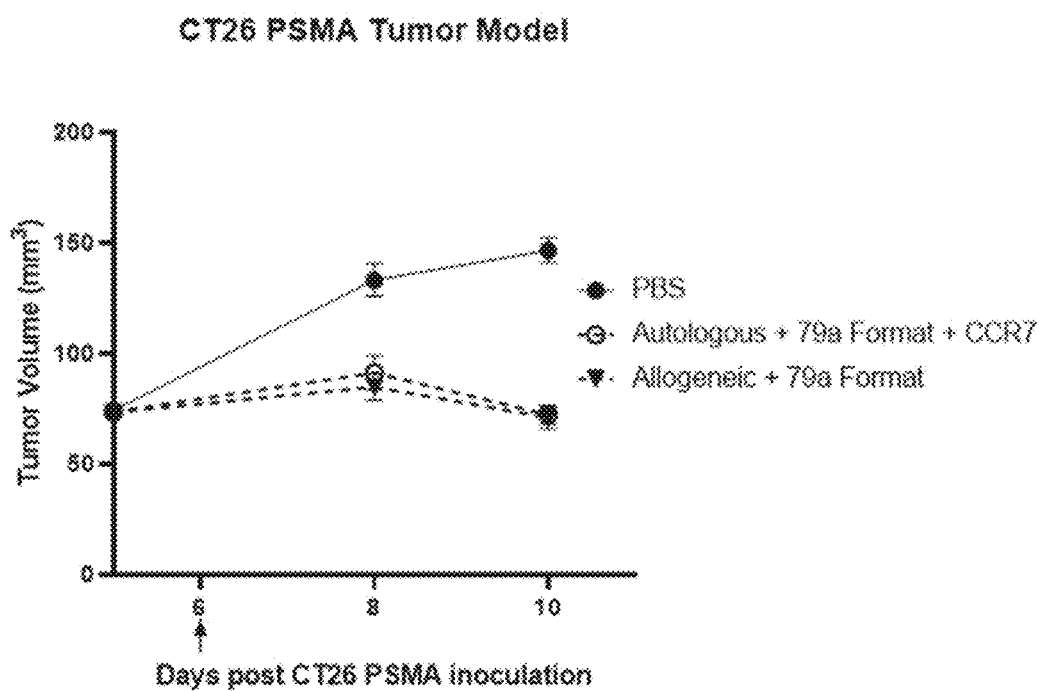
FIG. 15 illustrates the efficacy of PSMA-specific CAR engineered allogenic B cells on tumor volume and survival in BALB/c mice with CT26-PSMA tumors.

Example 14—Allogenic B Cells Expressing a PSMA-Specific CAR Reduce Tumor Growth in CT26-PSMA Tumors Mouse Tumor Model. A BALB/c CT26-PSMA tumor model engineered to express human PSMA was used to evaluate the efficacy of PSMA-specific CAR engineered allogeneic murine B cells on tumor volume and survival. Eight-week-old BALB/c mice were injected on one hind flank with $1.0 \times 10^6$ CT26-PSMA tumor cells in a volume of 50 µl. On day 5 when the tumor volume reached approximately 70 mm$^3$ the mice were distributed equally into 3 groups of 10 mice. Treatment of mice was started on day 6 using autologous murine B cells engineered with mRNA encoding a PSMA-specific CAR and an mRNA encoding CCR7 or allogeneic murine B cells engineered with mRNA encoding a PSMA-specific CAR administered intravenously at a dose of $1.5\times10^6$ cells in 100 µl, or saline. Tumor volume was measured using calipers on day 5, 8, and 10. There was a statistically significant tumor reduction of 51% in the allogeneic and autologous engineered B cell groups relative to saline on day 10 (FIG. 15). ($p<0.005$).

Engineering of Murine B Cells. Mouse splenocytes were isolated from autologous BALB/c and allogeneic C57Bl/6 donor spleens by manual cell separation through a 70 micron nylon cell strainer. B cells were then isolated from splenocytes via immunomagnetic negative selection using EasySep Mouse B cell Isolation Kit (Stem Cell Technologies, Cat #19854). B cells were stimulated for 24 hours in growth media (RPMI, 10% FBS, 25 mM HEPES, 1% Pen/Strep, recombinant mouse IL-4, 100 µM beta-mercaptoethanol) with anti-CD40 (250 ng/ml). Cells were then electroporated with 20 ug CAR mRNA construct per $3.6\times10^6$ B cells using BTX AgilePulse electroporation system set at 280V for 1 ms. Cells were washed and resuspended in PBS at a concentration of $15\times10^6$ B cells/ml. 100 µl of cell suspension were used per dose.

Example 15—the Antitumor Activity of PSMA-CAR-Engineered B Cells Depends on an Intact Host Immune System Mouse Tumor Models. The effect of antitumor PSMA-CAR B cells was studied in WT and immunocompromised NSG mice.

WT Mice. A BALB/c CT26-PSMA tumor model engineered to express human PSMA was used to evaluate the efficacy of PSMA-specific CAR engineered murine B cells on tumor volume and survival in WT mice. Eight-week-old BALB/c mice were injected on one hind flank with $1.0\times10^6$ CT26-PSMA tumor cells in a volume of 50 µl. On day 5 when the tumor volume reached approximately 60 mm$^3$ the mice were distributed equally into 4 groups of 10 mice. Treatment of mice was started on day 6 using murine B cells engineered with mRNA encoding two different PSMA-specific CAR formats or un-engineered B cells administered intravenously at a dose of $1.5\times10^6$ cells in 100 µl, or saline on day 6. Tumor volume was measured using calipers on day 5, 9, 11, and 13. There was a statistically significant tumor reduction of 57% in the PSMA-CAR group (format 79a) relative to saline on day 13. There was not a significant reduction of tumor volume on day 13 in the PSMA-CAR treatment group (format 79b) or un-engineered B cells, relative to saline (FIG. 14).

NSG Mice. A BALB/c CT26-PSMA tumor model engineered to express human PSMA was used to evaluate the efficacy of PSMA-specific CAR engineered murine B cells on tumor volume and survival in immunocompromised mice. Eight-week-old NSG mice were injected on one hind flank with $1.0\times10^6$ CT26-PSMA tumor cells in a volume of 50 µl. On day 5 when the tumor volume reached approximately 60 mm$^3$ the mice were distributed equally into 2 groups of mice. Treatment of mice was started on day 6 using murine B cells engineered with mRNA encoding a PSMA-specific CAR format administered intravenously at a dose of $1.5\times10^6$ cells in 100 µl, or saline on day 6. Tumor volume was measured using calipers on day 5, 8, 10, and 13.

Figure 16:
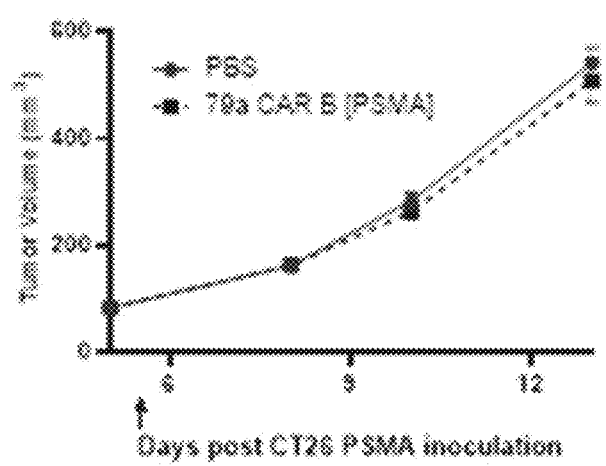
FIG. 16 illustrates the efficacy of PSMA-specific CAR engineered murine B cells on immunocompromised BALB/c mice with CT26-PSMA tumors.

There was no significant reduction in tumor volume in the PSMA-CAR group (format 79a) relative to saline on day 13 (FIG. 16B).

Engineering of Murine B Cells. Mouse splenocytes were isolated from autologous BALB/c and allogeneic C57Bl/6 donor spleens by manual cell separation through a 70 micron nylon cell strainer. B cells were then isolated from splenocytes via immunomagnetic negative selection using EasySep Mouse B cell Isolation Kit (Stem Cell Technologies, Cat #19854). B cells were stimulated for 24 hours in growth media (RPMI, 10% FBS, 25 mM HEPES, 1% Pen/Strep, recombinant mouse IL-4, 100 µM beta-mercaptoethanol) with anti-CD40 (250 ng/ml). Cells were then electroporated with 20 ug CAR mRNA construct per $3.6\times10^6$ B cells using BTX AgilePulse electroporation system set at 280V for 1 ms. Cells were washed and resuspended in PBS at a concentration of $15\times10^6$ B cells/ml. 100 µl of cell suspension were used per dose.

PSMA construct CD79a: pmRNA_d7_13_anti hPSMA (XENP14484) scFv-mCD8H-mCD28M-mCD79aE #ab-1

PSMA construct CD79b: pmRNA_d7_13_anti hPSMA (XENP14484) scFv-mCD8H-mCD28M-mCD79bE #ac-1

Figure 17:
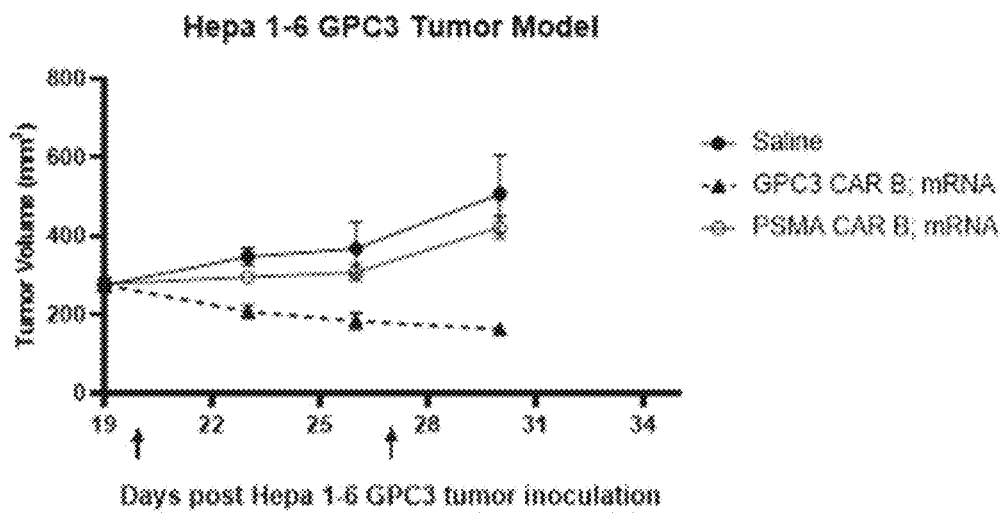
FIG. 17 illustrates the efficacy of murine B cells on tumor volume and survival in C57Bl/6 mice with HEPA 1-6 GPC3 tumors.

Example 16—B Cells Expressing a GPC3-Specific CAR Reduce Tumor Growth in HEPA 1-6 GPC3 Tumors Mouse Tumor Model. A C57Bl/6 HEPA 1-6 tumor model engineered to express human GPC3 (HEPA 1-6-GPC3) was used to evaluate the efficacy of murine B cells on tumor volume and survival. Eight-week-old C57Bl/6 mice were injected on one hind flank with $5.0\times10^6$ HEPA 1-6-GPC3 tumor cells at a volume of 200 µl. On day 19 when the tumors volume reached approximately 250 mm$^3$ the mice were distributed equally into 3 groups of 10 mice. Treatment of mice was started on day 20 using murine B cells engineered with mRNA encoding a GPC3-specific CAR or a PSMA-specific CAR administered intravenously at a dose of $1.5\times10^6$ cells in 100 µl, or saline on day 20 and day 27. Tumor volume was measured using calipers on day 19, 23, 26, and 30. There was a statistically significant tumor reduction of 68% in the GPC3-CAR group relative to saline on day 30. There was not a significant reduction of tumor volume on day 30 in the PSMA-CAR treatment group relative to saline. (note: this study is still in progress on 1-19-2021) (FIG. 17).

Engineering of Murine B Cells. Mouse splenocytes were isolated from C57Bl/6 donor spleens by manual cell separation through a 70 micron nylon cell strainer. B cells were then isolated from splenocytes via immunomagnetic negative selection using EasySep Mouse B cell Isolation Kit (Stem Cell Technologies, Cat #19854). B cells were stimulated for 24 hours in growth media (RPMI, 10% FBS, 25 mM HEPES, 1% Pen/Strep, 5 ng/ml recombinant mouse IL-4, 100 µM beta-mercaptoethanol) with anti-CD40 (250 ng/ml). Cells were then electroporated with 20 µg CAR mRNA construct per $3.6\times10^6$ B cells using BTX AgilePulse electroporation system set at 280V for 1 ms. Cells were washed and resuspended in PBS at a concentration of 15×106 B cells/ml. 100 µl of cell suspension were used per dose.

GPC3 mRNA construct: pmRNA_d7_13_anti-hGPC3 scFv-mCD8H-mCD28M-mCD79aE #15-1

PSMA construct: pmRNA_d7_13_anti hPSMA (XENP14484) scFv-mCD8H-mCD28M-mCD79aE #ab-1

Example 17—Multimerized GPC3 can Activate NFκB Expression of Luciferase in Cells Expressing a GPC3 CAR in a Dose-Responsive Manner CAR-B Construct Design. Five CAR-B constructs were designed using three basic formats (i) CAR 2 (an scFv, a hinge domain, a transmembrane domain and a signaling domain (see FIG XA)); (ii) CAR 3 (a multimerized receptor complex with 2 of each of the following: an scFv, a hinge domain, an FC domain, a transmembrane domain and a cytoplasmic tail (see FIG XB)); (iii) CAR 4 (a multimerized receptor complex with 2 of each of the following: (a FAB domain, a hinge domain, an FC domain, a transmembrane domain and a cytoplasmic tail (see FIG XC). The five CAR-B constructs are as follows:

TABLE 12

| | |
|---|---|
| pWF-506 (SEQ ID NO. 140/141) | pmRNA_d7_13_anti-hGPC3 scFv-hIgG1 Fc [TM + cyto] A-1 (CAR 3) |
| pWF-507 (SEQ ID NO. 142/143)/ pWF-508 (SEQ ID NO. 144/145) | pmRNA_d7_13_anti-hGPC3 vl-hcLamda/ pmRNA_d7_13_anti-hGPC3 vH-hIgHg1 [TM + cyto] (CAR 4) |
| pWF-509 (SEQ ID NO. 146/147) | pmRNA_d7_13_anti-hGPC3 scFv-hCD8H-hCD28M-hCD79bE (CAR 2) |
| pWF-510 (SEQ ID NO. 148/149) | pmRNA_d7_13_anti-hGPC3 scFv-hCD8H-hCD28M-hCD79aE (CAR 2) |

Figure 18:
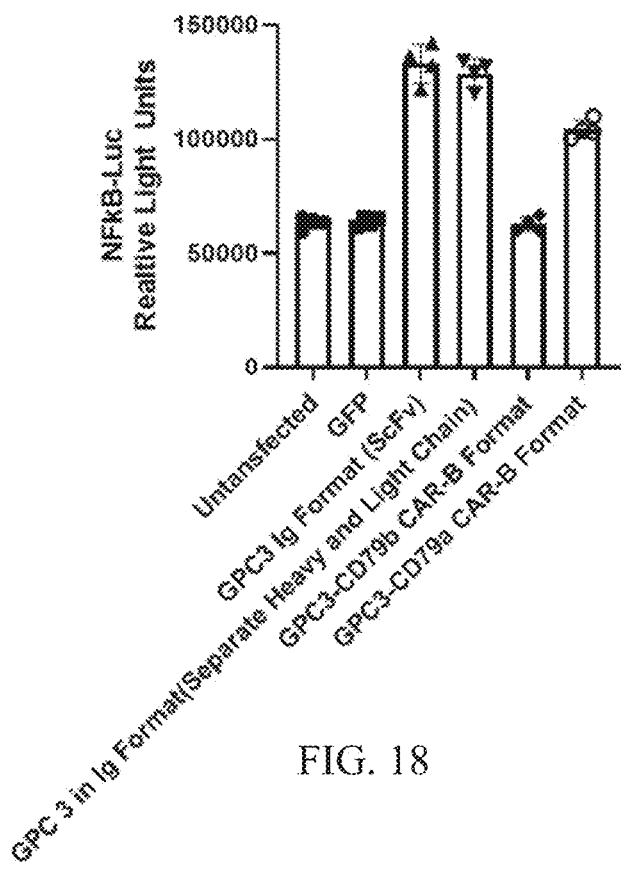
FIG. 18 illustrates NFKb signaling in luciferase reporter cells in B cells engineered with four different CAR constructs that recognized GPC3, using GFP as a control.

NFκB Reporter Assay: Antigen induced signaling. Ramos NFκB-luciferase reporter cells were transduced with mRNA coding for one of the CAR-B constructs listed above. Ramos NFκB-luciferase reporter cells were transfected at 280 V and 1 msec with 10 μg of RNA in 200 μL, of electroporation buffer followed by culturing overnight in growth medium. The cells were left at room temperature for 4 hours to quiesce the cells to reduce background. 30,000 of the transfected cells were transferred to each well in a multi-well plate in a volume of 30 μL per well. The transfected Ramos cells were then incubated with GPC3 protein multimerized with streptavidin, streptavidin control or GPC3-Fc protein for 3 hours in growth medium. 30 μL of Bioglo substrate (Promega) was added to each well and the plate was read within 5 minutes using a luminometer. As demonstrated in FIG. 18, multimerized GPC3 was capable of activating NFκB expression of luciferase in cells expressing three of the four GPC3 CAR-Bs except pWF-509 (GPC3-CD79b). All four constructs displayed good binding to GPC3 in FACS assays. Therefore, CD79b was an example where a CAR, which had good binding affinity, did not signal.

Figure 19:
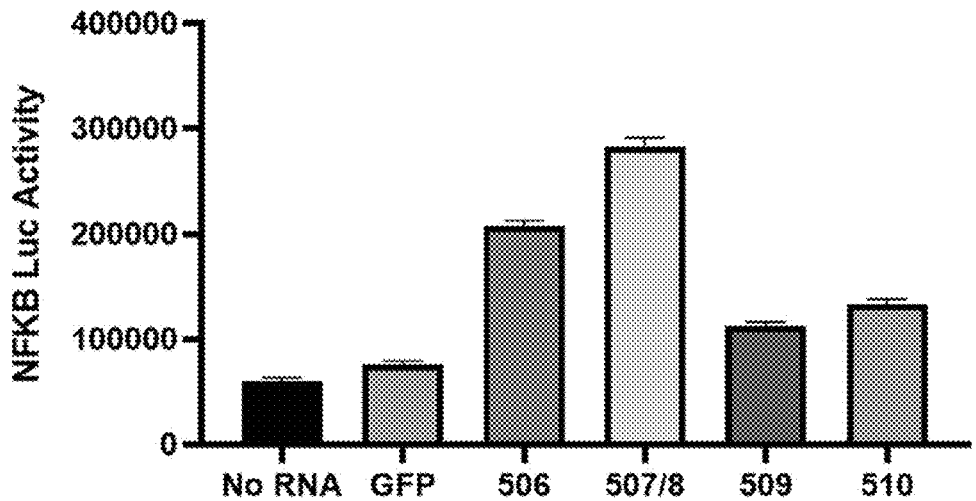
FIG. 19 illustrates basal or tonic NFKb activity in the absence of cognate target antigen in CAR constructs expressed in human B cell reporter line.

NFκB Reporter Assay: Tonic Signaling. Tonic signaling was also assessed, using the NFκB Reporter Assay. CAR constructs, which induced elevated tonic signaling in the absence of cognate antigen binding, were generated. FIG. 19 shows that the four CAR-B constructs were expressed in a human B cell reporter line and NFκB luciferase activity was measured in the absence of cognate target antigen. Each construct displayed significant tonic signaling activity. Engineered B cells with tonic signaling CAR Bs remained at a high number in vivo and led to high and durable expression of replacement factors or other payloads.

Figure 20:
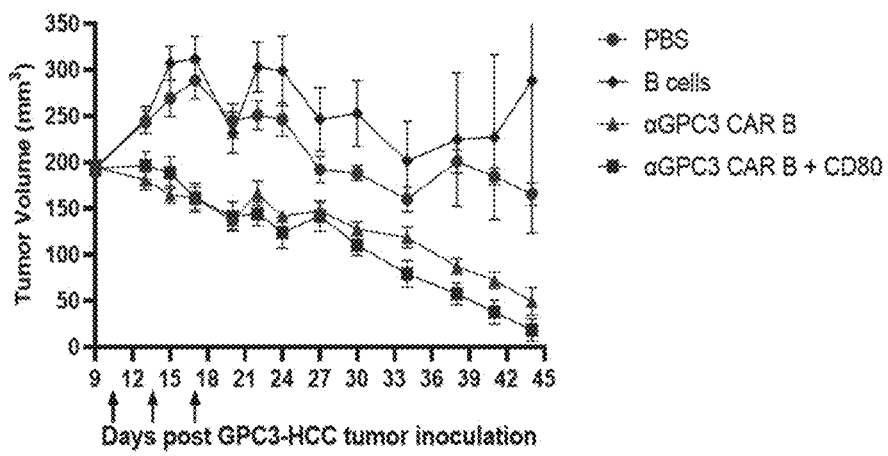
FIG. 20 illustrates the efficacy of murine B cells electroporated with anti-GPC3CAR-CD79a and a CD80 payload mRNAs in syngeneic C57Bl/6 mice with HEPA1-6GPC3 tumors.

Example 18—a CD80 Payload Enhances the Antitumor Activity of Anti-GPC3CAR-CD79a B Cells Experimental Design. A syngeneic C57Bl/6 mouse HEPA1-6GPC3 tumor is a model of human HCC engineered to express human GPC3. This model was used to evaluate the efficacy of murine B cells electroporated with anti-GPC3CAR-CD79a and a CD80 payload mRNAs. Mice were injected on one hind flank with $5.0 \times 10^6$ HEPA1-6GPC3 tumor cells at a volume of 200 ul in matrigel. On day 11,14, and 17 the mice were administered a 200 ul IV dose of $1.5 \times 10^6$ B cells, B cells engineered with anti-GPC3CAR-CD79a, B cells engineered with anti-GPC3CAR-CD79a and CD80, or saline as indicated in FIG. 20. The B cells were engineered with mRNA as described below. Tumor volume was monitored on multiple days as indicated in FIG. 20.

Figures 21A, 21B, 21C:
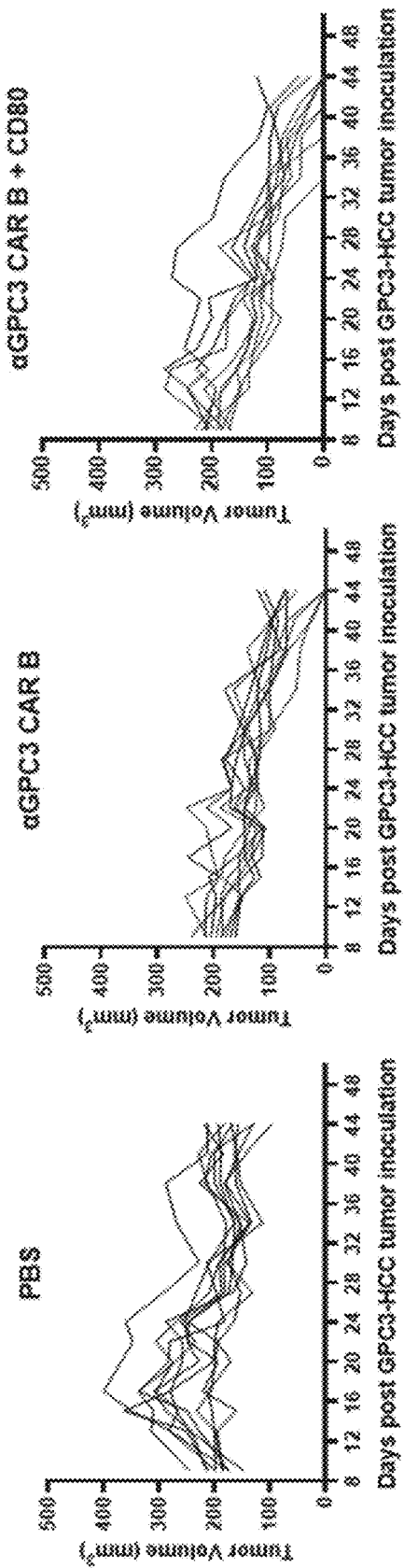
FIGS. 21A-21C illustrate the responses of the saline control, anti-GPC3CAR-CD79a, and anti-GPC3CAR-CD79a plus CD80 combo B cell groups.

In FIG. 20, both the anti-GPC3CAR-CD79a, and anti-GPC3CAR-CD79a plus CD80 combo displayed a statistically significant effect relative to saline or un-engineered B cells on day 44 and at multiple earlier time points. Additionally, by day 44 there were no complete responses in the saline control or B cell control groups but the anti-GPC3CAR-CD79a, and anti-GPC3CAR-CD79a plus CD80 combo resulted in 4 and 7 complete responses, respectively, as indicated in FIGS. 21A-21C. These data demonstrate that inclusion of the CD80 payload as mRNA potentiated the antitumor activity of B cells co-electroporated with an antigen-specific GPC3 CAR.

B Cell preparation. Mouse splenocytes were isolated from C57Bl/6 donor spleens by mechanical cell separation through a 70 micron nylon cell strainer. B cells were then isolated from splenocytes via immunomagnetic negative selection using EasySep Mouse B cell Isolation Kit (Stem Cell Technologies, Cat #19854). B cells were stimulated for 24 hours in growth media (RPMI, 10% FBS, 1% Pen/Strep, 5 ng/ml recombinant mouse IL-4, 100 uM beta-mercaptoethanol) with 250 ng/ml CD40 antibody (anti-murine CD40 Ab). Cells were then electroporated with 20 ug mRNA per $1.0 \times 10^7$ B cells using BTX AgilePulse electroporation system set at 400V for 1 ms, 2 ms interval for 5 pulses. When two mRNA's were cotransfected, 20 ug of each mRNA was used. Immediately after electroporation, the cells were washed in PBS and prepared for IV administration at a dose of $1.0 \times 10^7$ per 200 ul. The electroporated cells were administered to mice within 90 minutes after electroporation.

Figure 22C:
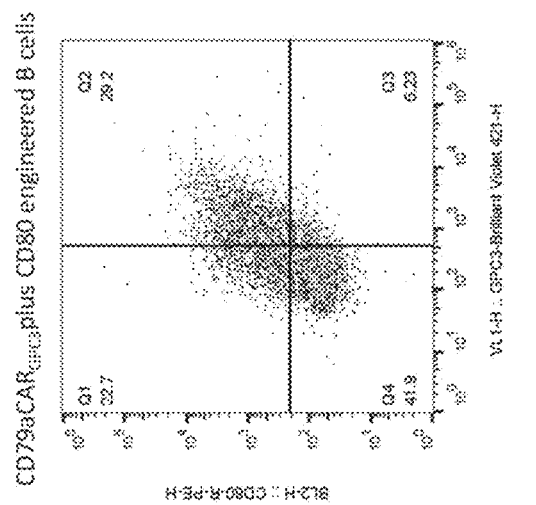
FIGS. 22A-22C illustrate the expression of the GPC3 CAR post-electroporation, using FACS plots.
Figure 22B:
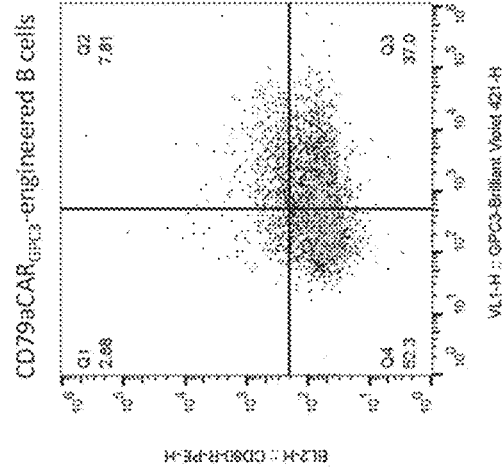
Figure 22A:
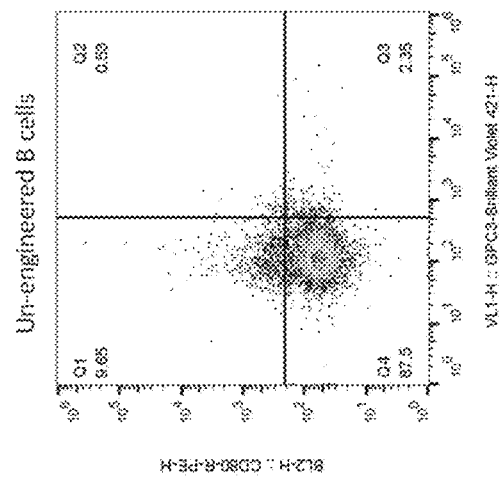

Twelve hours after electroporation, a small aliquot of the cells were stained for expression of anti-GPC3CAR-CD79a and CD80 expression. For detection of anti-GPC3CAR-CD79a expression, GPC3-Avitag and Streptavidin-BV421 were used. CD80 expression was measured with an anti-CD80-PE FACS antibody. The FACS plots in FIGS. 22A-22C show expression of the GPC3 CAR post-electroporation. CD80 was expressed at a basal level in un-engineered B cells, thus accounting for the ~10% positivity. This level remained in the CAR sample, but was increased dramatically in the CAR+CD80 sample. The latter suggested efficient expression of CD80.

What is claimed:

1. A modified B cell comprising a chimeric receptor, wherein said chimeric receptor comprises
a) an extracellular domain comprising an extracellular binding domain;
b) a transmembrane domain; and
c) a cytoplasmic domain comprising a signaling domain, said signaling domain comprising CD79a,
wherein, upon binding of the extracellular binding domain to a target antigen or protein, the modified B cell is activated and presents an antigen or an antigen-derived epitope in an HLA or MHC complex.

2. The modified B cell of claim 1 wherein said extracellular binding domain recognizes at least one target antigen or protein, or an epitope of the target antigen, expressed on the surface of a target cell.

3. The modified B cell of claim 1, wherein the extracellular binding domain recognizes at least one target antigen that is a secreted protein.

4. The modified B cell of claim 3, wherein the secreted protein accumulates in an extracellular matrix.

5. The modified B cell of claim 2, wherein said target cell is selected from the group consisting of a tumor cell, a cardiac muscle cell, a skeletal muscle cell, a bone cell, a blood cell, a nerve cell, a fat cell, a skin cell, an endothelial cell, a hepatocyte, a pulmonary epithelial cell, and a fibroblast cell.

6. The modified B cell of claim 1, wherein said B cell expresses more than one chimeric receptor.

7. The modified B cell of claim 1, wherein said chimeric receptor comprises more than one extracellular binding domain.

8. The modified B cell of claim 1, wherein said extracellular binding domain is a single chain variable fragment (scFv), a full-length antibody, an antibody fragment, or an extracellular domain of a receptor or ligand.

9. The modified B cell of claim 1, wherein said extracellular binding domain binds to a target antigen or protein selected from the group consisting of: PSMA, GPC3, ASGR1 ASGR2, Sarcoglycan, Corin, FAP, MUC1 CEA153, JAM-1, LAF-1, Mesothelin, and Her2.

10. The modified B cell of claim 1 wherein the extracellular domain further comprises a hinge domain derived from the group consisting of IgG, IgM, CD28 and CD8.

11. The modified B cell of claim 1, wherein said signaling domain comprises an immunoreceptor tyrosine-based activation motif (ITAM) of a CD79a.

12. The modified B cell of claim 1, wherein said cytoplasmic domain further comprises a costimulatory domain.

13. A modified B cell comprising a chimeric receptor, wherein said chimeric receptor comprises
a) an extracellular domain, wherein the extracellular domain comprises an extracellular binding domain;
b) a transmembrane domain; and
c) a cytoplasmic domain that comprises at least one signaling domain
wherein said at least one signaling domain comprises CD79a,
wherein, upon binding of the extracellular binding domain to a target antigen or protein, the modified B cell is activated and presents an antigen or an antigen-derived epitope in an HLA or MHC complex, and
wherein said modified B cell expresses a payload, wherein the payload is not naturally expressed in a B cell.

14. The modified B cell of claim 1, wherein, upon binding of the extracellular binding domain to the target antigen or protein, at least one effector function of the modified B cell is activated, and wherein the at least one effector function is selected from the group consisting of protein expression or secretion, antibody expression or secretion, receptor expression or secretion, integrin expression, transcription induction, RNA translation, dendritic cell activation or recruitment, T cell activation, initiation of dendritic cell or T cell homing to a site/target of interest, and tertiary lymphoid structure formation.

15. The modified B cell of claim 14, wherein the at least one effector function comprises expression or secretion of a payload, and wherein the payload is not naturally expressed in a B cell or is expressed at higher levels than is naturally expressed in a B cell.

16. The modified B cell of claim 1, wherein, upon binding of the extracellular binding domain to the target antigen or protein, the modified B cell expresses of NFκB and thereby activates an NFAT pathway.

17. The modified B cell of claim 14, wherein the at least one effector function comprises expression or secretion of at least one of a protein, antibody, receptor, cytokine, chemokine, costimulatory molecule, checkpoint inhibitor, Toll-like receptor (TLR), integrin, or homing antibody.

18. The modified B cell of claim 10, wherein the extracellular domain further comprises an Ig Fc domain.

19. The modified B cell of claim 18, where the Ig Fc domain comprises the hinge domain.

20. A modified B cell comprising:
a chimeric receptor comprising:
(a) an extracellular domain comprising an extracellular binding domain;
(b) a transmembrane domain; and
(c) a cytoplasmic domain that comprises a signaling domain of at least one of CD19 and CD40;
wherein the signaling domain further comprises CD79a operably linked in the cytoplasmic domain;
wherein, upon binding of the extracellular binding domain to a target antigen or protein, the modified B cell is activated and presents an antigen or an antigen-derived epitope, in an HLA or MHC complex.

21. The modified B cell of claim 20, wherein the signaling domain comprises CD79a in tandem with CD79b or in tandem with another CD79a domain.

22. The modified B cell of claim 20 wherein the signaling domain further comprises CD79b in tandem with CD79a or another CD79b domain.

23. The modified B cell of claim 20, wherein the transmembrane domain comprises at least one of CD8, CD28, CD79a, or CD79b.

24. The modified B cell of claim 1, wherein the signaling domain comprises CD79a operably linked to CD79b in the cytoplasmic domain.

25. The modified B cell of claim 1 wherein the signaling domain comprises CD79a in tandem with CD79b or in tandem with another CD79a domain.

26. The modified B cell of claim 1 wherein the signaling domain further comprises CD79b in tandem with CD79a or another CD79b domain.

27. The modified B cell of claim 1, wherein the transmembrane domain comprises at least one of CD8, CD28, CD79a, and CD79b.

28. The modified B cell of claim 1, wherein said cytoplasmic domain further comprises a signaling domain of at least one of CD19 and CD40.

29. The modified B cell of claim 28, wherein said cytoplasmic domain comprises two or more signaling domains, and wherein said two or more signaling domains are operably linked or in tandem.

30. A modified B cell comprising a chimeric receptor, wherein said chimeric receptor comprises
a) an extracellular domain comprising an extracellular binding domain;
b) a transmembrane domain; and
c) a cytoplasmic domain comprising at least one signaling domain,
wherein said cytoplasmic domain comprises a domain of CD79a,
wherein, upon binding of the extracellular binding domain to a target antigen or protein, the modified B cell is activated and presents an antigen or an antigen-derived epitope, in an HLA or MHC complex.

31. The modified B cell of claim 30, wherein said domain of CD79a comprises the at least one signaling domain.

32. The modified B cell of claim 30, wherein said at least one signaling domain is operably linked to or in tandem with said domain of at least one molecule selected from the group consisting of CD79a, CD79b, CD40, and CD19.

* * * * *